United States Patent
Heistracher et al.

[11] Patent Number: 5,939,558
[45] Date of Patent: Aug. 17, 1999

[54] N-PHENYLTETRAHYDROINDAZOLES, THEIR PREPARATION, AND THEIR USE AS CROP PROTECTION AGENTS

[75] Inventors: Elisabeth Heistracher, Ludwigshafen; Lothar Rüb, Speyer; Christoph-Sweder von dem Bussche-Hünnefeld, Mannheim; Gerhard Hamprecht, Weinheim; Ralf Klintz, Grünstadt; Peter Schäfer, Ottersheim; Karl-Otto Westphalen, Speyer; Matthias Gerber, Limburgerhof; Helmut Walter, Obrigheim, all of Germany

[73] Assignee: BASF Aktiengesellschaft, Ludwigshafen, Germany

[21] Appl. No.: 08/793,124

[22] PCT Filed: Aug. 18, 1995

[86] PCT No.: PCT/EP95/03286

§ 371 Date: Feb. 18, 1997

§ 102(e) Date: Feb. 18, 1997

[87] PCT Pub. No.: WO96/06830

PCT Pub. Date: Mar. 7, 1996

[30] Foreign Application Priority Data

Aug. 26, 1994 [DE] Germany .............. 44 30 287

[51] Int. Cl.⁶ .............. A01N 43/56; C07D 231/56
[52] U.S. Cl. .............. 548/360.1; 504/169; 504/281
[58] Field of Search .............. 548/360.1; 504/281

[56] References Cited

U.S. PATENT DOCUMENTS 4,608,080  8/1986  Haga et al. .............. 548/360.1
4,695,312  9/1987  Hayase et al. .............. 548/360.1

*Primary Examiner*—Robert W. Ramsuer
*Attorney, Agent, or Firm*—Keil & Weinkauf

[57] ABSTRACT

N-Phenyltetrahydroindazoles of formula (I), where $R_1$ is H or $C_{1-4}$-alkyl; $R^2$ is halogen, $C_{1-4}$-alkyl or $C_{1-4}$-haloalkyl; $R^3$ is H or halogen; $R^4$ is $NO_2$, halogen, $C_{1-4}$-alkyl or $C_{1-4}$-haloalkyl; $R^5$ is $-XR^6$; X is $-O-$, $-S-$, $-SO-$ or $-SO_2-$; $R^6$ is $-Alk-R^7$; Alk is a substituted or unsubstituted methylene, ethylene, propylene, butylene or pentamethylene chain, where one chain member can carry a spiro-linked 2- to 5-membered C chain or where 2 ring members can be bridged via a $C_{1-5}$-alkylene chain; $R^7$ is CN, SCN, halogen or $-YR^{11}$, where Y is $-O-$, $-S-$, $-SO-$ or $-SO_2-$; $R^{10}$ is H, OH, $C_1-C_4$-alkyl, $C_1-C_4$-haloalkyl, $C_3-C_5$-cycloalkyl, $C_1-C_4$-alkoxy, $C_1-C_4$-haloalkoxy, $C_3-C_5$-cycloalkoxy, $C_1-C_4$-alkylthio, $C_1-C_4$-haloalkylthio, $-NH-R^{12}$, $-N(C_1-C_4\text{-alkyl})-R^{12}$, $-N(C_3-C_4\text{-alkenyl})-R^{12}$, $-N(C_3-C_4\text{-alkynyl})-R^{12}$, pyrrolidin-1-yl, piperid-1-yl, morpholin-4-yl, azepan-1-yl, (i) unsubstituted or substituted phenyl, benzyl, phenoxy or benzyloxy; $R^{11}$ is $C_{1-6}$-alkyl, $C_{1-6}$-haloalkyl or $C_{1-6}$-cycloalkyl; $R^{12}$ is H, OH, $C_{1-4}$-alkyl, $C_{3-4}$-alkenyl, $C_{3-4}$-alkynyl, $C_{3-6}$-cycloalkyl, $C_{1-4}$-alkoxy, $C_{3-4}$-alkenyloxy, $C_{3-4}$-alkenyloxy, $C_{3-4}$-alkynyloxy, or substituted or unsubstituted phenyl or benzyl; and the agriculturally utilizable salts of formula (I), with the provisoes that the simultaneous meaning of $R^6$ as dihalomethyl, $R^2$ and $R^4$ as chlorine and $R^3$ as halogen is excluded; the simultaneous meaning of X as oxygen and $R^7$ as $-OR^{11}$ or $C_1-C_6$-alkylthio is excluded; Alk must not carry a spiro-linked three-membered ring if $R^7$ is halogen and $R^{11}$ is not $C_{1-6}$-alkyl if $R^1$ is H, $R^2$ is $C_{1-4}$-haloalkyl, $R^3$ is F, $R^4$ is halogen and $R^7$ is $-R^{11}$. Use: as herbicides; for desiccating/defoliating plants.

13 Claims, No Drawings

N-PHENYLTETRAHYDROINDAZOLES, THEIR PREPARATION, AND THEIR USE AS CROP PROTECTION AGENTS

The present invention relates to novel N-phenyltetrahydroindazoles of the formula I

I where
- $R^1$ is hydrogen or $C_{1-4}$-alkyl;
- $R^2$ is halogen, $C_{1-4}$-alkyl or $C_{1-4}$-haloalkyl;
- $R^3$ is hydrogen or halogen;
- $R^4$ is nitro, halogen, $C_{1-4}$-alkyl or $C_{1-4}$-haloalkyl;
- $R^5$ is —$XR^6$;
- X is oxygen, sulfur, —SO— or —$SO_2$—;
- $R^6$ is —Alk—$R^7$;
- Alk is a methylene, ethylene, propylene, butylene or pentamethylene chain, where one chain member can carry a spiro-linked 2- to 5-membered carbon chain or where 2 ring members can be bridged via a $C_{1-5}$-alkylene chain and/or where, if desired, any methylene unit which can be substituted can carry one or two of the following substituents ($R^8$, $R^9$): halogen, $C_{3-6}$-cycloalkyl, $C_{2-6}$-alkenyl, $C_{2-6}$-alkynyl, —CO—$R^{10}$, imino-$C_{1-4}$-alkyl, ($C_{1-4}$-alkyl)imino-$C_{1-4}$-alkyl, N-hydroxyimino-$C_{1-4}$-alkyl, ($C_{1-4}$-alkoxy)imino-$C_{1-4}$-alkyl, $C_{1-4}$-alkoxy-($C_{1-4}$-alkoxy)carbonyl, ($C_{1-4}$-alkoxy)carbonyl-($C_{1-4}$-alkoxy)carbonyl, $C_{1-6}$-alkyl, $C_{1-6}$-haloalkyl, $C_{1-6}$-alkoxy, $C_{1-6}$-haloalkoxy, $C_{1-6}$-alkylthio or $C_{1-6}$-haloalkylthio, where, if desired, the 6 last-mentioned radicals can additionally carry one of the following radicals:

$C_{3-6}$-cycloalkyl, $C_{1-6}$-alkoxy, $C_{1-6}$-haloalkoxy, $C_{1-6}$-alkylthio, $C_{1-6}$-haloalkylthio, —CO—$R^{10}$, imino-$C_{1-4}$-alkyl, $C_{1-4}$-alkylimino-$C_{1-4}$-alkyl, N-hydroxyimino-$C_{1-4}$-alkyl, ($C_{1-4}$-alkoxy)imino-$C_{1-4}$-alkyl, phenyl or heteroaryl, where, if desired, the phenyl radical and the heteroaryl radicals, in turn, can carry one to three substituents selected from the group consisting of nitro, cyano, halogen, $C_{1-4}$-alkyl, $C_{1-4}$-alkoxy, $C_{1-4}$-alkylthio, $C_{1-4}$-haloalkyl, $C_{1-4}$-haloalkoxy, $C_{1-4}$-haloalkylthio and ($C_{1-4}$-alkoxy) carbonyl;

phenyl, naphthyl or heteroaryl, where, if desired, these aromatic radicals can carry one to three substituents selected from the group consisting of nitro, cyano, halogen, $C_{1-4}$-alkyl, $C_{1-4}$-haloalkyl, $C_{1-4}$-alkoxy, $C_{1-4}$-haloalkoxy, $C_{1-4}$-alkylthio, $C_{1-4}$-haloalkylthio and ($C_{1-4}$-alkoxy)carbonyl;
- $R^7$ is halogen, cyano, thiocyanato or —$YR^{11}$, where Y is oxygen, sulfur, —SO— or —$SO_2$—;
- $R^{10}$ is hydrogen, hydroxyl, $C_1$–$C_4$-alkyl, $C_1$–$C_4$-haloalkyl, $C_3$–$C_6$-cycloalkyl, $C_1$–$C_4$-alkoxy, $C_1$–$C_4$-haloalkoxy, $C_3$–$C_6$-cycloalkoxy, $C_1$–$C_4$-alkylthio, $C_1$–$C_4$-haloalkylthio, —NH—$R^{12}$, —N($C_1$–$C_4$-alkyl)-$R^{12}$, —N($C_3$–$C_4$-alkenyl)-$R^{12}$, —N($C_3$–$C_4$-alkynyl)-$R^{12}$, pyrrolidin-1-yl, piperid-1-yl, morpholin-4-yl, azepan-1-yl, —N⟨ ⟩N—($C_1$—$C_4$-alkyl), phenyl, benzyl, phenoxy or benzyloxy, where, if desired, the phenyl rings can each carry 1 to 3 substituents selected from the group consisting of nitro, cyano, halogen, $C_{1-4}$-alkyl, $C_{1-4}$-haloalkyl, $C_{1-4}$-alkoxy, $C_{1-4}$-haloalkoxy, ($C_{1-4}$-alkoxy) carbonyl, $C_{1-4}$-alkylthio and $C_{1-4}$-haloalkylthio;
- $R^{11}$ is $C_{1-6}$-alkyl, $C_{1-6}$-haloalkyl or $C_{3-6}$-cycloalkyl;
- $R^{12}$ is hydrogen, hydroxyl, $C_{1-4}$-alkyl, $C_{3-4}$-alkenyl, $C_{3-4}$-alkynyl, $C_{3-6}$-cycloalkyl, $C_{1-4}$-alkoxy, $C_{3-4}$-alkenyloxy, $C_{3-4}$-alkynyloxy, phenyl or benzyl, where, if desired, the phenyl ring in both phenyl and benzyl can carry one to three substituents selected from the group consisting of nitro, cyano, halogen, $C_{1-4}$-alkyl, $C_{1-4}$-haloalkyl, $C_{1-4}$-alkoxy, $C_{1-4}$-haloalkoxy, ($C_{1-4}$-alkoxy)carbonyl, $C_{1-4}$-alkylthio and $C_{1-4}$-haloalkylthio;

and the agriculturally utilizable salts of the compounds I, with the provisoes that
- the simultaneous meaning of $R^6$ as dihalomethyl, $R^2$ and $R^4$ as chlorine and $R^3$ as halogen is excluded;
- the simultaneous meaning of X equals oxygen and $R^7$ as —$OR^{11}$ or $C_1$–$C_6$-alkylthio is excluded;
- Alk must not carry a spiro-linked three-membered ring if $R^7$ is halogen and
- $R_{11}$ is not $C_{1-6}$-alkyl if $R^1$ is hydrogen, $R^2$ is $C_{1-4}$-haloalkyl, $R^3$ is fluorine, $R^4$ is halogen and $R^7$ is —$OR^{11}$.

The invention furthermore relates to
- the use of the compounds I as herbicides and/or plant desiccants and/or defoliants,
- herbicides and plant desiccants and/or defoliants which comprise the compounds I as active ingredients,
- processes for the preparation of the compounds I and of herbicides and plant desiccants and/or defoliants using the compounds I, and
- methods of controlling undesirable vegetation and for desiccating and/or defoliating plants using the compounds I.

BE 847 340 discloses, inter alia, 3-chloro-2-(3-methoxyphenyl)- and 3-bromo-2-(3-methoxyphenyl)-tetrahydroindazoles in which the phenyl ring in the para position relative to the indazole radical has attached to it a fluorine, chlorine or bromine substituent. These compounds are disclosed as selective herbicides in rice and fruit.

In addition, EP-A 197 495 describes 3-chloro-2-[4-chloro-5-(dihalomethoxy-2-halogen-phenyl]-tetrahydroindazoles and their herbicidal action.

Furthermore, EP-A 105 721 discloses herbicidally active 3-chloro-2-(4-chloro-2-fluoro-phenyl)-, 3-methyl-2-(4-chloro-2-fluoro-phenyl)- and 3-chloro-2-(4-bromo-2-fluoro-phenyl)-tetrahydroindazoles which carry on the phenyl ring in the 5-position relative to the indazole radical, inter alia, a $C_1$–$C_4$-alkoxy, $C_3$–$C_4$-alkenyloxy, $C_3$–$C_4$-alkenyloxy, $C_1$–$C_6$-alkoxycarbonylmethoxy, $C_3$–$C_6$-cycloalkoxycarbonylmethoxy or $C_1$–$C_4$-haloalkoxycarbonylmethoxy substituent. EP-A 379 099 also relates to herbicidally active 3-chloro-2-[4-chloro-5-($C_2$–$C_7$-alkoxy)phenyl]-tetrahydroindazoles and also 3-chloro-2-(4-chlorophenyl)- and 3-chloro-2-(4-chloro-2- fluorophenyl)-tetrahydroindazoles which carry on the phenyl ring in the 5-position relative to the indazole radical, inter alia, a certain alkoxycarbonylalkoxy or heterocyclylalkoxy group.

Finally, EP-A 049 508 discloses, as herbicides, N-phenyl-3,4,5,6-tetrahydrophthalimides which have attached to them an alkoxy radical on the phenyl ring in the 5-position relative to the tetrahydrophthalimide.

However, the efficacy of these known herbicides against the harmful plants is not always entirely satisfactory, in particular at low application rates.

It is an object of the present invention to provide novel herbicidally active compounds which are more suitable for a tailor-made control of undesirable plants than the prior art.

We have found that this object is achieved by the N-phenyltetrahydroindazoles of the formula I and by herbicides which comprise the compounds I and which have a very good herbicidal action, and by processes for the preparation of these compositions and methods of controlling undesirable vegetation using the compounds I.

The compounds I according to the invention are furthermore useful for defoliating and desiccating parts of plants, for example cotton, ton, potatoes, oilseed rape, sunflowers, soya beans or field beans, in particular cotton. In this context, plant desiccants and/or defoliants, processes for the preparation thereof and methods for desiccating and/or defoliating plants using the compounds I have been found.

The compounds of the formula I can contain one or more chiral centers, in which case they are in the form of enantiomer/diastereomer mixtures. The invention relates to the pure enantiomers or diastereomers and also to mixtures of these.

The N-phenyltetrahydroindazoles of the formula I can be in the form of their agriculturally utilizable salts, in which case, as a rule, the nature of the salt is not critical. In general, suitable salts are those of bases and acid addition salts which do not adversely affect the herbicidal action in comparison with the free compound I.

Particularly useful basic salts are those of alkali metals, preferably sodium and potassium salts, of alkaline earth metals, preferably calcium and magnesium salts, those of the transition metals, preferably zinc and iron salts, and ammonium salts, where, if desired, the ammonium ion can have attached to it one to three $C_1$–$C_4$-alkyl, hydroxy-$C_1$–$C_4$-alkyl substituents and/or one phenyl or benzyl substituent, preferably diisopropylammonium, tetramethylammonium, tetrabutylammonium, trimethylbenzylammonium and trimethyl(2-hydroxyethyl)ammonium salts, furthermore phosphonium salts, sulfonium salts, such as, preferably, tri-($C_1$–$C_4$-alkyl)sulfonium salts, and sulfoxonium salts, such as, preferably, tri-($C_1$–$C_4$-alkyl)sulfoxonium salts.

The most important acid addition salts to be mentioned are the hydrochlorides and hydrobromides, the sulfates, nitrates, phosphates, oxalates, and the dodecylbenzenesulfonates.

The organic moieties mentioned for the substituents $R^1$ to $R^{12}$ or as radicals on phenyl rings, heterocycles or Alk, and the meaning halogen, are collective terms for individual enumerations of the individual members of a group. All carbon chains, ie. all alkyl, haloalkyl, alkenyl, alkynyl, alkoxy, alkylthio, haloalkoxy, haloalkylthio, alkenyloxy, alkynyloxy, alkoxycarbonyl, alkylimino or alkoxyimino moieties, can be straight-chain or branched. Halogenated substituents preferably contain one to five identical or different halogen atoms.

For example, halogen is fluorine, chlorine, bromine or iodine;

$C_{1-4}$-alkyl and the alkyl moiety of ($C_{1-4}$-alkyl)imino-$C_{1-4}$-alkyl are methyl, ethyl, n-propyl, 1-methylethyl, n-butyl, 1-methylpropyl, 2-methylpropyl or 1,1-dimethylethyl;

$C_{1-6}$-alkyl is a radical as mentioned under $C_{1-4}$-alkyl, or is n-pentyl, 1-methylbutyl, 2-methylbutyl, 3-methylbutyl, 2,2-dimethylpropyl, 1-ethylpropyl, 1,1-dimethylpropyl, 1,2-dimethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl;

$C_{1-4}$-haloalkyl is a $C_{1-4}$-alkyl radical as mentioned above which is partially or fully substituted by fluorine, chlorine, bromine and/or iodine, eg. chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl;

$C_{1-6}$-haloalkyl is a $C_{1-6}$-alkyl radical as mentioned above which is partially or fully substituted by fluorine, chlorine, bromine and/or iodine, eg. one of the radicals mentioned under $C_1$–$C_4$-haloalkyl, or 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl or dodecafluorohexyl;

$C_{3-6}$-cycloalkyl is cyclopropyl, cyclobutyl, cyclopentyl or cyclohexyl;

$C_{2-4}$-alkenyl is ethenyl, prop-1-en-1-yl, prop-2-en-1-yl, 1-methylethenyl, n-buten-1-yl, n-buten-2-yl, n-buten-3-yl, 1-methyl-prop-1-en-1-yl, 2-methyl-prop-1-en-1-yl, 1-methyl-prop-2-en-1-yl or 2-methyl-prop-2-en-1-yl;

$C_{2-6}$-alkenyl is a radical as mentioned under $C_{2-4}$-alkenyl, or is n-penten-1-yl, n-penten-2-yl, n-penten-3-yl, n-penten-4-yl, 1-methyl-but-1-en-1-yl, 2-methyl-but-1-en-1-yl, 3-methyl-but-1-en-1-yl, 1-methyl-but-2-en-1-yl, 2-methyl-but-2-en-1-yl, 3-methyl-but-2-en-1-yl, 1-methyl-but-3-en-1-yl, 2-methyl-but-3-en-1-yl, 3-methyl-but-3-en-1-yl, 1,1-dimethyl-prop-2-en-1-yl, 1,2-dimethyl-prop-1-en-1-yl, 1,2-dimethyl-prop-2-en-1-yl, 1-ethyl-prop-1-en-2-yl, 1-ethyl-prop-2-en-1-yl, n-hex-1-en-1-yl, n-hex-2-en-1-yl, n-hex-3-en-1-yl, n-hex-4-en-1-yl, n-hex-5-en-1-yl, 1-methyl-pent-1-en-1-yl, 2-methyl-pent-1-en-1-yl, 3-methyl-pent-1-en-1-yl, 4-methyl-pent-1-en-1-yl, 1-methyl-pent-2-en-1-yl, 2-methyl-pent-2-en-1-yl, 3-methyl-pent-2-en-1-yl, 4-methyl-pent-2-en-1-yl, 1-methyl-pent-3-en-1-yl, 2-methyl-pent-3-en-1-yl, 3-methyl-pent-3-en-1-yl, 4-methyl-pent-3-en-1-yl, 1-methyl-pent-4-en-1-yl, 2-methyl-pent-4-en-1-yl, 3-methyl-pent-4-en-1-yl, 4-methyl-pent-4-en-1-yl, 1,1-dimethyl-but-2-en-1-yl, 1,1-dimethyl-but-3-en-1-yl, 1,2-dimethyl-but-1-en-1-yl, 1,2-dimethyl-but-2-en-1-yl, 1,2-dimethyl-but-3-en-1-yl, 1,3-dimethyl-but-1-en-1-yl, 1,3-dimethyl-but-2-en-1-yl, 1,3-dimethyl-but-3-en-1-yl, 2,2-dimethyl-but-3-en-1-yl, 2,3-dimethyl-but-1-en-1-yl, 2,3-dimethyl-but-2-en-1-yl, 2,3-dimethyl-but-3-en-1-yl, 3,3-dimethyl-but-1-en-1-yl, 3,3-dimethyl-but-2-en-1-yl, 1-ethyl-but-1-en-1-yl, 1-ethyl-but-2-en-1-yl, 1-ethyl-but-3-en-1-yl, 2-ethyl-but-1-en-1-yl, 2-ethyl-but-2-en-1-yl, 2-ethyl-but-3-en-1-yl, 1,1,2-trimethyl-prop-2-en-1-yl, 1-ethyl-1-methyl-prop-2-en-1-yl, 1-ethyl-2-methyl-prop-1-en-1-yl or 1-ethyl-2-methyl-prop-2-en-1-yl;

$C_{2-4}$-alkynyl is ethynyl, prop-1-yn-1-yl, prop-2-yn-1-yl, but-1-yn-1-yl, but-1-yn-3-yl, but-1-yn-4-yl or but-2-yn-1-yl;

$C_{2-6}$-alkynyl is a radical as mentioned under $C_{2-4}$-alkynyl, or is n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methyl-but-1-yn-3-yl, 3-methyl-but-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methyl-pent-1-yn-1-yl, 3-methyl-pent-1-yn-3-yl, 3-methyl-pent-1-yn-4-yl, 3-methyl-pent-1-yn-5-yl, 4-methyl-pent-1-yn-1-yl, 4-methyl-pent-2-yn-4-yl or 4-methyl-pent-2-yn-5-yl;

$C_{1-4}$-alkoxy and the alkoxy moieties of ($C_{1-4}$-alkoxy)imino-$C_{1-4}$-alkyl and $C_{1-4}$-alkoxy-($C_{1-4}$-alkoxy)carbonyl are methoxy, ethoxy, n-propoxy, 1-methylethoxy, n-butoxy, 1-methyl-propoxy, 2-methylpropoxy or 1,1-dimethylethoxy;

$C_{1-6}$-alkoxy is a radical as mentioned under $C_{1-4}$-alkoxy, or is n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy;

$C_{1-4}$-haloalkoxy is $C_{1-4}$-alkoxy as mentioned above which is partially or fully substituted by fluorine, chlorine, bromine and/or iodine, eg. difluoromethoxy, trifluoromethoxy, chlorodifluoromethoxy, bromodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy or nonafluorobutoxy;

$C_{1-6}$-haloalkoxy is $C_{1-6}$-alkoxy as mentioned above which is partially or fully substituted by fluorine, chlorine, bromine and/or iodine, eg. one of the radicals mentioned under $C_{1-4}$-haloalkoxy, or 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy or dodecafluorohexoxy;

$C_{3-6}$-cycloalkoxy is cyclopropoxy, cyclobutoxy, cyclopentoxy or cyclohexoxy;

$C_3$- or $C_4$-alkenyloxy is prop-2-enyloxy, n-but-2-enyloxy, n-but-3-enyloxy, 1-methyl-prop-2-enyloxy or 2-methyl-prop-2-enyloxy;

$C_3$- or $C_4$-alkynyloxy is prop-2-ynoxy, 1-methyl-2-propynoxy, but-2-ynoxy or but-3-ynoxy;

$C_{1-4}$-alkylthio is methylthio, ethylthio, n-propylthio, 1-methylethylthio, n-butylthio, 1-methylpropylthio, 2-methylpropylthio or 1,1-dimethylethylthio;

$C_{1-6}$-alkylthio is $C_{1-4}$-alkylthio as mentioned above, or is n-pentylthio, 1-methylbutylthio, 2-methylbutylthio, 3-methylbutylthio, 2,2-di-methylpropylthio, 1-ethylpropylthio, n-hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

$C_{1-4}$-haloalkylthio is $C_{1-4}$-alkylthio as mentioned above which is partially or fully substituted by fluorine, chlorine, bromine and/or iodine, eg. difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio or 4-bromobutylthio;

$C_{1-6}$-haloalkylthio is a $C_{1-6}$-alkylthio radical as mentioned above which is partially or fully substituted by fluorine, chlorine, bromine and/or iodine, eg. one of the radicals mentioned under $C_{1-4}$-haloalkylthio or 5-fluoropentylthio, 5-chloropentylthio, 5-bromopentoxy, 5-iodopentoxy, undecafluoropentoxy, 6-fluorohexylthio or 6-chlorohexylthio;

($C_{1-4}$-alkoxy)carbonyl and the alkoxycarbonyl moiety of ($C_{1-4}$-alkoxy)carbonyl-($C_{1-4}$-alkoxy)carbonyl are methoxycarbonyl, ethoxycarbonyl, n-propoxycarbonyl, 1-methylethoxycarbonyl, n-butoxycarbonyl, 1-methylpropoxycarbonyl, 2-methylpropoxycarbonyl or 1,1-dimethylethoxycarbonyl;

imino-$C_{1-4}$-alkyl is iminomethyl, 1-iminoethyl, 2-iminoethyl, 1-iminoprop-1-yl, 2-iminoprop-1-yl, 3-iminoprop-1-yl, 1-iminobut-1-yl, 2-iminobut-1-yl, 3-iminobut-1-yl, 4-iminobut-1-yl, 1-iminobut-2-yl, 3-iminobut-2-yl, 4-iminobut-2-yl, 1-(iminomethyl)-eth-1-yl, 1-(iminomethyl)-1-(methyl)-eth-1-yl or 1-(iminomethyl)-prop-1-yl;

N-hydroxyimino-$C_{1-4}$-alkyl is N-hydroxyiminomethyl, 1-N-hydroxyiminoethyl, 2-(N-hydroxyimino)ethyl, 1-(N-hydroxyimino)-prop-1-yl, 2-(N-hydroxyimino)prop-1-yl, 3-(N-hydroxyimino)-prop-1-yl, 1-(N-hydroxyimino)but-1-yl, 2-(N-hydroxyimino)-but-1-yl, 3-(N-hydroxyimino)but-1-yl, 4-(N-hydroxyimino)-but-1-yl, 1-(N-hydroxyimino)but-2-yl, 3-(N-hydroxyimino)-but-2-yl, 4-(N-hydroxyimino)-but-2-yl, 1-(N-hydroxyiminomethyl)eth-1-yl, 1-(N-hydroxyiminomethyl)-1-(methyl)-eth-1-yl or 1-(N-hydroxyiminomethyl)-prop-1-yl.

Heteroaryl is preferably to be understood as meaning a 5- or 6-membered aromatic heterocycle which, if desired, can have fused to it a benzene ring. Particularly preferred heteroaromatics are 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl, 1,2,3,4-tetrazol-5-yl, 2-pyridyl, 3-pyridyl, 4-pyridyl, 3-pyridazinyl, 4-pyridazinyl, 2-pyrimidinyl, 4-pyrimidinyl, 5-pyrimidinyl, 2-pyrazinyl, 1,3,5-triazin-2-yl or 1,2,4-triazin-3-yl.

In connection with the use of the compounds of the formula I according to the invention as herbicides and/or for desiccating/defoliating plants, the variables preferably have the following meanings, either on their own or in combination:

$R^1$ is hydrogen, methyl, ethyl, n-propyl, 1-methylethyl, n-butyl, 1-methylpropyl, 2-methylpropyl or 1,1-dimethylethyl, in particular hydrogen or methyl;

$R^2$ is a substituent from amongst the group 2.01–2.30 (Table 1):

| No. | $R^2$ | No. | $R^2$ | No. | $R^2$ |
|---|---|---|---|---|---|
| 2.01 | F | 2.11 | sec-$C_4H_9$ | 2.21 | $CH_2CH_2F$ |
| 2.02 | Cl | 2.12 | t-$C_4H_9$ | 2.22 | $CH_2CHF_2$ |
| 2.03 | Br | 2.13 | $CH_2F$ | 2.23 | $CH_2CF_3$ |
| 2.04 | I | 2.14 | $CHF_2$ | 2.24 | $CHFCH_3$ |
| 2.05 | $CH_3$ | 2.15 | $CF_3$ | 2.25 | $CF_2CH_3$ |
| 2.06 | $C_2H_5$ | 2.16 | $CH_2Cl$ | 2.26 | $CF_2CF_3$ |
| 2.07 | n-$C_3H_7$ | 2.17 | $CHCl_2$ | 2.27 | $CH_2CH_2Cl$ |
| 2.08 | i-$C_3H_7$ | 2.18 | $CCl_3$ | 2.28 | $CH(Cl)CH_3$ |
| 2.09 | n-$C_4H_9$ | 2.19 | $CH_2Br$ | 2.29 | $CH_2CH_2Br$ |
| 2.10 | i-$C_4H_9$ | 2.20 | $CHBr_2$ | 2.30 | $CH(Br)CH_3$ | in particular 2.01–2.05 or 2.15;

$R^3$ is hydrogen, fluorine, chlorine, bromine or iodine, in particular hydrogen, fluorine or chlorine;

$R^4$ is a substituent from amongst the group 4.01–4.31 (Table 2):

| No. | $R^4$ | No. | $R^4$ | No. | $R^4$ |
|---|---|---|---|---|---|
| 4.01 | F | 4.11 | sec-$C_4H_9$ | 4.21 | $CH_2CH_2F$ |
| 4.02 | Cl | 4.12 | t-$C_4H_9$ | 4.22 | $CH_2CHF_2$ |
| 4.03 | Br | 4.13 | $CH_2F$ | 4.23 | $CH_2CF_3$ |
| 4.04 | I | 4.14 | $CHF_2$ | 4.24 | $CHFCH_3$ |
| 4.05 | $CH_3$ | 4.15 | $CF_3$ | 4.25 | $CF_2CH_3$ |
| 4.06 | $C_2H_5$ | 4.16 | $CH_2Cl$ | 4.26 | $CF_2CF_3$ |
| 4.07 | n-$C_3H_7$ | 4.17 | $CHCl_2$ | 4.27 | $CH_2CH_2Cl$ |
| 4.08 | i-$C_3H_7$ | 4.18 | $CCl_3$ | 4.28 | $CH(Cl)CH_3$ |
| 4.09 | n-$C_4H_9$ | 4.19 | $CH_2Br$ | 4.29 | $CH_2CH_2Br$ |
| 4.10 | i-$C_4H_9$ | 4.20 | $CHBr_2$ | 4.30 | $CH(Br)CH_3$ |
|  |  |  |  | 4.31 | $NO_2$ | in particular 4.01–4.04;

Alk is a methylene, ethylene, propylene, butylene or pentamethylene chain, where one chain member can be spiro-linked to one of the following chains: —$CH_2CH_2$—, —$CH_2CH_2CH_2$—, —$CH_2CH_2CH_2CH_2$—, —$CH_2CH(CH_3)CH_2$—, —$CH_2C(CH_3)_2CH_2$—, —$CH_2CH_2CH_2CH_2CH_2$— or —$CH(CH_3)CH_2CH_2$—;

2 ring members can be bridged via one of the following alkylenes: methylene, —$CH_2CH_2$—, —$CH(CH_3)$—, —$CH_2CH_2CH_2$—, —$CH_2CH_2CH_2CH_2$—, —$CH_2CH(CH_3)CH_2$—, —$CH_2C(CH_3)_2CH_2$—, —$CH_2CH_2CH_2CH_2CH_2$— or —$CH(CH_3)CH_2CH_2$—;

and, if desired, any methylene unit which can be substituted can carry one or two substituents which, independently of one another, are selected from Table 3:

TABLE 3

| No. | $R^8$ and/or $R^9$ |
|---|---|
| 8/9.01 | H |
| 8/9.02 | F |
| 8/9.03 | Cl |
| 8/9.04 | Br |
| 8/9.05 | I |
| 8/9.06 | cyclopropyl |
| 8/9.07 | cyclobutyl |
| 8/9.08 | cyclopentyl |
| 8/9.09 | cyclohexyl |
| 8/9.10 | $CH_3$ |
| 8/9.11 | $C_2H_5$ |
| 8/9.12 | n-$C_3H_7$ |
| 8/9.13 | i-$C_3H_7$ |
| 8/9.14 | n-$C_4H_9$ |
| 8/9.15 | i-$C_4H_9$ |
| 8/9.16 | s-$C_4H_9$ |
| 8/9.17 | tert-$C_4H_9$ |
| 8/9.18 | $CH_2F$ |
| 8/9.19 | $CHF_2$ |
| 8/9.20 | $CF_3$ |
| 8/9.21 | $CH_2Cl$ |
| 8/9.22 | $CHCl_2$ |
| 8/9.23 | $CCl_3$ |
| 8/9.24 | $CH_2Br$ |
| 8/9.25 | $CHBr_2$ |
| 8/9.26 | $CHF_2Cl$ |
| 8/9.27 | $CBrF_2$ |
| 8/9.28 | $CH_2CHF_2$ |
| 8/9.29 | $CH_2CF_3$ |
| 8/9.30 | $CHFCH_3$ |
| 8/9.31 | $CF_2CH_3$ |
| 8/9.32 | $CF_2CF_3$ |
| 8/9.33 | $CH_2CH_2Cl$ |
| 8/9.34 | $CH(Cl)CH_3$ |
| 8/9.35 | $CH_2CH_2Br$ |
| 8/9.36 | $CH(Br)CH_3$ |
| 8/9.37 | $CH(Cl)CH_2Cl$ |
| 8/9.38 | $CH_2CH_2CH_2F$ |
| 8/9.39 | $CH_2CH_2CH_2Cl$ |
| 8/9.40 | $CH_2CH_2CH_2Br$ |
| 8/9.41 | $OCH_3$ |
| 8/9.42 | $OC_2H_5$ |
| 8/9.43 | $OCH(CH_3)_2$ |

TABLE 3-continued

| No. | $R^8$ and/or $R^9$ |
|---|---|
| 8/9.44 | $OCH_2CH_2CH_3$ |
| 8/9.45 | $OC(CH_3)_3$ |
| 8/9.46 | $O\text{-}n\text{-}C_4H_9$ |
| 8/9.47 | $O\text{-}CH_2CH(CH_3)_2$ |
| 8/9.48 | $OCH(CH_3)C_2H_5$ |
| 8/9.49 | $O\text{-}n\text{-}C_5H_{11}$ |
| 8/9.50 | $O\text{-}n\text{-}C_6H_{13}$ |
| 8/9.51 | $OCH_2F$ |
| 8/9.52 | $OCHF_2$ |
| 8/9.53 | $OCF_3$ |
| 8/9.55 | $OCH_2Cl$ |
| 8/9.56 | $OClCF_2$ |
| 8/9.57 | $OCH_2CH_2F$ |
| 8/9.58 | $OCH_2CHF_2$ |
| 8/9.59 | $OCH_2CF_3$ |
| 8/9.60 | $OCHFCH_3$ |
| 8/9.61 | $OCF_2CH_3$ |
| 8/9.62 | $OCF_2CF_3$ |
| 8/9.63 | $OCH_2CH_2Cl$ |
| 8/9.64 | $OCH(Cl)CH_3$ |
| 8/9.65 | $OCH_2CH_2Br$ |
| 8/9.66 | $OCH(Br)CH_3$ |
| 8/9.67 | $OCH(Cl)CH_2Cl$ |
| 8/9.68 | $OCH_2CH_2CH_2F$ |
| 8/9.69 | $OCH_2CH_2CH_2Cl$ |
| 8/9.70 | $OCH_2CH_2CH_2Br$ |
| 8/9.71 | $SCH_3$ |
| 8/9.72 | $SC_2H_5$ |
| 8/9.73 | $SCH(CH_3)_2$ |
| 8/9.74 | $SCH_2CH_2CH_3$ |
| 8/9.75 | $SC(CH_3)_3$ |
| 8/9.76 | $S\text{-}n\text{-}C_4H_9$ |
| 8/9.77 | $SCF_3$ |
| 8/9.78 | $CH_2$-cyclopropyl |
| 8/9.79 | $CH_2$-cyclobutyl |
| 8/9.80 | $CH_2$-cyclopentyl |
| 8/9.81 | $CH_2$-cyclohexyl |
| 8/9.82 | $CH_2CH_2$-cyclopropyl |
| 8/9.83 | $CH_2\text{—}OCH_3$ |
| 8/9.84 | $CH_2CH_2\text{—}OCH_3$ |
| 819.85 | $CH_2\text{—}OC_2H_5$ |
| 8/9.86 | $CH_2CH_2\text{—}OC_2H_5$ |
| 8/9.87 | $CH_2CH_2CH_2\text{—}OCH_3$ |
| 8/9.88 | $CH_2\text{—}OCF_3$ |
| 8/9.89 | $CH_2CH_2\text{—}OCF_3$ |
| 8/9.90 | $CH_2CH_2\text{—}OCHF_2$ |
| 8/9.91 | $CH_2\text{—}OCHF_2$ |
| 8/9.92 | $CH_2\text{—}OCH_2CF_3$ |
| 8/9.93 | $CH_2CH_2\text{—}OCH_2CF_3$ |
| 8/9.94 | $CH_2CH_2\text{—}OCF_2Cl$ |
| 8/9.95 | $CH_2\text{—}OCF_2Cl$ |
| 8/9.96 | $CH_2\text{—}OCH_2CH_2Cl$ |
| 8/9.97 | $CH_2CH_2\text{—}OCH_2CH_2Cl$ |
| 8/9.98 | $CH_2\text{—}OCH_2CH_2F$ |
| 8/9.99 | $CH_2CH_2\text{—}OCH_2CH_2F$ |
| 8/9.100 | $CH_2\text{—}SCH_3$ |
| 8/9.101 | $CH_2\text{—}SC_2H_5$ |
| 8/9.102 | $CH_2CH_2\text{—}SCH_3$ |
| 8/9.103 | $CH_2CH_2\text{—}SC_2H_5$ |
| 8/9.104 | $CH_2\text{—}SCF_3$ |
| 8/9.105 | $CH_2\text{—}SCF_2H$ |
| 8/9.106 | $CH_2\text{—}SCF_2Cl$ |
| 8/9.107 | $CH_2\text{—}SCH_2CF_3$ |
| 8/9.108 | $CH_2\text{—}SCH_2CH_2F$ |
| 8/9.109 | $CH_2\text{—}SCH_2CH_2Cl$ |
| 8/9.110 | $CH_2CH_2\text{—}SCF_3$ |
| 8/9.111 | $CH_2CH_2\text{—}SCHF_2$ |
| 8/9.112 | $CH_2CH_2\text{—}SCF_2Cl$ |
| 8/9.113 | $CH_2CH_2\text{—}SCH_2CF_3$ |
| 8/9.114 | $CH_2CH_2\text{—}SCH_2CH_2F$ |
| 8/9.115 | $CH_2CH_2\text{—}SCH_2CH_2Cl$ |
| 8/9.116 | $CH_2\text{—}COCH_3$ |
| 8/9.117 | $CH_2CH_2\text{—}COCH_3$ |
| 8/9.118 | $CH_2CH_2\text{—}COC_2H_5$ |
| 8/9.119 | $CH(COCH_3)CH_3$ |
| 8/9.120 | $CH_2CHO$ |
| 8/9.121 | $CH_2CH_2CHO$ |
| 8/9.122 | $CH_2\text{—}COCF_3$ |
| 8/9.123 | $CH_2\text{—}COCH_2Cl$ |
| 8/9.124 | $CH_2\text{—}COCH_2Br$ |
| 8/9.125 | $CH_2CH_2\text{—}COCF_3$ |
| 8/9.126 | $CH_2CH_2\text{—}COCH_2Cl$ |
| 8/9.127 | $CH_2CH_2\text{—}COCH_2Br$ |
| 8/9.128 | $CH_2\text{—}CO$-cyclopropyl |
| 8/9.129 | $CH_2CH_2\text{—}CO$-cyclopropyl |
| 8/9.130 | $CH_2\text{—}CO\text{—}OCH_3$ |
| 8/9.131 | $CH_2\text{—}CO\text{—}OC_2H_5$ |
| 8/9.132 | $CH_2\text{—}CO\text{—}OCH(CH_3)_2$ |
| 8/9.133 | $CH_2\text{—}CO\text{—}OC(CH_3)_3$ |
| 8/9.134 | $CH_2CH_2\text{—}CO\text{—}OCH_3$ |
| 8/9.135 | $CH_2CH_2\text{—}CO\text{—}OC_2H_5$ |
| 8/9.136 | $CH_2CH_2\text{—}CO\text{—}OCH(CH_3)_2$ |
| 8/9.137 | $CH_2CH_2\text{—}CO\text{—}OC(CH_3)_3$ |
| 8/9.138 | $CH(CO\text{—}OCH_3)\text{—}CH_3$ |
| 8/9.139 | $CH(CO\text{—}OC_2H_5)\text{—}CH_3$ |
| 8/9.140 | $CH(CO\text{—}OCH(CH_3)_2)\text{—}CH_3$ |
| 8/9.141 | $CH(CO\text{—}OC(CH_3)_3)\text{—}CH_3$ |
| 8/9.142 | $CH_2\text{—}CO\text{—}OCH_2Cl$ |
| 8/9.143 | $CH_2\text{—}CO\text{—}OCH_2F$ |
| 8/9.144 | $CH_2\text{—}CO\text{—}O$-cyclopropyl |
| 8/9.145 | $CH_2\text{—}CO\text{—}SCH_3$ |
| 8/9.146 | $CH_2\text{—}CO\text{—}SC_2H_5$ |
| 8/9.147 | $CH_2\text{—}CO\text{—}SCF_3$ |
| 8/9.148 | $CH_2CH_2\text{—}CO\text{—}OCH_2CH_2Cl$ |
| 8/9.149 | $CH_2CH_2\text{—}CO\text{—}OCH_2CH_2F$ |
| 8/9.150 | $CH_2CH_2\text{—}CO\text{—}O$-cyclopropyl |
| 8/9.151 | $CH_2CH_2\text{—}CO\text{—}SCH_3$ |
| 8/9.152 | $CH_2CH_2\text{—}CO\text{—}SC_2H_5$ |
| 8/9.153 | $CH_2CH_2\text{—}CO\text{—}SCF_3$ |
| 8/9.154 | $CH_2\text{—}COC_6H_5$ |
| 8/9.155 | $CH_2\text{—}COCH_2C_6H_5$ |
| 8/9.156 | $CH_2\text{—}CO\text{—}OC_6H_5$ |
| 8/9.157 | $CH_2\text{—}CO\text{—}OCH_2C_6H_5$ |
| 8/9.158 | $CH_2\text{—}CONH_2$ |
| 8/9.159 | $CH_2\text{—}CONH\text{—}CH_3$ |
| 8/9.160 | $CH_2\text{—}CONH\text{—}C_2H_5$ |
| 8/9.161 | $CH_2\text{—}CON(CH_3)_2$ |
| 8/9.162 | $CH_2\text{—}CON(C_2H_5)_2$ |
| 8/9.163 | $CH_2\text{—}COOH$ |
| 8/9.164 | $CH_2CH_2\text{—}COC_6H_5$ |
| 8/9.165 | $CH_2CH_2\text{—}COCH_2C_6H_5$ |
| 8/9.166 | $CH_2CH_2\text{—}COOC_6H_5$ |
| 8/9.167 | $CH_2CH_2\text{—}CO\text{—}OCH_2C_6H_5$ |
| 8/9.168 | $CH_2CH_2\text{—}CONH_2$ |
| 8/9.169 | $CH_2CH_2\text{—}CONH\text{—}CH_3$ |
| 8/9.170 | $CH_2CH_2\text{—}CONH\text{—}C_2H_5$ |
| 8/9.171 | $CH_2CH_2\text{—}CON(CH_3)_2$ |
| 8/9.172 | $CH_2CH_2\text{—}CON(C_2H_5)_2$ |
| 8/9.173 | $CH_2CH_2\text{—}COOH$ |
| 8/9.174 | $CH_2CH\text{=}N\text{—}CH_3$ |
| 8/9.175 | $CH_3C(CH_3)\text{=}N\text{—}CH_3$ |
| 8/9.176 | $CH_2CH\text{=}N\text{—}OCH_3$ |
| 8/9.177 | $CH_2CH\text{=}N\text{—}OC_2H_5$ |
| 8/9.178 | $CH_2C(CH_3)\text{=}N\text{—}OCH_3$ |
| 8/9.179 | $CH_2C(CH_3)\text{=}N\text{—}OC_2H_5$ |
| 8/9.180 | $CH_2CH_2CH\text{=}N\text{—}CH_3$ |
| 8/9.181 | $CH_2CH_2C(CH_3)\text{=}N\text{—}CH_3$ |
| 8/9.182 | $CH_2CH_2CH\text{=}N\text{—}OCH_3$ |
| 8/9.183 | $CH_2CH_2CH\text{=}N\text{—}OC_2H_5$ |
| 8/9.184 | $CH_2C(CH_3)\text{=}N\text{—}OCH_3$ |
| 8/9.185 | $CH_2C(CH_3)\text{=}N\text{—}OC_2H_5$ |
| 8/9.186 | $CH_2$-phenyl |
| 8/9.187 | $CH_2$-furanyl |
| 8/9.188 | $CH_2$-pyrolyl |
| 8/9.189 | $CH_2$-thienyl |
| 8/9.190 | $CH_2$-thiazolyl |
| 8/9.191 | $CH_2$-oxazolyl |
| 8/9.192 | $CH_2$-thiadiazolyl |
| 8/9.193 | $CH_2$-pyrazolyl |
| 8/9.194 | $CH_2$-triazolyl |
| 8/9.195 | $CH_2$-(methyl-imidazolyl) |
| 8/9.196 | $CH_2$-(methylpyrazolyl) |

TABLE 3-continued

| No. | R⁸ and/or R⁹ |
|---|---|
| 8/9.197 | CH₂-methyltriazolyl) |
| 8/9.198 | CH₂-(4-Cl—C₆H₄) |
| 8/9.199 | CH₂-(2,4-Cl₂—C₆H₃) |
| 8/9.200 | CH₂-(4-NO₂—C₆H₄) |
| 8/9.201 | CH₂-(4-CN—C₆H₄) |
| 8/9.202 | CH₂CH₂—C₆H₅ |
| 8/9.203 | CH₂CH₂-(4-Cl—C₆H₅) |
| 8/9.204 | CH(Cl)-cyclopropyl |
| 8/9.205 | CH(Cl)CH₂—OCH₃ |
| 8/9.206 | CH(Cl)CH₂CH₂OCH₃ |
| 8/9.207 | CH(Br)CH₂OCH₃ |
| 8/9.208 | CH(Cl)COCH₃ |
| 8/9.209 | CH(Br)COCH₃ |
| 8/9.210 | CH(Br)COCH₂Br |
| 8/9.211 | CH(Cl)CO₂CH₃ |
| 8/9.212 | CH(Br)CO—OC₂H₅ |
| 8/9.213 | CH(Cl)C₆H₅ |
| 8/9.214 | OCH₂-cyclopropyl |
| 8/9.215 | OCH₂CH₂OCH₃ |
| 8/9.216 | OCH₂CH₂OC₂H₅ |
| 8/9.217 | OCH₂CH₂OCHF₂ |
| 8/9.218 | OCH₂CH₂OCF₃ |
| 8/9.219 | OCH₂CH₂SCH₃ |
| 8/9.220 | OCH₂CO₂CH₃ |
| 8/9.221 | OCH(CH₃)CO—OCH₃ |
| 8/9.222 | OCH₂CO—OC₂H₅ |
| 8/9.223 | OCH(CH₃)CO—OC₂H₅ |
| 8/9.224 | OCH₂CONH₂ |
| 8/9.225 | OCH₂CH₂CO—OCH₃ |
| 8/9.226 | OCH₂CH₂CO—OC₂H₅ |
| 8/9.227 | OCH₂CH=NOCH₃ |
| 8/9.228 | OCH₂CH=NOC₂H₅ |
| 8/9.229 | OCH₂C₆H₅ |
| 8/9.230 | SCH₂-cyclopropyl |
| 8/9.231 | SCH₂CH₂—OCH₃ |
| 8/9.232 | SCH₂CH₂—OC₂H₅ |
| 8/9.233 | SCH₂CH₂—SCH₃ |
| 8/9.234 | SCH₂—CO—OCH₃ |
| 8/9.235 | SCH(CH₃)—CO—OCH₃ |
| 8/9.236 | SCH₂—CO—OC₂H₅ |
| 8/9.237 | SCH₂—C₆H₅ |
| 8/9.238 | CH=CH₂ |
| 8/9.239 | CH=CH—CH₃ |
| 8/9.240 | CH₂—CH=CH₂ |
| 8/9.241 | C(CH₃)=CH₂ |
| 8/9.242 | CH₂CH₂—CH=CH₂ |
| 8/9.243 | CH(CH₃)—CH=CH₂ |
| 8/9.244 | C≡CH |
| 8/9.245 | C≡C—CH₃ |
| 8/9.246 | CH(CH₃)—C≡CH |
| 8/9.247 | CH₂—C≡C—CH₃ |
| 8/9.248 | C₆H₅ |
| 8/9.249 | 2-Cl—C₆H₄ |
| 8/9.250 | 3-Cl—C₆H₄ |
| 8/9.251 | 4-Cl—C₆H₄ |
| 8/9.252 | 2-Br—C₆H₄ |
| 8/9.253 | 3-Br—C₆H₄ |
| 8/9.254 | 4-Br—C₆H₄ |
| 8/9.255 | 2-F—C₆H₄ |
| 8/9.256 | 3-F—C₆H₄ |
| 8/9.257 | 4-F—C₆H₄ |
| 8/9.258 | 2,4-Cl₂—C₆H₃ |
| 8/9.259 | 2,6-Cl₂—C₆H₃ |
| 8/9.260 | 3,4-Cl₂—C₆H₃ |
| 8/9.261 | 3,5-Cl₂—C₆H₃ |
| 8/9.262 | 4-CN—C₆H₄ |
| 8/9.263 | 4-NO₂—C₆H₄ |
| 8/9.264 | 4-CH₃—C₆H₄ |
| 8/9.265 | 4-CF₃—C₆H₄ |
| 8/9.266 | 3-CF₃—C₆H₄ |
| 8/9.267 | 4-OCF₃—C₆H₄ |
| 8/9.268 | CHO |
| 8/9.269 | COCH₃ |
| 8/9.270 | COC₂H₅ |
| 8/9.271 | COCF₃ |
| 8/9.272 | COCH₂Cl |
| 8/9.273 | COCH₂Br |

TABLE 3-continued

| No. | R⁸ and/or R⁹ |
|---|---|
| 8/9.274 | CO-cyclopropyl |
| 8/9.275 | CO—OCH₃ |
| 8/9.276 | CO—OC₂H₅ |
| 8/9.277 | CO—OCH(CH₃)₂ |
| 8/9.278 | CO—OC₄H₉ |
| 8/9.279 | CO—OCH₂CH₂Cl |
| 8/9.280 | CO—OCH₂CH₂Br |
| 8/9.281 | CO—OCH₂CH₂F |
| 8/9.282 | CO—OCH₂CF₃ |
| 8/9.283 | CO—O-cyclopropyl |
| 8/9.284 | CO—SCH₃ |
| 8/9.285 | CO—SC₂H₅ |
| 8/9.286 | CO—C₆H₅ |
| 8/9.287 | CO—OC₆H₅ |
| 8/9.288 | CO—CH₂C₆H₅ |
| 8/9.289 | CO—OCH₂C₆H₅ |
| 8/9.290 | CONH₂ |
| 8/9.291 | CONH—CH₃ |
| 8/9.292 | CON(CH₃)₂ |
| 8/9.293 | CONH—C₂H₅ |
| 8/9.294 | CON(C₂H₅)₂ |
| 8/9.295 | CONH-n-C₃H₇ |
| 8/9.296 | CONH—CH(CH₃)₂ |
| 8/9.297 | CONH-n-C₄H₉ |
| 8/9.298 | CONH—CH₂CH=CH₂ |
| 8/9.299 | CONH—CH₂C≡CH |
| 8/9.300 | CO—(piperidin-1-yl) |
| 8/9.301 | CO—(pyrrolidin-1-yl) |
| 8/9.302 | CH=N—CH₃ |
| 8/9.303 | C(CH₃)=N—CH₃ |
| 8/9.304 | CH=N—C₂H₅ |
| 8/9.304 | CH₂CH=N—OCH₃ |
| 8/9.306 | CH=N—OC₂H₅ |
| 8/9.307 | CH₂CH=N—OCH₃ |
| 8/9.308 | C(CH₃)=N—OCH₃ |
| 8/9.309 | C(CH₃)=N—OC₂H₅ |
| 8/9.310 | CO—OCH₂CH₂—OCH₃ |
| 8/9.311 | CO—OCH₂CH₂—OC₂H₅ |
| 8/9.312 | CO—OCH₂—CO—OCH₃ |
| 8/9.313 | CO—OCH₂—CO—OC₂H₅ |
| 8/9.314 | CO—OCH(CH₃)—CO—OCH₃ |
| 8/9.315 | CO—OCH₂CH₂—CO—OCH₃ |

$R^7$ is a substituent from amongst the group 7.01–7.119 (Table 4):

TABLE 4

| No. | R⁷ |
|---|---|
| 7.01 | F |
| 7.02 | Cl |
| 7.03 | Br |
| 7.04 | I |
| 7.05 | CN |
| 7.06 | SCN |
| 7.07 | SCF₃ |
| 7.08 | SCH₂F |
| 7.09 | SCHF₂ |
| 7.10 | SCH₂CH₂F |
| 7.11 | SCH₂CHF₂ |
| 7.12 | SCH₂CF₃ |
| 7.13 | SCHFCH₃ |
| 7.14 | SCF₂CH₃ |
| 7.15 | SCF₂CF₃ |
| 7.16 | SCHFCH₂CH₃ |
| 7.17 | SCH₂CH₂CH₂F |
| 7.18 | SCH₂CH₂CF₃ |
| 7.19 | SCH₂CH₂Cl |
| 7.20 | SCH₂CH₂CH₂Cl |
| 7.21 | S-cyclopropyl |
| 7.22 | s-cyclobutyl |
| 7.23 | S-cyclopentyl |
| 7.24 | S-cyclohexyl |
| 7.25 | SOCH₃ |

TABLE 4-continued

| No. | R⁷ |
|---|---|
| 7.26 | SOC₂H₅ |
| 7.27 | SOCH(CH₃)₂ |
| 7.28 | SOCH₂CH₂CH₃ |
| 7.29 | SOC(CH₃)₃ |
| 7.30 | SO-n-C₄H₉ |
| 7.31 | SOCH₂CH(CH₃)₂ |
| 7.32 | SO-n-C₅H₁₁ |
| 7.33 | SO-n-C₆H₁₃ |
| 7.34 | SOCF₃ |
| 7.35 | SOCH₂F |
| 7.36 | SOCHF₂ |
| 7.37 | SOCH₂CH₂F |
| 7.38 | SOCH₂CHF₂ |
| 7.39 | SOCH₂CF₃ |
| 7.40 | SOCHFCH₃ |
| 7.41 | SOCF₂CH₃ |
| 7.42 | SOCF₂CF₃ |
| 7.43 | SOCHFCH₂CH₃ |
| 7.44 | SOCH₂CH₂CH₂F |
| 7.45 | SOCH₂CH₂CF₃ |
| 7.46 | SOCH₂CH₂Cl |
| 7.47 | SOCH₂CH₂CH₂Cl |
| 7.48 | SO-cyclopropyl |
| 7.49 | SO-cyclobutyl |
| 7.50 | SO-cyclopentyl |
| 7.51 | SO-cyclohexyl |
| 7.52 | SO₂—CH₃ |
| 7.53 | SO₂—C₂H₅ |
| 7.54 | SO₂—CH(CH₃)₂ |
| 7.55 | SO₂—CH₂CH₂CH₃ |
| 7.56 | SO₂-n-C₄H₉ |
| 7.57 | SO₂—CH₂CH(CH₃)₂ |
| 7.58 | SO₂-n-C₅H₁₁ |
| 7.59 | SO₂-n-C₆H₁₃ |
| 7.60 | SO₂—CF₃ |
| 7.61 | SO₂—CH₂F |
| 7.62 | SO₂—CHF₂ |
| 7.63 | SO₂—CH₂CH₂F |
| 7.64 | SO₂—CH₂CHF₂ |
| 7.65 | SO₂—CH₂CF₃ |
| 7.66 | SO₂—CHFCH₃ |
| 7.67 | SO₂—CF₂CH₃ |
| 7.68 | SO₂—CF₂CF₃ |
| 7.69 | SO₂—CHFCH₂CH₃ |
| 7.70 | SO₂—CH₂CH₂CH₂F |
| 7.71 | SO₂—CH₂CH₂CF₃ |
| 7.72 | SO₂—CH₂CH₂Cl |
| 7.73 | SO₂—CH₂CH₂CH₂Cl |
| 7.74 | SO₂-cyclopropyl |
| 7.75 | SO₂-cyclobutyl |
| 7.76 | SO₂-cyclopentyl |
| 7.77 | SO₂-cyclohexyl |
| 7.78 | OCH₃ |
| 7.79 | OC₂H₅ |
| 7.80 | OCH(CH₃)₂ |
| 7.81 | OCH₂CH₂CH₃ |
| 7.82 | OC(CH₃)₃ |
| 7.83 | O-n-C₄H₉ |
| 7.84 | O—CH₂CH(CH₃)₂ |
| 7.85 | O—CH(CH₃)C₂H₅ |
| 7.86 | O-n-C₅H₁₁ |
| 7.87 | O-n-C₆H₁₃ |
| 7.88 | OCF₃ |
| 7.89 | OCH₂F |
| 7.90 | OCHF₂ |
| 7.91 | OC(Cl)F₂ |
| 7.92 | OCH₂CH₂F |
| 7.93 | OCH₂CHF₂ |
| 7.94 | OCH₂CF₃ |
| 7.95 | OCHFCH₃ |
| 7.96 | OCF₂CH₃ |
| 7.97 | OCF₂CF₃ |
| 7.98 | OCHFCH₂CH₃ |
| 7.99 | OCH₂CH₂CH₂F |
| 7.100 | OCH₂CH₂CF₃ |
| 7.101 | OCH₂CH₂Cl |
| 7.102 | OCH₂CH₂CH₂Cl |
| 7.103 | OCH₂CH(Cl)CH₃ |
| 7.104 | OCH₂CH₂Br |
| 7.105 | OC(Br)F₂ |
| 7.106 | O-cyclopropyl |
| 7.107 | O-cyclobutyl |
| 7.108 | O-cyclopentyl |
| 7.109 | O-cyclohexyl |
| 7.110 | SCH₃ |
| 7.111 | SC₂H₅ |
| 7.112 | SCH(CH₃)₂ |
| 7.113 | SCH₂CH₂CH₃ |
| 7.114 | SC(CH₃)₃ |
| 7.115 | S-n-C₄H₉ |
| 7.116 | S—CH₂CH(CH₃)₂ |
| 7.117 | S—CH(CH₃)C₂H₅ |
| 7.118 | S-n-C₅H₁₁ |
| 7.119 | S-n-C₆H₁₃ |

Compounds I which are very particularly preferred with regard to their herbicidal action are those listed in Table 5.

TABLE 5

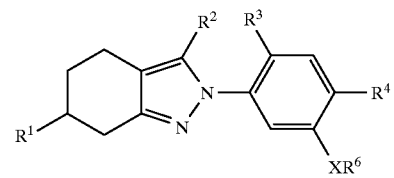

($R^1$ = H; $R^2$ = Cl; X = O)

| No. | R³ | R⁴ | R⁶ |
|---|---|---|---|
| Ia.001 | H | Cl | CH₂F |
| Ia.002 | F | Cl | CH₂F |
| Ia.003 | Cl | Cl | CH₂F |
| Ia.004 | H | Cl | CH₂Cl |
| Ia.005 | F | Cl | CH₂Cl |
| Ia.006 | Cl | Cl | CH₂Cl |
| Ia.007 | H | Cl | CH₂CN |
| Ia.008 | F | Cl | CH₂CN |
| Ia.009 | Cl | Cl | CH₂CN |
| Ia.010 | H | Cl | CH₂SCN |
| Ia.011 | F | Cl | CH₂SCN |
| Ia.012 | Cl | Cl | CH₂SCN |
| Ia.013 | H | Cl | CH₂SCF₃ |
| Ia.014 | F | Cl | CH₂SCF₃ |
| Ia.015 | Cl | Cl | CH₂SCF₃ |
| Ia.016 | H | Cl | CH₂SCHF₂ |
| Ia.017 | F | Cl | CH₂SCHF₂ |
| Ia.018 | Cl | Cl | CH₂SCHF₂ |
| Ia.019 | H | Cl | CH₂SOCH₃ |
| Ia.020 | F | Cl | CH₂SOCH₃ |
| Ia.021 | Cl | Cl | CH₂SOCH₃ |
| Ia.022 | H | Cl | CH₂SOC₂H₅ |
| Ia.023 | F | Cl | CH₂SOC₂H₅ |
| Ia.024 | Cl | Cl | CH₂SOC₂H₅ |
| Ia.025 | H | Cl | CH₂SOCF₃ |
| Ia.026 | F | Cl | CH₂SOCF₃ |
| Ia.027 | Cl | Cl | CH₂SOCF₃ |
| Ia.028 | H | Cl | CH₂SOCHF₂ |
| Ia.029 | F | Cl | CH₂SOCHF₂ |
| Ia.030 | Cl | Cl | CH₂SOCHF₂ |
| Ia.031 | H | Cl | CH₂SO₂CH₃ |
| Ia.032 | F | Cl | CH₂SO₂CH₃ |
| Ia.033 | Cl | Cl | CH₂SO₂CH₃ |
| Ia.034 | H | Cl | CH₂SO₂C₂H₅ |
| Ia.035 | F | Cl | CH₂SO₂C₂H₅ |
| Ia.036 | Cl | Cl | CH₂SO₂C₂H₅ |
| Ia.037 | H | Cl | CHF₂ |

TABLE 5-continued

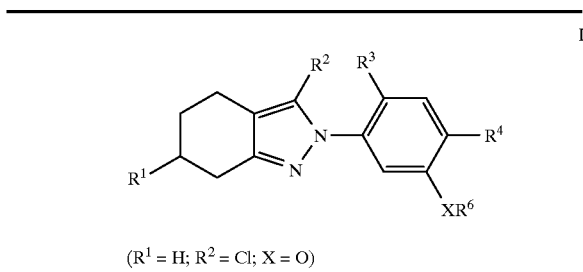

($R^1$ = H; $R^2$ = Cl; X = O)

| No. | $R^3$ | $R^4$ | $R^6$ |
|---|---|---|---|
| Ia.038 | H | Cl | $CHCl_2$ |
| Ia.039 | Cl | Cl | $CH_2CH_2F$ |
| Ia.040 | H | Cl | $CH_2CH_2F$ |
| Ia.041 | F | Cl | $CH_2CH_2F$ |
| Ia.042 | Cl | Cl | $CH(CH_3)F$ |
| Ia.043 | H | Cl | $CH(CH_3)F$ |
| Ia.044 | F | Cl | $CH(CH_3)F$ |
| Ia.045 | Cl | Cl | $CH_2CH_2Cl$ |
| Ia.046 | H | Cl | $CH_2CH_2Cl$ |
| Ia.047 | F | Cl | $CH_2CH_2Cl$ |
| Ia.048 | Cl | Cl | $CH(CH_3)Cl$ |
| Ia.049 | H | Cl | $CH(CH_3)Cl$ |
| Ia.050 | F | Cl | $CH(CH_3)Cl$ |
| Ia.051 | Cl | Cl | $CH_2CH_2Br$ |
| Ia.052 | H | Cl | $CH_2CH_2Br$ |
| Ia.053 | F | Cl | $CH_2CH_2Br$ |
| Ia.054 | Cl | Cl | $CH_2CH_2I$ |
| Ia.055 | H | Cl | $CH_2CH_2I$ |
| Ia.056 | F | Cl | $CH_2CH_2I$ |
| Ia.057 | Cl | Cl | $CH(CH_3)CN$ |
| Ia.058 | H | Cl | $CH(CH_3)CN$ |
| Ia.059 | F | Cl | $CH(CH_3)CN$ |
| Ia.060 | Cl | Cl | $CH_2CH_2SCN$ |
| Ia.061 | H | Cl | $CH_2CH_2SCN$ |
| Ia.062 | F | Cl | $CH_2CH_2SCN$ |
| Ia.063 | Cl | Cl | $CH(CH_3)SCN$ |
| Ia.064 | H | Cl | $CH(CH_3)SCN$ |
| Ia.065 | F | Cl | $CH(CH_3)SCN$ |
| Ia.066 | Cl | Cl | $CH_2CH_2SCHF_2$ |
| Ia.067 | H | Cl | $CH_2CH_2SCHF_2$ |
| Ia.068 | F | Cl | $CH_2CH_2SCHF_2$ |
| Ia.069 | Cl | Cl | $CH(CH_3)SCHF_2$ |
| Ia.070 | H | Cl | $CH(CH_3)SCHF_2$ |
| Ia.071 | F | Cl | $CH(CH_3)SCHF_2$ |
| Ia.072 | Cl | Cl | $CH_2CH_2SCF_3$ |
| Ia.073 | H | Cl | $CH_2CH_2SCF_3$ |
| Ia.074 | F | Cl | $CH_2CH_2SCF_3$ |
| Ia.075 | Cl | Cl | $CH(CH_3)SCF_3$ |
| Ia.076 | H | Cl | $CH(CH_3)SCF_3$ |
| Ia.077 | F | Cl | $CH(CH_3)SCF_3$ |
| Ia.078 | Cl | Cl | $CH_2CH_2SOCHF_2$ |
| Ia.079 | H | Cl | $CH_2CH_2SOCHF_2$ |
| Ia.080 | F | Cl | $CH_2CH_2SOCHF_2$ |
| Ia.081 | Cl | Cl | $CH(CH_3)SOCHF_2$ |
| Ia.082 | H | Cl | $CH(CH_3)SOCHF_2$ |
| Ia.083 | F | Cl | $CH(CH_3)SOCHF_2$ |
| Ia.084 | Cl | Cl | $CH_2CH_2SOCF_3$ |
| Ia.085 | H | Cl | $CH_2CH_2SOCF_3$ |
| Ia.086 | F | Cl | $CH_2CH_2SOCF_3$ |
| Ia.087 | Cl | Cl | $CH_2CH_2SO_2CHF_2$ |
| Ia.088 | H | Cl | $CH_2CH_2SO_2CHF_2$ |
| Ia.089 | F | Cl | $CH_2CH_2SO_2CHF_2$ |
| Ia.090 | Cl | Cl | $CH(CH_3)SO_2CHF_2$ |
| Ia.091 | H | Cl | $CH(CH_3)SO_2CHF_2$ |
| Ia.092 | F | Cl | $CH(CH_3)SO_2CHF_2$ |
| Ia.093 | Cl | Cl | $CH_2CH_2SO_2CF_3$ |
| Ia.094 | H | Cl | $CH_2CH_2SO_2CF_3$ |
| Ia.095 | F | Cl | $CH_2CH_2SO_2CF_3$ |
| Ia.096 | Cl | Cl | $CH(CH_3)SO_2CF_3$ |
| Ia.097 | H | Cl | $CH(CH_3)SO_2CF_3$ |
| Ia.098 | F | Cl | $CH(CH_3)SO_2CF_3$ |
| Ia.099 | Cl | Cl | $CH_2CH_2S$-cyclopropyl |
| Ia.100 | H | Cl | $CH_2CH_2S$-cyclopropyl |
| Ia.101 | F | Cl | $CH_2CH_2S$-cyclopropyl |

TABLE 5-continued

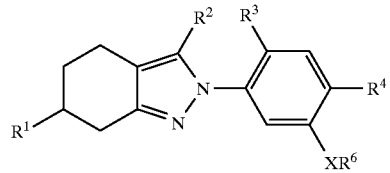

($R^1$ = H; $R^2$ = Cl; X = O)

| No. | $R^3$ | $R^4$ | $R^6$ |
|---|---|---|---|
| Ia.102 | Cl | Cl | $CH_2CH_3)S$-cyclopropyl |
| Ia.103 | H | Cl | $CH_2CH_3)S$-cyclopropyl |
| Ia.104 | F | Cl | $CH_2CH_3)S$-cyclopropyl |
| Ia.105 | Cl | Cl | $CH_2CH_2SO$-cyclopropyl |
| Ia.106 | H | Cl | $CH_2CH_2SO$-cyclopropyl |
| Ia.107 | F | Cl | $CH_2CH_2SO$-cyclopropyl |
| Ia.108 | Cl | Cl | $CH(CH_3)SO$-cyclopropyl |
| Ia.109 | H | Cl | $CH(CH_3)SO$-cyclopropyl |
| Ia.110 | F | Cl | $CH(CH_3)SO$-cyclopropyl |
| Ia.111 | Cl | Cl | $CH_2CH_2SO_2$-cyclopropyl |
| Ia.112 | H | Cl | $CH_2CH_2SO_2$-cyclopropyl |
| Ia.113 | F | Cl | $CH_2CH_2SO_2$-cyclopropyl |
| Ia.114 | Cl | Cl | $CH(CH_3)SO_2$-cyclopropyl |
| Ia.115 | H | Cl | $CH(CH_3)SO_2$-cyclopropyl |
| Ia.116 | F | Cl | $CH(CH_3)SO_2$-cyclopropyl |
| Ia.117 | Cl | Cl | $CH_2CH_2SOCH_3$ |
| Ia.118 | H | Cl | $CH_2CH_2SOCH_3$ |
| Ia.119 | F | Cl | $CH_2CH_2SOCH_3$ |
| Ia.120 | Cl | Cl | $CH(CH_3)SOCH_3$ |
| Ia.121 | H | Cl | $CH(CH_3)SOCH_3$ |
| Ia.122 | F | Cl | $CH(CH_3)SOCH_3$ |
| Ia.123 | Cl | Cl | $CH_2CH_2SO_2CH_3$ |
| Ia.124 | H | Cl | $CH_2CH_2SO_2CH_3$ |
| Ia.125 | F | Cl | $CH_2CH_2SO_2CH_3$ |
| Ia.126 | Cl | Cl | $CH(CH_3)SO_2CH_3$ |
| Ia.127 | H | Cl | $CH(CH_3)SO_2CH_3$ |
| Ia.128 | F | Cl | $CH(CH_3)SO_2CH_3$ |
| Ia.129 | Cl | Cl | $CH_2CH_2SOCH_2CH_3$ |
| Ia.130 | H | Cl | $CH_2CH_2SOCH_2CH_3$ |
| Ia.131 | F | Cl | $CH_2CH_2SOCH_2CH_3$ |
| Ia.132 | Cl | Cl | $CH(CH_3)SOCH_2CH_3$ |
| Ia.133 | H | Cl | $CH(CH_3)SOCH_2CH_3$ |
| Ia.134 | F | Cl | $CH(CH_3)SOCH_2CH_3$ |
| Ia.135 | Cl | Cl | $CH_2CH_2SO_2CH_2CH_3$ |
| Ia.136 | H | Cl | $CH_2CH_2SO_2CH_2CH_3$ |
| Ia.137 | F | Cl | $CH_2CH_2SO_2CH_2CH_3$ |
| Ia.138 | Cl | Cl | $CH(CH_3)SO_2CH_2CH_3$ |
| Ia.139 | H | Cl | $CH(CH_3)SO_2CH_2CH_3$ |
| Ia.140 | F | Cl | $CH(CH_3)SO_2CH_2CH_3$ |
| Ia.141 | Cl | Cl | $CH_2CH_2CH_2F$ |
| Ia.142 | H | Cl | $CH_2CH_2CH_2F$ |
| Ia.143 | F | Cl | $CH_2CH_2CH_2F$ |
| Ia.144 | Cl | Cl | $CH_2CH_2CH_2Cl$ |
| Ia.145 | H | Cl | $CH_2CH_2CH_2Cl$ |
| Ia.146 | F | Cl | $CH_2CH_2CH_2Cl$ |
| Ia.147 | Cl | Cl | $CH_2CH_2CH_2Br$ |
| Ia.148 | H | Cl | $CH_2CH_2CH_2Br$ |
| Ia.149 | F | Cl | $CH_2CH_2CH_2Br$ |
| Ia.150 | Cl | Cl | $CH_2CH_2CH_2I$ |
| Ia.151 | H | Cl | $CH_2CH_2CH_2I$ |
| Ia.152 | F | Cl | $CH_2CH_2CH_2I$ |
| Ia.153 | Cl | Cl | $CH(CH_3)CH_2F$ |
| Ia.154 | H | Cl | $CH(CH_3)CH_2F$ |
| Ia.155 | F | Cl | $CH(CH_3)CH_2F$ |
| Ia.156 | Cl | Cl | $CH(CH_3)CH_2Cl$ |
| Ia.157 | H | Cl | $CH(CH_3)CH_2Cl$ |
| Ia.158 | F | Cl | $CH(CH_3)CH_2Cl$ |
| Ia.159 | Cl | Cl | $CH(CH_3)CH_2Br$ |
| Ia.160 | H | Cl | $CH(CH_3)CH_2Br$ |
| Ia.161 | F | Cl | $CH(CH_3)CH_2Br$ |
| Ia.162 | Cl | Cl | $CH(CH_3)CH_2I$ |
| Ia.163 | H | Cl | $CH(CH_3)CH_2I$ |
| Ia.164 | F | Cl | $CH(CH_3)CH_2I$ |
| Ia.165 | Cl | Cl | $CH_2CH(CH_3)F$ |

TABLE 5-continued ($R^1$ = H; $R^2$ = Cl; X = O)

| No. | $R^3$ | $R^4$ | $R^6$ |
|---|---|---|---|
| Ia.166 | H | Cl | $CH_2CH(CH_3)F$ |
| Ia.167 | F | Cl | $CH_2CH(CH_3)F$ |
| Ia.168 | Cl | Cl | $CH_2CH(CH_3)Cl$ |
| Ia.169 | H | Cl | $CH_2CH(CH_3)Cl$ |
| Ia.170 | F | Cl | $CH_2CH(CH_3)Cl$ |
| Ia.171 | Cl | Cl | $CH_2CH(CH_3)Br$ |
| Ia.172 | H | Cl | $CH_2CH(CH_3)Br$ |
| Ia.173 | F | Cl | $CH_2CH(CH_3)Br$ |
| Ia.174 | Cl | Cl | $CH_2CH(CH_3)I$ |
| Ia.175 | H | Cl | $CH_2CH(CH_3)I$ |
| Ia.176 | F | Cl | $CH_2CH(CH_3)I$ |
| Ia.177 | Cl | Cl | $CH_2CH_2CH_2CN$ |
| Ia.178 | H | Cl | $CH_2CH_2CH_2CN$ |
| Ia.179 | F | Cl | $CH_2CH_2CH_2CN$ |
| Ia.180 | Cl | Cl | $CH(CH_3)CH_2CN$ |
| Ia.181 | H | Cl | $CH(CH_3)CH_2CN$ |
| Ia.182 | F | Cl | $CH(CH_3)CH_2CN$ |
| Ia.183 | Cl | Cl | $CH_2CH(CH_3)CN$ |
| Ia.184 | H | Cl | $CH_2CH(CH_3)CN$ |
| Ia.185 | F | Cl | $CH_2CH(CH_3)CN$ |
| Ia.186 | Cl | Cl | $CH_2CH_2CH_2SCN$ |
| Ia.187 | H | Cl | $CH_2CH_2CH_2SCN$ |
| Ia.188 | F | Cl | $CH_2CH_2CH_2SCN$ |
| Ia.189 | Cl | Cl | $CH(CH_3)CH_2SCN$ |
| Ia.190 | H | Cl | $CH(CH_3)CH_2SCN$ |
| Ia.191 | F | Cl | $CH(CH_3)CH_2SCN$ |
| Ia.192 | Cl | Cl | $CH_2CH(CH_3)SCN$ |
| Ia.193 | H | Cl | $CH_2CH(CH_3)SCN$ |
| Ia.194 | F | Cl | $CH_2CH(CH_3)SCN$ |
| Ia.195 | Cl | Cl | $CH_2CH_2CH_2SCHF_2$ |
| Ia.196 | H | Cl | $CH_2CH_2CH_2SCHF_2$ |
| Ia.197 | F | Cl | $CH_2CH_2CH_2SCHF_2$ |
| Ia.198 | Cl | Cl | $CH(CH_3)CH_2SCHF_2$ |
| Ia.199 | H | Cl | $CH(CH_3)CH_2SCHF_2$ |
| Ia.200 | F | Cl | $CH(CH_3)CH_2SCHF_2$ |
| Ia.201 | Cl | Cl | $CH_2CH(CH_3)SCHF_2$ |
| Ia.202 | H | Cl | $CH_2CH(CH_3)SCHF_2$ |
| Ia.203 | F | Cl | $CH_2CH(CH_3)SCHF_2$ |
| Ia.204 | Cl | Cl | $CH_2CH_2CH_2SCF_3$ |
| Ia.205 | H | Cl | $CH_2CH_2CH_2SCF_3$ |
| Ia.206 | F | Cl | $CH_2CH_2CH_2SCF_3$ |
| Ia.207 | Cl | Cl | $CH(CH_3)CH_2SCF_3$ |
| Ia.208 | H | Cl | $CH(CH_3)CH_2SCF_3$ |
| Ia.209 | F | Cl | $CH(CH_3)CH_2SCF_3$ |
| Ia.210 | Cl | Cl | $CH_2CH(CH_3)SCF_3$ |
| Ia.211 | H | Cl | $CH_2CH(CH_3)SCF_3$ |
| Ia.212 | F | Cl | $CH_2CH(CH_3)SCF_3$ |
| Ia.213 | Cl | Cl | $CH_2CH_2CH_2SOCHF_2$ |
| Ia.214 | H | Cl | $CH_2CH_2CH_2SOCHF_2$ |
| Ia.215 | F | Cl | $CH_2CH_2CH_2SOCHF_2$ |
| Ia.216 | Cl | Cl | $CH(CH_3)CH_2SOCHF_2$ |
| Ia.217 | H | Cl | $CH(CH_3)CH_2SOCHF_2$ |
| Ia.218 | F | Cl | $CH(CH_3)CH_2SOCHF_2$ |
| Ia.219 | Cl | Cl | $CH_2CH(CH_3)SOCHF_2$ |
| Ia.220 | H | Cl | $CH_2CH(CH_3)SOCHF_2$ |
| Ia.221 | F | Cl | $CH_2CH(CH_3)SOCHF_2$ |
| Ia.222 | Cl | Cl | $CH_2CH_2CH_2SOCF_3$ |
| Ia.223 | H | Cl | $CH_2CH_2CH_2SOCF_3$ |
| Ia.224 | F | Cl | $CH_2CH_2CH_2SOCF_3$ |
| Ia.225 | Cl | Cl | $CH(CH_3)CH_2SOCF_3$ |
| Ia.225 | Cl | Cl | $CH(CH_3)CH_2SOCF_3$ |
| Ia.226 | H | Cl | $CH(CH_3)CH_2SOCF_3$ |
| Ia.227 | F | Cl | $CH(CH_3)CH_2SOCF_3$ |
| Ia.228 | Cl | Cl | $CH_2CH(CH_3)SOCHF_3$ |
| Ia.229 | H | Cl | $CH_2CH(CH_3)SOCHF_3$ |
| Ia.230 | F | Cl | $CH_2CH(CH_3)SOCHF_3$ |
| Ia.231 | Cl | Cl | $CH_2CH_2CH_2SO_2CHF_2$ |
| Ia.232 | H | Cl | $CH_2CH_2CH_2SO_2CHF_2$ |
| Ia.233 | F | Cl | $CH_2CH_2CH_2SO_2CHF_2$ |
| Ia.234 | Cl | Cl | $CH(CH_3)CH_2SO_2CHF_2$ |
| Ia.235 | H | Cl | $CH(CH_3)CH_2SO_2CHF_2$ |
| Ia.236 | F | Cl | $CH(CH_3)CH_2SO_2CHF_2$ |
| Ia.237 | Cl | Cl | $CH_2CH(CH_3)SO_2CHF_2$ |
| Ia.238 | H | Cl | $CH_2CH(CH_3)SO_2CHF_2$ |
| Ia.239 | F | Cl | $CH_2CH(CH_3)SO_2CHF_2$ |
| Ia.240 | Cl | Cl | $CH_2CH_2CH_2SO_2CF_3$ |
| Ia.241 | H | Cl | $CH_2CH_2CH_2SO_2CF_3$ |
| Ia.242 | F | Cl | $CH_2CH_2CH_2SO_2CF_3$ |
| Ia.243 | Cl | Cl | $CH(CH_3)CH_2SO_2CF_3$ |
| Ia.244 | H | Cl | $CH(CH_3)CH_2SO_2CF_3$ |
| Ia.245 | F | Cl | $CH(CH_3)CH_2SO_2CF_3$ |
| Ia.246 | Cl | Cl | $CH_2CH(CH_3)SO_2CF_3$ |
| Ia.247 | H | Cl | $CH_2CH(CH_3)SO_2CF_3$ |
| Ia.248 | F | Cl | $CH_2CH(CH_3)SO_2CF_3$ |
| Ia.249 | Cl | Cl | $CH_2CH_2CH_2S$-cyclopropyl |
| Ia.250 | H | Cl | $CH_2CH_2CH_2S$-cyclopropyl |
| Ia.251 | F | Cl | $CH_2CH_2CH_2S$-cyclopropyl |
| Ia.252 | Cl | Cl | $CH(CH_3)CH_2S$-cyclopropyl |
| Ia.253 | H | Cl | $CH(CH_3)CH_2S$-cyclopropyl |
| Ia.254 | F | Cl | $CH(CH_3)CH_2S$-cyclopropyl |
| Ia.255 | Cl | Cl | $CH_2CH(CH_3)S$-cyclopropyl |
| Ia.256 | H | Cl | $CH_2CH(CH_3)S$-cyclopropyl |
| Ia.257 | F | Cl | $CH_2CH(CH_3)S$-cyclopropyl |
| Ia.258 | Cl | Cl | $CH_2CH_2CH_2SO$-cyclopropyl |
| Ia.259 | H | Cl | $CH_2CH_2CH_2SO$-cyclopropyl |
| Ia.260 | F | Cl | $CH_2CH_2CH_2SO$-cyclopropyl |
| Ia.261 | Cl | Cl | $CH(CH_3)CH_2SO$-cyclopropyl |
| Ia.262 | H | Cl | $CH(CH_3)CH_2SO$-cyclopropyl |
| Ia.263 | F | Cl | $CH(CH_3)CH_2SO$-cyclopropyl |
| Ia.264 | Cl | Cl | $CH_2CH(CH_3)SO$-cyclopropyl |
| Ia.265 | H | Cl | $CH_2CH(CH_3)SO$-cyclopropyl |
| Ia.266 | F | Cl | $CH_2CH(CH_3)SO$-cyclopropyl |
| Ia.267 | Cl | Cl | $CH_2CH_2CH_2SO_2$-cyclopropyl |
| Ia.268 | H | Cl | $CH_2CH_2CH_2SO_2$-cyclopropyl |
| Ia.269 | F | Cl | $CH_2CH_2CH_2SO_2$-cyclopropyl |
| Ia.270 | Cl | Cl | $CH(CH_3)CHSO_2$-cyclopropyl |
| Ia.271 | H | Cl | $CH(CH_3)CHSO_2$-cyclopropyl |
| Ia.272 | F | Cl | $CH(CH_3)CHSO_2$-cyclopropyl |
| Ia.273 | Cl | Cl | $CH_2CH_2(CH_3)SO_2$-cyclopropyl |
| Ia.274 | H | Cl | $CH_2CH_2(CH_3)SO_2$-cyclopropyl |
| Ia.275 | F | Cl | $CH_2CH_2(CH_3)SO_2$-cyclopropyl |
| Ia.276 | Cl | Cl | $CH_2CH_2CH_2SOCH_3$ |
| Ia.277 | H | Cl | $CH_2CH_2CH_2SOCH_3$ |
| Ia.278 | F | Cl | $CH_2CH_2CH_2SOCH_3$ |
| Ia.279 | Cl | Cl | $CH(CH_3)CH_2SOCH_3$ |
| Ia.280 | H | Cl | $CH(CH_3)CH_2SOCH_3$ |
| Ia.281 | F | Cl | $CH(CH_3)CH_2SOCH_3$ |
| Ia.282 | Cl | Cl | $CH_2CH(CH_3)SOCH_3$ |
| Ia.283 | H | Cl | $CH_2CH(CH_3)SOCH_3$ |
| Ia.284 | F | Cl | $CH_2CH(CH_3)SOCH_3$ |
| Ia.285 | Cl | Cl | $CH_2CH_2CH_2SOCH_2CH_3$ |
| Ia.286 | H | Cl | $CH_2CH_2CH_2SOCH_2CH_3$ |
| Ia.287 | F | Cl | $CH_2CH_2CH_2SOCH_2CH_3$ |
| Ia.288 | Cl | Cl | $CH(CH_3)CH_2SOCH_2CH_3$ |
| Ia.289 | H | Cl | $CH(CH_3)CH_2SOCH_2CH_3$ |
| Ia.290 | F | Cl | $CH(CH_3)CH_2SOCH_2CH_3$ |
| Ia.291 | Cl | Cl | $CH_2CH(CH_3)SOCH_2CH_3$ |
| Ia.292 | H | Cl | $CH_2CH(CH_3)SOCH_2CH_3$ |

TABLE 5-continued

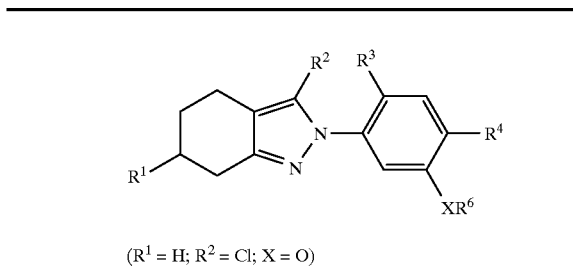

($R^1$ = H; $R^2$ = Cl; X = O)

| No. | $R^3$ | $R^4$ | $R^6$ |
|---|---|---|---|
| Ia.293 | F | Cl | $CH_2CH(CH_3)SOCH_2CH_3$ |
| Ia.294 | Cl | Cl | $CH_2CH_2CH_2SO_2CH_3$ |
| Ia.295 | H | Cl | $CH_2CH_2CH_2SO_2CH_3$ |
| Ia.296 | F | Cl | $CH_2CH_2CH_2SO_2CH_3$ |
| Ia.297 | Cl | Cl | $CH(CH_3)CH_2SO_2CH_3$ |
| Ia.298 | H | Cl | $CH(CH_3)CH_2SO_2CH_3$ |
| Ia.299 | F | Cl | $CH(CH_3)CH_2SO_2CH_3$ |
| Ia.300 | Cl | Cl | $CH_2CH(CH_3)SO_2CH_3$ |
| Ia.301 | H | Cl | $CH_2CH(CH_3)SO_2CH_3$ |
| Ia.302 | F | Cl | $CH_2CH(CH_3)SO_2CH_3$ |
| Ia.303 | Cl | Cl | $CH_2CH_2CH_2SO_2CH_2CH_3$ |
| Ia.304 | H | Cl | $CH_2CH_2CH_2SO_2CH_2CH_3$ |
| Ia.305 | F | Cl | $CH_2CH_2CH_2SO_2CH_2CH_3$ |
| Ia.306 | Cl | Cl | $CH(CH_3)CH_2SO_2CH_3$ |
| Ia.307 | H | Cl | $CH(CH_3)CH_2SO_2CH_3$ |
| Ia.308 | F | Cl | $CH(CH_3)CH_2SO_2CH_3$ |
| Ia.309 | Cl | Cl | $CH_2CH(CH_3)SO_2CH_2CH_3$ |
| Ia.310 | H | Cl | $CH_2CH(CH_3)SO_2CH_2CH_3$ |
| Ia.311 | F | Cl | $CH_2CH(CH_3)SO_2CH_2CH_3$ |
| Ia.312 | Cl | Cl | $CH(CH_2CH_3)F$ |
| Ia.313 | H | Cl | $CH(CH_2CH_3)F$ |
| Ia.314 | F | Cl | $CH(CH_2CH_3)F$ |
| Ia.315 | Cl | Cl | $CH(CH_2CH_3)Cl$ |
| Ia.316 | H | Cl | $CH(CH_2CH_3)Cl$ |
| Ia.317 | F | Cl | $CH(CH_2CH_3)Cl$ |
| Ia.318 | Cl | Cl | $CH(CH_2CH_3)Br$ |
| Ia.319 | H | Cl | $CH(CH_2CH_3)Br$ |
| Ia.320 | F | Cl | $CH(CH_2CH_3)Br$ |
| Ia.321 | Cl | Cl | $CH(CH_2CH_3)I$ |
| Ia.322 | H | Cl | $CH(CH_2CH_3)I$ |
| Ia.323 | F | Cl | $CH(CH_2CH_3)I$ |
| Ia.324 | Cl | Cl | $CH(CH_2CH_3)CN$ |
| Ia.325 | H | Cl | $CH(CH_2CH_3)CN$ |
| Ia.326 | F | Cl | $CH(CH_2CH_3)CN$ |
| Ia.327 | Cl | Cl | $CH(CH_2CH_3)SCN$ |
| Ia.328 | H | Cl | $CH(CH_2CH_3)SCN$ |
| Ia.329 | F | Cl | $CH(CH_2CH_3)SCN$ |
| Ia.330 | Cl | Cl | $CH(CH_2CH_3)SCHF_2$ |
| Ia.331 | H | Cl | $CH(CH_2CH_3)SCHF_2$ |
| Ia.332 | F | Cl | $CH(CH_2CH_3)SCHF_2$ |
| Ia.333 | Cl | Cl | $CH(CH_2CH_3)SOCHF_2$ |
| Ia.334 | H | Cl | $CH(CH_2CH_3)SOCHF_2$ |
| Ia.335 | F | Cl | $CH(CH_2CH_3)SOCHF_2$ |
| Ia.336 | Cl | Cl | $CH(CH_2CH_3)SO_2CHF_2$ |
| Ia.337 | H | Cl | $CH(CH_2CH_3)SO_2CHF_2$ |
| Ia.338 | F | Cl | $CH(CH_2CH_3)SO_2CHF_2$ |
| Ia.339 | Cl | Cl | $CH(CH_2CH_3)SCF_3$ |
| Ia.340 | H | Cl | $CH(CH_2CH_3)SCF_3$ |
| Ia.341 | F | Cl | $CH(CH_2CH_3)SCF_3$ |
| Ia.342 | Cl | Cl | $CH(CH_2CH_3)SOCF_3$ |
| Ia.343 | H | Cl | $CH(CH_2CH_3)SOCF_3$ |
| Ia.344 | F | Cl | $CH(CH_2CH_3)SOCF_3$ |
| Ia.345 | Cl | Cl | $CH(CH_2CH_3)SO_2CF_3$ |
| Ia.346 | H | Cl | $CH(CH_2CH_3)SO_2CF_3$ |
| Ia.347 | F | Cl | $CH(CH_2CH_3)SO_2CF_3$ |
| Ia.348 | Cl | Cl | $CH(CH_2CH_3)$S-cyclopropyl |
| Ia.349 | H | Cl | $CH(CH_2CH_3)$S-cyclopropyl |
| Ia.350 | F | Cl | $CH(CH_2CH_3)$S-cyclopropyl |
| Ia.351 | Cl | Cl | $CH(CH_2CH_3)$SO-cyclopropyl |
| Ia.352 | H | Cl | $CH(CH_2CH_3)$SO-cyclopropyl |
| Ia.353 | F | Cl | $CH(CH_2CH_3)$SO-cyclopropyl |
| Ia.354 | Cl | Cl | $CH(CH_2CH_3)SO_2$-cyclopropyl |
| Ia.355 | H | Cl | $CH(CH_2CH_3)SO_2$-cyclopropyl |
| Ia.356 | F | Cl | $CH(CH_2CH_3)SO_2$-cyclopropyl |

TABLE 5-continued

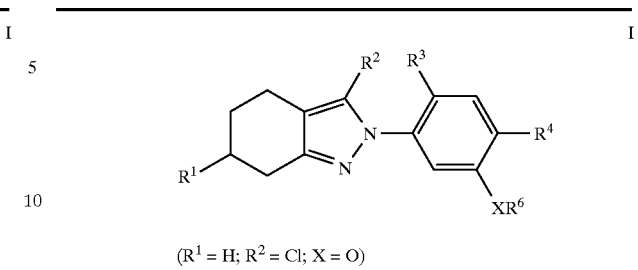

($R^1$ = H; $R^2$ = Cl; X = O)

| No. | $R^3$ | $R^4$ | $R^6$ |
|---|---|---|---|
| Ia.357 | Cl | Cl | $CH(CH_2CH_3)SOCH_3$ |
| Ia.358 | H | Cl | $CH(CH_2CH_3)SOCH_3$ |
| Ia.359 | F | Cl | $CH(CH_2CH_3)SOCH_3$ |
| Ia.360 | Cl | Cl | $CH(CH_2CH_3)SO_2CH_3$ |
| Ia.361 | H | Cl | $CH(CH_2CH_3)SO_2CH_3$ |
| Ia.362 | F | Cl | $CH(CH_2CH_3)SO_2CH_3$ |
| Ia.363 | Cl | Cl | $CH(CH_2CH_3)SOCH_2CH_3$ |
| Ia.364 | H | Cl | $CH(CH_2CH_3)SOCH_2CH_3$ |
| Ia.365 | F | Cl | $CH(CH_2CH_3)SOCH_2CH_3$ |
| Ia.366 | Cl | Cl | $CH(CH_2CH_3)SO_2CH_2CH_3$ |
| Ia.367 | H | Cl | $CH(CH_2CH_3)SO_2CH_2CH_3$ |
| Ia.368 | F | Cl | $CH(CH_2CH_3)SO_2CH_2CH_3$ |
| Ia.369 | Cl | Cl | $C(CH_3)_2F$ |
| Ia.370 | H | Cl | $C(CH_3)_2F$ |
| Ia.371 | F | Cl | $C(CH_3)_2F$ |
| Ia.372 | Cl | Cl | $C(CH_3)_2Cl$ |
| Ia.373 | H | Cl | $C(CH_3)_2Cl$ |
| Ia.374 | F | Cl | $C(CH_3)_2Cl$ |
| Ia.375 | Cl | Cl | $C(CH_3)_2Br$ |
| Ia.376 | H | Cl | $C(CH_3)_2Br$ |
| Ia.377 | F | Cl | $C(CH_3)_2Br$ |
| Ia.378 | Cl | Cl | $C(CH_3)_2I$ |
| Ia.379 | H | Cl | $C(CH_3)_2I$ |
| Ia.380 | F | Cl | $C(CH_3)_2I$ |
| Ia.381 | Cl | Cl | $C(CH_3)_2CN$ |
| Ia.382 | H | Cl | $C(CH_3)_2CN$ |
| Ia.383 | F | Cl | $C(CH_3)_2CN$ |
| Ia.384 | Cl | Cl | $C(CH_3)_2SCN$ |
| Ia.385 | H | Cl | $C(CH_3)_2SCN$ |
| Ia.386 | F | Cl | $C(CH_3)_2SCN$ |
| Ia.387 | Cl | Cl | $C(CH_3)_2SCHF_2$ |
| Ia.388 | H | Cl | $C(CH_3)_2SCHF_2$ |
| Ia.389 | F | Cl | $C(CH_3)_2SCHF_2$ |
| Ia.390 | Cl | Cl | $C(CH_3)_2SCF_3$ |
| Ia.391 | H | Cl | $C(CH_3)_2SCF_3$ |
| Ia.392 | F | Cl | $C(CH_3)_2SCF_3$ |
| Ia.393 | Cl | Cl | $C(CH_3)_2SOCHF_2$ |
| Ia.394 | H | Cl | $C(CH_3)_2SOCHF_2$ |
| Ia.395 | F | Cl | $C(CH_3)_2SOCHF_2$ |
| Ia.396 | Cl | Cl | $C(CH_3)_2SO_2CHF_2$ |
| Ia.397 | H | Cl | $C(CH_3)_2SO_2CHF_2$ |
| Ia.398 | F | Cl | $C(CH_3)_2SO_2CHF_2$ |
| Ia.399 | Cl | Cl | $C(CH_3)_2SOCF_3$ |
| Ia.400 | H | Cl | $C(CH_3)_2SOCF_3$ |
| Ia.401 | F | Cl | $C(CH_3)_2SOCF_3$ |
| Ia.402 | Cl | Cl | $C(CH_3)_2SO_2CF_3$ |
| Ia.403 | H | Cl | $C(CH_3)_2SO_2CF_3$ |
| Ia.404 | F | Cl | $C(CH_3)_2SO_2CF_3$ |
| Ia.405 | Cl | Cl | $C(CH_3)_2SOCH_3$ |
| Ia.406 | H | Cl | $C(CH_3)_2SOCH_3$ |
| Ia.407 | F | Cl | $C(CH_3)_2SOCH_3$ |
| Ia.408 | Cl | Cl | $C(CH_3)_2SO_2CH_3$ |
| Ia.409 | H | Cl | $C(CH_3)_2SO_2CH_3$ |
| Ia.410 | F | Cl | $C(CH_3)_2SO_2CH_3$ |
| Ia.411 | Cl | Cl | $C(CH_3)_2SOCH_2CH_3$ |
| Ia.412 | H | Cl | $C(CH_3)_2SOCH_2CH_3$ |
| Ia.413 | F | Cl | $C(CH_3)_2SOCH_2CH_3$ |
| Ia.414 | C | Cl | $CH_2CH_2CH_2F$ |
| Ia.415 | H | Cl | $CH_2CH_2CH_2F$ |
| Ia.416 | F | Cl | $CH_2CH_2CH_2F$ |
| Ia.417 | Cl | Cl | $CH_2CH_2CH_2Cl$ |
| Ia.418 | H | Cl | $CH_2CH_2CH_2Cl$ |
| Ia.419 | F | Cl | $CH_2CH_2CH_2Cl$ |
| Ia.420 | Cl | Cl | $CH_2CH_2CH_2Br$ |

TABLE 5-continued

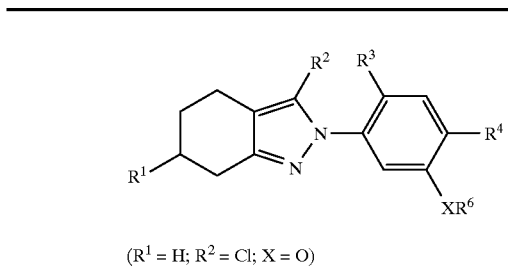

($R^1$ = H; $R^2$ = Cl; X = O)

| No. | $R^3$ | $R^4$ | $R^6$ |
|---|---|---|---|
| Ia.421 | H | Cl | $CH_2CH_2CH_2CH_2Br$ |
| Ia.422 | F | Cl | $CH_2CH_2CH_2CH_2Br$ |
| Ia.423 | Cl | Cl | $CH_2CH_2CH_2CH_2I$ |
| Ia.424 | H | Cl | $CH_2CH_2CH_2CH_2I$ |
| Ia.425 | F | Cl | $CH_2CH_2CH_2CH_2I$ |
| Ia.426 | Cl | Cl | $CH_2CH_2CH_2CH_2CN$ |
| Ia.427 | H | Cl | $CH_2CH_2CH_2CH_2CN$ |
| Ia.428 | F | Cl | $CH_2CH_2CH_2CH_2CN$ |
| Ia.429 | Cl | Cl | $CH_2CH_2CH_2CH_2SCN$ |
| Ia.430 | H | Cl | $CH_2CH_2CH_2CH_2SCN$ |
| Ia.431 | F | Cl | $CH_2CH_2CH_2CH_2SCN$ |
| Ia.432 | Cl | Cl | $CH_2CH_2CH_2CH_2SCHF_2$ |
| Ia.433 | H | Cl | $CH_2CH_2CH_2CH_2SCHF_2$ |
| Ia.434 | F | Cl | $CH_2CH_2CH_2CH_2SCHF_2$ |
| Ia.435 | Cl | Cl | $C(CH_3)_2SO_2CH_2CH_3$ |
| Ia.436 | H | Cl | $C(CH_3)_2SO_2CH_2CH_3$ |
| Ia.437 | F | Cl | $C(CH_3)_2SO_2CH_2CH_3$ |
| Ia.438 | Cl | Cl | $CH_2CH_2CH_2CH_2SCF_3$ |
| Ia.439 | H | Cl | $CH_2CH_2CH_2CH_2SCF_3$ |
| Ia.440 | F | Cl | $CH_2CH_2CH_2CH_2SCF_3$ |
| Ia.441 | Cl | Cl | $CH_2CH_2CH_2CH_2$S-cyclopropyl |
| Ia.442 | H | Cl | $CH_2CH_2CH_2CH_2$S-cyclopropyl |
| Ia.443 | F | Cl | $CH_2CH_2CH_2CH_2$S-cyclopropyl |
| Ia.444 | Cl | Cl | $CH_2CH_2CH_2CH_2SOCHF_2$ |
| Ia.445 | H | Cl | $CH_2CH_2CH_2CH_2SOCHF_2$ |
| Ia.446 | F | Cl | $CH_2CH_2CH_2CH_2SOCHF_2$ |
| Ia.447 | Cl | Cl | $CH_2CH_2CH_2CH_2SOCF_3$ |
| Ia.448 | H | Cl | $CH_2CH_2CH_2CH_2SOCF_3$ |
| Ia.449 | F | Cl | $CH_2CH_2CH_2CH_2SOCF_3$ |
| Ia.450 | Cl | Cl | $CH_2CH_2CH_2CH_2$SO-cyclopropyl |
| Ia.451 | H | Cl | $CH_2CH_2CH_2CH_2$SO-cyclopropyl |
| Ia.452 | F | Cl | $CH_2CH_2CH_2CH_2$SO-cyclopropyl |
| Ia.453 | Cl | Cl | $CH_2CH_2CH_2CH_2SOCH_3$ |
| Ia.454 | H | Cl | $CH_2CH_2CH_2CH_2SOCH_3$ |
| Ia.455 | F | Cl | $CH_2CH_2CH_2CH_2SOCH_3$ |
| Ia.456 | Cl | Cl | $CH_2CH_2CH_2CH_2SOCH_2CH_3$ |
| Ia.457 | H | Cl | $CH_2CH_2CH_2CH_2SOCH_2CH_3$ |
| Ia.458 | F | Cl | $CH_2CH_2CH_2CH_2SOCH_2CH_3$ |
| Ia.459 | Cl | Cl | $CH_2CH_2CH_2CH_2SOCHF_2$ |
| Ia.460 | H | Cl | $CH_2CH_2CH_2CH_2SOCHF_2$ |
| Ia.461 | F | Cl | $CH_2CH_2CH_2CH_2SOCHF_2$ |
| Ia.462 | Cl | Cl | $CH_2CH_2CH_2CH_2SO_2CF_3$ |
| Ia.463 | H | Cl | $CH_2CH_2CH_2CH_2SO_2CF_3$ |
| Ia.464 | F | Cl | $CH_2CH_2CH_2CH_2SO_2CF_3$ |
| Ia.465 | Cl | Cl | $CH_2CH_2CH_2CH_2SO_2$-cyclopropyl |
| Ia.466 | H | Cl | $CH_2CH_2CH_2CH_2SO_2$-cyclopropyl |
| Ia.467 | F | Cl | $CH_2CH_2CH_2CH_2SO_2$-cyclopropyl |
| Ia.468 | Cl | Cl | $CH_2CH_2CH_2CH_2SO_2CH_3$ |
| Ia.469 | H | Cl | $CH_2CH_2CH_2CH_2SO_2CH_3$ |
| Ia.470 | F | Cl | $CH_2CH_2CH_2CH_2SO_2CH_3$ |
| Ia.471 | Cl | Cl | $CH_2CH_2CH_2CH_2SO_2CH_2CH_3$ |
| Ia.472 | H | Cl | $CH_2CH_2CH_2CH_2SO_2CH_2CH_3$ |
| Ia.473 | F | Cl | $CH_2CH_2CH_2CH_2SO_2CH_2CH_3$ |
| Ia.474 | Cl | Cl | $CH(CH_3)CH_2CH_2F$ |
| Ia.475 | H | Cl | $CH(CH_3)CH_2CH_2F$ |
| Ia.476 | F | Cl | $CH(CH_3)CH_2CH_2F$ |
| Ia.477 | Cl | Cl | $CH(CH_3)CH_2CH_2Cl$ |
| Ia.478 | H | Cl | $CH(CH_3)CH_2CH_2Cl$ |
| Ia.479 | F | Cl | $CH(CH_3)CH_2CH_2Cl$ |
| Ia.480 | Cl | Cl | $CH(CH_3)CH_2CH_2Br$ |
| Ia.481 | H | Cl | $CH(CH_3)CH_2CH_2Br$ |
| Ia.482 | F | Cl | $CH(CH_3)CH_2CH_2Br$ |
| Ia.483 | Cl | Cl | $CH(CH_3)CH_2CH_2I$ |
| Ia.484 | H | Cl | $CH(CH_3)CH_2CH_2I$ |
| Ia.485 | F | Cl | $CH(CH_3)CH_2CH_2I$ |
| Ia.486 | Cl | Cl | $CH(CH_3)CH_2CH_2CN$ |
| Ia.487 | H | Cl | $CH(CH_3)CH_2CH_2CN$ |
| Ia.488 | F | Cl | $CH(CH_3)CH_2CH_2CN$ |
| Ia.489 | Cl | Cl | $CH(CH_3)CH_2CH_2SCN$ |
| Ia.490 | H | Cl | $CH(CH_3)CH_2CH_2SCN$ |
| Ia.491 | F | Cl | $CH(CH_3)CH_2CH_2SCN$ |
| Ia.492 | Cl | Cl | $CH(CH_3)CH_2CH_2SCHF_2$ |
| Ia.493 | H | Cl | $CH(CH_3)CH_2CH_2SCHF_2$ |
| Ia.494 | F | Cl | $CH(CH_3)CH_2CH_2SCHF_2$ |
| Ia.495 | Cl | Cl | $CH(CH_3)CH_2CH_2SCF_3$ |
| Ia.496 | H | Cl | $CH(CH_3)CH_2CH_2SCF_3$ |
| Ia.497 | F | Cl | $CH(CH_3)CH_2CH_2SCF_3$ |
| Ia.498 | Cl | Cl | $CH(CH_3)CH_2CH_2$—S-cyclopropyl |
| Ia.499 | H | Cl | $CH(CH_3)CH_2CH_2$—S-cyclopropyl |
| Ia.500 | F | Cl | $CH(CH_3)CH_2CH_2$—S-cyclopropyl |
| Ia.501 | Cl | Cl | $CH(CH_3)CH_2CH_2SOCHF_2$ |
| Ia.502 | H | Cl | $CH(CH_3)CH_2CH_2SOCHF_2$ |
| Ia.503 | F | Cl | $CH(CH_3)CH_2CH_2SOCHF_2$ |
| Ia.504 | Cl | Cl | $CH(CH_3)CH_2CH_2SOCF_3$ |
| Ia.505 | H | Cl | $CH(CH_3)CH_2CH_2SOCF_3$ |
| Ia.506 | F | Cl | $CH(CH_3)CH_2CH_2SOCF_3$ |
| Ia.507 | Cl | Cl | $CH(CH_3)CH_2CH_2$SO-cyclopropyl |
| Ia.508 | H | Cl | $CH(CH_3)CH_2CH_2$SO-cyclopropyl |
| Ia.509 | F | Cl | $CH(CH_3)CH_2CH_2$SO-cyclopropyl |
| Ia.510 | Cl | Cl | $CH(CH_3)CH_2CH_2SOCH_3$ |
| Ia.511 | H | Cl | $CH(CH_3)CH_2CH_2SOCH_3$ |
| Ia.512 | F | Cl | $CH(CH_3)CH_2CH_2SOCH_3$ |
| Ia.513 | Cl | Cl | $CH(CH_3)CH_2CH_2SOCH_2CH_3$ |
| Ia.514 | H | Cl | $CH(CH_3)CH_2CH_2SOCH_2CH_3$ |
| Ia.515 | F | Cl | $CH(CH_3)CH_2CH_2SOCH_2CH_3$ |
| Ia.516 | Cl | Cl | $CH(CH_3)CH_2CH_2SO_2CHF_2$ |
| Ia.517 | H | Cl | $CH(CH_3)CH_2CH_2SO_2CHF_2$ |
| Ia.518 | F | Cl | $CH(CH_3)CH_2CH_2SO_2CHF_2$ |
| Ia.519 | Cl | Cl | $CH(CH_3)CH_2CH_2SO_2CF_3$ |
| Ia.520 | H | Cl | $CH(CH_3)CH_2CH_2SO_2CF_3$ |
| Ia.521 | F | Cl | $CH(CH_3)CH_2CH_2SO_2CF_3$ |
| Ia.522 | Cl | Cl | $CH(CH_3)CH_2CH_2SO_2$-cyclopropyl |
| Ia.523 | H | Cl | $CH(CH_3)CH_2CH_2SO_2$-cyclopropyl |
| Ia.524 | F | Cl | $CH(CH_3)CH_2CH_2SO_2$-cyclopropyl |
| Ia.525 | Cl | Cl | $CH(CH_3)CH_2CH_2SO_2CH_3$ |
| Ia.526 | H | Cl | $CH(CH_3)CH_2CH_2SO_2CH_3$ |
| Ia.527 | F | Cl | $CH(CH_3)CH_2CH_2SO_2CH_3$ |
| Ia.528 | Cl | Cl | $CH(CH_3)CH_2CH_2SO_2CH_2CH_3$ |
| Ia.529 | H | Cl | $CH(CH_3)CH_2CH_2SO_2CH_2CH_3$ |
| Ia.530 | F | Cl | $CH(CH_3)CH_2CH_2SO_2CH_2CH_3$ |
| Ia.531 | Cl | Cl | $CH_2CH(CH_3)CH_2F$ |
| Ia.532 | H | Cl | $CH_2CH(CH_3)CH_2F$ |
| Ia.533 | F | Cl | $CH_2CH(CH_3)CH_2F$ |
| Ia.534 | Cl | Cl | $CH_2CH(CH_3)CH_2Cl$ |
| Ia.535 | H | Cl | $CH_2CH(CH_3)CH_2Cl$ |
| Ia.536 | F | Cl | $CH_2CH(CH_3)CH_2Cl$ |
| Ia.537 | Cl | Cl | $CH_2CH(CH_3)CH_2Br$ |
| Ia.538 | H | Cl | $CH_2CH(CH_3)CH_2Br$ |
| Ia.539 | F | Cl | $CH_2CH(CH_3)CH_2Br$ |
| Ia.540 | Cl | Cl | $CH_2CH(CH_3)CH_2I$ |
| Ia.541 | H | Cl | $CH_2CH(CH_3)CH_2I$ |
| Ia.542 | F | Cl | $CH_2CH(CH_3)CH_2I$ |
| Ia.543 | Cl | Cl | $CH_2CH(CH_3)CH_2CN$ |
| Ia.544 | H | Cl | $CH_2CH(CH_3)CH_2CN$ |
| Ia.545 | F | Cl | $CH_2CH(CH_3)CH_2CN$ |
| Ia.546 | Cl | Cl | $CH_2CH(CH_3)CH_2SCN$ |
| Ia.547 | H | Cl | $CH_2CH(CH_3)CH_2SCN$ |
| Ia.548 | F | Cl | $CH_2CH(CH_3)CH_2SCN$ |

TABLE 5-continued

I (R¹ = H; R² = Cl; X = O)

| No. | R³ | R⁴ | R⁶ |
|---|---|---|---|
| Ia.549 | Cl | Cl | $CH_2CH(CH_3)CH_2SCHF_2$ |
| Ia.550 | H | Cl | $CH_2CH(CH_3)CH_2SCHF_2$ |
| Ia.551 | F | Cl | $CH_2CH(CH_3)CH_2SCHF_2$ |
| Ia.552 | Cl | Cl | $CH_2CH(CH_3)CH_2SCF_3$ |
| Ia.553 | H | Cl | $CH_2CH(CH_3)CH_2SCF_3$ |
| Ia.554 | F | Cl | $CH_2CH(CH_3)CH_2SCF_3$ |
| Ia.555 | Cl | Cl | $CH_2CH(CH_3)CH_2S$-cyclopropyl |
| Ia.556 | H | Cl | $CH_2CH(CH_3)CH_2S$-cyclopropyl |
| Ia.557 | F | Cl | $CH_2CH(CH_3)CH_2S$-cyclopropyl |
| Ia.558 | Cl | Cl | $Ch_2CH(CH_3)CH_2SOCHF_2$ |
| Ia.559 | H | Cl | $Ch_2CH(CH_3)CH_2SOCHF_2$ |
| Ia.560 | F | Cl | $CH_2CH(CH_3)CH_2SOCHF_2$ |
| Ia.561 | Cl | Cl | $CH_2CH(CH_3)CH_2SOCF_3$ |
| Ia.562 | H | Cl | $CH_2CH(CH_3)CH_2SOCF_3$ |
| Ia.563 | F | Cl | $CH_2CH(CH_3)CH_2SOCF_3$ |
| Ia.564 | Cl | Cl | $CH_2CH(CH_3)CH_2SO$-cyclopropyl |
| Ia.565 | H | Cl | $CH_2CH(CH_3)CH_2SO$-cyclopropyl |
| Ia.566 | F | Cl | $CH_2CH(CH_3)CH_2SO$-cyclopropyl |
| Ia.567 | Cl | Cl | $CH_2CH(CH_3)CH_2SOCH_3$ |
| Ia.568 | H | Cl | $CH_2CH(CH_3)CH_2SOCH_3$ |
| Ia.569 | F | Cl | $CH_2CH(CH_3)CH_2SOCH_3$ |
| Ia.570 | Cl | Cl | $CH_2CH(CH_3)CH_2SOCH_2CH_3$ |
| Ia.571 | H | Cl | $CH_2CH(CH_3)CH_2SOCH_2CH_3$ |
| Ia.572 | F | Cl | $CH_2CH(CH_3)CH_2SOCH_2CH_3$ |
| Ia.573 | Cl | Cl | $CH_2CH(CH_3)CH_2SO_2CHF_2$ |
| Ia.574 | H | Cl | $CH_2CH(CH_3)CH_2SO_2CHF_2$ |
| Ia.575 | F | Cl | $CH_2CH(CH_3)CH_2SO_2CHF_2$ |
| Ia.576 | Cl | Cl | $CH_2CH(CH_3)CH_2SO_2CF_3$ |
| Ia.577 | H | Cl | $CH_2CH(CH_3)CH_2SO_2CF_3$ |
| Ia.578 | F | Cl | $CH_2CH(CH_3)CH_2SO_2CF_3$ |
| Ia.579 | Cl | Cl | $CH_2CH(CH_3)CH_2SO_2$-cyclopropyl |
| Ia.580 | H | Cl | $CH_2CH(CH_3)CH_2SO_2$-cyclopropyl |
| Ia.581 | F | Cl | $CH_2CH(CH_3)CH_2SO_2$-cyclopropyl |
| Ia.582 | Cl | Cl | $CH_2CH(CH_3)CH_2SO_2CH_3$ |
| Ia.583 | H | Cl | $CH_2CH(CH_3)CH_2SO_2CH_3$ |
| Ia.584 | F | Cl | $CH_2CH(CH_3)CH_2SO_2CH_3$ |
| Ia.585 | Cl | Cl | $CH_2CH(CH_3)CH_2SO_2CH_2CH_3$ |
| Ia.586 | H | Cl | $CH_2CH(CH_3)CH_2SO_2CH_2CH_3$ |
| Ia.587 | F | Cl | $CH_2CH(CH_3)CH_2SO_2CH_2CH_3$ |
| Ia.588 | Cl | Cl | $CH_2CH_2CH(CH_3)Cl$ |
| Ia.589 | H | Cl | $CH_2CH_2CH(CH_3)Cl$ |
| Ia.590 | F | Cl | $CH_2CH_2CH(CH_3)Cl$ |
| Ia.591 | Cl | Cl | $CH_2CH_2CH(CH_3)Br$ |
| Ia.592 | H | Cl | $CH_2CH_2CH(CH_3)Br$ |
| Ia.593 | F | Cl | $CH_2CH_2CH(CH_3)Br$ |
| Ia.594 | Cl | Cl | $CH_2CH_2CH(CH_3)I$ |
| Ia.595 | H | Cl | $CH_2CH_2CH(CH_3)I$ |
| Ia.596 | F | Cl | $CH_2CH_2CH(CH_3)I$ |
| Ia.597 | Cl | Cl | $CH_2CH_2CH(CH_3)CN$ |
| Ia.598 | H | Cl | $CH_2CH_2CH(CH_3)CN$ |
| Ia.599 | F | Cl | $CH_2CH_2CH(CH_3)CN$ |
| Ia.600 | Cl | Cl | $CH_2CH_2CH(CH_3)SCN$ |
| Ia.601 | H | Cl | $CH_2CH_2CH(CH_3)SCN$ |
| Ia.602 | F | Cl | $CH_2CH_2CH(CH_3)SCN$ |
| Ia.603 | Cl | Cl | $CH_2CH_2CH(CH_3)F$ |
| Ia.604 | H | Cl | $CH_2CH_2CH(CH_3)F$ |
| Ia.605 | F | Cl | $CH_2CH_2CH(CH_3)F$ |
| Ia.606 | Cl | Cl | $CH_2CH_2CH(CH_3)SCHF_2$ |
| Ia.607 | Cl | Cl | $CH_2CH_2CH(CH_3)SCHF_2$ |
| Ia.608 | H | Cl | $CH_2CH_2CH(CH_3)SCHF_2$ |
| Ia.609 | F | Cl | $CH_2CH_2CH(CH_3)SCF_3$ |
| Ia.610 | Cl | Cl | $CH_2CH_2CH(CH_3)SCF_3$ |
| Ia.611 | H | Cl | $CH_2CH_2CH(CH_3)SCF_3$ |
| Ia.612 | F | Cl | $CH_2CH_2CH(CH_3)S$-cyclopropyl |
| Ia.613 | Cl | Cl | $CH_2CH_2CH(CH_3)S$-cyclopropyl |
| Ia.614 | H | Cl | $CH_2CH_2CH(CH_3)S$-cyclopropyl |
| Ia.615 | F | Cl | $CH_2CH_2CH(CH_3)SOCHF_2$ |
| Ia.616 | Cl | Cl | $CH_2CH_2CH(CH_3)SOCHF_2$ |
| Ia.617 | H | Cl | $CH_2CH_2CH(CH_3)SOCHF_2$ |
| Ia.618 | F | Cl | $CH_2CH_2CH(CH_3)SOCF_2$ |
| Ia.619 | Cl | Cl | $CH_2CH_2CH(CH_3)SOCF_2$ |
| Ia.620 | H | Cl | $CH_2CH_2CH(CH_3)SOCF_2$ |
| Ia.621 | F | Cl | $CH_2CH_2CH(CH_3)SO$-cyclopropyl |
| Ia.622 | Cl | Cl | $CH_2CH_2CH(CH_3)SO$-cyclopropyl |
| Ia.623 | H | Cl | $CH_2CH_2CH(CH_3)SO$-cyclopropyl |
| Ia.624 | F | Cl | $CH_2CH_2CH(CH_3)SOCH_3$ |
| Ia.625 | Cl | Cl | $CH_2CH_2CH(CH_3)SOCH_3$ |
| Ia.626 | H | Cl | $CH_2CH_2CH(CH_3)SOCH_3$ |
| Ia.627 | F | Cl | $CH_2CH_2CH(CH_3)SOCH_2CH_3$ |
| Ia.628 | Cl | Cl | $CH_2CH_2CH(CH_3)SOCH_2CH_3$ |
| Ia.629 | H | Cl | $CH_2CH_2CH(CH_3)SOCH_2CH_3$ |
| Ia.630 | F | Cl | $CH_2CH_2CH(CH_3)SO_2CHF_2$ |
| Ia.631 | Cl | Cl | $CH_2CH_2CH(CH_3)SO_2CHF_2$ |
| Ia.632 | H | Cl | $CH_2CH_2CH(CH_3)SO_2CHF_2$ |
| Ia.633 | F | Cl | $CH_2CH_2CH(CH_3)SO_2CF_3$ |
| Ia.634 | Cl | Cl | $CH_2CH_2CH(CH_3)SO_2CF_3$ |
| Ia.635 | H | Cl | $CH_2CH_2CH(CH_3)SO_2CF_3$ |
| Ia.636 | F | Cl | $CH_2CH_2CH(CH_3)SO_2$-cyclopropyl |
| Ia.637 | Cl | Cl | $CH_2CH_2CH(CH_3)SO_2$-cyclopropyl |
| Ia.638 | H | Cl | $CH_2CH_2CH(CH_3)SO_2$-cyclopropyl |
| Ia.639 | F | Cl | $CH_2CH_2CH(CH_3)SO_2CH_3$ |
| Ia.640 | Cl | Cl | $CH_2CH_2CH(CH_3)SO_2CH_3$ |
| Ia.641 | H | Cl | $CH_2CH_2CH(CH_3)SO_2CH_3$ |
| Ia.642 | F | Cl | $CH_2CH_2CH(CH_3)SO_2CH_2CH_3$ |
| Ia.643 | Cl | Cl | $CH_2CH_2CH(CH_3)SO_2CH_2CH_3$ |
| Ia.644 | H | Cl | $CH_2CH_2CH(CH_3)SO_2CH_2CH_3$ |
| Ia.645 | F | Cl | $CH(CH_2CH_3)CH_2F$ |
| Ia.646 | Cl | Cl | $CH(CH_2CH_3)CH_2F$ |
| Ia.647 | H | Cl | $CH(CH_2CH_3)CH_2F$ |
| Ia.648 | F | Cl | $CH(CH_2CH_3)CH_2Cl$ |
| Ia.649 | Cl | Cl | $CH(CH_2CH_3)CH_2Cl$ |
| Ia.650 | H | Cl | $CH(CH_2CH_3)CH_2Cl$ |
| Ia.651 | F | Cl | $CH(CH_2CH_3)CH_2Br$ |
| Ia.652 | Cl | Cl | $CH(CH_2CH_3)CH_2Br$ |
| Ia.653 | H | Cl | $CH(CH_2CH_3)CH_2Br$ |
| Ia.654 | F | Cl | $CH(CH_2CH_3)CH_2I$ |
| Ia.655 | Cl | Cl | $CH(CH_2CH_3)CH_2I$ |
| Ia.656 | H | Cl | $CH(CH_2CH_3)CH_2I$ |
| Ia.657 | F | Cl | $CH(CH_2CH_3)CH_2CN$ |
| Ia.658 | Cl | Cl | $CH(CH_2CH_3)CH_2CN$ |
| Ia.659 | H | Cl | $CH(CH_2CH_3)CH_2CN$ |
| Ia.660 | F | Cl | $CH(CH_2CH_3)CH_2SCN$ |
| Ia.661 | Cl | Cl | $CH(CH_2CH_3)CH_2SCN$ |
| Ia.662 | H | Cl | $CH(CH_2CH_3)CH_2SCN$ |
| Ia.663 | F | Cl | $CH(CH_2CH_3)CH_2SCHF_2$ |
| Ia.664 | Cl | Cl | $CH(CH_2CH_3)CH_2SCHF_2$ |
| Ia.665 | H | Cl | $CH(CH_2CH_3)CH_2SCHF_2$ |
| Ia.666 | F | Cl | $CH(CH_2CH_3)CH_2SCF_3$ |
| Ia.667 | Cl | Cl | $CH(CH_2CH_3)CH_2SCF_3$ |
| Ia.668 | H | Cl | $CH(CH_2CH_3)CH_2SCF_3$ |
| Ia.669 | F | Cl | $CH(CH_2CH_3)CH_2S$-cyclopropyl |
| Ia.670 | Cl | Cl | $CH(CH_2CH_3)CH_2S$-cyclopropyl |
| Ia.671 | H | Cl | $CH(CH_2CH_3)CH_2S$-cyclopropyl |
| Ia.672 | F | Cl | $CH(CH_2CH_3)CH_2SOCHF_2$ |
| Ia.673 | Cl | Cl | $CH(CH_2CH_3)CH_2SOCHF_2$ |
| Ia.674 | H | Cl | $CH(CH_2CH_3)CH_2SOCHF_2$ |
| Ia.675 | F | Cl | $CH(CH_2CH_3)CH_2SOCF_3$ |
| Ia.676 | Cl | Cl | $CH(CH_2CH_3)CH_2SOCF_3$ |

TABLE 5-continued

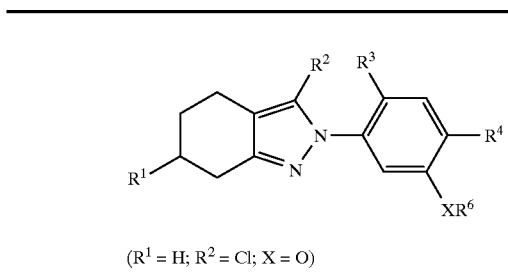

($R^1$ = H; $R^2$ = Cl; X = O)

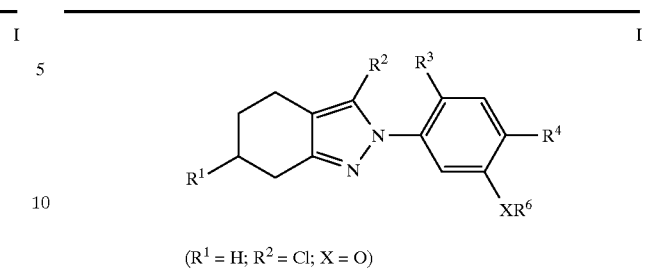

($R^1$ = H; $R^2$ = Cl; X = O)

| No. | $R^3$ | $R^4$ | $R^6$ |
|---|---|---|---|
| Ia.677 | H | Cl | $CH(CH_2CH_3)CH_2SOCF_3$ |
| Ia.678 | F | Cl | $CH(CH_2CH_3)CH_2SO$-cyclopropyl |
| Ia.679 | Cl | Cl | $CH(CH_2CH_3)CH_2SO$-cyclopropyl |
| Ia.680 | H | Cl | $CH(CH_2CH_3)CH_2SO$-cyclopropyl |
| Ia.681 | F | Cl | $CH(CH_2CH_3)CH_2SOCH_3$ |
| Ia.682 | Cl | Cl | $CH(CH_2CH_3)CH_2SOCH_3$ |
| Ia.683 | H | Cl | $CH(CH_2CH_3)CH_2SOCH_3$ |
| Ia.684 | F | Cl | $CH(CH_2CH_3)CH_2SOCH_2CH_3$ |
| Ia.685 | Cl | Cl | $CH(CH_2CH_3)CH_2SOCH_2CH_3$ |
| Ia.686 | H | Cl | $CH(CH_2CH_3)CH_2SOCH_2CH_3$ |
| Ia.687 | F | Cl | $CH(CH_2CH_3)CH_2SO_2CHF_2$ |
| Ia.688 | Cl | Cl | $CH(CH_2CH_3)CH_2SO_2CHF_2$ |
| Ia.689 | H | Cl | $CH(CH_2CH_3)CH_2SO_2CHF_2$ |
| Ia.690 | F | Cl | $CH(CH_2CH_3)CH_2SO_2CF_3$ |
| Ia.691 | Cl | Cl | $CH(CH_2CH_3)CH_2SO_2CF_3$ |
| Ia.692 | H | Cl | $CH(CH_2CH_3)CH_2SO_2CF_3$ |
| Ia.693 | F | Cl | $CH(CH_2CH_3)CH_2SO_2$-cyclopropyl |
| Ia.694 | Cl | Cl | $CH(CH_2CH_3)CH_2SO_2$-cyclopropyl |
| Ia.695 | H | Cl | $CH(CH_2CH_3)CH_2SO_2$-cyclopropyl |
| Ia.696 | F | Cl | $CH(CH_2CH_3)CH_2SO_2CH_3$ |
| Ia.697 | Cl | Cl | $CH(CH_2CH_3)CH_2SO_2CH_3$ |
| Ia.698 | H | Cl | $CH(CH_2CH_3)CH_2SO_2CH_3$ |
| Ia.699 | F | Cl | $CH(CH_2CH_3)CH_2SO_2CH_2CH_3$ |
| Ia.700 | Cl | Cl | $CH(CH_2CH_3)CH_2SO_2CH_2CH_3$ |
| Ia.701 | H | Cl | $CH(CH_2CH_3)CH_2SO_2CH_2CH_3$ |
| Ia.702 | F | Cl | $CH_2CH(CH_2CH_3)F$ |
| Ia.703 | Cl | Cl | $CH_2CH(CH_2CH_3)F$ |
| Ia.704 | H | Cl | $CH_2CH(CH_2CH_3)F$ |
| Ia.705 | F | Cl | $CH_2CH(CH_2CH_3)Cl$ |
| Ia.706 | Cl | Cl | $CH_2CH(CH_2CH_3)Cl$ |
| Ia.707 | H | Cl | $CH_2CH(CH_2CH_3)Cl$ |
| Ia.708 | F | Cl | $CH_2CH(CH_2CH_3)Br$ |
| Ia.709 | Cl | Cl | $CH_2CH(CH_2CH_3)Br$ |
| Ia.710 | H | Cl | $CH_2CH(CH_2CH_3)Br$ |
| Ia.711 | F | Cl | $CH_2CH(CH_2CH_3)I$ |
| Ia.712 | Cl | Cl | $CH_2CH(CH_2CH_3)I$ |
| Ia.713 | H | Cl | $CH_2CH(CH_2CH_3)I$ |
| Ia.714 | F | Cl | $CH_2CH(CH_2CH_3)CN$ |
| Ia.715 | Cl | Cl | $CH_2CH(CH_2CH_3)CN$ |
| Ia.716 | H | Cl | $CH_2CH(CH_2CH_3)CN$ |
| Ia.717 | F | Cl | $CH_2CH(CH_2CH_3)SCN$ |
| Ia.718 | Cl | Cl | $CH_2CH(CH_2CH_3)SCN$ |
| Ia.719 | H | Cl | $CH_2CH(CH_2CH_3)SCN$ |
| Ia.720 | F | Cl | $CH_2CH(CH_2CH_3)SCHF_2$ |
| Ia.721 | Cl | Cl | $CH_2CH(CH_2CH_3)SCHF_2$ |
| Ia.722 | H | Cl | $CH_2CH(CH_2CH_3)SCHF_2$ |
| Ia.723 | F | Cl | $CH_2CH(CH_2CH_3)SCF_3$ |
| Ia.724 | Cl | Cl | $CH_2CH(CH_2CH_3)SCF_3$ |
| Ia.725 | H | Cl | $CH_2CH(CH_2CH_3)SCF_3$ |
| Ia.726 | F | Cl | $CH_2CH(CH_2CH_3)S$-cyclopropyl |
| Ia.727 | Cl | Cl | $CH_2CH(CH_2CH_3)S$-cyclopropyl |
| Ia.728 | H | Cl | $CH_2CH(CH_2CH_3)S$-cyclopropyl |
| Ia.729 | F | Cl | $CH_2CH(CH_2CH_3)SOCHF_2$ |
| Ia.730 | Cl | Cl | $CH_2CH(CH_2CH_3)SOCHF_2$ |
| Ia.731 | H | Cl | $CH_2CH(CH_2CH_3)SOCHF_2$ |
| Ia.732 | F | Cl | $CH_2CH(CH_2CH_3)SOCF_3$ |
| Ia.733 | Cl | Cl | $CH_2CH(CH_2CH_3)SOCF_3$ |
| Ia.734 | H | Cl | $CH_2CH(CH_2CH_3)SOCF_3$ |
| Ia.735 | F | Cl | $CH_2CH(CH_2CH_3)SO$-cyclopropyl |
| Ia.736 | Cl | Cl | $CH_2CH(CH_2CH_3)SO$-cyclopropyl |
| Ia.737 | H | Cl | $CH_2CH(CH_2CH_3)SO$-cyclopropyl |
| Ia.738 | F | Cl | $CH_2CH(CH_2CH_3)SOCH_3$ |
| Ia.739 | Cl | Cl | $CH_2CH(CH_2CH_3)SOCH_3$ |
| Ia.740 | H | Cl | $CH_2CH(CH_2CH_3)SOCH_3$ |
| Ia.741 | F | Cl | $CH_2CH(CH_2CH_3)SOCH_2CH_3$ |
| Ia.742 | Cl | Cl | $CH_2CH(CH_2CH_3)SOCH_2CH_3$ |
| Ia.743 | H | Cl | $CH_2CH(CH_2CH_3)SOCH_2CH_3$ |
| Ia.744 | F | Cl | $CH_2CH(CH_2CH_3)SO_2CHF_2$ |
| Ia.745 | Cl | Cl | $CH_2CH(CH_2CH_3)SO_2CHF_2$ |
| Ia.746 | H | Cl | $CH_2CH(CH_2CH_3)SO_2CHF_2$ |
| Ia.747 | F | Cl | $CH_2CH(CH_2CH_3)SO_2CF_3$ |
| Ia.748 | Cl | Cl | $CH_2CH(CH_2CH_3)SO_2CF_3$ |
| Ia.749 | H | Cl | $CH_2CH(CH_2CH_3)SO_2CF_3$ |
| Ia.750 | F | Cl | $CH_2CH(CH_2CH_3)SO_2$-cyclopropyl |
| Ia.751 | Cl | Cl | $CH_2CH(CH_2CH_3)SO_2$-cyclopropyl |
| Ia.752 | H | Cl | $CH_2CH(CH_2CH_3)SO_2$-cyclopropyl |
| Ia.753 | F | Cl | $CH_2CH(CH_2CH_3)SO_2CH_3$ |
| Ia.754 | Cl | Cl | $CH_2CH(CH_2CH_3)SO_2CH_3$ |
| Ia.755 | H | Cl | $CH_2CH(CH_2CH_3)SO_2CH_3$ |
| Ia.756 | F | Cl | $CH_2CH(CH_2CH_3)SO_2CH_2CH_3$ |
| Ia.757 | Cl | Cl | $CH_2CH(CH_2CH_3)SO_2CH_2CH_3$ |
| Ia.758 | H | Cl | $CH_2CH(CH_2CH_3)SO_2CH_2CH_3$ |
| Ia.759 | F | Cl | $CH(CH_2CH_2CH_3)F$ |
| Ia.760 | Cl | Cl | $CH(CH_2CH_2CH_3)F$ |
| Ia.761 | H | Cl | $CH(CH_2CH_2CH_3)F$ |
| Ia.762 | F | Cl | $CH(CH_2CH_2CH_3)Cl$ |
| Ia.763 | Cl | Cl | $CH(CH_2CH_2CH_3)Cl$ |
| Ia.764 | H | Cl | $CH(CH_2CH_2CH_3)Cl$ |
| Ia.765 | F | Cl | $CH(CH_2CH_2CH_3)Br$ |
| Ia.766 | Cl | Cl | $CH(CH_2CH_2CH_3)Br$ |
| Ia.767 | H | Cl | $CH(CH_2CH_2CH_3)Br$ |
| Ia.768 | F | Cl | $CH(CH_2CH_2CH_3)I$ |
| Ia.769 | Cl | Cl | $CH(CH_2CH_2CH_3)I$ |
| Ia.770 | H | Cl | $CH(CH_2CH_2CH_3)I$ |
| Ia.771 | F | Cl | $CH(CH_2CH_2CH_3)CN$ |
| Ia.772 | Cl | Cl | $CH(CH_2CH_2CH_3)CN$ |
| Ia.773 | H | Cl | $CH(CH_2CH_2CH_3)CN$ |
| Ia.774 | F | Cl | $CH(CH_2CH_2CH_3)SCN$ |
| Ia.775 | Cl | Cl | $CH(CH_2CH_2CH_3)SCN$ |
| Ia.776 | H | Cl | $CH(CH_2CH_2CH_3)SCN$ |
| Ia.777 | F | Cl | $CH(CH_2CH_2CH_3)SCHF_2$ |
| Ia.778 | Cl | Cl | $CH(CH_2CH_2CH_3)SCHF_2$ |
| Ia.779 | H | Cl | $CH(CH_2CH_2CH_3)SCHF_2$ |
| Ia.780 | F | Cl | $CH(CH_2CH_2CH_3)SCF_3$ |
| Ia.781 | Cl | Cl | $CH(CH_2CH_2CH_3)SCF_3$ |
| Ia.782 | H | Cl | $CH(CH_2CH_2CH_3)SCF_3$ |
| Ia.783 | F | Cl | $CH(CH_2CH_2CH_3)S$-cyclopropyl |
| Ia.784 | Cl | Cl | $CH(CH_2CH_2CH_3)S$-cyclopropyl |
| Ia.785 | H | Cl | $CH(CH_2CH_2CH_3)S$-cyclopropyl |
| Ia.786 | F | Cl | $CH(CH_2CH_2CH_3)SOCHF_2$ |
| Ia.787 | Cl | Cl | $CH(CH_2CH_2CH_3)SOCHF_2$ |
| Ia.788 | H | Cl | $CH(CH_2CH_2CH_3)SOCHF_2$ |
| Ia.789 | F | Cl | $CH(CH_2CH_2CH_3)SOCF_3$ |
| Ia.790 | Cl | Cl | $CH(CH_2CH_2CH_3)SOCF_3$ |
| Ia.791 | H | Cl | $CH(CH_2CH_2CH_3)SOCF_3$ |
| Ia.792 | F | Cl | $CH(CH_2CH_2CH_3)SO$-cyclopropyl |
| Ia.793 | Cl | Cl | $CH(CH_2CH_2CH_3)SO$-cyclopropyl |
| Ia.794 | H | Cl | $CH(CH_2CH_2CH_3)SO$-cyclopropyl |
| Ia.795 | F | Cl | $CH(CH_2CH_2CH_3)SOCH_3$ |
| Ia.796 | Cl | Cl | $CH(CH_2CH_2CH_3)SOCH_3$ |
| Ia.797 | H | Cl | $CH(CH_2CH_2CH_3)SOCH_3$ |
| Ia.798 | F | Cl | $CH(CH_2CH_2CH_3)SOCH_2CH_3$ |
| Ia.799 | Cl | Cl | $CH(CH_2CH_2CH_3)SOCH_2CH_3$ |
| Ia.800 | H | Cl | $CH(CH_2CH_2CH_3)SOCH_2CH_3$ |
| Ia.801 | F | Cl | $CH(CH_2CH_2CH_3)SO_2CHF_2$ |
| Ia.802 | Cl | Cl | $CH(CH_2CH_2CH_3)SO_2CHF_2$ |
| Ia.803 | H | Cl | $CH(CH_2CH_2CH_3)SO_2CHF_2$ |
| Ia.804 | F | Cl | $CH(CH_2CH_2CH_3)SO_2CHF_2$ |

TABLE 5-continued

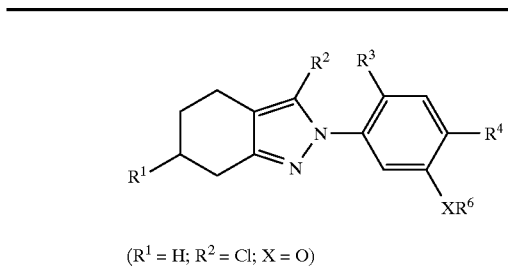

($R^1$ = H; $R^2$ = Cl; X = O)

| No. | $R^3$ | $R^4$ | $R^6$ |
|---|---|---|---|
| Ia.805 | Cl | Cl | $CH(CH_2CH_2CH_3)SO_2CHF_2$ |
| Ia.806 | H | Cl | $CH(CH_2CH_2CH_3)SO_2CHF_2$ |
| Ia.807 | F | Cl | $CH(CH_2CH_2CH_3)SO_2$-cyclopropyl |
| Ia.808 | Cl | Cl | $CH(CH_2CH_2CH_3)SO_2$-cyclopropyl |
| Ia.809 | H | Cl | $CH(CH_2CH_2CH_3)SO_2$-cyclopropyl |
| Ia.810 | F | Cl | $CH(CH_2CH_2CH_3)SO_2CH_3$ |
| Ia.811 | Cl | Cl | $CH(CH_2CH_2CH_3)SO_2CH_3$ |
| Ia.812 | H | Cl | $CH(CH_2CH_2CH_3)SO_2CH_3$ |
| Ia.813 | F | Cl | $CH(CH_2CH_2CH_3)SO_2CH_2CH_3$ |
| Ia.814 | Cl | Cl | $CH(CH_2CH_2CH_3)SO_2CH_2CH_3$ |
| Ia.815 | H | Cl | $CH(CH_2CH_2CH_3)SO_2CH_2CH_3$ |
| Ia.816 | F | Cl | $CH(CH(CH_3)_2)F$ |
| Ia.817 | Cl | Cl | $CH(CH(CH_3)_2)F$ |
| Ia.818 | H | Cl | $CH(CH(CH_3)_2)F$ |
| Ia.819 | F | Cl | $CH(CH(CH_3)_2)Cl$ |
| Ia.820 | Cl | Cl | $CH(CH(CH_3)_2)Cl$ |
| Ia.821 | H | Cl | $CH(CH(CH_3)_2)Cl$ |
| Ia.822 | F | Cl | $CH(CH(CH_3)_2)Br$ |
| Ia.823 | Cl | Cl | $CH(CH(CH_3)_2)Br$ |
| Ia.824 | H | Cl | $CH(CH(CH_3)_2)Br$ |
| Ia.825 | F | Cl | $CH(CH(CH_3)_2)I$ |
| Ia.826 | Cl | Cl | $CH(CH(CH_3)_2)I$ |
| Ia.827 | H | Cl | $CH(CH(CH_3)_2)I$ |
| Ia.828 | F | Cl | $CH(CH(CH_3)_2)CN$ |
| Ia.829 | Cl | Cl | $CH(CH(CH_3)_2)CN$ |
| Ia.830 | H | Cl | $CH(CH(CH_3)_2)CN$ |
| Ia.831 | F | Cl | $CH(CH(CH_3)_2)SCN$ |
| Ia.832 | Cl | Cl | $CH(CH(CH_3)_2)SCN$ |
| Ia.833 | H | Cl | $CH(CH(CH_3)_2)SCN$ |
| Ia.834 | F | Cl | $CH(CH(CH_3)_2)SCHF_2$ |
| Ia.835 | Cl | Cl | $CH(CH(CH_3)_2)SCHF_2$ |
| Ia.836 | H | Cl | $CH(CH(CH_3)_2)SCHF_2$ |
| Ia.837 | F | Cl | $CH(CH(CH_3)_2)SCF_3$ |
| Ia.838 | Cl | Cl | $CH(CH(CH_3)_2)SCF_3$ |
| Ia.839 | H | Cl | $CH(CH(CH_3)_2)SCF_3$ |
| Ia.840 | F | Cl | $CH(CH(CH_3)_2)S$-cyclopropyl |
| Ia.841 | Cl | Cl | $CH(CH(CH_3)_2)S$-cyclopropyl |
| Ia.842 | H | Cl | $CH(CH(CH_3)_2)S$-cyclopropyl |
| Ia.843 | F | Cl | $CH(CH(CH_3)_2)SOCHF_2$ |
| Ia.844 | Cl | Cl | $CH(CH(CH_3)_2)SOCHF_2$ |
| Ia.845 | H | Cl | $CH(CH(CH_3)_2)SOCHF_2$ |
| Ia.846 | F | Cl | $CH(CH(CH_3)_2)SOCF_3$ |
| Ia.847 | Cl | Cl | $CH(CH(CH_3)_2)SOCF_3$ |
| Ia.848 | H | Cl | $CH(CH(CH_3)_2)SOCF_3$ |
| Ia.849 | F | Cl | $CH(CH(CH_3)_2)SO$-cyclopropyl |
| Ia.850 | Cl | Cl | $CH(CH(CH_3)_2)SO$-cyclopropyl |
| Ia.851 | H | Cl | $CH(CH(CH_3)_2)SO$-cyclopropyl |
| Ia.852 | F | Cl | $CH(CH(CH_3)_2)SOCH_2CH_3$ |
| Ia.853 | Cl | Cl | $CH(CH(CH_3)_2)SOCH_2CH_3$ |
| Ia.854 | H | Cl | $CH(CH(CH_3)_2)SOCH_2CH_3$ |
| Ia.855 | F | Cl | $CH(CH(CH_3)_2)SOCH_3$ |
| Ia.856 | Cl | Cl | $CH(CH(CH_3)_2)SOCH_3$ |
| Ia.857 | H | Cl | $CH(CH(CH_3)_2)SOCH_3$ |
| Ia.858 | F | Cl | $CH(CH(CH_3)_2)SO_2CHF_2$ |
| Ia.859 | Cl | Cl | $CH(CH(CH_3)_2)SO_2CHF_2$ |
| Ia.860 | H | Cl | $CH(CH(CH_3)_2)SO_2CHF_2$ |
| Ia.861 | F | Cl | $CH(CH(CH_3)_2)SO_2CF_3$ |
| Ia.862 | Cl | Cl | $CH(CH(CH_3)_2)SO_2CF_3$ |
| Ia.863 | H | Cl | $CH(CH(CH_3)_2)SO_2CF_3$ |
| Ia.864 | F | Cl | $CH(CH(CH_3)_2)SO_2$-cyclopropyl |
| Ia.865 | Cl | Cl | $CH(CH(CH_3)_2)SO_2$-cyclopropyl |
| Ia.866 | H | Cl | $CH(CH(CH_3)_2)SO_2$-cyclopropyl |
| Ia.867 | F | Cl | $CH(CH(CH_3)_2)SO_2CH_3$ |
| Ia.868 | Cl | Cl | $CH(CH(CH_3)_2)SO_2CH_3$ |
| Ia.869 | H | Cl | $CH(CH(CH_3)_2)SO_2CH_3$ |
| Ia.870 | F | Cl | $CH(CH(CH_3)_2)SO_2CH_2CH_3$ |
| Ia.871 | Cl | Cl | $CH(CH(CH_3)_2)SO_2CH_2CH_3$ |
| Ia.872 | H | Cl | $CH(CH(CH_3)_2)SO_2CH_2CH_3$ |
| Ia.873 | F | Cl | $CH(CH_3)CH(CH_3)F$ |
| Ia.874 | Cl | Cl | $CH(CH_3)CH(CH_3)F$ |
| Ia.875 | H | Cl | $CH(CH_3)CH(CH_3)F$ |
| Ia.876 | F | Cl | $CH(CH_3)CH(CH_3)Cl$ |
| Ia.877 | Cl | Cl | $CH(CH_3)CH(CH_3)Cl$ |
| Ia.878 | H | Cl | $CH(CH_3)CH(CH_3)Cl$ |
| Ia.879 | F | Cl | $CH(CH_3)CH(CH_3)Br$ |
| Ia.880 | Cl | Cl | $CH(CH_3)CH(CH_3)Br$ |
| Ia.881 | H | Cl | $CH(CH_3)CH(CH_3)Br$ |
| Ia.882 | F | Cl | $CH(CH_3)CH(CH_3)I$ |
| Ia.883 | Cl | Cl | $CH(CH_3)CH(CH_3)I$ |
| Ia.884 | H | Cl | $CH(CH_3)CH(CH_3)I$ |
| Ia.885 | F | Cl | $CH(CH_3)CH(CH_3)CN$ |
| Ia.886 | Cl | Cl | $CH(CH_3)CH(CH_3)CN$ |
| Ia.887 | H | Cl | $CH(CH_3)CH(CH_3)CN$ |
| Ia.888 | F | Cl | $CH(CH_3)CH(CH_3)SCN$ |
| Ia.889 | Cl | Cl | $CH(CH_3)CH(CH_3)SCN$ |
| Ia.890 | H | Cl | $CH(CH_3)CH(CH_3)SCN$ |
| Ia.891 | F | Cl | $CH(CH_3)CH(CH_3)SCHF_2$ |
| Ia.892 | Cl | Cl | $CH(CH_3)CH(CH_3)SCHF_2$ |
| Ia.893 | H | Cl | $CH(CH_3)CH(CH_3)SCHF_2$ |
| Ia.894 | F | Cl | $CH(CH_3)CH(CH_3)SOCHF_2$ |
| Ia.895 | Cl | Cl | $CH(CH_3)CH(CH_3)SOCHF_2$ |
| Ia.896 | H | Cl | $CH(CH_3)CH(CH_3)SOCHF_2$ |
| Ia.897 | F | Cl | $CH(CH_3)CH(CH_3)SO_2CHF_2$ |
| Ia.898 | Cl | Cl | $CH(CH_3)CH(CH_3)SO_2CHF_2$ |
| Ia.899 | H | Cl | $CH(CH_3)CH(CH_3)SO_2CHF_2$ |
| Ia.900 | F | Cl | $CH(CH_3)CH(CH_3)SCF_3$ |
| Ia.901 | Cl | Cl | $CH(CH_3)CH(CH_3)SCF_3$ |
| Ia.902 | H | Cl | $CH(CH_3)CH(CH_3)SCF_3$ |
| Ia.903 | F | Cl | $CH(CH_3)CH(CH_3)SOCF_3$ |
| Ia.904 | Cl | Cl | $CH(CH_3)CH(CH_3)SOCF_3$ |
| Ia.905 | H | Cl | $CH(CH_3)CH(CH_3)SOCF_3$ |
| Ia.906 | F | Cl | $CH(CH_3)CH(CH_3)SO_2CF_3$ |
| Ia.907 | Cl | Cl | $CH(CH_3)CH(CH_3)SO_2CF_3$ |
| Ia.908 | H | Cl | $CH(CH_3)CH(CH_3)SO_2CF_3$ |
| Ia.909 | F | Cl | $CH(CH_3)CH(CH_3)S$-cyclopropyl |
| Ia.910 | Cl | Cl | $CH(CH_3)CH(CH_3)S$-cyclopropyl |
| Ia.911 | H | Cl | $CH(CH_3)CH(CH_3)S$-cyclopropyl |
| Ia.912 | F | Cl | $CH(CH_3)CH(CH_3)SO$-cyclopropyl |
| Ia.913 | Cl | Cl | $CH(CH_3)CH(CH_3)SO$-cyclopropyl |
| Ia.914 | H | Cl | $CH(CH_3)CH(CH_3)SO$-cyclopropyl |
| Ia.915 | F | Cl | $CH(CH_3)CH(CH_3)SO_2$-cyclopropyl |
| Ia.916 | Cl | Cl | $CH(CH_3)CH(CH_3)SO_2$-cyclopropyl |
| Ia.917 | H | Cl | $CH(CH_3)CH(CH_3)SO_2$-cyclopropyl |
| Ia.918 | F | Cl | $CH(CH_3)CH(CH_3)SOCH_3$ |
| Ia.919 | Cl | Cl | $CH(CH_3)CH(CH_3)SOCH_3$ |
| Ia.920 | H | Cl | $CH(CH_3)CH(CH_3)SOCH_3$ |
| Ia.921 | F | Cl | $CH(CH_3)CH(CH_3)SO_2CH_3$ |
| Ia.922 | Cl | Cl | $CH(CH_3)CH(CH_3)SO_2CH_3$ |
| Ia.923 | H | Cl | $CH(CH_3)CH(CH_3)SO_2CH_3$ |
| Ia.924 | F | Cl | $CH(CH_3)CH(CH_3)SOCH_2CH_3$ |
| Ia.925 | Cl | Cl | $CH(CH_3)CH(CH_3)SOCH_2CH_3$ |
| Ia.926 | H | Cl | $CH(CH_3)CH(CH_3)SOCH_2CH_3$ |
| Ia.927 | F | Cl | $CH(CH_3)CH(CH_3)SO_2CH_2CH_3$ |
| Ia.928 | Cl | Cl | $CH(CH_3)CH(CH_3)SO_2CH_2CH_3$ |
| Ia.929 | H | Cl | $CH(CH_3)CH(CH_3)SO_2CH_2CH_3$ |
| Ia.930 | F | Cl | $C(CH_3)_2CH_2F$ |
| Ia.931 | Cl | Cl | $C(CH_3)_2CH_2F$ |
| Ia.932 | H | Cl | $C(CH_3)_2CH_2F$ |

TABLE 5-continued

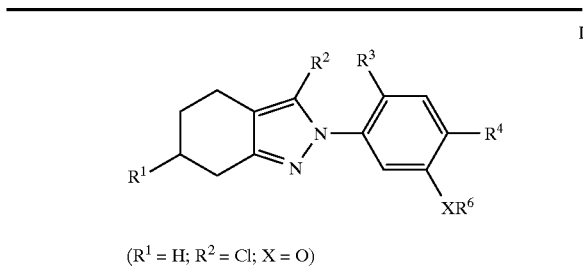

$(R^1 = H; R^2 = Cl; X = O)$

| No. | $R^3$ | $R^4$ | $R^6$ |
|---|---|---|---|
| Ia.933 | F | Cl | C(CH₃)₂CH₂Cl |
| Ia.934 | Cl | Cl | C(CH₃)₂CH₂Cl |
| Ia.935 | H | Cl | C(CH₃)₂CH₂Cl |
| Ia.936 | F | Cl | C(CH₃)₂CH₂Br |
| Ia.937 | Cl | Cl | C(CH₃)₂CH₂Br |
| Ia.938 | H | Cl | C(CH₃)₂CH₂Br |
| Ia.939 | F | Cl | C(CH₃)₂CH₂I |
| Ia.940 | Cl | Cl | C(CH₃)₂CH₂I |
| Ia.941 | H | Cl | C(CH₃)₂CH₂I |
| Ia.942 | F | Cl | C(CH₃)₂CH₂CN |
| Ia.943 | Cl | Cl | C(CH₃)₂CH₂CN |
| Ia.944 | H | Cl | C(CH₃)₂CH₂CN |
| Ia.945 | F | Cl | C(CH₃)₂CH₂SCN |
| Ia.946 | Cl | Cl | C(CH₃)₂CH₂SCN |
| Ia.947 | H | Cl | C(CH₃)₂CH₂SCN |
| Ia.948 | F | Cl | C(CH₃)₂CH₂SCHF₂ |
| Ia.949 | Cl | Cl | C(CH₃)₂CH₂SCHF₂ |
| Ia.950 | H | Cl | C(CH₃)₂CH₂SCHF₂ |
| Ia.951 | F | Cl | C(CH₃)₂CH₂SCF₃ |
| Ia.952 | Cl | Cl | C(CH₃)₂CH₂SCF₃ |
| Ia.953 | H | Cl | C(CH₃)₂CH₂SCF₃ |
| Ia.954 | F | Cl | C(CH₃)₂CH₂SOCHF₂ |
| Ia.955 | Cl | Cl | C(CH₃)₂CH₂SOCHF₂ |
| Ia.956 | H | Cl | C(CH₃)₂CH₂SOCHF₂ |
| Ia.957 | F | Cl | C(CH₃)₂CH₂SO₂CHF₂ |
| Ia.958 | Cl | Cl | C(CH₃)₂CH₂SO₂CHF₂ |
| Ia.959 | H | Cl | C(CH₃)₂CH₂SO₂CHF₂ |
| Ia.960 | F | Cl | C(CH₃)₂CH₂SOCF₃ |
| Ia.961 | Cl | Cl | C(CH₃)₂CH₂SOCF₃ |
| Ia.962 | H | Cl | C(CH₃)₂CH₂SOCF₃ |
| Ia.963 | F | Cl | C(CH₃)₂CH₂SO₂CF₃ |
| Ia.964 | Cl | Cl | C(CH₃)₂CH₂SO₂CF₃ |
| Ia.965 | H | Cl | C(CH₃)₂CH₂SO₂CF₃ |
| Ia.966 | F | Cl | C(CH₃)₂CH₂SOCH₃ |
| Ia.967 | Cl | Cl | C(CH₃)₂CH₂SOCH₃ |
| Ia.968 | H | Cl | C(CH₃)₂CH₂SOCH₃ |
| Ia.969 | F | Cl | C(CH₃)₂CH₂SO₂CH₃ |
| Ia.970 | Cl | Cl | C(CH₃)₂CH₂SO₂CH₃ |
| Ia.971 | H | Cl | C(CH₃)₂CH₂SO₂CH₃ |
| Ia.972 | F | Cl | C(CH₃)₂CH₂SOCH₂CH₃ |
| Ia.973 | Cl | Cl | C(CH₃)₂CH₂SOCH₂CH₃ |
| Ia.974 | H | Cl | C(CH₃)₂CH₂SOCH₂CH₃ |
| Ia.975 | F | Cl | C(CH₃)₂CH₂SO₂CH₂CH₃ |
| Ia.976 | Cl | Cl | C(CH₃)₂CH₂SO₂CH₂CH₃ |
| Ia.977 | H | Cl | C(CH₃)₂CH₂SO₂CH₂CH₃ |
| Ia.978 | F | Cl | CH₂C(CH₃)₂F |
| Ia.979 | Cl | Cl | CH₂C(CH₃)₂F |
| Ia.980 | H | Cl | CH₂C(CH₃)₂F |
| Ia.981 | F | Cl | CH₂C(CH₃)₂Cl |
| Ia.982 | Cl | Cl | CH₂C(CH₃)₂Cl |
| Ia.983 | H | Cl | CH₂C(CH₃)₂Cl |
| Ia.984 | F | Cl | CH₂C(CH₃)₂Br |
| Ia.985 | Cl | Cl | CH₂C(CH₃)₂Br |
| Ia.986 | H | Cl | CH₂C(CH₃)₂Br |
| Ia.987 | F | Cl | CH₂C(CH₃)₂I |
| Ia.988 | Cl | Cl | CH₂C(CH₃)₂I |
| Ia.989 | H | Cl | CH₂C(CH₃)₂I |
| Ia.990 | F | Cl | CH₂C(CH₃)₂CN |
| Ia.991 | Cl | Cl | CH₂C(CH₃)₂CN |
| Ia.992 | H | Cl | CH₂C(CH₃)₂CN |
| Ia.993 | F | Cl | CH₂C(CH₃)₂SCN |
| Ia.994 | Cl | Cl | CH₂C(CH₃)₂SCN |
| Ia.995 | H | Cl | CH₂C(CH₃)₂SCN |
| Ia.996 | F | Cl | CH₂C(CH₃)₂SCHF₂ |
| Ia.997 | Cl | Cl | CH₂C(CH₃)₂SCHF₂ |
| Ia.998 | H | Cl | CH₂C(CH₃)₂SCHF₂ |
| Ia.999 | F | Cl | CH₂C(CH₃)₂SCF₃ |
| Ia.1000 | Cl | Cl | CH₂C(CH₃)₂SCF₃ |
| Ia.1001 | H | Cl | CH₂C(CH₃)₂SCF₃ |
| Ia.1002 | F | Cl | CH₂C(CH₃)₂S-cyclopropyl |
| Ia.1003 | Cl | Cl | CH₂C(CH₃)₂S-cyclopropyl |
| Ia.1004 | H | Cl | CH₂C(CH₃)₂S-cyclopropyl |
| Ia.1005 | F | Cl | CH₂C(CH₃)₂SOCHF₂ |
| Ia.1006 | Cl | Cl | CH₂C(CH₃)₂SOCHF₂ |
| Ia.1007 | H | Cl | CH₂C(CH₃)₂SOCHF₂ |
| Ia.1008 | F | Cl | CH₂C(CH₃)₂SOCF₃ |
| Ia.1009 | Cl | Cl | CH₂C(CH₃)₂SOCF₃ |
| Ia.1010 | H | Cl | CH₂C(CH₃)₂SOCF₃ |
| Ia.1011 | F | Cl | CH₂C(CH₃)₂SO-cyclopropyl |
| Ia.1012 | Cl | Cl | CH₂C(CH₃)₂SO-cyclopropyl |
| Ia.1013 | H | Cl | CH₂C(CH₃)₂SO-cyclopropyl |
| Ia.1014 | F | Cl | CH₂C(CH₃)₂SOCH₃ |
| Ia.1015 | Cl | Cl | CH₂C(CH₃)₂SOCH₃ |
| Ia.1016 | H | Cl | CH₂C(CH₃)₂SOCH₃ |
| Ia.1017 | F | Cl | CH₂C(CH₃)₂SOCH₂CH₃ |
| Ia.1018 | Cl | Cl | CH₂C(CH₃)₂SOCH₂CH₃ |
| Ia.1019 | H | Cl | CH₂C(CH₃)₂SOCH₂CH₃ |
| Ia.1020 | F | Cl | CH₂C(CH₃)₂SO₂CHF₂ |
| Ia.1021 | Cl | Cl | CH₂C(CH₃)₂SO₂CHF₂ |
| Ia.1022 | H | Cl | CH₂C(CH₃)₂SO₂CHF₂ |
| Ia.1023 | F | Cl | CH₂C(CH₃)₂SO₂CF₃ |
| Ia.1024 | Cl | Cl | CH₂C(CH₃)₂SO₂CF₃ |
| Ia.1025 | H | Cl | CH₂C(CH₃)₂SO₂CF₃ |
| Ia.1026 | F | Cl | CH₂C(CH₃)₂SO₂-cyclopropyl |
| Ia.1027 | Cl | Cl | CH₂C(CH₃)₂SO₂-cyclopropyl |
| Ia.1028 | H | Cl | CH₂C(CH₃)₂SO₂-cyclopropyl |
| Ia.1029 | F | Cl | CH₂C(CH₃)₂SO₂CH₃ |
| Ia.1030 | Cl | Cl | CH₂C(CH₃)₂SO₂CH₃ |
| Ia.1031 | H | Cl | CH₂C(CH₃)₂SO₂CH₃ |
| Ia.1032 | F | Cl | CH₂C(CH₃)₂SO₂CH₂CH₃ |
| Ia.1033 | Cl | Cl | CH₂C(CH₃)₂SO₂CH₂CH₃ |
| Ia.1034 | H | Cl | CH₂C(CH₃)₂SO₂CH₂CH₃ |
| Ia.1035 | F | Cl | C(CH₃)₂CH₂S-cyclopropyl |
| Ia.1036 | Cl | Cl | C(CH₃)₂CH₂S-cyclopropyl |
| Ia.1037 | H | Cl | C(CH₃)₂CH₂S-cyclopropyl |
| Ia.1038 | F | Cl | C(CH₃)₂CH₂SO-cyclopropyl |
| Ia.1039 | Cl | Cl | C(CH₃)₂CH₂SO-cyclopropyl |
| Ia.1040 | H | Cl | C(CH₃)₂CH₂SO-cyclopropyl |
| Ia.1041 | F | Cl | C(CH₃)₂CH₂SO₂-cyclopropyl |
| Ia.1042 | Cl | Cl | C(CH₃)₂CH₂SO₂-cyclopropyl |
| Ia.1043 | H | Cl | C(CH₃)₂CH₂SO₂-cyclopropyl |
| Ia.1044 | F | Cl | CH₂CH₂CH₂CH₂CH₂F |
| Ia.1045 | Cl | Cl | CH₂CH₂CH₂CH₂CH₂F |
| Ia.1046 | H | Cl | CH₂CH₂CH₂CH₂CH₂F |
| Ia.1047 | F | Cl | CH₂CH₂CH₂CH₂CH₂Cl |
| Ia.1048 | Cl | Cl | CH₂CH₂CH₂CH₂CH₂Cl |
| Ia.1049 | H | Cl | CH₂CH₂CH₂CH₂CH₂Cl |
| Ia.1050 | F | Cl | CH₂CH₂CH₂CH₂CH₂Br |
| Ia.1051 | Cl | Cl | CH₂CH₂CH₂CH₂CH₂Br |
| Ia.1052 | H | Cl | CH₂CH₂CH₂CH₂CH₂Br |
| Ia.1053 | F | Cl | CH₂CH₂CH₂CH₂CH₂I |
| Ia.1054 | Cl | Cl | CH₂CH₂CH₂CH₂CH₂I |
| Ia.1055 | H | Cl | CH₂CH₂CH₂CH₂CH₂I |
| Ia.1056 | F | Cl | CH₂CH₂CH₂CH₂CH₂CN |
| Ia.1057 | Cl | Cl | CH₂CH₂CH₂CH₂CH₂CN |
| Ia.1058 | H | Cl | CH₂CH₂CH₂CH₂CH₂CN |
| Ia.1059 | F | Cl | CH₂CH₂CH₂CH₂CH₂SCN |
| Ia.1060 | Cl | Cl | CH₂CH₂CH₂CH₂CH₂SCN |

TABLE 5-continued $$\text{(structure I with } R^1 = H; R^2 = Cl; X = O\text{)}$$

| No. | $R^3$ | $R^4$ | $R^6$ |
|---|---|---|---|
| Ia.1061 | H | Cl | $CH_2CH_2CH_2CH_2CH_2SCN$ |
| Ia.1062 | F | Cl | $CH_2CH_2CH_2CH_2CH_2SCHF_2$ |
| Ia.1063 | Cl | Cl | $CH_2CH_2CH_2CH_2CH_2SCHF_2$ |
| Ia.1064 | H | Cl | $CH_2CH_2CH_2CH_2CH_2SCHF_2$ |
| Ia.1065 | F | Cl | $CH_2CH_2CH_2CH_2CH_2SCF_3$ |
| Ia.1066 | Cl | Cl | $CH_2CH_2CH_2CH_2CH_2SCF_3$ |
| Ia.1067 | H | Cl | $CH_2CH_2CH_2CH_2CH_2SCF_3$ |
| Ia.1068 | F | Cl | $CH_2CH_2CH_2CH_2CH_2S\text{-cyclopropyl}$ |
| Ia.1069 | Cl | Cl | $CH_2CH_2CH_2CH_2CH_2S\text{-cyclopropyl}$ |
| Ia.1070 | H | Cl | $CH_2CH_2CH_2CH_2CH_2S\text{-cyclopropyl}$ |
| Ia.1071 | F | Cl | $CH_2CH_2CH_2CH_2CH_2SOCHF_2$ |
| Ia.1072 | Cl | Cl | $CH_2CH_2CH_2CH_2CH_2SOCHF_2$ |
| Ia.1073 | H | Cl | $CH_2CH_2CH_2CH_2CH_2SOCHF_2$ |
| Ia.1074 | F | Cl | $CH_2CH_2CH_2CH_2CH_2SOCF_3$ |
| Ia.1075 | Cl | Cl | $CH_2CH_2CH_2CH_2CH_2SOCF_3$ |
| Ia.1076 | H | Cl | $CH_2CH_2CH_2CH_2CH_2SOCF_3$ |
| Ia.1077 | F | Cl | $CH_2CH_2CH_2CH_2CH_2SO\text{-cyclopropyl}$ |
| Ia.1078 | Cl | Cl | $CH_2CH_2CH_2CH_2CH_2SO\text{-cyclopropyl}$ |
| Ia.1079 | H | Cl | $CH_2CH_2CH_2CH_2CH_2SO\text{-cyclopropyl}$ |
| Ia.1080 | F | Cl | $CH_2CH_2CH_2CH_2CH_2SOCH_3$ |
| Ia.1081 | Cl | Cl | $CH_2CH_2CH_2CH_2CH_2SOCH_3$ |
| Ia.1082 | H | Cl | $CH_2CH_2CH_2CH_2CH_2SOCH_3$ |
| Ia.1083 | F | Cl | $CH_2CH_2CH_2CH_2CH_2SOCH_2CH_3$ |
| Ia.1084 | Cl | Cl | $CH_2CH_2CH_2CH_2CH_2SOCH_2CH_3$ |
| Ia.1085 | H | Cl | $CH_2CH_2CH_2CH_2CH_2SOCH_2CH_3$ |
| Ia.1086 | F | Cl | $CH_2CH_2CH_2CH_2CH_2SO_2CHF_2$ |
| Ia.1087 | Cl | Cl | $CH_2CH_2CH_2CH_2CH_2SO_2CHF_2$ |
| Ia.1088 | H | Cl | $CH_2CH_2CH_2CH_2CH_2SO_2CHF_2$ |
| Ia.1089 | F | Cl | $CH_2CH_2CH_2CH_2CH_2SO_2CF_3$ |
| Ia.1090 | Cl | Cl | $CH_2CH_2CH_2CH_2CH_2SO_2CF_3$ |
| Ia.1091 | H | Cl | $CH_2CH_2CH_2CH_2CH_2SO_2CF_3$ |
| Ia.1092 | F | Cl | $CH_2CH_2CH_2CH_2CH_2SO_2\text{-cyclopropyl}$ |
| Ia.1093 | Cl | Cl | $CH_2CH_2CH_2CH_2CH_2SO_2\text{-cyclopropyl}$ |
| Ia.1094 | H | Cl | $CH_2CH_2CH_2CH_2CH_2SO_2\text{-cyclopropyl}$ |
| Ia.1095 | F | Cl | $CH_2CH_2CH_2CH_2CH_2SO_2CH_3$ |
| Ia.1096 | Cl | Cl | $CH_2CH_2CH_2CH_2CH_2SO_2CH_3$ |
| Ia.1097 | H | Cl | $CH_2CH_2CH_2CH_2CH_2SO_2CH_3$ |
| Ia.1098 | F | Cl | $CH_2CH_2CH_2CH_2CH_2SO_2CH_2CH_3$ |
| Ia.1099 | Cl | Cl | $CH_2CH_2CH_2CH_2CH_2SO_2CH_2CH_3$ |
| Ia.1100 | H | Cl | $CH_2CH_2CH_2CH_2CH_2SO_2CH_2CH_3$ |
| Ia.1101 | F | Cl | $CH(CH_3)CH_2CH_2CH_2F$ |
| Ia.1102 | Cl | Cl | $CH(CH_3)CH_2CH_2CH_2F$ |
| Ia.1103 | H | Cl | $CH(CH_3)CH_2CH_2CH_2F$ |
| Ia.1104 | F | Cl | $CH(CH_3)CH_2CH_2CH_2Cl$ |
| Ia.1105 | Cl | Cl | $CH(CH_3)CH_2CH_2CH_2Cl$ |
| Ia.1106 | H | Cl | $CH(CH_3)CH_2CH_2CH_2Cl$ |
| Ia.1107 | F | Cl | $CH(CH_3)CH_2CH_2CH_2Br$ |
| Ia.1108 | Cl | Cl | $CH(CH_3)CH_2CH_2CH_2Br$ |
| Ia.1109 | H | Cl | $CH(CH_3)CH_2CH_2CH_2Br$ |
| Ia.1110 | F | Cl | $CH(CH_3)CH_2CH_2CH_2I$ |
| Ia.1111 | Cl | Cl | $CH(CH_3)CH_2CH_2CH_2I$ |
| Ia.1112 | H | Cl | $CH(CH_3)CH_2CH_2CH_2I$ |
| Ia.1113 | F | Cl | $CH(CH_3)CH_2CH_2CH_2CN$ |
| Ia.1114 | Cl | Cl | $CH(CH_3)CH_2CH_2CH_2CN$ |
| Ia.1115 | H | Cl | $CH(CH_3)CH_2CH_2CH_2CN$ |
| Ia.1116 | F | Cl | $CH(CH_3)CH_2CH_2CH_2SCN$ |
| Ia.1117 | Cl | Cl | $CH(CH_3)CH_2CH_2CH_2SCN$ |
| Ia.1118 | H | Cl | $CH(CH_3)CH_2CH_2CH_2SCN$ |
| Ia.1119 | F | Cl | $CH(CH_3)CH_2CH_2CH_2SCHF_2$ |
| Ia.1120 | Cl | Cl | $CH(CH_3)CH_2CH_2CH_2SCHF_2$ |
| Ia.1121 | H | Cl | $CH(CH_3)CH_2CH_2CH_2SCHF_2$ |
| Ia.1122 | F | Cl | $CH(CH_3)CH_2CH_2CH_2SCF_3$ |
| Ia.1123 | Cl | Cl | $CH(CH_3)CH_2CH_2CH_2SCF_3$ |
| Ia.1124 | H | Cl | $CH(CH_3)CH_2CH_2CH_2SCF_3$ |
| Ia.1125 | F | Cl | $CH(CH_3)CH_2CH_2CH_2S\text{-cyclopropyl}$ |
| Ia.1126 | Cl | Cl | $CH(CH_3)CH_2CH_2CH_2S\text{-cyclopropyl}$ |
| Ia.1127 | H | Cl | $CH(CH_3)CH_2CH_2CH_2S\text{-cyclopropyl}$ |
| Ia.1128 | F | Cl | $CH(CH_3)CH_2CH_2CH_2SOCHF_2$ |
| Ia.1129 | Cl | Cl | $CH(CH_3)CH_2CH_2CH_2SOCHF_2$ |
| Ia.1130 | H | Cl | $CH(CH_3)CH_2CH_2CH_2SOCHF_2$ |
| Ia.1131 | F | Cl | $CH(CH_3)CH_2CH_2CH_2SOCF_3$ |
| Ia.1132 | Cl | Cl | $CH(CH_3)CH_2CH_2CH_2SOCF_3$ |
| Ia.1133 | H | Cl | $CH(CH_3)CH_2CH_2CH_2SOCF_3$ |
| Ia.1134 | F | Cl | $CH(CH_3)CH_2CH_2CH_2SO\text{-cyclopropyl}$ |
| Ia.1135 | Cl | Cl | $CH(CH_3)CH_2CH_2CH_2SO\text{-cyclopropyl}$ |
| Ia.1136 | H | Cl | $CH(CH_3)CH_2CH_2CH_2SO\text{-cyclopropyl}$ |
| Ia.1137 | F | Cl | $CH(CH_3)CH_2CH_2CH_2SOCH_3$ |
| Ia.1138 | Cl | Cl | $CH(CH_3)CH_2CH_2CH_2SOCH_3$ |
| Ia.1139 | H | Cl | $CH(CH_3)CH_2CH_2CH_2SOCH_3$ |
| Ia.1140 | F | Cl | $CH(CH_3)CH_2CH_2CH_2SOCH_2CH_3$ |
| Ia.1141 | Cl | Cl | $CH(CH_3)CH_2CH_2CH_2SOCH_2CH_3$ |
| Ia.1142 | H | Cl | $CH(CH_3)CH_2CH_2CH_2SOCH_2CH_3$ |
| Ia.1143 | F | Cl | $CH(CH_3)CH_2CH_2CH_2SOCHF_2$ |
| Ia.1144 | Cl | Cl | $CH(CH_3)CH_2CH_2CH_2SOCHF_2$ |
| Ia.1145 | H | Cl | $CH(CH_3)CH_2CH_2CH_2SOCHF_2$ |
| Ia.1146 | F | Cl | $CH(CH_3)CH_2CH_2CH_2SO_2CF_3$ |
| Ia.1147 | Cl | Cl | $CH(CH_3)CH_2CH_2CH_2SO_2CF_3$ |
| Ia.1148 | H | Cl | $CH(CH_3)CH_2CH_2CH_2SO_2CF_3$ |
| Ia.1149 | F | Cl | $CH(CH_3)CH_2CH_2CH_2SO_2\text{-cyclopropyl}$ |
| Ia.1150 | Cl | Cl | $CH(CH_3)CH_2CH_2CH_2SO_2\text{-cyclopropyl}$ |
| Ia.1151 | H | Cl | $CH(CH_3)CH_2CH_2CH_2SO_2\text{-cyclopropyl}$ |
| Ia.1152 | F | Cl | $CH(CH_3)CH_2CH_2CH_2SO_2CH_3$ |
| Ia.1153 | Cl | Cl | $CH(CH_3)CH_2CH_2CH_2SO_2CH_3$ |
| Ia.1154 | H | Cl | $CH(CH_3)CH_2CH_2CH_2SO_2CH_3$ |
| Ia.1155 | F | Cl | $CH(CH_3)CH_2CH_2CH_2SO_2CH_2CH_3$ |
| Ia.1156 | Cl | Cl | $CH(CH_3)CH_2CH_2CH_2SO_2CH_2CH_3$ |
| Ia.1157 | H | Cl | $CH(CH_3)CH_2CH_2CH_2SO_2CH_2CH_3$ |
| Ia.1158 | F | Cl | $CH_2CH(CH_3)CH_2CH_2F$ |
| Ia.1159 | Cl | Cl | $CH_2CH(CH_3)CH_2CH_2F$ |
| Ia.1160 | H | Cl | $CH_2CH(CH_3)CH_2CH_2F$ |
| Ia.1161 | F | Cl | $CH_2CH(CH_3)CH_2CH_2Cl$ |
| Ia.1162 | Cl | Cl | $CH_2CH(CH_3)CH_2CH_2Cl$ |
| Ia.1163 | H | Cl | $CH_2CH(CH_3)CH_2CH_2Cl$ |
| Ia.1164 | F | Cl | $CH_2CH(CH_3)CH_2CH_2Br$ |
| Ia.1165 | Cl | Cl | $CH_2CH(CH_3)CH_2CH_2Br$ |
| Ia.1166 | H | Cl | $CH_2CH(CH_3)CH_2CH_2Br$ |
| Ia.1167 | F | Cl | $CH_2CH(CH_3)CH_2CH_2I$ |
| Ia.1168 | Cl | Cl | $CH_2CH(CH_3)CH_2CH_2I$ |
| Ia.1169 | H | Cl | $CH_2CH(CH_3)CH_2CH_2I$ |
| Ia.1170 | F | Cl | $CH_2CH(CH_3)CH_2CH_2CN$ |
| Ia.1171 | Cl | Cl | $CH_2CH(CH_3)CH_2CH_2CN$ |
| Ia.1172 | H | Cl | $CH_2CH(CH_3)CH_2CH_2CN$ |
| Ia.1173 | F | Cl | $CH_2CH(CH_3)CH_2CH_2SCN$ |
| Ia.1174 | Cl | Cl | $CH_2CH(CH_3)CH_2CH_2SCN$ |
| Ia.1175 | H | Cl | $CH_2CH(CH_3)CH_2CH_2SCN$ |
| Ia.1176 | F | Cl | $CH_2CH(CH_3)CH_2CH_2SCHF_2$ |
| Ia.1177 | Cl | Cl | $CH_2CH(CH_3)CH_2CH_2SCHF_2$ |
| Ia.1178 | H | Cl | $CH_2CH(CH_3)CH_2CH_2SCHF_2$ |
| Ia.1179 | F | Cl | $CH_2CH(CH_3)CH_2CH_2SCF_3$ |
| Ia.1180 | Cl | Cl | $CH_2CH(CH_3)CH_2CH_2SCF_3$ |
| Ia.1181 | H | Cl | $CH_2CH(CH_3)CH_2CH_2SCF_3$ |
| Ia.1182 | F | Cl | $CH_2CH(CH_3)CH_2CH_2S\text{-cyclopropyl}$ |
| Ia.1183 | Cl | Cl | $CH_2CH(CH_3)CH_2CH_2S\text{-cyclopropyl}$ |
| Ia.1184 | H | Cl | $CH_2CH(CH_3)CH_2CH_2S\text{-cyclopropyl}$ |
| Ia.1185 | F | Cl | $CH_2CH(CH_3)CH_2CH_2SOCHF_2$ |
| Ia.1186 | Cl | Cl | $CH_2CH(CH_3)CH_2CH_2SOCHF_2$ |
| Ia.1187 | H | Cl | $CH_2CH(CH_3)CH_2CH_2SOCHF_2$ |
| Ia.1188 | F | Cl | $CH_2CH(CH_3)CH_2CH_2SOCF_3$ |

TABLE 5-continued

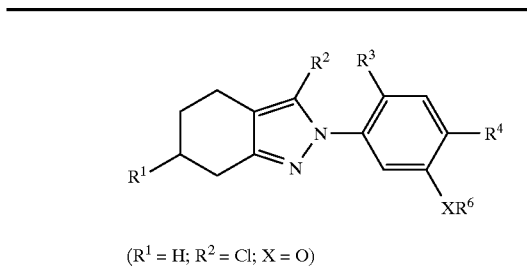

($R^1$ = H; $R^2$ = Cl; X = O)

| No. | $R^3$ | $R^4$ | $R^6$ |
|---|---|---|---|
| Ia.1189 | Cl | Cl | $CH_2CH(CH_3)CH_2CH_2SOCF_3$ |
| Ia.1190 | H | Cl | $CH_2CH(CH_3)CH_2CH_2SOCF_3$ |
| Ia.1191 | F | Cl | $CH_2CH(CH_3)CH_2CH_2SO$-cyclopropyl |
| Ia.1192 | Cl | Cl | $CH_2CH(CH_3)CH_2CH_2SO$-cyclopropyl |
| Ia.1193 | H | Cl | $CH_2CH(CH_3)CH_2CH_2SO$-cyclopropyl |
| Ia.1194 | F | Cl | $CH_2CH(CH_3)CH_2CH_2SOCH_3$ |
| Ia.1195 | Cl | Cl | $CH_2CH(CH_3)CH_2CH_2SOCH_3$ |
| Ia.1196 | H | Cl | $CH_2CH(CH_3)CH_2CH_2SOCH_3$ |
| Ia.1197 | F | Cl | $CH_2CH(CH_3)CH_2CH_2SOCH_2CH_3$ |
| Ia.1198 | Cl | Cl | $CH_2CH(CH_3)CH_2CH_2SOCH_2CH_3$ |
| Ia.1199 | H | Cl | $CH_2CH(CH_3)CH_2CH_2SOCH_2CH_3$ |
| Ia.1200 | F | Cl | $CH_2CH(CH_3)CH_2CH_2SO_2CHF_2$ |
| Ia.1201 | Cl | Cl | $CH_2CH(CH_3)CH_2CH_2SO_2CHF_2$ |
| Ia.1202 | H | Cl | $CH_2CH(CH_3)CH_2CH_2SO_2CHF_2$ |
| Ia.1203 | F | Cl | $CH_2CH(CH_3)CH_2CH_2SO_2CF_3$ |
| Ia.1204 | Cl | Cl | $CH_2CH(CH_3)CH_2CH_2SO_2CF_3$ |
| Ia.1205 | H | Cl | $CH_2CH(CH_3)CH_2CH_2SO_2CF_3$ |
| Ia.1206 | F | Cl | $CH_2CH(CH_3)CH_2CH_2SO_2$-cyclopropyl |
| Ia.1207 | Cl | Cl | $CH_2CH(CH_3)CH_2CH_2SO_2$-cyclopropyl |
| Ia.1208 | H | Cl | $CH_2CH(CH_3)CH_2CH_2SO_2$-cyclopropyl |
| Ia.1209 | F | Cl | $CH_2CH(CH_3)CH_2CH_2SO_2CH_3$ |
| Ia.1210 | Cl | Cl | $CH_2CH(CH_3)CH_2CH_2SO_2CH_3$ |
| Ia.1211 | H | Cl | $CH_2CH(CH_3)CH_2CH_2SO_2CH_3$ |
| Ia.1212 | F | Cl | $CH_2CH(CH_3)CH_2CH_2SO_2CH_2CH_3$ |
| Ia.1213 | Cl | Cl | $CH_2CH(CH_3)CH_2CH_2SO_2CH_2CH_3$ |
| Ia.1214 | H | Cl | $CH_2CH(CH_3)CH_2CH_2SO_2CH_2CH_3$ |
| Ia.1215 | F | Cl | $CH_2CH_2CH(CH_3)CH_2F$ |
| Ia.1216 | Cl | Cl | $CH_2CH_2CH(CH_3)CH_2F$ |
| Ia.1217 | H | Cl | $CH_2CH_2CH(CH_3)CH_2F$ |
| Ia.1218 | F | Cl | $CH_2CH_2CH(CH_3)CH_2Cl$ |
| Ia.1219 | Cl | Cl | $CH_2CH_2CH(CH_3)CH_2Cl$ |
| Ia.1220 | H | Cl | $CH_2CH_2CH(CH_3)CH_2Cl$ |
| Ia.1221 | F | Cl | $CH_2CH_2CH(CH_3)CH_2Br$ |
| Ia.1222 | Cl | Cl | $CH_2CH_2CH(CH_3)CH_2Br$ |
| Ia.1223 | H | Cl | $CH_2CH_2CH(CH_3)CH_2Br$ |
| Ia.1224 | F | Cl | $CH_2CH_2CH(CH_3)CH_2I$ |
| Ia.1225 | Cl | Cl | $CH_2CH_2CH(CH_3)CH_2I$ |
| Ia.1226 | H | Cl | $CH_2CH_2CH(CH_3)CH_2I$ |
| Ia.1227 | F | Cl | $CH_2CH_2CH(CH_3)CH_2CN$ |
| Ia.1228 | Cl | Cl | $CH_2CH_2CH(CH_3)CH_2CN$ |
| Ia.1229 | H | Cl | $CH_2CH_2CH(CH_3)CH_2CN$ |
| Ia.1230 | F | Cl | $CH_2CH_2CH(CH_3)CH_2SCN$ |
| Ia.1231 | Cl | Cl | $CH_2CH_2CH(CH_3)CH_2SCN$ |
| Ia.1232 | H | Cl | $CH_2CH_2CH(CH_3)CH_2SCN$ |
| Ia.1233 | F | Cl | $CH_2CH_2CH(CH_3)CH_2SCHF_2$ |
| Ia.1234 | Cl | Cl | $CH_2CH_2CH(CH_3)CH_2SCHF_2$ |
| Ia.1235 | H | Cl | $CH_2CH_2CH(CH_3)CH_2SCHF_2$ |
| Ia.1236 | F | Cl | $CH_2CH_2CH(CH_3)CH_2SCF_3$ |
| Ia.1237 | Cl | Cl | $CH_2CH_2CH(CH_3)CH_2SCF_3$ |
| Ia.1238 | H | Cl | $CH_2CH_2CH(CH_3)CH_2SCF_3$ |
| Ia.1239 | F | Cl | $CH_2CH_2CH(CH_3)CH_2S$-cyclopropyl |
| Ia.1240 | Cl | Cl | $CH_2CH_2CH(CH_3)CH_2S$-cyclopropyl |
| Ia.1241 | H | Cl | $CH_2CH_2CH(CH_3)CH_2S$-cyclopropyl |
| Ia.1242 | F | Cl | $CH_2CH_2CH(CH_3)CH_2SOCHF_2$ |
| Ia.1243 | Cl | Cl | $CH_2CH_2CH(CH_3)CH_2SOCHF_2$ |
| Ia.1244 | H | Cl | $CH_2CH_2CH(CH_3)CH_2SOCHF_2$ |
| Ia.1245 | F | Cl | $CH_2CH_2CH(CH_3)CH_2SOCF_3$ |
| Ia.1246 | Cl | Cl | $CH_2CH_2CH(CH_3)CH_2SOCF_3$ |
| Ia.1247 | H | Cl | $CH_2CH_2CH(CH_3)CH_2SOCF_3$ |
| Ia.1248 | F | Cl | $CH_2CH_2CH(CH_3)CH_2SO$-cyclopropyl |
| Ia.1249 | Cl | Cl | $CH_2CH_2CH(CH_3)CH_2SO$-cyclopropyl |
| Ia.1250 | H | Cl | $CH_2CH_2CH(CH_3)CH_2SO$-cyclopropyl |
| Ia.1251 | F | Cl | $CH_2CH_2CH(CH_3)CH_2SOCH_3$ |
| Ia.1252 | Cl | Cl | $CH_2CH_2CH(CH_3)CH_2SOCH_3$ |
| Ia.1253 | H | Cl | $CH_2CH_2CH(CH_3)CH_2SOCH_3$ |
| Ia.1254 | F | Cl | $CH_2CH_2CH(CH_3)CH_2SOCH_2CH_3$ |
| Ia.1255 | Cl | Cl | $CH_2CH_2CH(CH_3)CH_2SOCH_2CH_3$ |
| Ia.1256 | H | Cl | $CH_2CH_2CH(CH_3)CH_2SOCH_2CH_3$ |
| Ia.1257 | F | Cl | $CH_2CH_2CH(CH_3)CH_2SO_2CHF_2$ |
| Ia.1258 | Cl | Cl | $CH_2CH_2CH(CH_3)CH_2SO_2CHF_2$ |
| Ia.1259 | H | Cl | $CH_2CH_2CH(CH_3)CH_2SO_2CHF_2$ |
| Ia.1260 | F | Cl | $CH_2CH_2CH(CH_3)CH_2SO_2CF_3$ |
| Ia.1261 | Cl | Cl | $CH_2CH_2CH(CH_3)CH_2SO_2CF_3$ |
| Ia.1262 | H | Cl | $CH_2CH_2CH(CH_3)CH_2SO_2CF_3$ |
| Ia.1263 | F | Cl | $CH_2CH_2CH(CH_3)CH_2SO_2$-cyclopropyl |
| Ia.1264 | Cl | Cl | $CH_2CH_2CH(CH_3)CH_2SO_2$-cyclopropyl |
| Ia.1265 | H | Cl | $CH_2CH_2CH(CH_3)CH_2SO_2$-cyclopropyl |
| Ia.1266 | F | Cl | $CH_2CH_2CH(CH_3)CH_2SO_2CH_3$ |
| Ia.1267 | Cl | Cl | $CH_2CH_2CH(CH_3)CH_2SO_2CH_3$ |
| Ia.1268 | H | Cl | $CH_2CH_2CH(CH_3)CH_2SO_2CH_3$ |
| Ia.1269 | F | Cl | $CH_2CH_2CH(CH_3)CH_2SO_2CH_2CH_3$ |
| Ia.1270 | Cl | Cl | $CH_2CH_2CH(CH_3)CH_2SO_2CH_2CH_3$ |
| Ia.1271 | H | Cl | $CH_2CH_2CH(CH_3)CH_2SO_2CH_2CH_3$ |
| Ia.1272 | F | Cl | $CH_2CH_2CH_2CH(CH_3)F$ |
| Ia.1273 | Cl | Cl | $CH_2CH_2CH_2CH(CH_3)F$ |
| Ia.1274 | H | Cl | $CH_2CH_2CH_2CH(CH_3)F$ |
| Ia.1275 | F | Cl | $CH_2CH_2CH_2CH(CH_3)Cl$ |
| Ia.1276 | Cl | Cl | $CH_2CH_2CH_2CH(CH_3)Cl$ |
| Ia.1277 | H | Cl | $CH_2CH_2CH_2CH(CH_3)Cl$ |
| Ia.1278 | F | Cl | $CH_2CH_2CH_2CH(CH_3)Br$ |
| Ia.1279 | Cl | Cl | $CH_2CH_2CH_2CH(CH_3)Br$ |
| Ia.1280 | H | Cl | $CH_2CH_2CH_2CH(CH_3)Br$ |
| Ia.1281 | F | Cl | $CH_2CH_2CH_2CH(CH_3)I$ |
| Ia.1282 | Cl | Cl | $CH_2CH_2CH_2CH(CH_3)I$ |
| Ia.1283 | H | Cl | $CH_2CH_2CH_2CH(CH_3)I$ |
| Ia.1284 | F | Cl | $CH_2CH_2CH_2CH(CH_3)CN$ |
| Ia.1285 | Cl | Cl | $CH_2CH_2CH_2CH(CH_3)CN$ |
| Ia.1286 | H | Cl | $CH_2CH_2CH_2CH(CH_3)CN$ |
| Ia.1287 | F | Cl | $CH_2CH_2CH_2CH(CH_3)SCN$ |
| Ia.1288 | Cl | Cl | $CH_2CH_2CH_2CH(CH_3)SCN$ |
| Ia.1289 | H | Cl | $CH_2CH_2CH_2CH(CH_3)SCN$ |
| Ia.1290 | F | Cl | $CH_2CH_2CH_2CH(CH_3)SCHF_2$ |
| Ia.1291 | Cl | Cl | $CH_2CH_2CH_2CH(CH_3)SCHF_2$ |
| Ia.1292 | H | Cl | $CH_2CH_2CH_2CH(CH_3)SCHF_2$ |
| Ia.1293 | F | Cl | $CH_2CH_2CH_2CH(CH_3)SCF_3$ |
| Ia.1294 | Cl | Cl | $CH_2CH_2CH_2CH(CH_3)SCF_3$ |
| Ia.1295 | H | Cl | $CH_2CH_2CH_2CH(CH_3)SCF_3$ |
| Ia.1296 | F | Cl | $CH_2CH_2CH_2CH(CH_3)S$-cyclopropyl |
| Ia.1297 | Cl | Cl | $CH_2CH_2CH_2CH(CH_3)S$-cyclopropyl |
| Ia.1298 | H | Cl | $CH_2CH_2CH_2CH(CH_3)S$-cyclopropyl |
| Ia.1299 | F | Cl | $CH_2CH_2CH_2CH(CH_3)SOCHF_2$ |
| Ia.1300 | Cl | Cl | $CH_2CH_2CH_2CH(CH_3)SOCHF_2$ |
| Ia.1301 | H | Cl | $CH_2CH_2CH_2CH(CH_3)SOCHF_2$ |
| Ia.1302 | F | Cl | $CH_2CH_2CH_2CH(CH_3)SOCF_3$ |
| Ia.1303 | Cl | Cl | $CH_2CH_2CH_2CH(CH_3)SOCF_3$ |
| Ia.1304 | H | Cl | $CH_2CH_2CH_2CH(CH_3)SOCF_3$ |
| Ia.1305 | F | Cl | $CH_2CH_2CH_2CH(CH_3)SO$-cyclopropyl |
| Ia.1306 | Cl | Cl | $CH_2CH_2CH_2CH(CH_3)SO$-cyclopropyl |
| Ia.1307 | H | Cl | $CH_2CH_2CH_2CH(CH_3)SO$-cyclopropyl |
| Ia.1308 | F | Cl | $CH_2CH_2CH_2CH(CH_3)SOCH_3$ |
| Ia.1309 | Cl | Cl | $CH_2CH_2CH_2CH(CH_3)SOCH_3$ |
| Ia.1310 | H | Cl | $CH_2CH_2CH_2CH(CH_3)SOCH_3$ |
| Ia.1311 | F | Cl | $CH_2CH_2CH_2CH(CH_3)SOCH_2CH_3$ |
| Ia.1312 | Cl | Cl | $CH_2CH_2CH_2CH(CH_3)SOCH_2CH_3$ |
| Ia.1313 | H | Cl | $CH_2CH_2CH_2CH(CH_3)SOCH_2CH_3$ |
| Ia.1314 | F | Cl | $CH_2CH_2CH_2CH(CH_3)SO_2CHF_2$ |
| Ia.1315 | Cl | Cl | $CH_2CH_2CH_2CH(CH_3)SO_2CHF_2$ |
| Ia.1316 | H | Cl | $CH_2CH_2CH_2CH(CH_3)SO_2CHF_2$ |

TABLE 5-continued $$(R^1 = H; R^2 = Cl; X = O)$$

| No. | $R^3$ | $R^4$ | $R^6$ |
|---|---|---|---|
| Ia.1317 | F | Cl | CH₂CH₂CH₂CH(CH₃)SO₂CF₃ |
| Ia.1318 | Cl | Cl | CH₂CH₂CH₂CH(CH₃)SO₂CF₃ |
| Ia.1319 | H | Cl | CH₂CH₂CH₂CH(CH₃)SO₂CF₃ |
| Ia.1320 | F | Cl | CH₂CH₂CH₂CH(CH₃)SO₂-cyclopropyl |
| Ia.1321 | Cl | Cl | CH₂CH₂CH₂CH(CH₃)SO₂-cyclopropyl |
| Ia.1322 | H | Cl | CH₂CH₂CH₂CH(CH₃)SO₂-cyclopropyl |
| Ia.1323 | F | Cl | CH₂CH₂CH₂CH(CH₃)SO₂CH₃ |
| Ia.1324 | Cl | Cl | CH₂CH₂CH₂CH(CH₃)SO₂CH₃ |
| Ia.1325 | H | Cl | CH₂CH₂CH₂CH(CH₃)SO₂CH₃ |
| Ia.1326 | F | Cl | CH₂CH₂CH₂CH(CH₃)SO₂CH₂CH₃ |
| Ia.1327 | Cl | Cl | CH₂CH₂CH₂CH(CH₃)SO₂CH₂CH₃ |
| Ia.1328 | H | Cl | CH₂CH₂CH₂CH(CH₃)SO₂CH₂CH₃ |
| Ia.1329 | F | Cl | CH(CH₂CH₃)CH₂CH₂F |
| Ia.1330 | Cl | Cl | CH(CH₂CH₃)CH₂CH₂F |
| Ia.1331 | H | Cl | CH(CH₂CH₃)CH₂CH₂F |
| Ia.1332 | H | Cl | CH(CH₂CH₃)CH₂CH₂Cl |
| Ia.1333 | F | Cl | CH(CH₂CH₃)CH₂CH₂Cl |
| Ia.1334 | Cl | Cl | CH(CH₂CH₃)CH₂CH₂Cl |
| Ia.1335 | H | Cl | CH(CH₂CH₃)CH₂CH₂Br |
| Ia.1336 | F | Cl | CH(CH₂CH₃)CH₂CH₂Br |
| Ia.1337 | Cl | Cl | CH(CH₂CH₃)CH₂CH₂Br |
| Ia.1338 | H | Cl | CH(CH₂CH₃)CH₂CH₂I |
| Ia.1339 | F | Cl | CH(CH₂CH₃)CH₂CH₂I |
| Ia.1340 | Cl | Cl | CH(CH₂CH₃)CH₂CH₂I |
| Ia.1341 | H | Cl | CH(CH₂CH₃)CH₂CH₂CN |
| Ia.1342 | F | Cl | CH(CH₂CH₃)CH₂CH₂CN |
| Ia.1343 | Cl | Cl | CH(CH₂CH₃)CH₂CH₂CN |
| Ia.1344 | H | Cl | CH(CH₂CH₃)CH₂CH₂SCN |
| Ia.1345 | F | Cl | CH(CH₂CH₃)CH₂CH₂SCN |
| Ia.1346 | Cl | Cl | CH(CH₂CH₃)CH₂CH₂SCN |
| Ia.1347 | H | Cl | CH(CH₂CH₃)CH₂CH₂SCHF₂ |
| Ia.1348 | F | Cl | CH(CH₂CH₃)CH₂CH₂SCHF₂ |
| Ia.1349 | Cl | Cl | CH(CH₂CH₃)CH₂CH₂SCHF₂ |
| Ia.1350 | H | Cl | CH(CH₂CH₃)CH₂CH₂SCF₃ |
| Ia.1351 | F | Cl | CH(CH₂CH₃)CH₂CH₂SCF₃ |
| Ia.1352 | Cl | Cl | CH(CH₂CH₃)CH₂CH₂SCF₃ |
| Ia.1353 | H | Cl | CH(CH₂CH₃)CH₂CH₂S-cyclopropyl |
| Ia.1354 | F | Cl | CH(CH₂CH₃)CH₂CH₂S-cyclopropyl |
| Ia.1355 | Cl | Cl | CH(CH₂CH₃)CH₂CH₂S-cyclopropyl |
| Ia.1356 | H | Cl | CH(CH₂CH₃)CH₂CH₂SOCHF₂ |
| Ia.1357 | F | Cl | CH(CH₂CH₃)CH₂CH₂SOCHF₂ |
| Ia.1358 | Cl | Cl | CH(CH₂CH₃)CH₂CH₂SOCHF₂ |
| Ia.1359 | H | Cl | CH(CH₂CH₃)CH₂CH₂SOCF₃ |
| Ia.1360 | F | Cl | CH(CH₂CH₃)CH₂CH₂SOCF₃ |
| Ia.1361 | Cl | Cl | CH(CH₂CH₃)CH₂CH₂SOCF₃ |
| Ia.1362 | H | Cl | CH(CH₂CH₃)CH₂CH₂SO-cyclopropyl |
| Ia.1363 | F | Cl | CH(CH₂CH₃)CH₂CH₂SO-cyclopropyl |
| Ia.1364 | Cl | Cl | CH(CH₂CH₃)CH₂CH₂SO-cyclopropyl |
| Ia.1365 | H | Cl | CH(CH₂CH₃)CH₂CH₂SOCH₃ |
| Ia.1366 | F | Cl | CH(CH₂CH₃)CH₂CH₂SOCH₃ |
| Ia.1367 | Cl | Cl | CH(CH₂CH₃)CH₂CH₂SOCH₃ |
| Ia.1368 | H | Cl | CH(CH₂CH₃)CH₂CH₂SOCH₂CH₃ |
| Ia.1369 | F | Cl | CH(CH₂CH₃)CH₂CH₂SOCH₂CH₃ |
| Ia.1370 | Cl | Cl | CH(CH₂CH₃)CH₂CH₂SOCH₂CH₃ |
| Ia.1371 | H | Cl | CH(CH₂CH₃)CH₂CH₂SO₂CHF₂ |
| Ia.1372 | F | Cl | CH(CH₂CH₃)CH₂CH₂SO₂CHF₂ |
| Ia.1373 | Cl | Cl | CH(CH₂CH₃)CH₂CH₂SO₂CHF₂ |
| Ia.1374 | H | Cl | CH(CH₂CH₃)CH₂CH₂SO₂CF₃ |
| Ia.1375 | F | Cl | CH(CH₂CH₃)CH₂CH₂SO₂CF₃ |
| Ia.1376 | Cl | Cl | CH(CH₂CH₃)CH₂CH₂SO₂CF₃ |
| Ia.1377 | H | Cl | CH(CH₂CH₃)CH₂CH₂SO₂-cyclopropyl |
| Ia.1378 | F | Cl | CH(CH₂CH₃)CH₂CH₂SO₂-cyclopropyl |
| Ia.1379 | Cl | Cl | CH(CH₂CH₃)CH₂CH₂SO₂-cyclopropyl |
| Ia.1380 | H | Cl | CH(CH₂CH₃)CH₂CH₂SO₂CH₃ |
| Ia.1381 | F | Cl | CH(CH₂CH₃)CH₂CH₂SO₂CH₃ |
| Ia.1382 | Cl | Cl | CH(CH₂CH₃)CH₂CH₂SO₂CH₃ |
| Ia.1383 | H | Cl | CH(CH₂CH₃)CH₂CH₂SO₂CH₂CH₃ |
| Ia.1384 | F | Cl | CH(CH₂CH₃)CH₂CH₂SO₂CH₂CH₃ |
| Ia.1385 | Cl | Cl | CH(CH₂CH₃)CH₂CH₂SO₂CH₂CH₃ |
| Ia.1386 | H | Cl | CH₂CH(CH₂CH₃)CH₂F |
| Ia.1387 | F | Cl | CH₂CH(CH₂CH₃)CH₂F |
| Ia.1388 | Cl | Cl | CH₂CH(CH₂CH₃)CH₂F |
| Ia.1389 | H | Cl | CH₂CH(CH₂CH₃)CH₂Cl |
| Ia.1390 | F | Cl | CH₂CH(CH₂CH₃)CH₂Cl |
| Ia.1391 | Cl | Cl | CH₂CH(CH₂CH₃)CH₂Cl |
| Ia.1392 | H | Cl | CH₂CH(CH₂CH₃)CH₂Br |
| Ia.1393 | F | Cl | CH₂CH(CH₂CH₃)CH₂Br |
| Ia.1394 | Cl | Cl | CH₂CH(CH₂CH₃)CH₂Br |
| Ia.1395 | H | Cl | CH₂CH(CH₂CH₃)CH₂I |
| Ia.1396 | F | Cl | CH₂CH(CH₂CH₃)CH₂I |
| Ia.1397 | Cl | Cl | CH₂CH(CH₂CH₃)CH₂I |
| Ia.1398 | H | Cl | CH₂CH(CH₂CH₃)CH₂CN |
| Ia.1399 | F | Cl | CH₂CH(CH₂CH₃)CH₂CN |
| Ia.1400 | Cl | Cl | CH₂CH(CH₂CH₃)CH₂CN |
| Ia.1401 | H | Cl | CH₂CH(CH₂CH₃)CH₂SCN |
| Ia.1402 | F | Cl | CH₂CH(CH₂CH₃)CH₂SCN |
| Ia.1403 | Cl | Cl | CH₂CH(CH₂CH₃)CH₂SCN |
| Ia.1404 | H | Cl | CH₂CH(CH₂CH₃)CH₂SCHF₂ |
| Ia.1405 | F | Cl | CH₂CH(CH₂CH₃)CH₂SCHF₂ |
| Ia.1406 | Cl | Cl | CH₂CH(CH₂CH₃)CH₂SCHF₂ |
| Ia.1407 | H | Cl | CH₂CH(CH₂CH₃)CH₂SCF₃ |
| Ia.1408 | F | Cl | CH₂CH(CH₂CH₃)CH₂SCF₃ |
| Ia.1409 | Cl | Cl | CH₂CH(CH₂CH₃)CH₂SCF₃ |
| Ia.1410 | H | Cl | CH₂CH(CH₂CH₃)CH₂S-cyclopropyl |
| Ia.1411 | F | Cl | CH₂CH(CH₂CH₃)CH₂S-cyclopropyl |
| Ia.1412 | Cl | Cl | CH₂CH(CH₂CH₃)CH₂S-cyclopropyl |
| Ia.1413 | H | Cl | CH₂CH(CH₂CH₃)CH₂SOCHF₂ |
| Ia.1414 | F | Cl | CH₂CH(CH₂CH₃)CH₂SOCHF₂ |
| Ia.1415 | Cl | Cl | CH₂CH(CH₂CH₃)CH₂SOCHF₂ |
| Ia.1416 | H | Cl | CH₂CH(CH₂CH₃)CH₂SOCF₃ |
| Ia.1417 | F | Cl | CH₂CH(CH₂CH₃)CH₂SOCF₃ |
| Ia.1418 | Cl | Cl | CH₂CH(CH₂CH₃)CH₂SOCF₃ |
| Ia.1419 | H | Cl | CH₂CH(CH₂CH₃)CH₂SO-cyclopropyl |
| Ia.1420 | F | Cl | CH₂CH(CH₂CH₃)CH₂SO-cyclopropyl |
| Ia.1421 | Cl | Cl | CH₂CH(CH₂CH₃)CH₂SO-cyclopropyl |
| Ia.1422 | H | Cl | CH₂CH(CH₂CH₃)CH₂SOCH₃ |
| Ia.1423 | F | Cl | CH₂CH(CH₂CH₃)CH₂SOCH₃ |
| Ia.1424 | Cl | Cl | CH₂CH(CH₂CH₃)CH₂SOCH₃ |
| Ia.1425 | H | Cl | CH₂CH(CH₂CH₃)CH₂SOCH₂CH₃ |
| Ia.1426 | F | Cl | CH₂CH(CH₂CH₃)CH₂SOCH₂CH₃ |
| Ia.1427 | Cl | Cl | CH₂CH(CH₂CH₃)CH₂SOCH₂CH₃ |
| Ia.1428 | H | Cl | CH₂CH(CH₂CH₃)CH₂SO₂CHF₂ |
| Ia.1429 | F | Cl | CH₂CH(CH₂CH₃)CH₂SO₂CHF₂ |
| Ia.1430 | Cl | Cl | CH₂CH(CH₂CH₃)CH₂SO₂CHF₂ |
| Ia.1431 | H | Cl | CH₂CH(CH₂CH₃)CH₂SO₂CF₃ |
| Ia.1432 | F | Cl | CH₂CH(CH₂CH₃)CH₂SO₂CF₃ |
| Ia.1433 | Cl | Cl | CH₂CH(CH₂CH₃)CH₂SO₂CF₃ |
| Ia.1434 | H | Cl | CH₂CH(CH₂CH₃)CH₂SO₂-cyclopropyl |
| Ia.1435 | F | Cl | CH₂CH(CH₂CH₃)CH₂SO₂-cyclopropyl |
| Ia.1436 | Cl | Cl | CH₂CH(CH₂CH₃)CH₂SO₂-cyclopropyl |
| Ia.1437 | H | Cl | CH₂CH(CH₂CH₃)CH₂SO₂CH₃ |
| Ia.1438 | F | Cl | CH₂CH(CH₂CH₃)CH₂SO₂CH₃ |
| Ia.1439 | Cl | Cl | CH₂CH(CH₂CH₃)CH₂SO₂CH₃ |
| Ia.1440 | H | Cl | CH₂CH(CH₂CH₃)CH₂SO₂CH₂CH₃ |
| Ia.1441 | F | Cl | CH₂CH(CH₂CH₃)CH₂SO₂CH₂CH₃ |
| Ia.1442 | Cl | Cl | CH₂CH(CH₂CH₃)CH₂SO₂CH₂CH₃ |
| Ia.1443 | H | Cl | CH₂CH₂CH(CH₂CH₃)F |
| Ia.1444 | F | Cl | CH₂CH₂CH(CH₂CH₃)F |

TABLE 5-continued

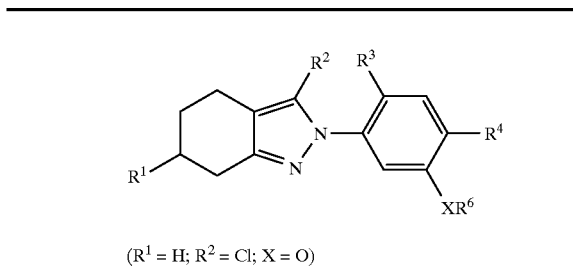

($R^1$ = H; $R^2$ = Cl; X = O)

| No. | $R^3$ | $R^4$ | $R^6$ |
|---|---|---|---|
| Ia.1445 | Cl | Cl | $CH_2CH_2CH(CH_2CH_3)F$ |
| Ia.1446 | H | Cl | $CH_2CH_2CH(CH_2CH_3)Cl$ |
| Ia.1447 | F | Cl | $CH_2CH_2CH(CH_2CH_3)Cl$ |
| Ia.1448 | Cl | Cl | $CH_2CH_2CH(CH_2CH_3)Cl$ |
| Ia.1449 | H | Cl | $CH_2CH_2CH(CH_2CH_3)Br$ |
| Ia.1450 | F | Cl | $CH_2CH_2CH(CH_2CH_3)Br$ |
| Ia.1451 | Cl | Cl | $CH_2CH_2CH(CH_2CH_3)Br$ |
| Ia.1452 | H | Cl | $CH_2CH_2CH(CH_2CH_3)I$ |
| Ia.1453 | F | Cl | $CH_2CH_2CH(CH_2CH_3)I$ |
| Ia.1454 | Cl | Cl | $CH_2CH_2CH(CH_2CH_3)I$ |
| Ia.1455 | H | Cl | $CH_2CH_2CH(CH_2CH_3)CN$ |
| Ia.1456 | F | Cl | $CH_2CH_2CH(CH_2CH_3)CN$ |
| Ia.1457 | Cl | Cl | $CH_2CH_2CH(CH_2CH_3)CN$ |
| Ia.1458 | H | Cl | $CH_2CH_2CH(CH_2CH_3)SCN$ |
| Ia.1459 | F | Cl | $CH_2CH_2CH(CH_2CH_3)SCN$ |
| Ia.1460 | Cl | Cl | $CH_2CH_2CH(CH_2CH_3)SCN$ |
| Ia.1461 | H | Cl | $CH_2CH_2CH(CH_2CH_3)SCHF_2$ |
| Ia.1462 | F | Cl | $CH_2CH_2CH(CH_2CH_3)SCHF_2$ |
| Ia.1463 | Cl | Cl | $CH_2CH_2CH(CH_2CH_3)SCHF_2$ |
| Ia.1464 | H | Cl | $CH_2CH_2CH(CH_2CH_3)SCF_3$ |
| Ia.1465 | F | Cl | $CH_2CH_2CH(CH_2CH_3)SCF_3$ |
| Ia.1466 | Cl | Cl | $CH_2CH_2CH(CH_2CH_3)SCF_3$ |
| Ia.1467 | H | Cl | $CH_2CH_2CH(CH_2CH_3)$S-cyclopropyl |
| Ia.1468 | F | Cl | $CH_2CH_2CH(CH_2CH_3)$S-cyclopropyl |
| Ia.1469 | Cl | Cl | $CH_2CH_2CH(CH_2CH_3)$S-cyclopropyl |
| Ia.1470 | H | Cl | $CH_2CH_2CH(CH_2CH_3)SOCHF_2$ |
| Ia.1471 | F | Cl | $CH_2CH_2CH(CH_2CH_3)SOCHF_2$ |
| Ia.1472 | Cl | Cl | $CH_2CH_2CH(CH_2CH_3)SOCHF_2$ |
| Ia.1473 | H | Cl | $CH_2CH_2CH(CH_2CH_3)SOCF_3$ |
| Ia.1474 | F | Cl | $CH_2CH_2CH(CH_2CH_3)SOCF_3$ |
| Ia.1475 | Cl | Cl | $CH_2CH_2CH(CH_2CH_3)SOCF_3$ |
| Ia.1476 | H | Cl | $CH_2CH_2CH(CH_2CH_3)$SO-cyclopropyl |
| Ia.1477 | F | Cl | $CH_2CH_2CH(CH_2CH_3)$SO-cyclopropyl |
| Ia.1478 | Cl | Cl | $CH_2CH_2CH(CH_2CH_3)$SO-cyclopropyl |
| Ia.1479 | H | Cl | $CH_2CH_2CH(CH_2CH_3)SOCH_3$ |
| Ia.1480 | F | Cl | $CH_2CH_2CH(CH_2CH_3)SOCH_3$ |
| Ia.1481 | Cl | Cl | $CH_2CH_2CH(CH_2CH_3)SOCH_3$ |
| Ia.1482 | H | Cl | $CH_2CH_2CH(CH_2CH_3)SOCH_2CH_3$ |
| Ia.1483 | F | Cl | $CH_2CH_2CH(CH_2CH_3)SOCH_2CH_3$ |
| Ia.1484 | Cl | Cl | $CH_2CH_2CH(CH_2CH_3)SOCH_2CH_3$ |
| Ia.1485 | H | Cl | $CH_2CH_2CH(CH_2CH_3)SO_2CHF_2$ |
| Ia.1486 | F | Cl | $CH_2CH_2CH(CH_2CH_3)SO_2CHF_2$ |
| Ia.1487 | Cl | Cl | $CH_2CH_2CH(CH_2CH_3)SO_2CHF_2$ |
| Ia.1488 | H | Cl | $CH_2CH_2CH(CH_2CH_3)SO_2CF_3$ |
| Ia.1489 | F | Cl | $CH_2CH_2CH(CH_2CH_3)SO_2CF_3$ |
| Ia.1490 | Cl | Cl | $CH_2CH_2CH(CH_2CH_3)SO_2CF_3$ |
| Ia.1491 | H | Cl | $CH_2CH_2CH(CH_2CH_3)SO_2$-cyclopropyl |
| Ia.1492 | F | Cl | $CH_2CH_2CH(CH_2CH_3)SO_2$-cyclopropyl |
| Ia.1493 | Cl | Cl | $CH_2CH_2CH(CH_2CH_3)SO_2$-cyclopropyl |
| Ia.1494 | H | Cl | $CH_2CH_2CH(CH_2CH_3)SO_2CH_3$ |
| Ia.1495 | F | Cl | $CH_2CH_2CH(CH_2CH_3)SO_2CH_3$ |
| Ia.1496 | Cl | Cl | $CH_2CH_2CH(CH_2CH_3)SO_2CH_3$ |
| Ia.1497 | H | Cl | $CH_2CH_2CH(CH_2CH_3)SO_2CH_2CH_3$ |
| Ia.1498 | F | Cl | $CH_2CH_2CH(CH_2CH_3)SO_2CH_2CH_3$ |
| Ia.1499 | Cl | Cl | $CH_2CH_2CH(CH_2CH_3)SO_2CH_2CH_3$ |
| Ia.1500 | H | Cl | $CH(CH_2CH_2CH_3)CH_2F$ |
| Ia.1501 | F | Cl | $CH(CH_2CH_2CH_3)CH_2F$ |
| Ia.1502 | Cl | Cl | $CH(CH_2CH_2CH_3)CH_2F$ |
| Ia.1503 | H | Cl | $CH(CH_2CH_2CH_3)CH_2Cl$ |
| Ia.1504 | F | Cl | $CH(CH_2CH_2CH_3)CH_2Cl$ |
| Ia.1505 | Cl | Cl | $CH(CH_2CH_2CH_3)CH_2Cl$ |
| Ia.1506 | H | Cl | $CH(CH_2CH_2CH_3)CH_2Br$ |
| Ia.1507 | F | Cl | $CH(CH_2CH_2CH_3)CH_2Br$ |
| Ia.1508 | Cl | Cl | $CH(CH_2CH_2CH_3)CH_2Br$ |
| Ia.1509 | H | Cl | $CH(CH_2CH_2CH_3)CH_2I$ |
| Ia.1510 | F | Cl | $CH(CH_2CH_2CH_3)CH_2I$ |
| Ia.1511 | Cl | Cl | $CH(CH_2CH_2CH_3)CH_2I$ |
| Ia.1512 | H | Cl | $CH(CH_2CH_2CH_3)CH_2CN$ |
| Ia.1513 | F | Cl | $CH(CH_2CH_2CH_3)CH_2CN$ |
| Ia.1514 | Cl | Cl | $CH(CH_2CH_2CH_3)CH_2CN$ |
| Ia.1515 | H | Cl | $CH(CH_2CH_2CH_3)CH_2SCN$ |
| Ia.1516 | F | Cl | $CH(CH_2CH_2CH_3)CH_2SCN$ |
| Ia.1517 | Cl | Cl | $CH(CH_2CH_2CH_3)CH_2SCN$ |
| Ia.1518 | H | Cl | $CH(CH_2CH_2CH_3)CH_2SCHF_2$ |
| Ia.1519 | F | Cl | $CH(CH_2CH_2CH_3)CH_2SCHF_2$ |
| Ia.1520 | Cl | Cl | $CH(CH_2CH_2CH_3)CH_2SCHF_2$ |
| Ia.1521 | H | Cl | $CH(CH_2CH_2CH_3)CH_2SCF_3$ |
| Ia.1522 | F | Cl | $CH(CH_2CH_2CH_3)CH_2SCF_3$ |
| Ia.1523 | Cl | Cl | $CH(CH_2CH_2CH_3)CH_2SCF_3$ |
| Ia.1524 | H | Cl | $CH(CH_2CH_2CH_3)CH_2$S-cyclopropyl |
| Ia.1525 | F | Cl | $CH(CH_2CH_2CH_3)CH_2$S-cyclopropyl |
| Ia.1526 | Cl | Cl | $CH(CH_2CH_2CH_3)CH_2$S-cyclopropyl |
| Ia.1527 | H | Cl | $CH(CH_2CH_2CH_3)CH_2SOCHF_2$ |
| Ia.1528 | F | Cl | $CH(CH_2CH_2CH_3)CH_2SOCHF_2$ |
| Ia.1529 | Cl | Cl | $CH(CH_2CH_2CH_3)CH_2SOCHF_2$ |
| Ia.1530 | H | Cl | $CH(CH_2CH_2CH_3)CH_2SOCF_3$ |
| Ia.1531 | F | Cl | $CH(CH_2CH_2CH_3)CH_2SOCF_3$ |
| Ia.1532 | Cl | Cl | $CH(CH_2CH_2CH_3)CH_2SOCF_3$ |
| Ia.1533 | H | Cl | $CH(CH_2CH_2CH_3)CH_2$SO-cyclopropyl |
| Ia.1534 | F | Cl | $CH(CH_2CH_2CH_3)CH_2$SO-cyclopropyl |
| Ia.1535 | Cl | Cl | $CH(CH_2CH_2CH_3)CH_2$SO-cyclopropyl |
| Ia.1536 | H | Cl | $CH(CH_2CH_2CH_3)CH_2SOCH_3$ |
| Ia.1537 | F | Cl | $CH(CH_2CH_2CH_3)CH_2SOCH_3$ |
| Ia.1538 | Cl | Cl | $CH(CH_2CH_2CH_3)CH_2SOCH_3$ |
| Ia.1539 | H | Cl | $CH(CH_2CH_2CH_3)CH_2SOCH_2CH_3$ |
| Ia.1540 | F | Cl | $CH(CH_2CH_2CH_3)CH_2SOCH_2CH_3$ |
| Ia.1541 | Cl | Cl | $CH(CH_2CH_2CH_3)CH_2SOCH_2CH_3$ |
| Ia.1542 | H | Cl | $CH(CH_2CH_2CH_3)CH_2SO_2CHF_2$ |
| Ia.1543 | F | Cl | $CH(CH_2CH_2CH_3)CH_2SO_2CHF_2$ |
| Ia.1544 | Cl | Cl | $CH(CH_2CH_2CH_3)CH_2SO_2CHF_2$ |
| Ia.1545 | H | Cl | $CH(CH_2CH_2CH_3)CH_2SO_2CF_3$ |
| Ia.1546 | F | Cl | $CH(CH_2CH_2CH_3)CH_2SO_2CF_3$ |
| Ia.1547 | Cl | Cl | $CH(CH_2CH_2CH_3)CH_2SO_2CF_3$ |
| Ia.1548 | H | Cl | $CH(CH_2CH_2CH_3)CH_2SO_2$-cyclopropyl |
| Ia.1549 | F | Cl | $CH(CH_2CH_2CH_3)CH_2SO_2$-cyclopropyl |
| Ia.1550 | Cl | Cl | $CH(CH_2CH_2CH_3)CH_2SO_2$-cyclopropyl |
| Ia.1551 | H | Cl | $CH(CH_2CH_2CH_3)CH_2SO_2CH_3$ |
| Ia.1552 | F | Cl | $CH(CH_2CH_2CH_3)CH_2SO_2CH_3$ |
| Ia.1553 | Cl | Cl | $CH(CH_2CH_2CH_3)CH_2SO_2CH_3$ |
| Ia.1554 | H | Cl | $CH(CH_2CH_2CH_3)CH_2SO_2CH_2CH_3$ |
| Ia.1555 | F | Cl | $CH(CH_2CH_2CH_3)CH_2SO_2CH_2CH_3$ |
| Ia.1556 | Cl | Cl | $CH(CH_2CH_2CH_3)CH_2SO_2CH_2CH_3$ |
| Ia.1557 | H | Cl | $CH_2CH(CH_2CH_2CH_3)F$ |
| Ia.1558 | F | Cl | $CH_2CH(CH_2CH_2CH_3)F$ |
| Ia.1559 | Cl | Cl | $CH_2CH(CH_2CH_2CH_3)F$ |
| Ia.1560 | H | Cl | $CH_2CH(CH_2CH_2CH_3)Cl$ |
| Ia.1561 | F | Cl | $CH_2CH(CH_2CH_2CH_3)Cl$ |
| Ia.1562 | Cl | Cl | $CH_2CH(CH_2CH_2CH_3)Cl$ |
| Ia.1563 | H | Cl | $CH_2CH(CH_2CH_2CH_3)Br$ |
| Ia.1564 | F | Cl | $CH_2CH(CH_2CH_2CH_3)Br$ |
| Ia.1565 | Cl | Cl | $CH_2CH(CH_2CH_2CH_3)Br$ |
| Ia.1566 | H | Cl | $CH_2CH(CH_2CH_2CH_3)I$ |
| Ia.1567 | F | Cl | $CH_2CH(CH_2CH_2CH_3)I$ |
| Ia.1568 | Cl | Cl | $CH_2CH(CH_2CH_2CH_3)I$ |
| Ia.1569 | H | Cl | $CH_2CH(CH_2CH_2CH_3)CN$ |
| Ia.1570 | F | Cl | $CH_2CH(CH_2CH_2CH_3)CN$ |
| Ia.1571 | Cl | Cl | $CH_2CH(CH_2CH_2CH_3)CN$ |
| Ia.1572 | H | Cl | $CH_2CH(CH_2CH_2CH_3)SCN$ |

TABLE 5-continued

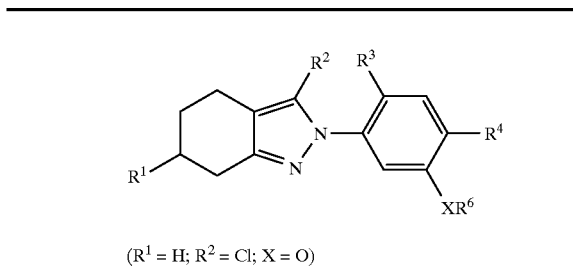

($R^1$ = H; $R^2$ = Cl; X = O)

| No. | $R^3$ | $R^4$ | $R^6$ |
|---|---|---|---|
| Ia.1573 | F | Cl | $CH_2CH(CH_2CH_2CH_3)SCN$ |
| Ia.1574 | Cl | Cl | $CH_2CH(CH_2CH_2CH_3)SCN$ |
| Ia.1575 | H | Cl | $CH_2CH(CH_2CH_2CH_3)SCHF_2$ |
| Ia.1576 | F | Cl | $CH_2CH(CH_2CH_2CH_3)SCHF_2$ |
| Ia.1577 | Cl | Cl | $CH_2CH(CH_2CH_2CH_3)SCHF_2$ |
| Ia.1578 | H | Cl | $CH_2CH(CH_2CH_2CH_3)SCF_3$ |
| Ia.1579 | F | Cl | $CH_2CH(CH_2CH_2CH_3)SCF_3$ |
| Ia.1580 | Cl | Cl | $CH_2CH(CH_2CH_2CH_3)SCF_3$ |
| Ia.1581 | H | Cl | $CH_2CH(CH_2CH_2CH_3)$S-cyclopropyl |
| Ia.1582 | F | Cl | $CH_2CH(CH_2CH_2CH_3)$S-cyclopropyl |
| Ia.1583 | Cl | Cl | $CH_2CH(CH_2CH_2CH_3)$S-cyclopropyl |
| Ia.1584 | H | Cl | $CH_2CH(CH_2CH_2CH_3)SOCHF_2$ |
| Ia.1585 | F | Cl | $CH_2CH(CH_2CH_2CH_3)SOCHF_2$ |
| Ia.1586 | Cl | Cl | $CH_2CH(CH_2CH_2CH_3)SOCHF_2$ |
| Ia.1587 | H | Cl | $CH_2CH(CH_2CH_2CH_3)SOCF_3$ |
| Ia.1588 | F | Cl | $CH_2CH(CH_2CH_2CH_3)SOCF_3$ |
| Ia.1589 | Cl | Cl | $CH_2CH(CH_2CH_2CH_3)SOCF_3$ |
| Ia.1590 | H | Cl | $CH_2CH(CH_2CH_2CH_3)$SO-cyclopropyl |
| Ia.1591 | F | Cl | $CH_2CH(CH_2CH_2CH_3)$SO-cyclopropyl |
| Ia.1592 | Cl | Cl | $CH_2CH(CH_2CH_2CH_3)$SO-cyclopropyl |
| Ia.1593 | H | Cl | $CH_2CH(CH_2CH_2CH_3)SOCH_3$ |
| Ia.1594 | F | Cl | $CH_2CH(CH_2CH_2CH_3)SOCH_3$ |
| Ia.1595 | Cl | Cl | $CH_2CH(CH_2CH_2CH_3)SOCH_3$ |
| Ia.1596 | H | Cl | $CH_2CH(CH_2CH_2CH_3)SOCH_2CH_3$ |
| Ia.1597 | F | Cl | $CH_2CH(CH_2CH_2CH_3)SOCH_2CH_3$ |
| Ia.1598 | Cl | Cl | $CH_2CH(CH_2CH_2CH_3)SOCH_2CH_3$ |
| Ia.1599 | H | Cl | $CH_2CH(CH_2CH_2CH_3)SO_2CHF_2$ |
| Ia.1600 | F | Cl | $CH_2CH(CH_2CH_2CH_3)SO_2CHF_2$ |
| Ia.1601 | Cl | Cl | $CH_2CH(CH_2CH_2CH_3)SO_2CHF_2$ |
| Ia.1602 | H | Cl | $CH_2CH(CH_2CH_2CH_3)SO_2CF_3$ |
| Ia.1603 | F | Cl | $CH_2CH(CH_2CH_2CH_3)SO_2CF_3$ |
| Ia.1604 | Cl | Cl | $CH_2CH(CH_2CH_2CH_3)SO_2CF_3$ |
| Ia.1605 | H | Cl | $CH_2CH(CH_2CH_2CH_3)SO_2$-cyclopropyl |
| Ia.1606 | F | Cl | $CH_2CH(CH_2CH_2CH_3)SO_2$-cyclopropyl |
| Ia.1607 | Cl | Cl | $CH_2CH(CH_2CH_2CH_3)SO_2$-cyclopropyl |
| Ia.1608 | H | Cl | $CH_2CH(CH_2CH_2CH_3)SO_2CH_3$ |
| Ia.1609 | F | Cl | $CH_2CH(CH_2CH_2CH_3)SO_2CH_3$ |
| Ia.1610 | Cl | Cl | $CH_2CH(CH_2CH_2CH_3)SO_2CH_3$ |
| Ia.1611 | H | Cl | $CH_2CH(CH_2CH_2CH_3)SO_2CH_3CH_3$ |
| Ia.1612 | F | Cl | $CH_2CH(CH_2CH_2CH_3)SO_2CH_3CH_3$ |
| Ia.1613 | Cl | Cl | $CH_2CH(CH_2CH_2CH_3)SO_2CH_3CH_3$ |
| Ia.1614 | H | Cl | $CH(CH_2CH_2CH_2CH_3)F$ |
| Ia.1615 | F | Cl | $CH(CH_2CH_2CH_2CH_3)F$ |
| Ia.1616 | Cl | Cl | $CH(CH_2CH_2CH_2CH_3)F$ |
| Ia.1617 | H | Cl | $CH(CH_2CH_2CH_2CH_3)Cl$ |
| Ia.1618 | F | Cl | $CH(CH_2CH_2CH_2CH_3)Cl$ |
| Ia.1619 | Cl | Cl | $CH(CH_2CH_2CH_2CH_3)Cl$ |
| Ia.1620 | H | Cl | $CH(CH_2CH_2CH_2CH_3)Br$ |
| Ia.1621 | F | Cl | $CH(CH_2CH_2CH_2CH_3)Br$ |
| Ia.1622 | Cl | Cl | $CH(CH_2CH_2CH_2CH_3)Br$ |
| Ia.1623 | H | Cl | $CH(CH_2CH_2CH_2CH_3)I$ |
| Ia.1624 | F | Cl | $CH(CH_2CH_2CH_2CH_3)I$ |
| Ia.1625 | Cl | Cl | $CH(CH_2CH_2CH_2CH_3)I$ |
| Ia.1626 | H | Cl | $CH(CH_2CH_2CH_2CH_3)CN$ |
| Ia.1627 | F | Cl | $CH(CH_2CH_2CH_2CH_3)CN$ |
| Ia.1628 | Cl | Cl | $CH(CH_2CH_2CH_2CH_3)CN$ |
| Ia.1629 | H | Cl | $CH(CH_2CH_2CH_2CH_3)SCN$ |
| Ia.1630 | F | Cl | $CH(CH_2CH_2CH_2CH_3)SCN$ |
| Ia.1631 | Cl | Cl | $CH(CH_2CH_2CH_2CH_3)SCN$ |
| Ia.1632 | H | Cl | $CH(CH_2CH_2CH_2CH_3)SCHF_2$ |
| Ia.1633 | F | Cl | $CH(CH_2CH_2CH_2CH_3)SCHF_2$ |
| Ia.1634 | Cl | Cl | $CH(CH_2CH_2CH_2CH_3)SCHF_2$ |
| Ia.1635 | H | Cl | $CH(CH_2CH_2CH_2CH_3)SCF_3$ |
| Ia.1636 | F | Cl | $CH(CH_2CH_2CH_2CH_3)SCF_3$ |
| Ia.1637 | Cl | Cl | $CH(CH_2CH_2CH_2CH_3)SCF_3$ |
| Ia.1638 | H | Cl | $CH(CH_2CH_2CH_2CH_3)$S-cyclopropyl |
| Ia.1639 | F | Cl | $CH(CH_2CH_2CH_2CH_3)$S-cyclopropyl |
| Ia.1640 | Cl | Cl | $CH(CH_2CH_2CH_2CH_3)$S-cyclopropyl |
| Ia.1641 | H | Cl | $CH(CH_2CH_2CH_2CH_3)SOCH_3$ |
| Ia.1642 | F | Cl | $CH(CH_2CH_2CH_2CH_3)SOCH_3$ |
| Ia.1643 | Cl | Cl | $CH(CH_2CH_2CH_2CH_3)SOCH_3$ |
| Ia.1644 | H | Cl | $CH(CH_2CH_2CH_2CH_3)SOCH_2CH_3$ |
| Ia.1645 | F | Cl | $CH(CH_2CH_2CH_2CH_3)SOCH_2CH_3$ |
| Ia.1646 | Cl | Cl | $CH(CH_2CH_2CH_2CH_3)SOCH_2CH_3$ |
| Ia.1647 | H | Cl | $CH(CH_2CH_2CH_2CH_3)SO_2CHF_2$ |
| Ia.1648 | F | Cl | $CH(CH_2CH_2CH_2CH_3)SO_2CHF_2$ |
| Ia.1649 | Cl | Cl | $CH(CH_2CH_2CH_2CH_3)SO_2CHF_2$ |
| Ia.1650 | H | Cl | $CH(CH_2CH_2CH_2CH_3)SO_2CF_3$ |
| Ia.1651 | F | Cl | $CH(CH_2CH_2CH_2CH_3)SO_2CF_3$ |
| Ia.1652 | Cl | Cl | $CH(CH_2CH_2CH_2CH_3)SO_2CF_3$ |
| Ia.1653 | H | Cl | $CH(CH_2CH_2CH_2CH_3)SO_2$-cyclopropyl |
| Ia.1654 | F | Cl | $CH(CH_2CH_2CH_2CH_3)SO_2$-cyclopropyl |
| Ia.1655 | Cl | Cl | $CH(CH_2CH_2CH_2CH_3)SO_2$-cyclopropyl |
| Ia.1656 | H | Cl | $CH(CH_2CH_2CH_2CH_3)SO_2CH_3$ |
| Ia.1657 | F | Cl | $CH(CH_2CH_2CH_2CH_3)SO_2CH_3$ |
| Ia.1658 | Cl | Cl | $CH(CH_2CH_2CH_2CH_3)SO_2CH_3$ |
| Ia.1659 | H | Cl | $CH(CH_2CH_2CH_2CH_3)SO_2CH_2CH_3$ |
| Ia.1660 | F | Cl | $CH(CH_2CH_2CH_2CH_3)SO_2CH_2CH_3$ |
| Ia.1661 | Cl | Cl | $CH(CH_2CH_2CH_2CH_3)SO_2CH_2CH_3$ |
| Ia.1662 | H | Cl | $CH(CH_2CH_2CH_2CH_3)SOCHF_2$ |
| Ia.1663 | F | Cl | $CH(CH_2CH_2CH_2CH_3)SOCHF_2$ |
| Ia.1664 | Cl | Cl | $CH(CH_2CH_2CH_2CH_3)SOCHF_2$ |
| Ia.1665 | H | Cl | $CH(CH_2CH_2CH_2CH_3)SOCF_3$ |
| Ia.1666 | F | Cl | $CH(CH_2CH_2CH_2CH_3)SOCF_3$ |
| Ia.1667 | Cl | Cl | $CH(CH_2CH_2CH_2CH_3)SOCF_3$ |
| Ia.1668 | H | Cl | $CH(CH_2CH_2CH_2CH_3)$SO-cyclopropyl |
| Ia.1669 | F | Cl | $CH(CH_2CH_2CH_2CH_3)$SO-cyclopropyl |
| Ia.1670 | Cl | Cl | $CH(CH_2CH_2CH_2CH_3)$SO-cyclopropyl |
| Ia.1671 | H | Cl | $C(CH_3)_2CH_2CH_2F$ |
| Ia.1672 | F | Cl | $C(CH_3)_2CH_2CH_2F$ |
| Ia.1673 | Cl | Cl | $C(CH_3)_2CH_2CH_2F$ |
| Ia.1674 | H | Cl | $C(CH_3)_2CH_2CH_2Cl$ |
| Ia.1675 | F | Cl | $C(CH_3)_2CH_2CH_2Cl$ |
| Ia.1676 | Cl | Cl | $C(CH_3)_2CH_2CH_2Cl$ |
| Ia.1677 | H | Cl | $C(CH_3)_2CH_2CH_2Br$ |
| Ia.1678 | F | Cl | $C(CH_3)_2CH_2CH_2Br$ |
| Ia.1679 | Cl | Cl | $C(CH_3)_2CH_2CH_2Br$ |
| Ia.1680 | H | Cl | $C(CH_3)_2CH_2CH_2I$ |
| Ia.1681 | F | Cl | $C(CH_3)_2CH_2CH_2I$ |
| Ia.1682 | Cl | Cl | $C(CH_3)_2CH_2CH_2I$ |
| Ia.1683 | H | Cl | $C(CH_3)_2CH_2CH_2CN$ |
| Ia.1684 | F | Cl | $C(CH_3)_2CH_2CH_2CN$ |
| Ia.1685 | Cl | Cl | $C(CH_3)_2CH_2CH_2CN$ |
| Ia.1686 | H | Cl | $C(CH_3)_2CH_2CH_2SCN$ |
| Ia.1687 | F | Cl | $C(CH_3)_2CH_2CH_2SCN$ |
| Ia.1688 | Cl | Cl | $C(CH_3)_2CH_2CH_2SCN$ |
| Ia.1689 | H | Cl | $C(CH_3)_2CH_2CH_2SCHF_2$ |
| Ia.1690 | F | Cl | $C(CH_3)_2CH_2CH_2SCHF_2$ |
| Ia.1691 | Cl | Cl | $C(CH_3)_2CH_2CH_2SCHF_2$ |
| Ia.1692 | H | Cl | $C(CH_3)_2CH_2CH_2SCF_3$ |
| Ia.1693 | F | Cl | $C(CH_3)_2CH_2CH_2SCF_3$ |
| Ia.1694 | Cl | Cl | $C(CH_3)_2CH_2CH_2SCF_3$ |
| Ia.1695 | H | Cl | $C(CH_3)_2CH_2CH_2$S-cyclopropyl |
| Ia.1696 | F | Cl | $C(CH_3)_2CH_2CH_2$S-cyclopropyl |
| Ia.1697 | Cl | Cl | $C(CH_3)_2CH_2CH_2$S-cyclopropyl |
| Ia.1698 | H | Cl | $C(CH_3)_2CH_2CH_2SOCHF_2$ |
| Ia.1699 | F | Cl | $C(CH_3)_2CH_2CH_2SOCHF_2$ |
| Ia.1700 | Cl | Cl | $C(CH_3)_2CH_2CH_2SOCHF_2$ |

TABLE 5-continued $$\text{(structure I)}$$

(R¹ = H; R² = Cl; X = O)

| No. | R³ | R⁴ | R⁶ |
|---|---|---|---|
| Ia.1701 | H | Cl | C(CH₃)₂CH₂CH₂SOCF₃ |
| Ia.1702 | F | Cl | C(CH₃)₂CH₂CH₂SOCF₃ |
| Ia.1703 | Cl | Cl | C(CH₃)₂CH₂CH₂SOCF₃ |
| Ia.1704 | H | Cl | C(CH₃)₂CH₂CH₂SO-cyclopropyl |
| Ia.1705 | F | Cl | C(CH₃)₂CH₂CH₂SO-cyclopropyl |
| Ia.1706 | Cl | Cl | C(CH₃)₂CH₂CH₂SO-cyclopropyl |
| Ia.1707 | H | Cl | C(CH₃)₂CH₂CH₂SOCH₂CH₃ |
| Ia.1708 | F | Cl | C(CH₃)₂CH₂CH₂SOCH₂CH₃ |
| Ia.1709 | Cl | Cl | C(CH₃)₂CH₂CH₂SOCH₂CH₃ |
| Ia.1710 | H | Cl | C(CH₃)₂CH₂CH₂SO₂CHF₂ |
| Ia.1711 | F | Cl | C(CH₃)₂CH₂CH₂SO₂CHF₂ |
| Ia.1712 | Cl | Cl | C(CH₃)₂CH₂CH₂SO₂CHF₂ |
| Ia.1713 | H | Cl | C(CH₃)₂CH₂CH₂SO₂CF₃ |
| Ia.1714 | F | Cl | C(CH₃)₂CH₂CH₂SO₂CF₃ |
| Ia.1715 | Cl | Cl | C(CH₃)₂CH₂CH₂SO₂CF₃ |
| Ia.1716 | H | Cl | C(CH₃)₂CH₂CH₂SO₂-cyclopropyl |
| Ia.1717 | F | Cl | C(CH₃)₂CH₂CH₂SO₂-cyclopropyl |
| Ia.1718 | Cl | Cl | C(CH₃)₂CH₂CH₂SO₂-cyclopropyl |
| Ia.1719 | H | Cl | C(CH₃)₂CH₂CH₂SO₂CH₃ |
| Ia.1720 | F | Cl | C(CH₃)₂CH₂CH₂SO₂CH₃ |
| Ia.1721 | Cl | Cl | C(CH₃)₂CH₂CH₂SO₂CH₃ |
| Ia.1722 | H | Cl | C(CH₃)₂CH₂CH₂SO₂CH₂CH₃ |
| Ia.1723 | F | Cl | C(CH₃)₂CH₂CH₂SO₂CH₂CH₃ |
| Ia.1724 | Cl | Cl | C(CH₃)₂CH₂CH₂SO₂CH₂CH₃ |
| Ia.1725 | H | Cl | CH₂C(CH₃)₂CH₂F |
| Ia.1726 | F | Cl | CH₂C(CH₃)₂CH₂F |
| Ia.1727 | Cl | Cl | CH₂C(CH₃)₂CH₂F |
| Ia.1728 | H | Cl | CH₂C(CH₃)₂CH₂Cl |
| Ia.1729 | F | Cl | CH₂C(CH₃)₂CH₂Cl |
| Ia.1730 | Cl | Cl | CH₂C(CH₃)₂CH₂Cl |
| Ia.1731 | H | Cl | CH₂C(CH₃)₂CH₂Br |
| Ia.1732 | F | Cl | CH₂C(CH₃)₂CH₂Br |
| Ia.1733 | Cl | Cl | CH₂C(CH₃)₂CH₂Br |
| Ia.1734 | H | Cl | CH₂C(CH₃)₂CH₂I |
| Ia.1735 | F | Cl | CH₂C(CH₃)₂CH₂I |
| Ia.1736 | Cl | Cl | CH₂C(CH₃)₂CH₂I |
| Ia.1737 | H | Cl | CH₂C(CH₃)₂CH₂CN |
| Ia.1738 | F | Cl | CH₂C(CH₃)₂CH₂CN |
| Ia.1739 | Cl | Cl | CH₂C(CH₃)₂CH₂CN |
| Ia.1740 | H | Cl | CH₂C(CH₃)₂CH₂SCN |
| Ia.1741 | F | Cl | CH₂C(CH₃)₂CH₂SCN |
| Ia.1742 | Cl | Cl | CH₂C(CH₃)₂CH₂SCN |
| Ia.1743 | H | Cl | CH₂C(CH₃)₂CH₂SCHF₂ |
| Ia.1744 | F | Cl | CH₂C(CH₃)₂CH₂SCHF₂ |
| Ia.1745 | Cl | Cl | CH₂C(CH₃)₂CH₂SCHF₂ |
| Ia.1746 | H | Cl | CH₂C(CH₃)₂CH₂SCF₃ |
| Ia.1747 | F | Cl | CH₂C(CH₃)₂CH₂SCF₃ |
| Ia.1748 | Cl | Cl | CH₂C(CH₃)₂CH₂SCF₃ |
| Ia.1749 | H | Cl | CH₂C(CH₃)₂CH₂S-cyclopropyl |
| Ia.1750 | F | Cl | CH₂C(CH₃)₂CH₂S-cyclopropyl |
| Ia.1751 | Cl | Cl | CH₂C(CH₃)₂CH₂S-cyclopropyl |
| Ia.1752 | H | Cl | CH₂C(CH₃)₂CH₂SOCHF₂ |
| Ia.1753 | F | Cl | CH₂C(CH₃)₂CH₂SOCHF₂ |
| Ia.1754 | Cl | Cl | CH₂C(CH₃)₂CH₂SOCHF₂ |
| Ia.1755 | H | Cl | CH₂C(CH₃)₂CH₂SOCF₃ |
| Ia.1756 | F | Cl | CH₂C(CH₃)₂CH₂SOCF₃ |
| Ia.1757 | Cl | Cl | CH₂C(CH₃)₂CH₂SOCF₃ |
| Ia.1758 | H | Cl | CH₂C(CH₃)₂CH₂-cyclopropyl |
| Ia.1759 | F | Cl | CH₂C(CH₃)₂CH₂-cyclopropyl |
| Ia.1760 | Cl | Cl | CH₂C(CH₃)₂CH₂-cyclopropyl |
| Ia.1761 | H | Cl | CH₂C(CH₃)₂CH₂SOCH₃ |
| Ia.1762 | F | Cl | CH₂C(CH₃)₂CH₂SOCH₃ |
| Ia.1763 | Cl | Cl | CH₂C(CH₃)₂CH₂SOCH₃ |
| Ia.1764 | H | Cl | CH₂C(CH₃)₂CH₂SOCH₂CH₃ |
| Ia.1765 | F | Cl | CH₂C(CH₃)₂CH₂SOCH₂CH₃ |
| Ia.1766 | Cl | Cl | CH₂C(CH₃)₂CH₂SOCH₂CH₃ |
| Ia.1767 | H | Cl | CH₂C(CH₃)₂CH₂SO₂CHF₂ |
| Ia.1768 | F | Cl | CH₂C(CH₃)₂CH₂SO₂CHF₂ |
| Ia.1769 | Cl | Cl | CH₂C(CH₃)₂CH₂SO₂CHF₂ |
| Ia.1770 | H | Cl | CH₂C(CH₃)₂CH₂SO₂CF₃ |
| Ia.1771 | F | Cl | CH₂C(CH₃)₂CH₂SO₂CF₃ |
| Ia.1772 | Cl | Cl | CH₂C(CH₃)₂CH₂SO₂CF₃ |
| Ia.1773 | H | Cl | CH₂C(CH₃)₂CH₂SO₂-cyclopropyl |
| Ia.1774 | F | Cl | CH₂C(CH₃)₂CH₂SO₂-cyclopropyl |
| Ia.1775 | Cl | Cl | CH₂C(CH₃)₂CH₂SO₂-cyclopropyl |
| Ia.1776 | H | Cl | CH₂C(CH₃)₂CH₂SO₂CH₃ |
| Ia.1777 | F | Cl | CH₂C(CH₃)₂CH₂SO₂CH₃ |
| Ia.1778 | Cl | Cl | CH₂C(CH₃)₂CH₂SO₂CH₃ |
| Ia.1779 | H | Cl | CH₂C(CH₃)₂CH₂SO₂CH₂CH₃ |
| Ia.1780 | F | Cl | CH₂C(CH₃)₂CH₂SO₂CH₂CH₃ |
| Ia.1781 | Cl | Cl | CH₂C(CH₃)₂CH₂SO₂CH₂CH₃ |
| Ia.1782 | H | Cl | CH₂CH₂C(CH₃)₂F |
| Ia.1783 | F | Cl | CH₂CH₂C(CH₃)₂F |
| Ia.1784 | Cl | Cl | CH₂CH₂C(CH₃)₂F |
| Ia.1785 | H | Cl | CH₂CH₂C(CH₃)₂Cl |
| Ia.1786 | F | Cl | CH₂CH₂C(CH₃)₂Cl |
| Ia.1787 | Cl | Cl | CH₂CH₂C(CH₃)₂Cl |
| Ia.1788 | H | Cl | CH₂CH₂C(CH₃)₂Br |
| Ia.1789 | F | Cl | CH₂CH₂C(CH₃)₂Br |
| Ia.1790 | Cl | Cl | CH₂CH₂C(CH₃)₂Br |
| Ia.1791 | H | Cl | CH₂CH₂C(CH₃)₂I |
| Ia.1792 | F | Cl | CH₂CH₂C(CH₃)₂I |
| Ia.1793 | Cl | Cl | CH₂CH₂C(CH₃)₂I |
| Ia.1794 | H | Cl | CH₂CH₂C(CH₃)₂CN |
| Ia.1795 | F | Cl | CH₂CH₂C(CH₃)₂CN |
| Ia.1796 | Cl | Cl | CH₂CH₂C(CH₃)₂CN |
| Ia.1797 | H | Cl | CH₂CH₂C(CH₃)₂SCN |
| Ia.1798 | F | Cl | CH₂CH₂C(CH₃)₂SCN |
| Ia.1799 | Cl | Cl | CH₂CH₂C(CH₃)₂SCN |
| Ia.1800 | H | Cl | CH₂CH₂C(CH₃)₂SCHF₂ |
| Ia.1801 | F | Cl | CH₂CH₂C(CH₃)₂SCHF₂ |
| Ia.1802 | Cl | Cl | CH₂CH₂C(CH₃)₂SCHF₂ |
| Ia.1803 | H | Cl | CH₂CH₂C(CH₃)₂SCF₂ |
| Ia.1804 | F | Cl | CH₂CH₂C(CH₃)₂SCF₂ |
| Ia.1805 | Cl | Cl | CH₂CH₂C(CH₃)₂SCF₂ |
| Ia.1806 | H | Cl | CH₂CH₂C(CH₃)₂S-cyclopropyl |
| Ia.1807 | F | Cl | CH₂CH₂C(CH₃)₂S-cyclopropyl |
| Ia.1808 | Cl | Cl | CH₂CH₂C(CH₃)₂S-cyclopropyl |
| Ia.1809 | H | Cl | CH₂CH₂C(CH₃)₂SOCHF₂ |
| Ia.1810 | F | Cl | CH₂CH₂C(CH₃)₂SOCHF₂ |
| Ia.1811 | Cl | Cl | CH₂CH₂C(CH₃)₂SOCHF₂ |
| Ia.1812 | H | Cl | CH₂CH₂C(CH₃)₂SOCF₂ |
| Ia.1813 | F | Cl | CH₂CH₂C(CH₃)₂SOCF₂ |
| Ia.1814 | Cl | Cl | CH₂CH₂C(CH₃)₂SOCF₂ |
| Ia.1815 | H | Cl | CH₂CH₂C(CH₃)₂SO-cyclopropyl |
| Ia.1816 | F | Cl | CH₂CH₂C(CH₃)₂SO-cyclopropyl |
| Ia.1817 | Cl | Cl | CH₂CH₂C(CH₃)₂SO-cyclopropyl |
| Ia.1818 | H | Cl | CH₂CH₂C(CH₃)₂SOCH₃ |
| Ia.1819 | F | Cl | CH₂CH₂C(CH₃)₂SOCH₃ |
| Ia.1820 | Cl | Cl | CH₂CH₂C(CH₃)₂SOCH₃ |
| Ia.1821 | H | Cl | CH₂CH₂C(CH₃)₂SOCH₂CH₃ |
| Ia.1822 | F | Cl | CH₂CH₂C(CH₃)₂SOCH₂CH₃ |
| Ia.1823 | Cl | Cl | CH₂CH₂C(CH₃)₂SOCH₂CH₃ |
| Ia.1824 | H | Cl | CH₂CH₂C(CH₃)₂SO₂CHF₂ |
| Ia.1825 | F | Cl | CH₂CH₂C(CH₃)₂SO₂CHF₂ |
| Ia.1826 | Cl | Cl | CH₂CH₂C(CH₃)₂SO₂CHF₂ |
| Ia.1827 | H | Cl | CH₂CH₂C(CH₃)₂SO₂CF₃ |
| Ia.1828 | F | Cl | CH₂CH₂C(CH₃)₂SO₂CF₃ |

TABLE 5-continued

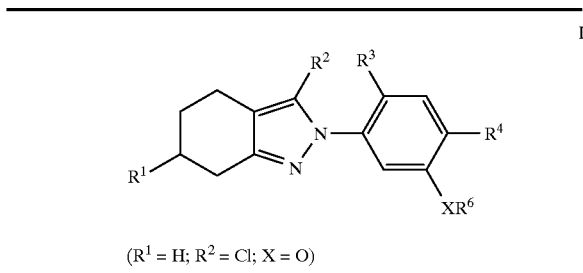

($R^1$ = H; $R^2$ = Cl; X = O)

| No. | $R^3$ | $R^4$ | $R^6$ |
|---|---|---|---|
| Ia.1829 | Cl | Cl | $CH_2CH_2C(CH_3)_2SO_2CF_3$ |
| Ia.1830 | H | Cl | $CH_2CH_2C(CH_3)_2SO_2$-cyclopropyl |
| Ia.1831 | F | Cl | $CH_2CH_2C(CH_3)_2SO_2$-cyclopropyl |
| Ia.1832 | Cl | Cl | $CH_2CH_2C(CH_3)_2SO_2$-cyclopropyl |
| Ia.1833 | H | Cl | $CH_2CH_2C(CH_3)_2SO_2CH_3$ |
| Ia.1834 | F | Cl | $CH_2CH_2C(CH_3)_2SO_2CH_3$ |
| Ia.1835 | Cl | Cl | $CH_2CH_2C(CH_3)_2SO_2CH_3$ |
| Ia.1836 | H | Cl | $CH_2CH_2C(CH_3)_2SO_2CH_3CH_3$ |
| Ia.1837 | F | Cl | $CH_2CH_2C(CH_3)_2SO_2CH_3CH_3$ |
| Ia.1838 | Cl | Cl | $CH_2CH_2C(CH_3)_2SO_2CH_3CH_3$ |
| Ia.1839 | H | Cl | $CH(CH_3)CH(CH_3)CH_2F$ |
| Ia.1840 | F | Cl | $CH(CH_3)CH(CH_3)CH_2F$ |
| Ia.1841 | Cl | Cl | $CH(CH_3)CH(CH_3)CH_2F$ |
| Ia.1842 | H | Cl | $CH(CH_3)CH(CH_3)CH_2Cl$ |
| Ia.1843 | F | Cl | $CH(CH_3)CH(CH_3)CH_2Cl$ |
| Ia.1844 | Cl | Cl | $CH(CH_3)CH(CH_3)CH_2Cl$ |
| Ia.1845 | H | Cl | $CH(CH_3)CH(CH_3)CH_2Br$ |
| Ia.1846 | F | Cl | $CH(CH_3)CH(CH_3)CH_2Br$ |
| Ia.1847 | Cl | Cl | $CH(CH_3)CH(CH_3)CH_2Br$ |
| Ia.1848 | H | Cl | $CH(CH_3)CH(CH_3)CH_2I$ |
| Ia.1849 | F | Cl | $CH(CH_3)CH(CH_3)CH_2I$ |
| Ia.1850 | Cl | Cl | $CH(CH_3)CH(CH_3)CH_2I$ |
| Ia.1851 | H | Cl | $CH(CH_3)CH(CH_3)CH_2CN$ |
| Ia.1852 | F | Cl | $CH(CH_3)CH(CH_3)CH_2CN$ |
| Ia.1853 | Cl | Cl | $CH(CH_3)CH(CH_3)CH_2CN$ |
| Ia.1854 | H | Cl | $CH(CH_3)CH(CH_3)CH_2SCN$ |
| Ia.1855 | F | Cl | $CH(CH_3)CH(CH_3)CH_2SCN$ |
| Ia.1856 | Cl | Cl | $CH(CH_3)CH(CH_3)CH_2SCN$ |
| Ia.1857 | H | Cl | $CH(CH_3)CH(CH_3)CH_2SCHF_2$ |
| Ia.1858 | F | Cl | $CH(CH_3)CH(CH_3)CH_2SCHF_2$ |
| Ia.1859 | Cl | Cl | $CH(CH_3)CH(CH_3)CH_2SCHF_2$ |
| Ia.1860 | H | Cl | $CH(CH_3)CH(CH_3)CH_2SCF_3$ |
| Ia.1861 | F | Cl | $CH(CH_3)CH(CH_3)CH_2SCF_3$ |
| Ia.1862 | Cl | Cl | $CH(CH_3)CH(CH_3)CH_2SCF_3$ |
| Ia.1863 | H | Cl | $CH(CH_3)CH(CH_3)CH_2S$-cyclopropyl |
| Ia.1864 | F | Cl | $CH(CH_3)CH(CH_3)CH_2S$-cyclopropyl |
| Ia.1865 | Cl | Cl | $CH(CH_3)CH(CH_3)CH_2S$-cyclopropyl |
| Ia.1866 | H | Cl | $CH(CH_3)CH(CH_3)CH_2SOCHF_2$ |
| Ia.1867 | F | Cl | $CH(CH_3)CH(CH_3)CH_2SOCHF_2$ |
| Ia.1868 | Cl | Cl | $CH(CH_3)CH(CH_3)CH_2SOCHF_2$ |
| Ia.1869 | H | Cl | $CH(CH_3)CH(CH_3)CH_2SOCF_3$ |
| Ia.1870 | F | Cl | $CH(CH_3)CH(CH_3)CH_2SOCF_3$ |
| Ia.1871 | Cl | Cl | $CH(CH_3)CH(CH_3)CH_2SOCF_3$ |
| Ia.1872 | H | Cl | $CH(CH_3)CH(CH_3)CH_2$—SO-cyclopropyl |
| Ia.1873 | F | Cl | $CH(CH_3)CH(CH_3)CH_2$—SO-cyclopropyl |
| Ia.1874 | Cl | Cl | $CH(CH_3)CH(CH_3)CH_2$—SO-cyclopropyl |
| Ia.1875 | H | Cl | $CH(CH_3)CH(CH_3)CH_2$—$SOCH_3$ |
| Ia.1876 | F | Cl | $CH(CH_3)CH(CH_3)CH_2$—$SOCH_3$ |
| Ia.1877 | Cl | Cl | $CH(CH_3)CH(CH_3)CH_2$—$SOCH_3$ |
| Ia.1878 | H | Cl | $CH(CH_3)CH(CH_3)SO_2CH_2CH_3$ |
| Ia.1879 | F | Cl | $CH(CH_3)CH(CH_3)SO_2CH_2CH_3$ |
| Ia.1880 | Cl | Cl | $CH(CH_3)CH(CH_3)SO_2CH_2CH_3$ |
| Ia.1881 | H | Cl | $CH(CH_3)CH(CH_3)CH_2SO_2CHF_2$ |
| Ia.1882 | F | Cl | $CH(CH_3)CH(CH_3)CH_2SO_2CHF_2$ |
| Ia.1883 | Cl | Cl | $CH(CH_3)CH(CH_3)CH_2SO_2CHF_2$ |
| Ia.1884 | H | Cl | $CH(CH_3)CH(CH_3)CH_2SO_2CF_3$ |
| Ia.1885 | F | Cl | $CH(CH_3)CH(CH_3)CH_2SO_2CF_3$ |
| Ia.1886 | Cl | Cl | $CH(CH_3)CH(CH_3)CH_2SO_2CF_3$ |
| Ia.1887 | H | Cl | $CH(CH_3)CH(CH_3)CH_2SO_2$-cyclopropyl |
| Ia.1888 | F | Cl | $CH(CH_3)CH(CH_3)CH_2SO_2$-cyclopropyl |
| Ia.1889 | Cl | Cl | $CH(CH_3)CH(CH_3)CH_2SO_2$-cyclopropyl |
| Ia.1890 | H | Cl | $CH(CH_3)CH(CH_3)CH_2SO_2CH_3$ |
| Ia.1891 | F | Cl | $CH(CH_3)CH(CH_3)CH_2SO_2CH_3$ |
| Ia.1892 | Cl | Cl | $CH(CH_3)CH(CH_3)CH_2SO_2CH_3$ |
| Ia.1893 | H | Cl | $CH(CH_3)CH(CH_3)CH_2SO_2CH_2CH_3$ |
| Ia.1894 | F | Cl | $CH(CH_3)CH(CH_3)CH_2SO_2CH_2CH_3$ |
| Ia.1895 | Cl | Cl | $CH(CH_3)CH(CH_3)CH_2SO_2CH_2CH_3$ |
| Ia.1896 | H | Cl | $CH_2CH(CH_3)CH(CH_3)F$ |
| Ia.1897 | F | Cl | $CH_2CH(CH_3)CH(CH_3)F$ |
| Ia.1898 | Cl | Cl | $CH_2CH(CH_3)CH(CH_3)F$ |
| Ia.1899 | H | Cl | $CH_2CH(CH_3)CH(CH_3)Cl$ |
| Ia.1900 | F | Cl | $CH_2CH(CH_3)CH(CH_3)Cl$ |
| Ia.1901 | Cl | Cl | $CH_2CH(CH_3)CH(CH_3)Cl$ |
| Ia.1902 | H | Cl | $CH_2CH(CH_3)CH(CH_3)Br$ |
| Ia.1903 | F | Cl | $CH_2CH(CH_3)CH(CH_3)Br$ |
| Ia.1904 | Cl | Cl | $CH_2CH(CH_3)CH(CH_3)Br$ |
| Ia.1905 | H | Cl | $CH_2CH(CH_3)CH(CH_3)I$ |
| Ia.1906 | F | Cl | $CH_2CH(CH_3)CH(CH_3)I$ |
| Ia.1907 | Cl | Cl | $CH_2CH(CH_3)CH(CH_3)I$ |
| Ia.1908 | H | Cl | $CH_2CH(CH_3)CH(CH_3)CN$ |
| Ia.1909 | F | Cl | $CH_2CH(CH_3)CH(CH_3)CN$ |
| Ia.1910 | Cl | Cl | $CH_2CH(CH_3)CH(CH_3)CN$ |
| Ia.1911 | H | Cl | $CH_2CH(CH_3)CH(CH_3)SCN$ |
| Ia.1912 | F | Cl | $CH_2CH(CH_3)CH(CH_3)SCN$ |
| Ia.1913 | Cl | Cl | $CH_2CH(CH_3)CH(CH_3)SCN$ |
| Ia.1914 | H | Cl | $CH_2CH(CH_3)CH(CH_3)SCHF_2$ |
| Ia.1915 | F | Cl | $CH_2CH(CH_3)CH(CH_3)SCHF_2$ |
| Ia.1916 | Cl | Cl | $CH_2CH(CH_3)CH(CH_3)SCHF_2$ |
| Ia.1917 | H | Cl | $CH_2CH(CH_3)CH(CH_3)SCF_3$ |
| Ia.1918 | F | Cl | $CH_2CH(CH_3)CH(CH_3)SCF_3$ |
| Ia.1919 | Cl | Cl | $CH_2CH(CH_3)CH(CH_3)SCF_3$ |
| Ia.1920 | H | Cl | $CH_2CH(CH_3)CH(CH_3)S$-cyclopropyl |
| Ia.1921 | F | Cl | $CH_2CH(CH_3)CH(CH_3)S$-cyclopropyl |
| Ia.1922 | Cl | Cl | $CH_2CH(CH_3)CH(CH_3)S$-cyclopropyl |
| Ia.1923 | H | Cl | $CH_2CH(CH_3)CH(CH_3)SOCHF_2$ |
| Ia.1924 | F | Cl | $CH_2CH(CH_3)CH(CH_3)SOCHF_2$ |
| Ia.1925 | Cl | Cl | $CH_2CH(CH_3)CH(CH_3)SOCHF_2$ |
| Ia.1926 | H | Cl | $CH_2CH(CH_3)CH(CH_3)SOCF_3$ |
| Ia.1927 | F | Cl | $CH_2CH(CH_3)CH(CH_3)SOCF_3$ |
| Ia.1928 | Cl | Cl | $CH_2CH(CH_3)CH(CH_3)SOCF_3$ |
| Ia.1929 | H | Cl | $CH_2CH(CH_3)CH(CH_3)SO$-cyclopropyl |
| Ia.1930 | F | Cl | $CH_2CH(CH_3)CH(CH_3)SO$-cyclopropyl |
| Ia.1931 | Cl | Cl | $CH_2CH(CH_3)CH(CH_3)SO$-cyclopropyl |
| Ia.1932 | H | Cl | $CH_2CH(CH_3)CH(CH_3)SOCH_3$ |
| Ia.1933 | F | Cl | $CH_2CH(CH_3)CH(CH_3)SOCH_3$ |
| Ia.1934 | Cl | Cl | $CH_2CH(CH_3)CH(CH_3)SOCH_3$ |
| Ia.1935 | H | Cl | $CH_2CH(CH_3)CH(CH_3)SOCH_2CH_3$ |
| Ia.1936 | F | Cl | $CH_2CH(CH_3)CH(CH_3)SOCH_2CH_3$ |
| Ia.1937 | Cl | Cl | $CH_2CH(CH_3)CH(CH_3)SOCH_2CH_3$ |
| Ia.1938 | H | Cl | $CH_2CH(CH_3)CH(CH_3)SO_2CHF_2$ |
| Ia.1939 | F | Cl | $CH_2CH(CH_3)CH(CH_3)SO_2CHF_2$ |
| Ia.1940 | Cl | Cl | $CH_2CH(CH_3)CH(CH_3)SO_2CHF_2$ |
| Ia.1941 | H | Cl | $CH_2CH(CH_3)CH(CH_3)SO_2CF_3$ |
| Ia.1942 | F | Cl | $CH_2CH(CH_3)CH(CH_3)SO_2CF_3$ |
| Ia.1943 | Cl | Cl | $CH_2CH(CH_3)CH(CH_3)SO_2CF_3$ |
| Ia.1944 | H | Cl | $CH_2CH(CH_3)CH(CH_3)SO_2CH_3$ |
| Ia.1945 | F | Cl | $CH_2CH(CH_3)CH(CH_3)SO_2CH_3$ |
| Ia.1946 | Cl | Cl | $CH_2CH(CH_3)CH(CH_3)SO_2CH_3$ |
| Ia.1947 | H | Cl | $CH_2CH(CH_3)CH(CH_3)SO_2CH_2CH_3$ |
| Ia.1948 | F | Cl | $CH_2CH(CH_3)CH(CH_3)SO_2CH_2CH_3$ |
| Ia.1949 | Cl | Cl | $CH_2CH(CH_3)CH(CH_3)SO_2CH_2CH_3$ |
| Ia.1950 | H | Cl | $CH_2CH(CH_3)CH(CH_3)SO_2$-cyclopropyl |
| Ia.1951 | F | Cl | $CH_2CH(CH_3)CH(CH_3)SO_2$-cyclopropyl |
| Ia.1952 | Cl | Cl | $CH_2CH(CH_3)CH(CH_3)SO_2$-cyclopropyl |
| Ia.1953 | H | Cl | $CH(CH_3)CH_2CH(CH_3)F$ |
| Ia.1954 | F | Cl | $CH(CH_3)CH_2CH(CH_3)F$ |
| Ia.1955 | Cl | Cl | $CH(CH_3)CH_2CH(CH_3)F$ |
| Ia.1956 | H | Cl | $CH(CH_3)CH_2CH(CH_3)Cl$ |

TABLE 5-continued

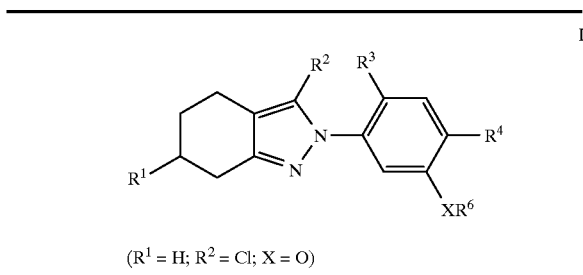

($R^1$ = H; $R^2$ = Cl; X = O)

| No. | $R^3$ | $R^4$ | $R^6$ |
|---|---|---|---|
| Ia.1957 | F | Cl | $CH(CH_3)CH_2CH(CH_3)Cl$ |
| Ia.1958 | Cl | Cl | $CH(CH_3)CH_2CH(CH_3)Cl$ |
| Ia.1959 | H | Cl | $CH(CH_3)CH_2CH(CH_3)Br$ |
| Ia.1960 | F | Cl | $CH(CH_3)CH_2CH(CH_3)Br$ |
| Ia.1961 | Cl | Cl | $CH(CH_3)CH_2CH(CH_3)Br$ |
| Ia.1962 | H | Cl | $CH(CH_3)CH_2CH(CH_3)I$ |
| Ia.1963 | F | Cl | $CH(CH_3)CH_2CH(CH_3)I$ |
| Ia.1964 | Cl | Cl | $CH(CH_3)CH_2CH(CH_3)I$ |
| Ia.1965 | H | Cl | $CH(CH_3)CH_2CH(CH_3)CN$ |
| Ia.1966 | F | Cl | $CH(CH_3)CH_2CH(CH_3)CN$ |
| Ia.1967 | Cl | Cl | $CH(CH_3)CH_2CH(CH_3)CN$ |
| Ia.1968 | H | Cl | $CH(CH_3)CH_2CH(CH_3)SCN$ |
| Ia.1969 | F | Cl | $CH(CH_3)CH_2CH(CH_3)SCN$ |
| Ia.1970 | Cl | Cl | $CH(CH_3)CH_2CH(CH_3)SCN$ |
| Ia.1971 | H | Cl | $CH(CH_3)CH_2CH(CH_3)SCHF_2$ |
| Ia.1972 | F | Cl | $CH(CH_3)CH_2CH(CH_3)SCHF_2$ |
| Ia.1973 | Cl | Cl | $CH(CH_3)CH_2CH(CH_3)SCHF_2$ |
| Ia.1974 | H | Cl | $CH(CH_3)CH_2CH(CH_3)SCF_3$ |
| Ia.1975 | F | Cl | $CH(CH_3)CH_2CH(CH_3)SCF_3$ |
| Ia.1976 | Cl | Cl | $CH(CH_3)CH_2CH(CH_3)SCF_3$ |
| Ia.1977 | H | Cl | $CH(CH_3)CH_2CH(CH_3)$S-cyclopropyl |
| Ia.1978 | F | Cl | $CH(CH_3)CH_2CH(CH_3)$S-cyclopropyl |
| Ia.1979 | Cl | Cl | $CH(CH_3)CH_2CH(CH_3)$S-cyclopropyl |
| Ia.1980 | H | Cl | $CH(CH_3)CH_2CH(CH_3)SOCHF_2$ |
| Ia.1981 | F | Cl | $CH(CH_3)CH_2CH(CH_3)SOCHF_2$ |
| Ia.1982 | Cl | Cl | $CH(CH_3)CH_2CH(CH_3)SOCHF_2$ |
| Ia.1983 | H | Cl | $CH(CH_3)CH_2CH(CH_3)SOCF_3$ |
| Ia.1984 | F | Cl | $CH(CH_3)CH_2CH(CH_3)SOCF_3$ |
| Ia.1985 | Cl | Cl | $CH(CH_3)CH_2CH(CH_3)SOCF_3$ |
| Ia.1986 | H | Cl | $CH(CH_3)CH_2CH(CH_3)$SO-cyclopropyl |
| Ia.1987 | F | Cl | $CH(CH_3)CH_2CH(CH_3)$SO-cyclopropyl |
| Ia.1988 | Cl | Cl | $CH(CH_3)CH_2CH(CH_3)$SO-cyclopropyl |
| Ia.1989 | H | Cl | $CH(CH_3)CH_2CH(CH_3)SOCH_3$ |
| Ia.1990 | F | Cl | $CH(CH_3)CH_2CH(CH_3)SOCH_3$ |
| Ia.1991 | Cl | Cl | $CH(CH_3)CH_2CH(CH_3)SOCH_3$ |
| Ia.1992 | H | Cl | $CH(CH_3)CH_2CH(CH_3)SOCH_2CH_3$ |
| Ia.1993 | F | Cl | $CH(CH_3)CH_2CH(CH_3)SOCH_2CH_3$ |
| Ia.1994 | Cl | Cl | $CH(CH_3)CH_2CH(CH_3)SOCH_2CH_3$ |
| Ia.1995 | H | Cl | $CH(CH_3)CH_2CH(CH_3)SO_2CHF_2$ |
| Ia.1996 | F | Cl | $CH(CH_3)CH_2CH(CH_3)SO_2CHF_2$ |
| Ia.1997 | Cl | Cl | $CH(CH_3)CH_2CH(CH_3)SO_2CHF_2$ |
| Ia.1998 | H | Cl | $CH(CH_3)CH_2CH(CH_3)SO_2CF_3$ |
| Ia.1999 | F | Cl | $CH(CH_3)CH_2CH(CH_3)SO_2CF_3$ |
| Ia.2000 | Cl | Cl | $CH(CH_3)CH_2CH(CH_3)SO_2CF_3$ |
| Ia.2001 | H | Cl | $CH(CH_3)CH_2CH(CH_3)SO_2$-cyclopropyl |
| Ia.2002 | F | Cl | $CH(CH_3)CH_2CH(CH_3)SO_2$-cyclopropyl |
| Ia.2003 | Cl | Cl | $CH(CH_3)CH_2CH(CH_3)SO_2$-cyclopropyl |
| Ia.2004 | H | Cl | $CH(CH_3)CH_2CH(CH_3)SO_2CH_3$ |
| Ia.2005 | F | Cl | $CH(CH_3)CH_2CH(CH_3)SO_2CH_3$ |
| Ia.2006 | Cl | Cl | $CH(CH_3)CH_2CH(CH_3)SO_2CH_3$ |
| Ia.2007 | H | Cl | $CH(CH_3)CH_2CH(CH_3)SO_2CH_2CH_3$ |
| Ia.2008 | F | Cl | $CH(CH_3)CH_2CH(CH_3)SO_2CH_2CH_3$ |
| Ia.2009 | Cl | Cl | $CH(CH_3)CH_2CH(CH_3)SO_2CH_2CH_3$ |
| Ia.2010 | H | Cl | $C(CH_3)(CH_2CH_3)CH_2F$ |
| Ia.2011 | F | Cl | $C(CH_3)(CH_2CH_3)CH_2F$ |
| Ia.2012 | Cl | Cl | $C(CH_3)(CH_2CH_3)CH_2F$ |
| Ia.2013 | H | Cl | $C(CH_3)(CH_2CH_3)CH_2Cl$ |
| Ia.2014 | F | Cl | $C(CH_3)(CH_2CH_3)CH_2Cl$ |
| Ia.2015 | Cl | Cl | $C(CH_3)(CH_2CH_3)CH_2Cl$ |
| Ia.2016 | H | Cl | $C(CH_3)(CH_2CH_3)CH_2Br$ |
| Ia.2017 | F | Cl | $C(CH_3)(CH_2CH_3)CH_2Br$ |
| Ia.2018 | Cl | Cl | $C(CH_3)(CH_2CH_3)CH_2Br$ |
| Ia.2019 | H | Cl | $C(CH_3)(CH_2CH_3)CH_2I$ |
| Ia.2020 | F | Cl | $C(CH_3)(CH_2CH_3)CH_2I$ |

TABLE 5-continued

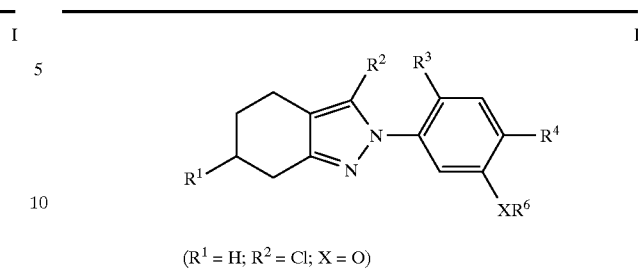

($R^1$ = H; $R^2$ = Cl; X = O)

| No. | $R^3$ | $R^4$ | $R^6$ |
|---|---|---|---|
| Ia.2021 | Cl | Cl | $C(CH_3)(CH_2CH_3)CH_2I$ |
| Ia.2022 | H | Cl | $C(CH_3)(CH_2CH_3)CH_2CN$ |
| Ia.2023 | F | Cl | $C(CH_3)(CH_2CH_3)CH_2CN$ |
| Ia.2024 | Cl | Cl | $C(CH_3)(CH_2CH_3)CH_2CN$ |
| Ia.2025 | H | Cl | $C(CH_3)(CH_2CH_3)CH_2SCN$ |
| Ia.2026 | F | Cl | $C(CH_3)(CH_2CH_3)CH_2SCN$ |
| Ia.2027 | Cl | Cl | $C(CH_3)(CH_2CH_3)CH_2SCN$ |
| Ia.2028 | H | Cl | $C(CH_3)(CH_2CH_3)CH_2SCHF_2$ |
| Ia.2029 | F | Cl | $C(CH_3)(CH_2CH_3)CH_2SCHF_2$ |
| Ia.2030 | Cl | Cl | $C(CH_3)(CH_2CH_3)CH_2SCHF_2$ |
| Ia.2031 | H | Cl | $C(CH_3)(CH_2CH_3)CH_2SCF_3$ |
| Ia.2032 | F | Cl | $C(CH_3)(CH_2CH_3)CH_2SCF_3$ |
| Ia.2033 | Cl | Cl | $C(CH_3)(CH_2CH_3)CH_2SCF_3$ |
| Ia.2034 | H | Cl | $C(CH_3)(CH_2CH_3)CH_2$S-cyclopropyl |
| Ia.2035 | F | Cl | $C(CH_3)(CH_2CH_3)CH_2$S-cyclopropyl |
| Ia.2036 | Cl | Cl | $C(CH_3)(CH_2CH_3)CH_2$S-cyclopropyl |
| Ia.2037 | H | Cl | $C(CH_3)(CH_2CH_3)CH_2SOCHF_2$ |
| Ia.2038 | F | Cl | $C(CH_3)(CH_2CH_3)CH_2SOCHF_2$ |
| Ia.2039 | Cl | Cl | $C(CH_3)(CH_2CH_3)CH_2SOCHF_2$ |
| Ia.2040 | H | Cl | $C(CH_3)(CH_2CH_3)CH_2SOCF_3$ |
| Ia.2041 | F | Cl | $C(CH_3)(CH_2CH_3)CH_2SOCF_3$ |
| Ia.2042 | Cl | Cl | $C(CH_3)(CH_2CH_3)CH_2SOCF_3$ |
| Ia.2043 | H | Cl | $C(CH_3)(CH_2CH_3)CH_2$SO-cyclopropyl |
| Ia.2044 | F | Cl | $C(CH_3)(CH_2CH_3)CH_2$SO-cyclopropyl |
| Ia.2045 | Cl | Cl | $C(CH_3)(CH_2CH_3)CH_2$SO-cyclopropyl |
| Ia.2046 | H | Cl | $C(CH_3)(CH_2CH_3)CH_2SOCH_3$ |
| Ia.2047 | F | Cl | $C(CH_3)(CH_2CH_3)CH_2SOCH_3$ |
| Ia.2048 | Cl | Cl | $C(CH_3)(CH_2CH_3)CH_2SOCH_3$ |
| Ia.2049 | H | Cl | $C(CH_3)(CH_2CH_3)CH_2SOCH_2CH_3$ |
| Ia.2050 | F | Cl | $C(CH_3)(CH_2CH_3)CH_2SOCH_2CH_3$ |
| Ia.2051 | Cl | Cl | $C(CH_3)(CH_2CH_3)CH_2SOCH_2CH_3$ |
| Ia.2052 | H | Cl | $C(CH_3)(CH_2CH_3)CH_2SO_2CHF_2$ |
| Ia.2053 | F | Cl | $C(CH_3)(CH_2CH_3)CH_2SO_2CHF_2$ |
| Ia.2054 | Cl | Cl | $C(CH_3)(CH_2CH_3)CH_2SO_2CHF_2$ |
| Ia.2055 | H | Cl | $C(CH_3)(CH_2CH_3)CH_2SO_2CF_3$ |
| Ia.2056 | F | Cl | $C(CH_3)(CH_2CH_3)CH_2SO_2CF_3$ |
| Ia.2057 | Cl | Cl | $C(CH_3)(CH_2CH_3)CH_2SO_2CF_3$ |
| Ia.2058 | H | Cl | $C(CH_3)(CH_2CH_3)CH_2SO_2$-cyclopropyl |
| Ia.2059 | F | Cl | $C(CH_3)(CH_2CH_3)CH_2SO_2$-cyclopropyl |
| Ia.2060 | Cl | Cl | $C(CH_3)(CH_2CH_3)CH_2SO_2$-cyclopropyl |
| Ia.2061 | H | Cl | $C(CH_3)(CH_2CH_3)CH_2SO_2CH_3$ |
| Ia.2062 | F | Cl | $C(CH_3)(CH_2CH_3)CH_2SO_2CH_3$ |
| Ia.2063 | Cl | Cl | $C(CH_3)(CH_2CH_3)CH_2SO_2CH_3$ |
| Ia.2064 | H | Cl | $C(CH_3)(CH_2CH_3)CH_2SO_2CH_2CH_3$ |
| Ia.2065 | F | Cl | $C(CH_3)(CH_2CH_3)CH_2SO_2CH_2CH_3$ |
| Ia.2066 | Cl | Cl | $C(CH_3)(CH_2CH_3)CH_2SO_2CH_2CH_3$ |
| Ia.2067 | H | Cl | $CH(CH_3)CH(CH_2CH_3)F$ |
| Ia.2068 | F | Cl | $CH(CH_3)CH(CH_2CH_3)F$ |
| Ia.2069 | Cl | Cl | $CH(CH_3)CH(CH_2CH_3)F$ |
| Ia.2070 | H | Cl | $CH(CH_3)CH(CH_2CH_3)Cl$ |
| Ia.2071 | F | Cl | $CH(CH_3)CH(CH_2CH_3)Cl$ |
| Ia.2072 | Cl | Cl | $CH(CH_3)CH(CH_2CH_3)Cl$ |
| Ia.2073 | H | Cl | $CH(CH_3)CH(CH_2CH_3)Br$ |
| Ia.2074 | F | Cl | $CH(CH_3)CH(CH_2CH_3)Br$ |
| Ia.2075 | Cl | Cl | $CH(CH_3)CH(CH_2CH_3)Br$ |
| Ia.2076 | H | Cl | $CH(CH_3)CH(CH_2CH_3)I$ |
| Ia.2077 | F | Cl | $CH(CH_3)CH(CH_2CH_3)I$ |
| Ia.2078 | Cl | Cl | $CH(CH_3)CH(CH_2CH_3)I$ |
| Ia.2079 | H | Cl | $CH(CH_3)CH(CH_2CH_3)CN$ |
| Ia.2080 | F | Cl | $CH(CH_3)CH(CH_2CH_3)CN$ |
| Ia.2081 | Cl | Cl | $CH(CH_3)CH(CH_2CH_3)CN$ |
| Ia.2082 | H | Cl | $CH(CH_3)CH(CH_2CH_3)SCN$ |
| Ia.2083 | F | Cl | $CH(CH_3)CH(CH_2CH_3)SCN$ |
| Ia.2084 | Cl | Cl | $CH(CH_3)CH(CH_2CH_3)SCN$ |

TABLE 5-continued $$I$$

(R$^1$ = H; R$^2$ = Cl; X = O)

| No. | R$^3$ | R$^4$ | R$^6$ |
|---|---|---|---|
| Ia.2085 | H | Cl | CH(CH$_3$)CH(CH$_2$CH$_3$)SCHF$_2$ |
| Ia.2086 | F | Cl | CH(CH$_3$)CH(CH$_2$CH$_3$)SCHF$_2$ |
| Ia.2087 | Cl | Cl | CH(CH$_3$)CH(CH$_2$CH$_3$)SCHF$_2$ |
| Ia.2088 | H | Cl | CH(CH$_3$)CH(CH$_2$CH$_3$)SCF$_3$ |
| Ia.2089 | F | Cl | CH(CH$_3$)CH(CH$_2$CH$_3$)SCF$_3$ |
| Ia.2090 | Cl | Cl | CH(CH$_3$)CH(CH$_2$CH$_3$)SCF$_3$ |
| Ia.2091 | H | Cl | CH(CH$_3$)CH(CH$_2$CH$_3$)S-cyclopropyl |
| Ia.2092 | F | Cl | CH(CH$_3$)CH(CH$_2$CH$_3$)S-cyclopropyl |
| Ia.2093 | Cl | Cl | CH(CH$_3$)CH(CH$_2$CH$_3$)S-cyclopropyl |
| Ia.2094 | H | Cl | CH(CH$_3$)CH(CH$_2$CH$_3$)SOCHF$_2$ |
| Ia.2095 | F | Cl | CH(CH$_3$)CH(CH$_2$CH$_3$)SOCHF$_2$ |
| Ia.2096 | Cl | Cl | CH(CH$_3$)CH(CH$_2$CH$_3$)SOCHF$_2$ |
| Ia.2097 | H | Cl | CH(CH$_3$)CH(CH$_2$CH$_3$)SOCF$_3$ |
| Ia.2098 | F | Cl | CH(CH$_3$)CH(CH$_2$CH$_3$)SOCF$_3$ |
| Ia.2099 | Cl | Cl | CH(CH$_3$)CH(CH$_2$CH$_3$)SOCF$_3$ |
| Ia.2100 | H | Cl | CH(CH$_3$)CH(CH$_2$CH$_3$)SO-cyclopropyl |
| Ia.2101 | F | Cl | CH(CH$_3$)CH(CH$_2$CH$_3$)SO-cyclopropyl |
| Ia.2102 | Cl | Cl | CH(CH$_3$)CH(CH$_2$CH$_3$)SO-cyclopropyl |
| Ia.2103 | H | Cl | CH(CH$_3$)CH(CH$_2$CH$_3$)SOCH$_3$ |
| Ia.2104 | F | Cl | CH(CH$_3$)CH(CH$_2$CH$_3$)SOCH$_3$ |
| Ia.2105 | Cl | Cl | CH(CH$_3$)CH(CH$_2$CH$_3$)SOCH$_3$ |
| Ia.2106 | H | Cl | CH(CH$_3$)CH(CH$_2$CH$_3$)SOCH$_2$CH$_3$ |
| Ia.2107 | F | Cl | CH(CH$_3$)CH(CH$_2$CH$_3$)SOCH$_2$CH$_3$ |
| Ia.2108 | Cl | Cl | CH(CH$_3$)CH(CH$_2$CH$_3$)SOCH$_2$CH$_3$ |
| Ia.2109 | H | Cl | CH(CH$_3$)CH(CH$_2$CH$_3$)SO$_2$CHF$_2$ |
| Ia.2110 | F | Cl | CH(CH$_3$)CH(CH$_2$CH$_3$)SO$_2$CHF$_2$ |
| Ia.2111 | Cl | Cl | CH(CH$_3$)CH(CH$_2$CH$_3$)SO$_2$CHF$_2$ |
| Ia.2112 | H | Cl | CH(CH$_3$)CH(CH$_2$CH$_3$)SO$_2$CF$_3$ |
| Ia.2113 | F | Cl | CH(CH$_3$)CH(CH$_2$CH$_3$)SO$_2$CF$_3$ |
| Ia.2114 | Cl | Cl | CH(CH$_3$)CH(CH$_2$CH$_3$)SO$_2$CF$_3$ |
| Ia.2115 | H | Cl | CH(CH$_3$)CH(CH$_2$CH$_3$)SO$_2$-cyclopropyl |
| Ia.2116 | F | Cl | CH(CH$_3$)CH(CH$_2$CH$_3$)SO$_2$-cyclopropyl |
| Ia.2117 | Cl | Cl | CH(CH$_3$)CH(CH$_2$CH$_3$)SO$_2$-cyclopropyl |
| Ia.2118 | H | Cl | CH(CH$_3$)CH(CH$_2$CH$_3$)SO$_2$CH$_3$ |
| Ia.2119 | F | Cl | CH(CH$_3$)CH(CH$_2$CH$_3$)SO$_2$CH$_3$ |
| Ia.2120 | Cl | Cl | CH(CH$_3$)CH(CH$_2$CH$_3$)SO$_2$CH$_3$ |
| Ia.2121 | H | Cl | CH(CH$_3$)CH(CH$_2$CH$_3$)SO$_2$CH$_2$CH$_3$ |
| Ia.2122 | F | Cl | CH(CH$_3$)CH(CH$_2$CH$_3$)SO$_2$CH$_2$CH$_3$ |
| Ia.2123 | Cl | Cl | CH(CH$_3$)CH(CH$_2$CH$_3$)SO$_2$CH$_2$CH$_3$ |
| Ia.2124 | H | Cl | CH(CH$_2$CH$_3$)CH(CH$_3$)F |
| Ia.2125 | F | Cl | CH(CH$_2$CH$_3$)CH(CH$_3$)F |
| Ia.2126 | Cl | Cl | CH(CH$_2$CH$_3$)CH(CH$_3$)F |
| Ia.2127 | H | Cl | CH(CH$_2$CH$_3$)CH(CH$_3$)Cl |
| Ia.2128 | F | Cl | CH(CH$_2$CH$_3$)CH(CH$_3$)Cl |
| Ia.2129 | Cl | Cl | CH(CH$_2$CH$_3$)CH(CH$_3$)Cl |
| Ia.2130 | H | Cl | CH(CH$_2$CH$_3$)CH(CH$_3$)Br |
| Ia.2131 | F | Cl | CH(CH$_2$CH$_3$)CH(CH$_3$)Br |
| Ia.2132 | Cl | Cl | CH(CH$_2$CH$_3$)CH(CH$_3$)Br |
| Ia.2133 | H | Cl | CH(CH$_2$CH$_3$)CH(CH$_3$)I |
| Ia.2134 | F | Cl | CH(CH$_2$CH$_3$)CH(CH$_3$)I |
| Ia.2135 | Cl | Cl | CH(CH$_2$CH$_3$)CH(CH$_3$)I |
| Ia.2136 | H | Cl | CH(CH$_2$CH$_3$)CH(CH$_3$)CN |
| Ia.2137 | F | Cl | CH(CH$_2$CH$_3$)CH(CH$_3$)CN |
| Ia.2138 | Cl | Cl | CH(CH$_2$CH$_3$)CH(CH$_3$)CN |
| Ia.2139 | H | Cl | CH(CH$_2$CH$_3$)CH(CH$_3$)SCN |
| Ia.2140 | F | Cl | CH(CH$_2$CH$_3$)CH(CH$_3$)SCN |
| Ia.2141 | Cl | Cl | CH(CH$_2$CH$_3$)CH(CH$_3$)SCN |
| Ia.2142 | H | Cl | CH(CH$_2$CH$_3$)CH(CH$_3$)SCHF$_2$ |
| Ia.2143 | F | Cl | CH(CH$_2$CH$_3$)CH(CH$_3$)SCHF$_2$ |
| Ia.2144 | Cl | Cl | CH(CH$_2$CH$_3$)CH(CH$_3$)SCHF$_2$ |
| Ia.2145 | H | Cl | CH(CH$_2$CH$_3$)CH(CH$_3$)SCF$_3$ |
| Ia.2146 | F | Cl | CH(CH$_2$CH$_3$)CH(CH$_3$)SCF$_3$ |
| Ia.2147 | Cl | Cl | CH(CH$_2$CH$_3$)CH(CH$_3$)SCF$_3$ |
| Ia.2148 | H | Cl | CH(CH$_2$CH$_3$)CH(CH$_3$)S-cyclopropyl |
| Ia.2149 | F | Cl | CH(CH$_2$CH$_3$)CH(CH$_3$)S-cyclopropyl |
| Ia.2150 | Cl | Cl | CH(CH$_2$CH$_3$)CH(CH$_3$)S-cyclopropyl |
| Ia.2151 | H | Cl | CH(CH$_2$CH$_3$)CH(CH$_3$)SOCHF$_2$ |
| Ia.2152 | F | Cl | CH(CH$_2$CH$_3$)CH(CH$_3$)SOCHF$_2$ |
| Ia.2153 | Cl | Cl | CH(CH$_2$CH$_3$)CH(CH$_3$)SOCHF$_2$ |
| Ia.2154 | H | Cl | CH(CH$_2$CH$_3$)CH(CH$_3$)SOCF$_3$ |
| Ia.2155 | F | Cl | CH(CH$_2$CH$_3$)CH(CH$_3$)SOCF$_3$ |
| Ia.2156 | Cl | Cl | CH(CH$_2$CH$_3$)CH(CH$_3$)SOCF$_3$ |
| Ia.2157 | H | Cl | CH(CH$_2$CH$_3$)CH(CH$_3$)SO-cyclopropyl |
| Ia.2158 | F | Cl | CH(CH$_2$CH$_3$)CH(CH$_3$)SO-cyclopropyl |
| Ia.2159 | Cl | Cl | CH(CH$_2$CH$_3$)CH(CH$_3$)SO-cyclopropyl |
| Ia.2160 | H | Cl | CH(CH$_2$CH$_3$)CH(CH$_3$)SOCH$_3$ |
| Ia.2161 | F | Cl | CH(CH$_2$CH$_3$)CH(CH$_3$)SOCH$_3$ |
| Ia.2162 | Cl | Cl | CH(CH$_2$CH$_3$)CH(CH$_3$)SOCH$_3$ |
| Ia.2163 | H | Cl | CH(CH$_2$CH$_3$)CH(CH$_3$)SOCH$_2$CH$_3$ |
| Ia.2164 | F | Cl | CH(CH$_2$CH$_3$)CH(CH$_3$)SOCH$_2$CH$_3$ |
| Ia.2165 | Cl | Cl | CH(CH$_2$CH$_3$)CH(CH$_3$)SOCH$_2$CH$_3$ |
| Ia.2166 | H | Cl | CH(CH$_2$CH$_3$)CH(CH$_3$)SO$_2$CHF$_2$ |
| Ia.2167 | F | Cl | CH(CH$_2$CH$_3$)CH(CH$_3$)SO$_2$CHF$_2$ |
| Ia.2168 | Cl | Cl | CH(CH$_2$CH$_3$)CH(CH$_3$)SO$_2$CHF$_2$ |
| Ia.2169 | H | Cl | CH(CH$_2$CH$_3$)CH(CH$_3$)SO$_2$CF$_3$ |
| Ia.2170 | F | Cl | CH(CH$_2$CH$_3$)CH(CH$_3$)SO$_2$CF$_3$ |
| Ia.2171 | Cl | Cl | CH(CH$_2$CH$_3$)CH(CH$_3$)SO$_2$CF$_3$ |
| Ia.2172 | H | Cl | CH(CH$_2$CH$_3$)CH(CH$_3$)SO$_2$-cyclopropyl |
| Ia.2173 | F | Cl | CH(CH$_2$CH$_3$)CH(CH$_3$)SO$_2$-cyclopropyl |
| Ia.2174 | Cl | Cl | CH(CH$_2$CH$_3$)CH(CH$_3$)SO$_2$-cyclopropyl |
| Ia.2175 | H | Cl | CH(CH$_2$CH$_3$)CH(CH$_3$)SO$_2$CH$_3$ |
| Ia.2176 | F | Cl | CH(CH$_2$CH$_3$)CH(CH$_3$)SO$_2$CH$_3$ |
| Ia.2177 | Cl | Cl | CH(CH$_2$CH$_3$)CH(CH$_3$)SO$_2$CH$_3$ |
| Ia.2178 | H | Cl | CH(CH$_2$CH$_3$)CH(CH$_3$)SO$_2$CH$_2$CH$_3$ |
| Ia.2179 | F | Cl | CH(CH$_2$CH$_3$)CH(CH$_3$)SO$_2$CH$_2$CH$_3$ |
| Ia.2180 | Cl | Cl | CH(CH$_2$CH$_3$)CH(CH$_3$)SO$_2$CH$_2$CH$_3$ |
| Ia.2181 | H | Cl | CH$_2$C(CH$_3$)(CH$_2$CH$_3$)F |
| Ia.2182 | F | Cl | CH$_2$C(CH$_3$)(CH$_2$CH$_3$)F |
| Ia.2183 | Cl | Cl | CH$_2$C(CH$_3$)(CH$_2$CH$_3$)F |
| Ia.2184 | H | Cl | CH$_2$C(CH$_3$)(CH$_2$CH$_3$)Cl |
| Ia.2185 | F | Cl | CH$_2$C(CH$_3$)(CH$_2$CH$_3$)Cl |
| Ia.2186 | Cl | Cl | CH$_2$C(CH$_3$)(CH$_2$CH$_3$)Cl |
| Ia.2187 | H | Cl | CH$_2$C(CH$_3$)(CH$_2$CH$_3$)Br |
| Ia.2188 | F | Cl | CH$_2$C(CH$_3$)(CH$_2$CH$_3$)Br |
| Ia.2189 | Cl | Cl | CH$_2$C(CH$_3$)(CH$_2$CH$_3$)Br |
| Ia.2190 | H | Cl | CH$_2$C(CH$_3$)(CH$_2$CH$_3$)I |
| Ia.2191 | F | Cl | CH$_2$C(CH$_3$)(CH$_2$CH$_3$)I |
| Ia.2192 | Cl | Cl | CH$_2$C(CH$_3$)(CH$_2$CH$_3$)I |
| Ia.2193 | H | Cl | CH$_2$C(CH$_3$)(CH$_2$CH$_3$)CN |
| Ia.2194 | F | Cl | CH$_2$C(CH$_3$)(CH$_2$CH$_3$)CN |
| Ia.2195 | Cl | Cl | CH$_2$C(CH$_3$)(CH$_2$CH$_3$)CN |
| Ia.2196 | H | Cl | CH$_2$C(CH$_3$)(CH$_2$CH$_3$)SCN |
| Ia.2197 | F | Cl | CH$_2$C(CH$_3$)(CH$_2$CH$_3$)SCN |
| Ia.2198 | Cl | Cl | CH$_2$C(CH$_3$)(CH$_2$CH$_3$)SCN |
| Ia.2199 | H | Cl | CH$_2$C(CH$_3$)(CH$_2$CH$_3$)SCHF$_2$ |
| Ia.2200 | F | Cl | CH$_2$C(CH$_3$)(CH$_2$CH$_3$)SCHF$_2$ |
| Ia.2201 | Cl | Cl | CH$_2$C(CH$_3$)(CH$_2$CH$_3$)SCHF$_2$ |
| Ia.2202 | H | Cl | CH$_2$C(CH$_3$)(CH$_2$CH$_3$)SCF$_3$ |
| Ia.2203 | F | Cl | CH$_2$C(CH$_3$)(CH$_2$CH$_3$)SCF$_3$ |
| Ia.2204 | Cl | Cl | CH$_2$C(CH$_3$)(CH$_2$CH$_3$)SCF$_3$ |
| Ia.2205 | H | Cl | CH$_2$C(CH$_3$)(CH$_2$CH$_3$)S-cyclopropyl |
| Ia.2206 | F | Cl | CH$_2$C(CH$_3$)(CH$_2$CH$_3$)S-cyclopropyl |
| Ia.2207 | Cl | Cl | CH$_2$C(CH$_3$)(CH$_2$CH$_3$)S-cyclopropyl |
| Ia.2208 | H | Cl | CH$_2$C(CH$_3$)(CH$_2$CH$_3$)SOCHF$_2$ |
| Ia.2209 | F | Cl | CH$_2$C(CH$_3$)(CH$_2$CH$_3$)SOCHF$_2$ |
| Ia.2210 | Cl | Cl | CH$_2$C(CH$_3$)(CH$_2$CH$_3$)SOCHF$_2$ |
| Ia.2211 | H | Cl | CH$_2$C(CH$_3$)(CH$_2$CH$_3$)SOCF$_3$ |
| Ia.2212 | F | Cl | CH$_2$C(CH$_3$)(CH$_2$CH$_3$)SOCF$_3$ |

TABLE 5-continued

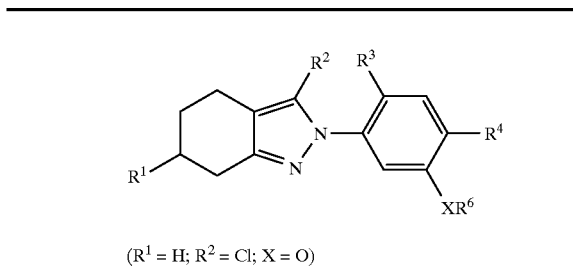

($R^1$ = H; $R^2$ = Cl; X = O)

| No. | $R^3$ | $R^4$ | $R^6$ |
|---|---|---|---|
| Ia.2213 | Cl | Cl | $CH_2C(CH_3)(CH_2CH_3)SOCF_3$ |
| Ia.2214 | H | Cl | $CH_2C(CH_3)(CH_2CH_3)SO$-cyclopropyl |
| Ia.2215 | F | Cl | $CH_2C(CH_3)(CH_2CH_3)SO$-cyclopropyl |
| Ia.2216 | Cl | Cl | $CH_2C(CH_3)(CH_2CH_3)SO$-cyclopropyl |
| Ia.2217 | H | Cl | $CH_2C(CH_3)(CH_2CH_3)SOCH_3$ |
| Ia.2218 | F | Cl | $CH_2C(CH_3)(CH_2CH_3)SOCH_3$ |
| Ia.2219 | Cl | Cl | $CH_2C(CH_3)(CH_2CH_3)SOCH_3$ |
| Ia.2220 | H | Cl | $CH_2C(CH_3)(CH_2CH_3)SOCH_2CH_3$ |
| Ia.2221 | F | Cl | $CH_2C(CH_3)(CH_2CH_3)SOCH_2CH_3$ |
| Ia.2222 | Cl | Cl | $CH_2C(CH_3)(CH_2CH_3)SOCH_2CH_3$ |
| Ia.2223 | H | Cl | $CH_2C(CH_3)(CH_2CH_3)SO_2CHF_2$ |
| Ia.2224 | F | Cl | $CH_2C(CH_3)(CH_2CH_3)SO_2CHF_2$ |
| Ia.2225 | Cl | Cl | $CH_2C(CH_3)(CH_2CH_3)SO_2CHF_2$ |
| Ia.2226 | H | Cl | $CH_2C(CH_3)(CH_2CH_3)SO_2CF_3$ |
| Ia.2227 | F | Cl | $CH_2C(CH_3)(CH_2CH_3)SO_2CF_3$ |
| Ia.2228 | Cl | Cl | $CH_2C(CH_3)(CH_2CH_3)SO_2CF_3$ |
| Ia.2229 | H | Cl | $CH_2C(CH_3)(CH_2CH_3)SO_2$-cyclopropyl |
| Ia.2230 | F | Cl | $CH_2C(CH_3)(CH_2CH_3)SO_2$-cyclopropyl |
| Ia.2231 | Cl | Cl | $CH_2C(CH_3)(CH_2CH_3)SO_2$-cyclopropyl |
| Ia.2232 | H | Cl | $CH_2C(CH_3)(CH_2CH_3)SO_2CH_3$ |
| Ia.2233 | F | Cl | $CH_2C(CH_3)(CH_2CH_3)SO_2CH_3$ |
| Ia.2234 | Cl | Cl | $CH_2C(CH_3)(CH_2CH_3)SO_2CH_3$ |
| Ia.2235 | H | Cl | $CH_2C(CH_3)(CH_2CH_3)SO_2CH_2CH_3$ |
| Ia.2236 | F | Cl | $CH_2C(CH_3)(CH_2CH_3)SO_2CH_2CH_3$ |
| Ia.2237 | Cl | Cl | $CH_2C(CH_3)(CH_2CH_3)SO_2CH_2CH_3$ |
| Ia.2238 | H | Cl | $CH(CH(CH_3)_2)CH_2F$ |
| Ia.2239 | F | Cl | $CH(CH(CH_3)_2)CH_2F$ |
| Ia.2240 | Cl | Cl | $CH(CH(CH_3)_2)CH_2F$ |
| Ia.2241 | H | Cl | $CH(CH(CH_3)_2)CH_2Cl$ |
| Ia.2242 | F | Cl | $CH(CH(CH_3)_2)CH_2Cl$ |
| Ia.2243 | Cl | Cl | $CH(CH(CH_3)_2)CH_2Cl$ |
| Ia.2244 | H | Cl | $CH(CH(CH_3)_2)CH_2Br$ |
| Ia.2245 | F | Cl | $CH(CH(CH_3)_2)CH_2Br$ |
| Ia.2246 | Cl | Cl | $CH(CH(CH_3)_2)CH_2Br$ |
| Ia.2247 | H | Cl | $CH(CH(CH_3)_2)CH_2I$ |
| Ia.2248 | F | Cl | $CH(CH(CH_3)_2)CH_2I$ |
| Ia.2249 | Cl | Cl | $CH(CH(CH_3)_2)CH_2I$ |
| Ia.2250 | H | Cl | $CH(CH(CH_3)_2)CH_2CN$ |
| Ia.2251 | F | Cl | $CH(CH(CH_3)_2)CH_2CN$ |
| Ia.2252 | Cl | Cl | $CH(CH(CH_3)_2)CH_2CN$ |
| Ia.2253 | H | Cl | $CH(CH(CH_3)_2)CH_2SCN$ |
| Ia.2254 | F | Cl | $CH(CH(CH_3)_2)CH_2SCN$ |
| Ia.2255 | Cl | Cl | $CH(CH(CH_3)_2)CH_2SCN$ |
| Ia.2256 | H | Cl | $CH(CH(CH_3)_2)CH_2SCHF_2$ |
| Ia.2257 | F | Cl | $CH(CH(CH_3)_2)CH_2SCHF_2$ |
| Ia.2258 | Cl | Cl | $CH(CH(CH_3)_2)CH_2SCHF_2$ |
| Ia.2259 | H | Cl | $CH(CH(CH_3)_2)CH_2SCF_3$ |
| Ia.2260 | F | Cl | $CH(CH(CH_3)_2)CH_2SCF_3$ |
| Ia.2261 | Cl | Cl | $CH(CH(CH_3)_2)CH_2SCF_3$ |
| Ia.2262 | H | Cl | $CH(CH(CH_3)_2)CH_2S$-cyclopropyl |
| Ia.2263 | F | Cl | $CH(CH(CH_3)_2)CH_2S$-cyclopropyl |
| Ia.2264 | Cl | Cl | $CH(CH(CH_3)_2)CH_2S$-cyclopropyl |
| Ia.2265 | H | Cl | $CH(CH(CH_3)_2)CH_2SOCHF_2$ |
| Ia.2266 | F | Cl | $CH(CH(CH_3)_2)CH_2SOCHF_2$ |
| Ia.2267 | Cl | Cl | $CH(CH(CH_3)_2)CH_2SOCHF_2$ |
| Ia.2268 | H | Cl | $CH(CH(CH_3)_2)CH_2SOCF_3$ |
| Ia.2269 | F | Cl | $CH(CH(CH_3)_2)CH_2SOCF_3$ |
| Ia.2270 | Cl | Cl | $CH(CH(CH_3)_2)CH_2SOCF_3$ |
| Ia.2271 | H | Cl | $CH(CH(CH_3)_2)CH_2SO$-cyclopropyl |
| Ia.2272 | F | Cl | $CH(CH(CH_3)_2)CH_2SO$-cyclopropyl |
| Ia.2273 | Cl | Cl | $CH(CH(CH_3)_2)CH_2SO$-cyclopropyl |
| Ia.2274 | H | Cl | $CH(CH(CH_3)_2)CH_2SOCH_3$ |
| Ia.2275 | F | Cl | $CH(CH(CH_3)_2)CH_2SOCH_3$ |
| Ia.2276 | Cl | Cl | $CH(CH(CH_3)_2)CH_2SOCH_3$ |
| Ia.2277 | H | Cl | $CH(CH(CH_3)_2)CH_2SOCH_2CH_3$ |
| Ia.2278 | F | Cl | $CH(CH(CH_3)_2)CH_2SOCH_2CH_3$ |
| Ia.2279 | Cl | Cl | $CH(CH(CH_3)_2)CH_2SOCH_2CH_3$ |
| Ia.2280 | H | Cl | $CH(CH(CH_3)_2)CH_2SOCHF_2$ |
| Ia.2281 | F | Cl | $CH(CH(CH_3)_2)CH_2SOCHF_2$ |
| Ia.2282 | Cl | Cl | $CH(CH(CH_3)_2)CH_2SOCHF_2$ |
| Ia.2283 | H | Cl | $CH(CH(CH_3)_2)CH_2SO_2CF_3$ |
| Ia.2284 | F | Cl | $CH(CH(CH_3)_2)CH_2SO_2CF_3$ |
| Ia.2285 | Cl | Cl | $CH(CH(CH_3)_2)CH_2SO_2CF_3$ |
| Ia.2286 | H | Cl | $CH(CH(CH_3)_2)CH_2SO_2CH_3$ |
| Ia.2287 | F | Cl | $CH(CH(CH_3)_2)CH_2SO_2CH_3$ |
| Ia.2288 | Cl | Cl | $CH(CH(CH_3)_2)CH_2SO_2CH_3$ |
| Ia.2289 | H | Cl | $CH(CH(CH_3)_2)CH_2SO_2CH_2CH_3$ |
| Ia.2290 | F | Cl | $CH(CH(CH_3)_2)CH_2SO_2CH_2CH_3$ |
| Ia.2291 | Cl | Cl | $CH(CH(CH_3)_2)CH_2SO_2CH_2CH_3$ |
| Ia.2292 | H | Cl | $CH(CH(CH_3)_2)CH_2SO_2$-cyclopropyl |
| Ia.2293 | F | Cl | $CH(CH(CH_3)_2)CH_2SO_2$-cyclopropyl |
| Ia.2294 | Cl | Cl | $CH(CH(CH_3)_2)CH_2SO_2$-cyclopropyl |
| Ia.2295 | H | Cl | $CH_2CH(CH(CH_3)_2)F$ |
| Ia.2296 | F | Cl | $CH_2CH(CH(CH_3)_2)F$ |
| Ia.2297 | Cl | Cl | $CH_2CH(CH(CH_3)_2)F$ |
| Ia.2298 | H | Cl | $CH_2CH(CH(CH_3)_2)Cl$ |
| Ia.2299 | F | Cl | $CH_2CH(CH(CH_3)_2)Cl$ |
| Ia.2300 | Cl | Cl | $CH_2CH(CH(CH_3)_2)Cl$ |
| Ia.2301 | H | Cl | $CH_2CH(CH(CH_3)_2)Br$ |
| Ia.2302 | F | Cl | $CH_2CH(CH(CH_3)_2)Br$ |
| Ia.2303 | Cl | Cl | $CH_2CH(CH(CH_3)_2)Br$ |
| Ia.2304 | H | Cl | $CH_2CH(CH(CH_3)_2)I$ |
| Ia.2305 | F | Cl | $CH_2CH(CH(CH_3)_2)I$ |
| Ia.2306 | Cl | Cl | $CH_2CH(CH(CH_3)_2)I$ |
| Ia.2307 | H | Cl | $CH_2CH(CH(CH_3)_2)CN$ |
| Ia.2308 | F | Cl | $CH_2CH(CH(CH_3)_2)CN$ |
| Ia.2309 | Cl | Cl | $CH_2CH(CH(CH_3)_2)CN$ |
| Ia.2310 | H | Cl | $CH_2CH(CH(CH_3)_2)SCN$ |
| Ia.2311 | F | Cl | $CH_2CH(CH(CH_3)_2)SCN$ |
| Ia.2312 | Cl | Cl | $CH_2CH(CH(CH_3)_2)SCN$ |
| Ia.2313 | H | Cl | $CH_2CH(CH(CH_3)_2)SCHF_2$ |
| Ia.2314 | F | Cl | $CH_2CH(CH(CH_3)_2)SCHF_2$ |
| Ia.2315 | Cl | Cl | $CH_2CH(CH(CH_3)_2)SCHF_2$ |
| Ia.2316 | H | Cl | $CH_2CH(CH(CH_3)_2)SCF_3$ |
| Ia.2317 | F | Cl | $CH_2CH(CH(CH_3)_2)SCF_3$ |
| Ia.2318 | Cl | Cl | $CH_2CH(CH(CH_3)_2)SCF_3$ |
| Ia.2319 | H | Cl | $CH_2CH(CH(CH_3)_2)S$-cyclopropyl |
| Ia.2320 | F | Cl | $CH_2CH(CH(CH_3)_2)S$-cyclopropyl |
| Ia.2321 | Cl | Cl | $CH_2CH(CH(CH_3)_2)S$-cyclopropyl |
| Ia.2322 | H | Cl | $CH_2CH(CH(CH_3)_2)SOCHF_2$ |
| Ia.2323 | F | Cl | $CH_2CH(CH(CH_3)_2)SOCHF_2$ |
| Ia.2324 | Cl | Cl | $CH_2CH(CH(CH_3)_2)SOCHF_2$ |
| Ia.2325 | H | Cl | $CH_2CH(CH(CH_3)_2)SOCF_3$ |
| Ia.2326 | F | Cl | $CH_2CH(CH(CH_3)_2)SOCF_3$ |
| Ia.2327 | Cl | Cl | $CH_2CH(CH(CH_3)_2)SOCF_3$ |
| Ia.2328 | H | Cl | $CH_2CH(CH(CH_3)_2)SO$-cyclopropyl |
| Ia.2329 | F | Cl | $CH_2CH(CH(CH_3)_2)SO$-cyclopropyl |
| Ia.2330 | Cl | Cl | $CH_2CH(CH(CH_3)_2)SO$-cyclopropyl |
| Ia.2331 | H | Cl | $CH_2CH(CH(CH_3)_2)SOCH_3$ |
| Ia.2332 | F | Cl | $CH_2CH(CH(CH_3)_2)SOCH_3$ |
| Ia.2333 | Cl | Cl | $CH_2CH(CH(CH_3)_2)SOCH_3$ |
| Ia.2334 | H | Cl | $CH_2CH(CH(CH_3)_2)SOCH_2CH_3$ |
| Ia.2335 | F | Cl | $CH_2CH(CH(CH_3)_2)SOCH_2CH_3$ |
| Ia.2336 | Cl | Cl | $CH_2CH(CH(CH_3)_2)SOCH_2CH_3$ |
| Ia.2337 | H | Cl | $CH_2CH(CH(CH_3)_2)SO_2CHF_2$ |
| Ia.2338 | F | Cl | $CH_2CH(CH(CH_3)_2)SO_2CHF_2$ |
| Ia.2339 | Cl | Cl | $CH_2CH(CH(CH_3)_2)SO_2CHF_2$ |
| Ia.2340 | H | Cl | $CH_2CH(CH(CH_3)_2)SO_2CF_3$ |

TABLE 5-continued $$I$$

(R¹ = H; R² = Cl; X = O)

| No. | R³ | R⁴ | R⁶ |
|---|---|---|---|
| Ia.2341 | F | Cl | CH$_2$CH(CH(CH$_3$)$_2$)SO$_2$CF$_3$ |
| Ia.2342 | Cl | Cl | CH$_2$CH(CH(CH$_3$)$_2$)SO$_2$CF$_3$ |
| Ia.2343 | H | Cl | CH$_2$CH(CH(CH$_3$)$_2$)SO$_2$-cyclopropyl |
| Ia.2344 | F | Cl | CH$_2$CH(CH(CH$_3$)$_2$)SO$_2$-cyclopropyl |
| Ia.2345 | Cl | Cl | CH$_2$CH(CH(CH$_3$)$_2$)SO$_2$-cyclopropyl |
| Ia.2346 | H | Cl | CH$_2$CH(CH(CH$_3$)$_2$)SO$_2$CH$_3$ |
| Ia.2347 | F | Cl | CH$_2$CH(CH(CH$_3$)$_2$)SO$_2$CH$_3$ |
| Ia.2348 | Cl | Cl | CH$_2$CH(CH(CH$_3$)$_2$)SO$_2$CH$_3$ |
| Ia.2349 | H | Cl | CH$_2$CH(CH(CH$_3$)$_2$)SO$_2$CH$_2$CH$_3$ |
| Ia.2350 | F | Cl | CH$_2$CH(CH(CH$_3$)$_2$)SO$_2$CH$_2$CH$_3$ |
| Ia.2351 | Cl | Cl | CH$_2$CH(CH(CH$_3$)$_2$)SO$_2$CH$_2$CH$_3$ |
| Ia.2352 | H | Cl | CH(CH$_2$CH(CH$_3$)$_2$)F |
| Ia.2353 | F | Cl | CH(CH$_2$CH(CH$_3$)$_2$)F |
| Ia.2354 | Cl | Cl | CH(CH$_2$CH(CH$_3$)$_2$)F |
| Ia.2355 | H | Cl | CH(CH$_2$CH(CH$_3$)$_2$)Cl |
| Ia.2356 | F | Cl | CH(CH$_2$CH(CH$_3$)$_2$)Cl |
| Ia.2357 | Cl | Cl | CH(CH$_2$CH(CH$_3$)$_2$)Cl |
| Ia.2358 | H | Cl | CH(CH$_2$CH(CH$_3$)$_2$)Br |
| Ia.2359 | F | Cl | CH(CH$_2$CH(CH$_3$)$_2$)Br |
| Ia.2360 | Cl | Cl | CH(CH$_2$CH(CH$_3$)$_2$)Br |
| Ia.2361 | H | Cl | CH(CH$_2$CH(CH$_3$)$_2$)I |
| Ia.2362 | F | Cl | CH(CH$_2$CH(CH$_3$)$_2$)I |
| Ia.2363 | Cl | Cl | CH(CH$_2$CH(CH$_3$)$_2$)I |
| Ia.2364 | H | Cl | CH(CH$_2$CH(CH$_3$)$_2$)CN |
| Ia.2365 | F | Cl | CH(CH$_2$CH(CH$_3$)$_2$)CN |
| Ia.2366 | Cl | Cl | CH(CH$_2$CH(CH$_3$)$_2$)CN |
| Ia.2367 | H | Cl | CH(CH$_2$CH(CH$_3$)$_2$)SCN |
| Ia.2368 | F | Cl | CH(CH$_2$CH(CH$_3$)$_2$)SCN |
| Ia.2369 | Cl | Cl | CH(CH$_2$CH(CH$_3$)$_2$)SCN |
| Ia.2370 | H | Cl | CH(CH$_2$CH(CH$_3$)$_2$)SCHF$_2$ |
| Ia.2371 | F | Cl | CH(CH$_2$CH(CH$_3$)$_2$)SCHF$_2$ |
| Ia.2372 | Cl | Cl | CH(CH$_2$CH(CH$_3$)$_2$)SCHF$_2$ |
| Ia.2373 | H | Cl | CH(CH$_2$CH(CH$_3$)$_2$)SCF$_3$ |
| Ia.2374 | F | Cl | CH(CH$_2$CH(CH$_3$)$_2$)SCF$_3$ |
| Ia.2375 | Cl | Cl | CH(CH$_2$CH(CH$_3$)$_2$)SCF$_3$ |
| Ia.2376 | H | Cl | CH(CH$_2$CH(CH$_3$)$_2$)S-cyclopropyl |
| Ia.2377 | F | Cl | CH(CH$_2$CH(CH$_3$)$_2$)S-cyclopropyl |
| Ia.2378 | Cl | Cl | CH(CH$_2$CH(CH$_3$)$_2$)S-cyclopropyl |
| Ia.2379 | H | Cl | CH(CH$_2$CH(CH$_3$)$_2$)SOCHF$_2$ |
| Ia.2380 | F | Cl | CH(CH$_2$CH(CH$_3$)$_2$)SOCHF$_2$ |
| Ia.2381 | Cl | Cl | CH(CH$_2$CH(CH$_3$)$_2$)SOCHF$_2$ |
| Ia.2382 | H | Cl | CH(CH$_2$CH(CH$_3$)$_2$)SOCF$_3$ |
| Ia.2383 | F | Cl | CH(CH$_2$CH(CH$_3$)$_2$)SOCF$_3$ |
| Ia.2384 | Cl | Cl | CH(CH$_2$CH(CH$_3$)$_2$)SOCF$_3$ |
| Ia.2385 | H | Cl | CH(CH$_2$CH(CH$_3$)$_2$)SO-cyclopropyl |
| Ia.2386 | F | Cl | CH(CH$_2$CH(CH$_3$)$_2$)SO-cyclopropyl |
| Ia.2387 | Cl | Cl | CH(CH$_2$CH(CH$_3$)$_2$)SO-cyclopropyl |
| Ia.2388 | H | Cl | CH(CH$_2$CH(CH$_3$)$_2$)SOCH$_3$ |
| Ia.2389 | F | Cl | CH(CH$_2$CH(CH$_3$)$_2$)SOCH$_3$ |
| Ia.2390 | Cl | Cl | CH(CH$_2$CH(CH$_3$)$_2$)SOCH$_3$ |
| Ia.2391 | H | Cl | CH(CH$_2$CH(CH$_3$)$_2$)SOCH$_2$CH$_3$ |
| Ia.2392 | F | Cl | CH(CH$_2$CH(CH$_3$)$_2$)SOCH$_2$CH$_3$ |
| Ia.2393 | Cl | Cl | CH(CH$_2$CH(CH$_3$)$_2$)SOCH$_2$CH$_3$ |
| Ia.2394 | H | Cl | CH(CH$_2$CH(CH$_3$)$_2$)SO$_2$CHF$_2$ |
| Ia.2395 | F | Cl | CH(CH$_2$CH(CH$_3$)$_2$)SO$_2$CHF$_2$ |
| Ia.2396 | Cl | Cl | CH(CH$_2$CH(CH$_3$)$_2$)SO$_2$CHF$_2$ |
| Ia.2397 | H | Cl | CH(CH$_2$CH(CH$_3$)$_2$)SO$_2$CF$_3$ |
| Ia.2398 | F | Cl | CH(CH$_2$CH(CH$_3$)$_2$)SO$_2$CF$_3$ |
| Ia.2399 | Cl | Cl | CH(CH$_2$CH(CH$_3$)$_2$)SO$_2$CF$_3$ |
| Ia.2400 | H | Cl | CH(CH$_2$CH(CH$_3$)$_2$)SO$_2$-cyclopropyl |
| Ia.2401 | F | Cl | CH(CH$_2$CH(CH$_3$)$_2$)SO$_2$-cyclopropyl |
| Ia.2402 | Cl | Cl | CH(CH$_2$CH(CH$_3$)$_2$)SO$_2$-cyclopropyl |
| Ia.2403 | H | Cl | CH(CH$_2$CH(CH$_3$)$_2$)SO$_2$CH$_3$ |
| Ia.2404 | F | Cl | CH(CH$_2$CH(CH$_3$)$_2$)SO$_2$CH$_3$ |
| Ia.2405 | Cl | Cl | CH(CH$_2$CH(CH$_3$)$_2$)SO$_2$CH$_3$ |
| Ia.2406 | H | Cl | CH(CH$_2$CH(CH$_3$)$_2$)SO$_2$CH$_2$CH$_3$ |
| Ia.2407 | F | Cl | CH(CH$_2$CH(CH$_3$)$_2$)SO$_2$CH$_2$CH$_3$ |
| Ia.2408 | Cl | Cl | CH(CH$_2$CH(CH$_3$)$_2$)SO$_2$CH$_2$CH$_3$ |
| Ia.2409 | H | Cl | CH$_2$CF$_3$ |
| Ia.2410 | F | Cl | CH$_2$CF$_3$ |
| Ia.2411 | Cl | Cl | CH$_2$CF$_3$ |
| Ia.2412 | H | Cl | CH$_2$CH$_2$CF$_3$ |
| Ia.2413 | F | Cl | CH$_2$CH$_2$CF$_3$ |
| Ia.2414 | Cl | Cl | CH$_2$CH$_2$CF$_3$ |
| Ia.2415 | H | Cl | CF$_2$CF$_3$ |
| Ia.2416 | F | Cl | CF$_2$CF$_3$ |
| Ia.2417 | Cl | Cl | CF$_2$CF$_3$ |
| Ia.2418 | H | Cl | CH(CF$_3$)$_2$ |
| Ia.2419 | F | Cl | CH(CF$_3$)$_2$ |
| Ia.2420 | Cl | Cl | CH(CF$_3$)$_2$ |
| Ia.2421 | H | Cl | CH$_2$CH(Cl)CH$_2$Cl |
| Ia.2422 | F | Cl | CH$_2$CH(Cl)CH$_2$Cl |
| Ia.2423 | Cl | Cl | CH$_2$CH(Cl)CH$_2$Cl |
| Ia.2424 | H | Cl | CH$_2$CH(CN)CH$_2$Cl |
| Ia.2425 | F | Cl | CH$_2$CH(CN)CH$_2$Cl |
| Ia.2426 | Cl | Cl | CH$_2$CH(CN)CH$_2$Cl |
| Ia.2427 | H | Cl | CH$_2$CH(Br)CH$_2$Br |
| Ia.2428 | F | Cl | CH$_2$CH(Br)CH$_2$Br |
| Ia.2429 | Cl | Cl | CH$_2$CH(Br)CH$_2$Br |
| Ia.2430 | H | Cl | CH$_2$CH(Cl)CH$_2$CN |
| Ia.2431 | F | Cl | CH$_2$CH(Cl)CH$_2$CN |
| Ia.2432 | Cl | Cl | CH$_2$CH(Cl)CH$_2$CN |
| Ia.2433 | H | Cl | CF$_2$CH$_3$ |
| Ia.2434 | F | Cl | CF$_2$CH$_3$ |
| Ia.2435 | Cl | Cl | CF$_2$CH$_3$ |
| Ia.2436 | H | Cl | CH(COOCH$_3$)CN |
| Ia.2437 | F | Cl | CH(COOCH$_3$)CN |
| Ia.2438 | Cl | Cl | CH(COOCH$_3$)CN |
| Ia.2439 | H | Cl | CH$_2$CH(Cl)COOCH$_3$ |
| Ia.2440 | F | Cl | CH$_2$CH(Cl)COOCH$_3$ |
| Ia.2441 | Cl | Cl | CH$_2$CH(Cl)COOCH$_3$ |
| Ia.2442 | H | Cl | CH(COOCH$_2$CH$_3$)CN |
| Ia.2443 | F | Cl | CH(COOCH$_2$CH$_3$)CN |
| Ia.2444 | Cl | Cl | CH(COOCH$_2$CH$_3$)CN |
| Ia.2445 | H | Cl | CH$_2$CH(Br)COOCH$_3$ |
| Ia.2446 | F | Cl | CH$_2$CH(Br)COOCH$_3$ |
| Ia.2447 | Cl | Cl | CH$_2$CH(Br)COOCH$_3$ |
| Ia.2448 | H | Cl | CH$_2$CH(I)COOCH$_3$ |
| Ia.2449 | F | Cl | CH$_2$CH(I)COOCH$_3$ |
| Ia.2450 | Cl | Cl | CH$_2$CH(I)COOCH$_3$ |
| Ia.2451 | H | Cl | CH$_2$CH(Cl)COOC$_2$H$_5$ |
| Ia.2452 | F | Cl | CH$_2$CH(Cl)COOC$_2$H$_5$ |
| Ia.2453 | Cl | Cl | CH$_2$CH(Cl)COOC$_2$H$_5$ |
| Ia.2454 | H | Cl | CH$_2$CH(Br)COOC$_2$C$_5$ |
| Ia.2455 | F | Cl | CH$_2$CH(Br)COOC$_2$H$_5$ |
| Ia.2456 | Cl | Cl | CH$_2$CH(Br)COOC$_2$H$_5$ |
| Ia.2457 | H | Cl | CH(COOCH$_3$)CH$_2$F |
| Ia.2458 | F | Cl | CH(COOCH$_3$)CH$_2$F |
| Ia.2459 | Cl | Cl | CH(COOCH$_3$)CH$_2$F |
| Ia.2460 | H | Cl | CH(COOCH$_3$)CH$_2$Cl |
| Ia.2461 | F | Cl | CH(COOCH$_3$)CH$_2$Cl |
| Ia.2462 | Cl | Cl | CH(COOCH$_3$)CH$_2$Cl |
| Ia.2463 | H | Cl | CH(COOCH$_3$)CH$_2$Br |
| Ia.2464 | F | Cl | CH(COOCH$_3$)CH$_2$Br |
| Ia.2465 | Cl | Cl | CH(COOCH$_3$)CH$_2$Br |
| Ia.2466 | H | Cl | CH(COOCH$_3$)CH$_2$I |
| Ia.2467 | F | Cl | CH(COOCH$_3$)CH$_2$I |
| Ia.2468 | Cl | Cl | CH(COOCH$_3$)CH$_2$I |

TABLE 5-continued

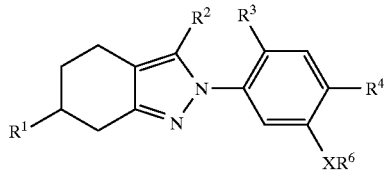

($R^1$ = H; $R^2$ = Cl; X = O)

| No. | $R^3$ | $R^4$ | $R^6$ |
|---|---|---|---|
| Ia.2469 | H | Cl | CH(COOC$_2$H$_5$)CH$_2$F |
| Ia.2470 | F | Cl | CH(COOC$_2$H$_5$)CH$_2$F |
| Ia.2471 | Cl | Cl | CH(COOC$_2$H$_5$)CH$_2$F |
| Ia.2472 | H | Cl | CH(COOC$_2$H$_5$)CH$_2$Cl |
| Ia.2473 | F | Cl | CH(COOC$_2$H$_5$)CH$_2$Cl |
| Ia.2474 | Cl | Cl | CH(COOC$_2$H$_5$)CH$_2$Cl |
| Ia.2475 | H | Cl | CH(COOC$_2$H$_5$)CH$_2$Br |
| Ia.2476 | F | Cl | CH(COOC$_2$H$_5$)CH$_2$Br |
| Ia.2477 | Cl | Cl | CH(COOC$_2$H$_5$)CH$_2$Br |
| Ia.2478 | H | Cl | CH(COOC$_2$H$_5$)CH$_2$I |
| Ia.2479 | F | Cl | CH(COOCH$_2$CH$_3$)CH$_2$I |
| Ia.2480 | Cl | Cl | CH(COOCH$_2$CH$_3$)CH$_2$I |
| Ia.2481 | H | Cl | CH$_2$CH(CN)CO—OCH$_3$ |
| Ia.2482 | F | Cl | CH$_2$CH(CN)CO—OCH$_3$ |
| Ia.2483 | Cl | Cl | CH$_2$CH(CN)CO—OCH$_3$ |
| Ia.2484 | H | Cl | CH(COOCH$_2$CH$_3$)CH$_2$CN |
| Ia.2485 | F | Cl | CH(COOCH$_2$CH$_3$)CH$_2$CN |
| Ia.2486 | Cl | Cl | CH(COOCH$_2$CH$_3$)CH$_2$CN |

Other particularly preferred N-phenyltetrahydroindazoles I are those which follow:

compounds Ib.001–Ib.2486, which differ from the compounds Ia.001–Ia.2486 in that $R^1$ is methyl:

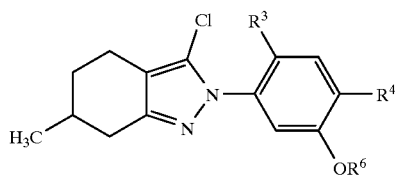

($R^1$ = CH$_3$;
$R^2$ = Cl;
X = O)

compounds Ic.001–Ic.2486, which differ from the compounds Ia.001–Ia.2486 in that $R^2$ is methyl:

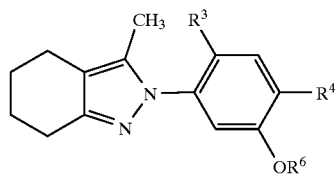

($R^1$ = H;
$R^2$ = CH$_3$;
X = O)

compounds Id.001–Id.2486, which differ from the compounds Ia.001–Ia.2486 in that $R^1$ and $R^2$ are methyl:

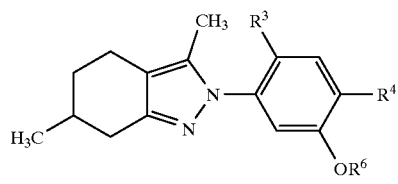

($R^1$ = CH$_3$;
$R^2$ = CH$_3$;
X = O)

compounds Ie.001–Ie.2486, which differ from the compounds Ia.001–Ia.2486 in that $R^2$ is trifluoromethyl:

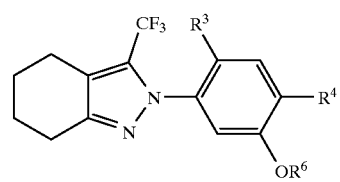

($R^1$ = H;
$R^2$ = CF$_3$;
X = O)

compounds If.001–If.2486, which differ from the compounds Ia.001–Ia.2486 in that R1 is methyl and $R^2$ is trifluoromethyl:

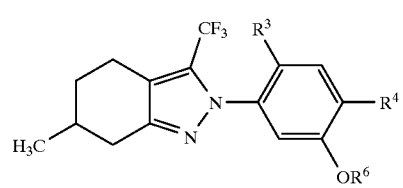

($R^1$ = CH$_3$;
$R^2$ = CF$_3$;
X = O)

compounds Ig.001–Ig.2486, which differ from the compounds Ia.001–Ia.2486 in that X is sulfur:

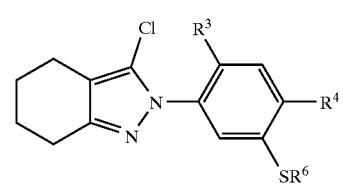

($R^1$ = H;
$R^2$ = Cl;
X = S)

compounds Ih.001–Ih.2486, which differ from the compounds Ia.001–Ia.2486 in that $R^1$ is methyl and X is sulfur:

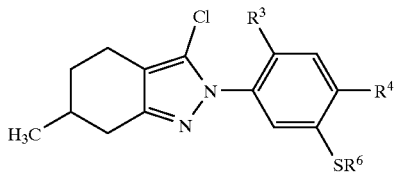

($R^1$ = $CH_3$;
$R^2$ = Cl;
X = S)

compounds Ii.001–Ii.2486, which differ from the compounds Ia.001–Ia.2486 in that X is —SO—:

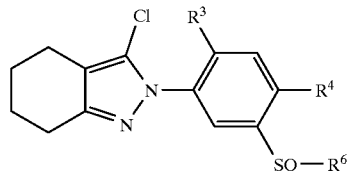

($R^1$ = H;
$R^2$ = Cl;
X = SO)

compounds Ik.001–Ik.2486, which differ from the compounds Ia.001–Ia.2486 in that X is —$SO_2$—:

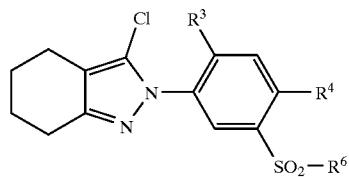

($R^1$ = H;
$R^2$ = Cl;
X = $SO_2$)

compounds Il.001–Il.2486, which differ from the compounds Ia.001–Ia.2486 in that $R^2$ is trifluoromethyl and $R^5$ is —$SR^6$:

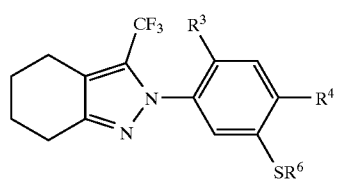

($R^1$ = H;
$R^2$ = $CF_3$;
X = S)

Very particularly preferred compounds of the formula I are those in which $R^2$ is halogen, X is oxygen or sulfur and $R^7$ is cyano or halogen.

The N-phenyltetrahydroindazoles I can be obtained by various routes, for example by one of the following processes (A–Q):

Process A

Conversion of alcohols or mercaptans II in a manner known per se (cf., for example, Houben-Weyl, Vol. VI/3, p. 24, and Vol. IX, pp. 103 et seq.) into compounds I where $R^7$ is —$OR^{11}$ or —$SR^{11}$:

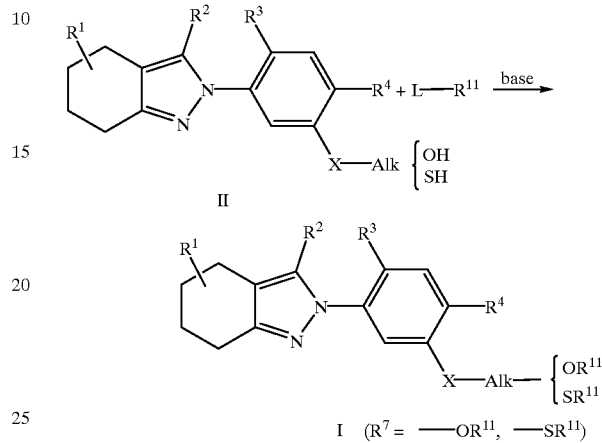

L is a customary leaving group, such as halogen, preferably chlorine, bromine or iodine, (halo)alkylsulfonyloxy, preferably methylsulfonyloxy or trifluoromethylsulfonyloxy, arylsulfonyloxy, preferably toluenesulfonyloxy, and alkoxysulfonyloxy, preferably methoxysulfonyloxy or ethoxysulfonyloxy.

The reaction is expediently carried out in an inert solvent, for example in an ether, such as diethyl ether, methyl tert-butyl ether, dimethoxyethane, diethylene glycol dimethyl ether, tetrahydrofuran and dioxane, a ketone, such as acetone, diethyl ketone, ethyl methyl ketone and cyclohexanone, a dipolar aprotic solvent, such as acetonitrile, dimethylformamide, N-methylpyrrolidone and dimethyl sulfoxide, a protic solvent, such as methanol and ethanol, an aromatic hydrocarbon which may be halogenated, such as benzene, chlorobenzene and 1,2-dichlorobenzene, a heteroaromatic solvent, such as pyridine and quinoline, or in a mixture of these. Preferred substances are tetrahydrofuran, acetone, diethyl ketone and dimethylformamide.

Suitable bases are, e.g., the hydroxides, hydrides, alkoxides, carbonates or hydrogen carbonates of alkali metal and alkaline earth metal cations, tertiary aliphatic amines, such as triethylamine, N-methylmorpholine and N-ethyl-N,N-diisopropylamine, bi- and tricyclic amines, such as diazabicycloundecane (DBU) and diazabicyclooctane (DABCO), or aromatic nitrogen bases, such as pyridine, 4-dimethylaminopyridine and quinoline. Combinations of different bases are also suitable. Preferred bases are sodium hydride, sodium hydroxide, sodium carbonate, potassium carbonate, sodium methoxide, sodium ethoxide and potassium tert-butoxide.

The starting materials are conventionally employed in an approximately stoichiometric ratio, but an excess of one or the other component may be advantageous as regards process control or as complete a reaction of II as possible.

The molar ratio of alcohol or mercaptan II to base is generally 1:1 to 1:3.

The concentration of the starting materials in the solvent is normally 0.1 to 5.0 mol/l.

The reaction can be carried out at from 0° C. to the reflux point of the solvent, or solvent mixture, in question.

Process B

Reaction of a compound III with an alcohol or thiol IV in a manner known per se (cf., for example, Houben-Weyl, Vol. VI/3, pp. 24 et seq., and Vol. IX, pp. 103 et seq.) in the presence of a base to give compounds I where $R^7$ is $-OR^{11}$ or $-SR^{11}$:

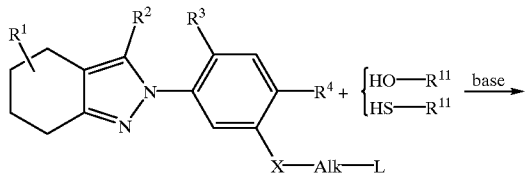

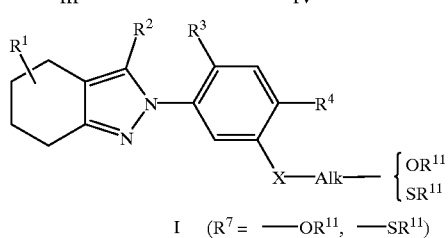

L is a customary leaving group. Examples are listed under process A).

With regard to the solvents, bases, the concentration of the starting materials in the solvent and the reaction temperature, the information given under process A) also applies here.

The starting materials are expediently employed in approximately stoichiometric amounts, but an excess of one or the other component may be advantageous with regard to process control or as complete a reaction of III as possible. The molar ratio of alcohol or thiol IV to base is preferably 1:1 to 1:3.

Process C

Oxidation of compounds V where $R^7$ is $-SR^{11}$ to give compounds I where $R^7$ is $-S-R^{11}$ in a manner known per se (cf., for example, Houben-Weyl, Methoden der Organischen Chemie, Vol. E11/1, pp. 702 et seq., and Vol. IX, p. 211):

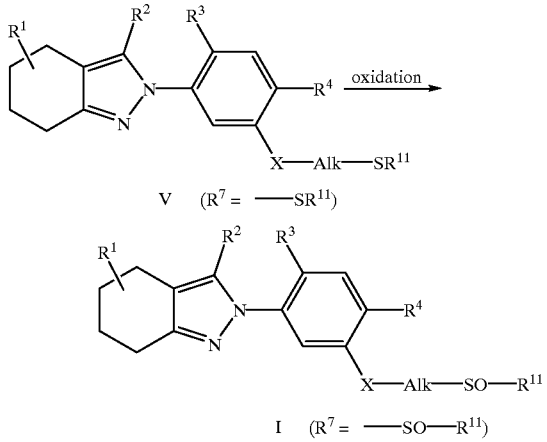

Suitable oxidants are, e.g., hydrogen peroxide, organic peroxides, such as peracetic acid, trifluoroperacetic acid, m-chloroperbenzoic acid, tert-butyl hydroperoxide and tert-butyl hypochlorite, and inorganic compounds, such as sodium metaiodate, chromic acid and nitric acid.

Depending on the oxidant, the process is generally carried out in an organic acid, such as acetic acid or trichloroacetic acid, in a chlorinated hydrocarbon, such as methylene chloride, chloroform or 1,2-dichloroethane, in an aromatic hydrocarbon, such as benzene, chlorobenzene or toluene, or in a protic solvent, such as methanol or ethanol. Mixtures of these are also suitable.

The reaction is generally carried out at from -30° C. to the boiling point of the reaction mixture in question, the lower temperature range normally being preferred.

Starting compound and oxidant are expediently employed in approximately stoichiometric ratio, but one or the other component can also be employed in an excess.

Process D

Oxidation of compounds VI in a manner known per se (cf., for example, Houben-Weyl, Methoden der Organischen Chemie, Vol. E11/2, pp. 1132 et seq., and Vol. IX, pp. 222 et seq.) to give compounds I where $R^7$ is $-SO_2-R^{11}$:

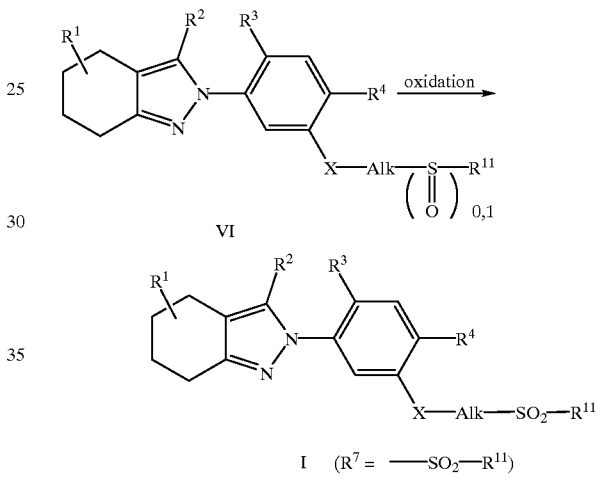

Suitable oxidants are, for example, hydrogen peroxide, organic peroxides, such as acetic acid peroxide, trifluoroacetic acid peroxide and m-chloroperbenzoic acid, and furthermore inorganic oxidants, such as potassium permanganate. The presence of a catalyst, for example tungstate, can have a positive effect on the course of the reaction.

As a rule, the reaction is carried out in an inert solvent. Depending on the oxidant, suitable substances are, for example, organic acids, such as acetic acid and propionic acid, chlorinated hydrocarbons, such as methylene chloride, chloroform and 1,2-dichloroethane, aromatic hydrocarbons or halohydrocarbons, such as benzene, chlorobenzene or toluene, or water. Mixtures of these are also suitable.

The process is normally carried out at from -30° C. to the boiling point of the reaction mixture in question, preferably at from 10° C. to the boiling point.

Starting compound VI ($R^7=-SR^{11}$ or $-S-R^{11}$) and oxidant are expediently employed in approximately stoichiometric amounts. However, an excess of oxidant can be advantageous for optimizing the conversion rate of the starting compound.

Process E

Reaction of a compound III in a manner known per se (cf., for example, Houben-Weyl, Methoden der Organischen Chemie, Vol. VIII, pp. 293 et seq., and Vol. IX, p. 857) with a cyanide or thiocyanate M-$R^7$:

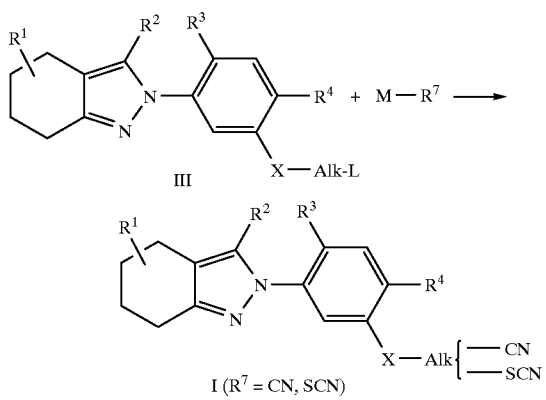

L is a customary leaving group. Examples are given under process A);

M is an alkali, alkaline earth or transition metal, in particular sodium, potassium, silver or copper.

The reaction can be carried out without a solvent or in an inert solvent. Depending on the starting compounds and on the solvent, it may be advantageous to carry out the process under phase-transfer conditions, a catalytic amount of phase-transfer catalyst, for example between 1 and 10 mol % based on III, generally being sufficient.

Suitable solvents are, for example, ethers, such as dimethoxyethane and diethylene glycol dimethyl ether, aromatic hydrocarbons, such as benzene and toluene, dipolar aprotic solvents, such as acetonitrile, dimethylformamide, diethylformamide, N-methylpyrrolidone and dimethyl sulfoxide, and protic solvents, e.g. water. Mixtures of these are also suitable.

Suitable phase-transfer catalysts are, for example, ammonium, sulfonium or phosphonium salts, the type of anion being of less importance. Examples which have proved to be expedient are benzyltrimethylammonium salts, such as benzyltrimethylammonium hydroxide, and tetrabutylammonium salts.

The process is normally carried out at from 0° C. to the boiling point of the reaction mixture, preferably in the upper temperature range.

The starting compounds III and M-R$^7$ are expediently employed in an approximately stoichiometric ratio. However, it is also possible to employ an excess of one of the components, for example so that the other component is converted as completely as possible, or to use one of the components simultaneously as the solvent.

Process F

Halogenation of a compound VII in a manner known per se (cf., for example, Houben-Weyl, Methoden der Organischen Chemie, Vol. 5/3 and Vol. 5/4):

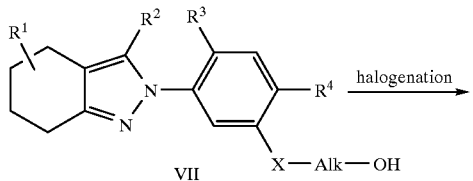

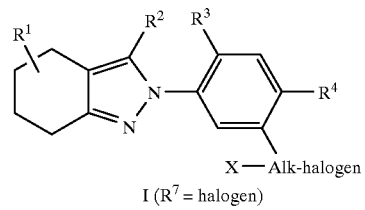

Suitable halogenating agents are, for example, hydrogen halides, such as hydrogen chloride, hydrogen bromide and hydrogen iodide, thionyl chloride, thionyl bromide, sulfuryl chloride, sulfuryl bromide, organic sulfonyl chlorides, such as tosyl chloride, furthermore phosphorus trichloride, phosphorus tribromide, phosphorus pentachloride, phosphorus pentabromide, diphosphorus tetraiodide, phosphorus oxychloride, phosphorus oxybromide, binary halogenating systems, such as tetrachloromethane/triphenylphosphine, tetrabromomethane/triphenylphosphine, and furthermore sulfur fluorine compounds, such as diethylamino sulfur trifluoride.

If a hydrogen halide is used, it may be advantageous to carry out the process in the presence of a dehydrater, such as sulfuric acid.

The reaction can be carried out in the absence of a solvent in an excess of the halogenating agent or else in an inert solvent which depends on the halogenating agent.

Suitable solvents are generally halogenated hydrocarbons, such as methylene chloride and chloroform, aromatic hydrocarbons and halohydrocarbons, such as benzene, toluene and chlorobenzene, dipolar aprotic solvents, such as acetonitrile, furthermore, carbon disulfide, ethers, such as diethyl ether, methyl tert-butyl ether and tetrahydrofuran, and mixtures of these.

The reaction can be carried out at from −30° C. to the boiling point of the reaction mixture. It is preferably carried out in the upper temperature range.

Depending on the halogenating agent, the starting compound VII is expediently employed in stoichiometric or substoichiometric amounts. If the process is carried out in the absence of a solvent, a large excess of halogenating agent will be useful.

Process G

Halogen exchange of compounds I where R$^7$ is chlorine or bromine in a manner known per se (cf., for example, Houben-Weyl, Methoden der Organischen Chemie, Vol. 5/3, pp. 145 et seq., and Vol. 5/4, pp. 595 et seq.):

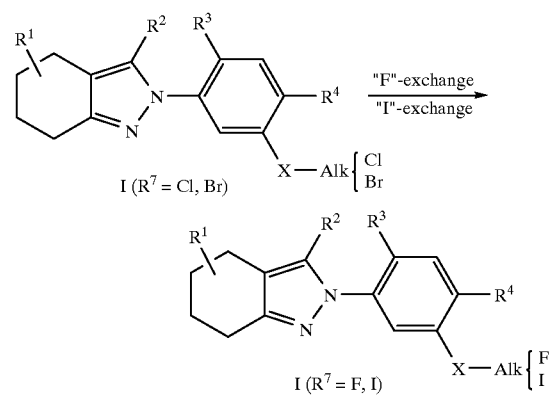

Suitable fluorinating and iodizing reagents are, for example, metal fluorides and iodides, in particular alkali metal fluorides and iodides, antimony fluoride, and organic fluorinating agents, such as diethylamino sulfur trifluoride.

The choice of solvent will depend on the fluorinating or iodizing agent. In general, aprotic solvents, such as acetone, diethyl ketone, methyl ethyl ketone, dimethylformamide, diethylformamide, N-methylpyrrolidone, dimethyl sulfoxide and sulfolane, chlorinated hydrocarbons, such as methylene chloride, chloroform and chlorobenzene, or mixtures of these are generally suitable.

The reaction is generally carried out at from −30° C. to the boiling point of the reaction mixture in question.

Starting compound and fluorinating or iodizing agent are conventionally employed in an approximately stoichiometric ratio. However, it may be advantageous to employ an excess of fluorinating or iodizing agent to optimize the conversion rate of I where $R^7$ is chlorine or bromine.

The starting compounds I where $R^7$ is chlorine or bromine can be obtained, for example, by one of processes F, H and L–Q.

Process H

Addition reaction of hydrogen chloride, hydrogen bromide or hydrogen iodide with an alkene VIII in a manner known per se (cf., for example, Houben-Weyl, Methoden der Organischen Chemie, Vols. 4 and 5):

The process is normally carried out in an inert organic solvent, for example an aromatic hydrocarbon or halohydrocarbon, such as benzene, toluene and chlorobenzene, in an ether, such as diethyl ether and methyl tert-butyl ether, or in a mixture of these.

The reaction is generally carried out at from 0° C. to the boiling point of the reaction mixture in question.

The hydrohalic acid is generally employed in a large excess, but it is also possible to employ VIII and hydrohalic acid in an approximately stoichiometric ratio.

Depending on the particular starting compound VIII, it may be advantageous to carry out the reaction under superatmospheric pressure.

Process I

Elimination of water from aldoximes IX in a manner known per se (cf., for example, Houben-Weyl, Methoden der Organischen Chemie, Vol. X/4, pp. 226 et seq., and Vol. E 5/2, pp. 1318 et seq.):

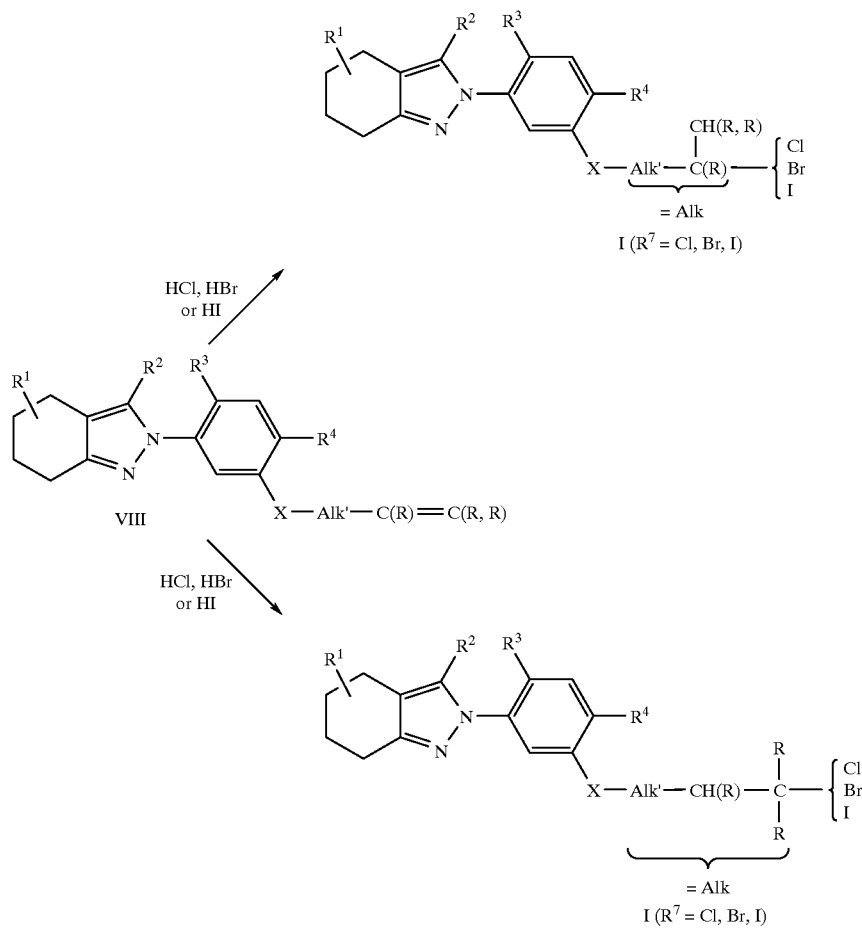

Alk' is a carbon chain which is shorter by 1 or 2 C atoms than the chain Alk desired in the end product I;

R radicals are in each case hydrogen or as defined for $R^8$ or $R^9$.

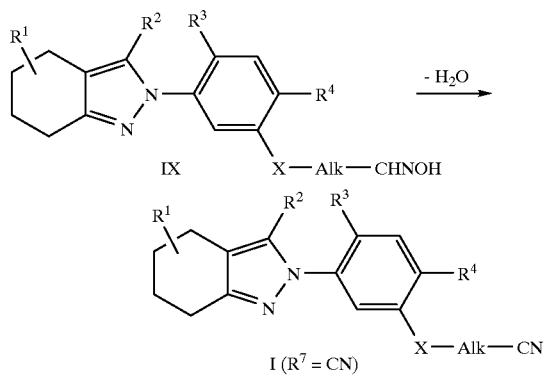

Water may be eliminated for example using anhydrides, such as acetic anhydride, trifluoroacetic anhydride and propionic anhydride, acid chlorides, such as mesyl chloride, trifluoromethylsulfonyl chloride, thionyl chloride, phosgene, diphosgene, phosphorus oxychloride and phosphorus pentachloride, or by means of carbonyl diimidazole or dicyclohexylcarbodiimide.

The reaction is carried out either in the absence of a solvent in an excess of dehydrater or else in an inert solvent or diluent.

Generally suitable as solvents or diluents are, for example, halogenated hydrocarbons, such as methylene chloride, chloroform and 1,2-dichloroethane, aromatic hydrocarbons, such as benzene, toluene and chlorobenzene, ethers, such as diethyl ether and methyl tert-butyl ether, and dipolar aprotic solvents, such as acetonitrile. Mixtures of these are also suitable.

Depending on the reactants, the presence of an organic base, such as triethylamine, pyridine, piperidine or quinoline, may be advantageous. An equimolar amount based on IX or an excess may be employed.

As a rule, the process is carried out using approximately equimolar amounts or an excess of dehydrater, based on the aldoxime IX.

The reaction is generally carried out at from $-20°$ C. to the boiling point of the reaction mixture.

The aldoxime IX, in turn, can be obtained in a manner known per se (cf., for example, Houben-Weyl, Methoden der Organischen Chemie, Vol. X/4, pp. 1 et seq.) by reacting aldehydes of the formula X with hydroxylamine or with suitable hydroxylamine derivatives, such as disodium hydroxylaminedisulfonate and hydroxylamine hydrochloride:

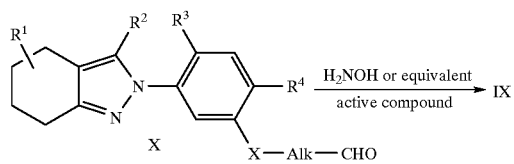

As a rule, the process is carried out in an inert, in particular a protic, solvent, for example in water, in an alcohol, such as methanol, ethanol and isopropanol, in a dipolar aprotic solvent, such as acetonitrile, or in a mixture of these.

Depending on which compound is chosen in place of hydroxylamine, the presence of a base, for example an alkali metal hydroxide or alkaline earth metal hydroxide, such as sodium hydroxide, potassium hydroxide or calcium hydroxide, an alkali metal hydride, such as sodium hydride or potassium hydride, an alkali metal carbonate or alkaline earth metal carbonate, such as sodium carbonate, potassium carbonate or calcium carbonate, or an alkali metal hydrogen carbonate, such as sodium hydrogen carbonate or potassium hydrogen carbonate, or of an acid, for example a hydrohalic acid, such as hydrochloric acid or hydrobromic acid, or an aliphatic carboxylic acid, such as acetic acid, may be advantageous.

Equimolar amounts of base or an excess of up to approximately 10 mol %, based on the amount of X, are preferred.

The starting materials are conventionally employed in an approximately stoichiometric ratio, but an excess of one or the other component may occasionally be advantageous.

The reaction can be carried out at $-30°$ C. to the boiling point of the reaction mixture in question.

Process K

Dehydration of carboxamides XI in a manner known per se (cf., for example, Houben-Weyl, Methoden der Organischen Chemie, Vol. VIII, p. 330 et seq.):

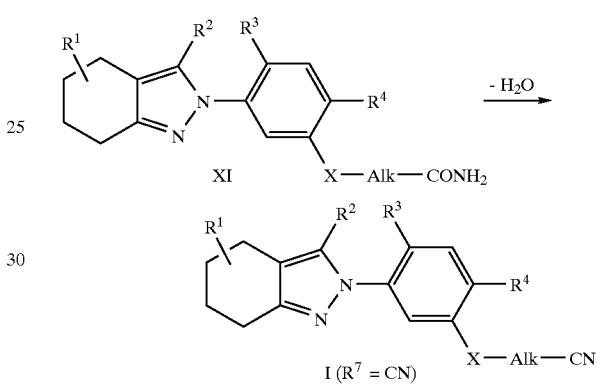

Dehydraters which can be used are, for example, "chlorinating agents", such as phosphorus pentachloride, phosphorus oxychloride, phosphorus trichloride, thionyl chloride, sulfuryl chloride, phosgene and diphosgene, anhydrides, such as acetic anhydride, trifluoroacetic anhydride, propionic anhydride and phosphorus pentoxide, furthermore sulfuric acid, phosphoric acid, sulfonic acids such as p-toluenesulfonic acid, trifluoromethylsulfonic acid and methanesulfonic acid, Lewis acids such as aluminum chloride and boron trifluoride, and also benzotrichloride in the presence of a catalyst such as zinc chloride and iron chloride. Thermal dehydration in the presence of catalysts such as aluminum oxide, sand, pumice and glass is also possible.

Depending on the dehydrater in question, it may be advantageous to carry out the process in the presence of a base, for example a tertiary amine or pyridine.

The reaction is carried out either in the absence of a solvent in an excess of dehydrater or else in an inert solvent or diluent.

Examples of suitable solvents or diluents are generally halogenated hydrocarbons, such as methylene chloride, chloroform and 1,2-dichloroethane, aromatic hydrocarbons and halohydrocarbons such as benzene, toluene and chlorobenzene, ethers, for example diethyl ether, methyl tert-butyl ether and tetrahydrofuran, dipolar aprotic solvents, such as acetonitrile, dimethylformamide and dimethyl sulfoxide, or mixtures of these.

Dehydraters and carboxamide XI are normally reacted with each other in an approximately stoichiometric ratio unless an excess of dehydrater is expedient for optimizing the conversion rate of XI.

In general, the process is carried out at from −30° C. to the boiling point of the reaction mixture in question.

Process L

Reaction of a phenol or thiophenol of the formula XII in a manner known per se (cf., for example, Houben-Weyl, Methoden der Organischen Chemie, Vol. VI/3, pp. 54 et seq., and Vol. IX, pp. 103 et seq.) with a compound of the formula XIII:

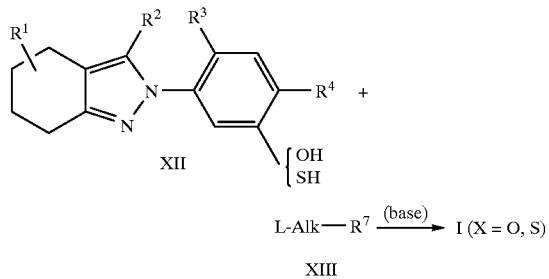

L is a customary leaving group. Examples have been mentioned under process A.

The process is generally carried out in an inert solvent or diluent, if desired in the presence of a base.

As regards solvents, bases, the concentration of the starting materials in the solvent and the reaction temperature, the information given under process A) applies.

It is expedient to employ the starting substances XII and XIII in approximately stoichiometric amounts, but an excess of one or the other component may be advantageous with regard to process control or as complete a conversion of XII or XIII as possible.

The molar ratio of phenol or thiophenol XII to base is preferably 1:1 to 1:3.

Process M

Reaction of phenols XIV with alcohols HO—Alk—$R^7$ (XV) by the method of Mitsunobu (cf. O. Mitsunobu, Synthesis 1981, 1) or by a variant of this method to give compounds I where X is oxygen:

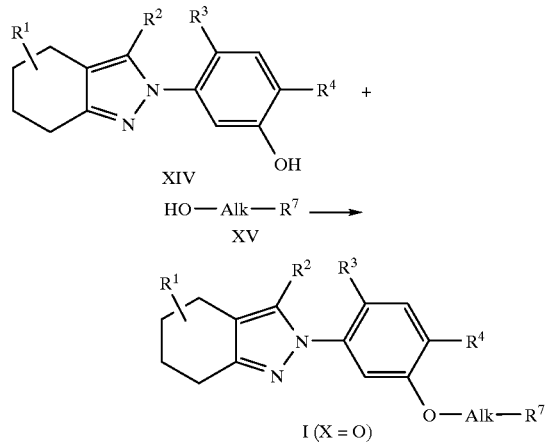

The process is normally carried out in an inert solvent, for example in an ether, such as diethyl ether, methyl tert-butyl ether, THF and dioxane, in a ketone, such as diethyl ketone, acetone and ethyl methyl ketone, in an aromatic hydrocarbon or halohydrocarbon, such as benzene, toluene or 1,2-dichlorobenzene, in a halogenated hydrocarbon, such as methylene chloride, chloroform or 1,2-dichloroethane, or in a mixture of these.

The reaction is generally carried out at from 0° C. to the boiling point of the reaction mixture in question.

The starting substances XIV and XV as well as the auxiliaries triphenylphosphine and azodicarboxylic ester (or compounds with an equivalent action), which are required for the Mitsunobu reaction, are generally employed in a stoichiometric ratio unless an excess of one or the other component is advantageous for optimizing the conversion rate of XIV or XV.

Process N

Oxidation of compounds I where X is sulfur in a manner known per se (cf., for example, Houben-Weyl, Methoden der Organischen Chemie, Vol. E11/1, p. 702 et seq., and Vol. IX, p. 211) to give compounds I where X is —S—:

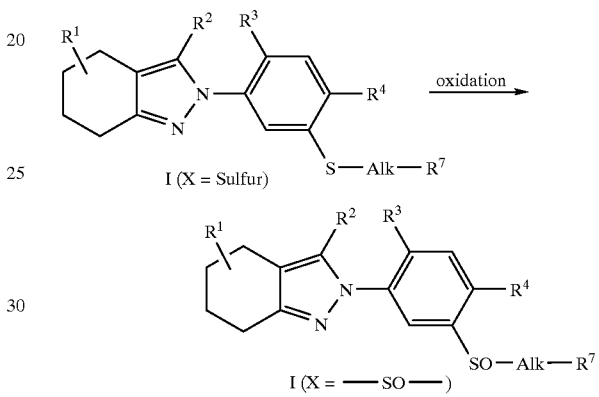

Suitable oxidants are, for example, hydrogen peroxide, organic peroxides, such as acetic acid peroxide, trifluoroacetic acid peroxide, m-chloroperbenzoic acid, tert-butyl hydroperoxide and tert-butyl hypochlorite, and furthermore organic oxidants, such as sodium metaiodate, chromic acid and nitric acid.

The compounds are generally reacted in an inert solvent, for example, organic acids, such as acetic acid and trifluoroacetic acid, chlorinated hydrocarbons, such as methylene chloride, chloroform and 1,2-dichloroethane, aromatic hydrocarbons or halohydrocarbons, such as benzene, chlorobenzene or toluene, and protic solvents, such as methanol and ethanol, depending on the oxidant used. Mixtures of these are also suitable.

The process is normally carried out at from −30° C. to the boiling point of the reaction mixture in question, preferably in the lower temperature range.

Starting compound I (X=S) and oxidant are expediently employed in approximately stoichiometric amounts. However, to optimize the conversion rate of the starting compound, an excess of oxidant may be advantageous.

Process O

Oxidation of compounds I where X is sulfur or —S—in a manner known per se (cf., for example, Houben-Weyl, Methoden der Organischen Chemie, Vol. E 11/2, pp. 1132 et seq., and Vol. IX, pp. 222 et seq.) to give compounds I where X is —$SO_2$—:

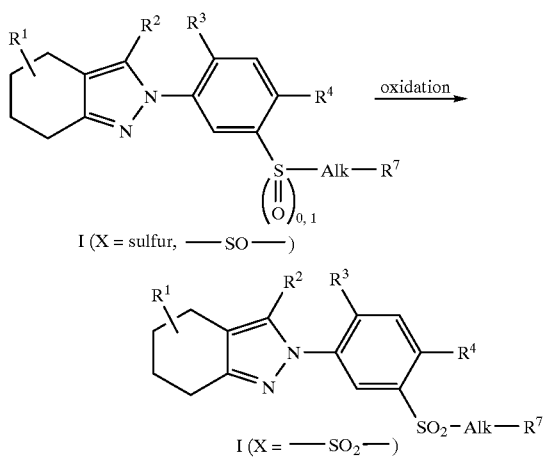

I (X = sulfur, —SO—)

I (X = —SO$_2$—)

Suitable oxidants are, for example, hydrogen peroxide, organic peroxides, such as acetic acid peroxide, trifluoroacetic acid peroxide and m-chloroperbenzoic acid, and furthermore inorganic oxidants, such as potassium permanganate.

Depending on the starting compound and the oxidant, it may be advantageous to carry out the process in the presence of a catalyst, for example tungstate.

The compounds are generally reacted in an inert solvent, for example, organic acids, such as acetic acid and propionic acid, chlorinated hydrocarbons, such as methylene chloride, chloroform and 1,2-dichloroethane, aromatic hydrocarbons or halohydrocarbons, such as benzene, chlorobenzene and toluene, and water, depending on the oxidant used. Mixtures of these are also suitable.

The process is normally carried out at from −30° C. to the boiling point of the reaction mixture in question, preferably at 10° C. to the boiling point.

Starting compound I (X=S or —S—) and oxidant are expediently employed in approximately stoichiometric amounts. However, to optimize the conversion rate of the starting compound, an excess of oxidant may be advantageous.

Process P

Reaction of a diketo compound XVI in a manner known per se (cf., for example, A. N. Kost, I.I. Grandberg, Advan. Heterocyclic Chem. 6, 358 (1966)) with a hydrazine XVII to give compounds I where $R^2$ is alkyl or haloalkyl:

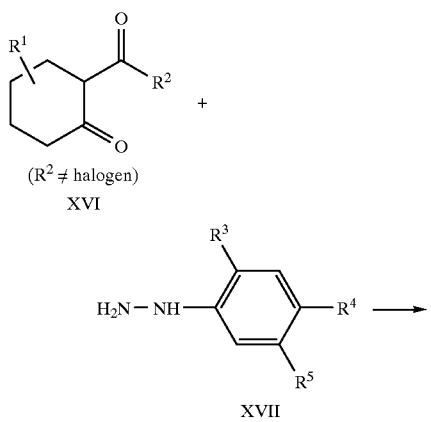

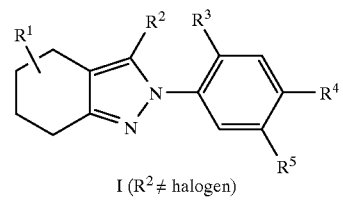

I ($R^2 \neq$ halogen)

The compounds are generally reacted in an inert solvent, for example in an organic acid, such as acetic acid, in a chlorinated hydrocarbon, such as methylene chloride and 1,2-dichloroethane, in an aromatic hydrocarbon or halohydrocarbon, such as benzene, toluene and chlorobenzene, a protic solvent, such as methanol, ethanol and isopropanol, or in water. Mixtures of these are also suitable.

Depending on the choice of the starting compounds and the particular solvent, it may be advantageous to carry out the process in the presence of catalytic amounts of acid, for example hydrochloric acid, sulfuric acid or p-toluenesulfonic acid.

The compounds are generally reacted at from −30° C. to the boiling point of the reaction mixture in question.

The two starting compounds are expediently employed in a stoichiometric ratio, but an excess of one or the other component is also possible.

Process Q

Halogenation of indazolones XVIII in a manner known per se (cf., for example, E. F. M. Stephenson, Org. Synth. Coll. Vol. III, 475 (1955)):

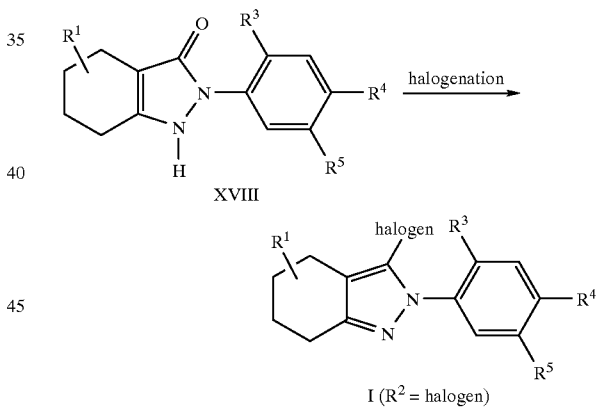

I ($R^2$ = halogen)

The reaction is carried out either in the absence of a solvent or in an inert solvent or diluent. If desired, it can be carried out in the presence of a base.

All customary halogenating agents are generally suitable. Examples which may be mentioned are oxychlorides, such as phosphorus oxychloride, oxybromides, such as phosphorus oxybromide, chlorides, such as phosphorus trichloride, phosphorus pentachloride and sulfur tetrachloride, bromides, such as phosphorus tribromide and phosphorus pentabromide, and furthermore thionyl chloride, thionyl bromide, phosgene and trichloromethyl chloroformate.

Useful solvents are, in particular, benzene, toluene and the xylenes.

Examples of suitable bases are tert-amines, such as triethylamine, diisopropylethylamine, N,N-dimethylaniline, N,N-dimethyl-p-aminopyridine, pyridine, isoquinoline, N-methylpyrrolidone, N,N,N',N'-tetramethylenediamine, 1,5-diazabicyclo(4,3,0)-non- 5-ene, 1,8-diazabicyclo(5,4,0) undec-7-ene, dimethylformamide and diethylformamide.

The reaction is preferably carried out at from 25 to 200° C., in particular at from 60 to 160° C.

For example, indazolone XVIII and halogenating agent can be employed in approximately stoichiometric amounts. If the reaction is carried out without an inert solvent, an excess of one of the components is generally used. To optimize the conversion rate of indazolone, an excess of halogenating agent may be advantageous.

The indazolones XVIII, in turn, can be obtained in a manner known per se by reacting cyclohexanonecarboxylic acid derivatives XIX with the hydrazines XVII in a suitable solvent:

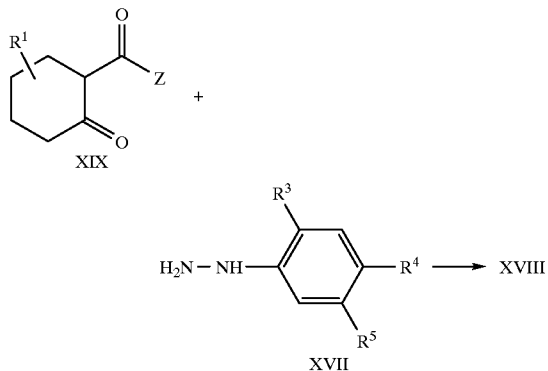

Z is a nucleophilic leaving group, such as halogen, e.g. chlorine or bromine, alcoholate, e.g. methanolate, ethanolate, propylate or isopropylate, or sulfonylate, e.g. mesylate or tosylate.

Customary solvents are lower alkanoic acids, such as acetic acid and propionic acid, or aprotic solvents, such as xylene, toluene and benzene. If desired, the process can be carried out in the presence of acidic catalysts, e.g. hydrochloric acid, sulfonic acid or p-toluenesulfonic acid. Mixtures of these are also suitable.

If, in formula XIX, Z is halogen, in particular chlorine or bromine, it may be advantageous to carry out the process in the presence of a tert-amine as the base. Examples of suitable tertamines are triethylamine, diisopropylethylamine, N,N-dimethylaniline, N,N-dimethyl-p-aminopyridine, pyridine, isoquinoline, N-methylpyrrolidone, N,N,N',N'-tetramethylenediamine, 1,5-diazabicyclo(4,3,0)non-5-ene, and 1,8-diazabicyclo(5,4, 0)undec-7-ene.

The compounds are normally reacted at from 0° C. to the reflux temperature of the reaction mixture in question.

The two starting compounds are expediently employed in approximately stoichiometric amounts, or a slight excess of one of the starting compounds is used.

Unless otherwise specified, all processes described above are expediently carried out under atmospheric pressure or under the inherent pressure of the reaction mixture in question.

Those starting compounds indicated for the individual processes which are not already known can be obtained in a manner known per se, for example also by one of the processes described.

When preparing the N-phenyltetrahydroindazoles of the formula I, mixtures of isomers may be obtained. If desired, these may be separated by the methods customary for this purpose, for example by means of crystallization or chromatography on an optically active adsorbate, to give the pure isomers. Pure optically active isomers can, for example, also be prepared from the corresponding optically active starting materials.

If desired, the N-phenyltetrahydroindazoles can be converted into acid addition salts or into their alkali metal salts.

Salts of the N-phenyltetrahydroindazoles I whose metal ion is other than an alkali metal ion can usually be prepared by double decomposition with the corresponding alkali metal salt.

Other metal salts, such as zinc, iron, calcium, magnesium and barium salts, can be prepared from the sodium salts in the customary manner, as can ammonium and phosphonium salts by means of ammonia or phosphonium, sulfonium or sulfoxonium hydroxides.

The compounds I and the agriculturally utilizable salts thereof are suitable as herbicides, both in the form of isomer mixtures and in the form of the pure isomers. They can very effectively control broad-leaf weeds and grass weeds in crops such as wheat, rice, maize, soya beans and cotton without damaging the crop plants to a more than negligible extent. This effect is observed especially at low application rates.

Depending on the method of application chosen, the compounds I, or herbicides comprising them, can be employed in other crop plants for eliminating undesirable plants. The following are examples of suitable crops:

Allium cepa, Ananas comosus, Arachis hypogaea, Asparagus officinalis, Beta vulgaris spp. altissima, Beta vulgaris spp. rapa, Brassica napus var. napus, Brassica napus var. napobrassica, Brassica rapa var. silvestris, Camellia sinensis, Carthamus tinctorius, Carya illinoensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus spp., Manihot esculenta, Medicago sativa, Musa spp., Nicotiana tabacum (N.rustica), Olea europaea, Oryza sativa, Phaseolus lunatus, Phaseolus vulgaris, Picea abies, Pinus spp., Pisum sativum, Prunus avium, Prunus persica, Pyrus communis, Ribes sylvestre, Ricinus communis, Saccharum officinarum, Secale cereale, Solanum tuberosum, Sorghum bicolor (S. vulgare), Theobroma cacao, Trifolium pratense, Triticum aestivum, Triticum durum, Vicia faba, Vitis vinifera and Zea mays.

In addition, the compounds I can be used in crops which have been rendered substantially resistant to the action of I by means of breeding and/or genetic engineering methods.

Moreover, the N-phenyltetrahydroindazoles I are also suitable for desiccating and/or defoliating plants.

As desiccants they are particularly suitable for desiccating the aerial parts of crop plants such as potatoes, oilseed rape, sunflower and soya beans. This allows completely mechanical harvesting of these important crop plants.

Another economically interesting aspect is facilitated harvesting, which is made possible by fall or reduced adherence to the tree of citrus fruit, olives and other species and varieties of pomaceous fruit, stone fruit and hard-shelled fruit being concentrated within a short period. The same mechanism, i.e. promotion of abscission tissue formation between fruit or leaf, on the one hand, and plant corm, on the other hand, is also important for readily controllable defoliation of useful plants, in particular cotton.

Moreover, a shortened period of time within which the individual cotton plants ripen also results in an improved post-harvest fiber quality.

The compounds I or the herbicides comprising them can be applied, for example, in the form of ready-to-spray aqueous solutions, powders, suspensions, even high-percentage aqueous, oily or other suspensions or dispersions, emulsions, oil dispersions, pastes, dusts, broadcasting agents or granules by means of spraying, atomizing, dusting, scattering or pouring. The use forms depend on the intended purpose; in any case they should guarantee as fine a distribution of the active compounds according to the invention as possible.

Suitable inert auxiliaries for the preparation of ready-to-spray solutions, emulsions, pastes or oil dispersions are mainly the following: mineral oil fractions of medium to high boiling point, such as kerosene and diesel oil, furthermore coaltar oils and oils of vegetable or animal origin, aliphatic, cyclic and aromatic hydrocarbons, e.g. paraffins, tetrahydronaphthalene, alkylated naphthalenes and derivatives thereof, alkylated benzenes and derivatives thereof, alcohols, e.g. methanol, ethanol, propanol, butanol and cyclohexanol, ketones, such as cyclohexanone, strongly polar solvents, e.g. amines, such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the substrates as such or dissolved in an oil or solvent can be homogenized in water with the aid of wetting agents, adhesives, dispersants or emulsifiers. However, concentrates may be prepared which are composed of active substance, wetting agent, adhesive, dispersant or emulsifier, and, if desired, solvent or oil and which are suitable for dilution with water.

Suitable surfactants are the alkali metal, alkaline earth metal and ammonium salts of aromatic sulfonic acids, e.g. lignosulfonic acid, phenolsulfonic acid, naphthalenesulfonic acid and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and of fatty alcohol glycol ether, condensation products of sulfonated naphthalene and derivatives thereof with formaldehyde, condensation products of naphthalene or naphthalenesulfonic acids with phenol and formaldehyde, polyoxyethylene octylphenol ether, ethoxylated isooctyl-, octyl- or nonylphenol, alkylphenol or tributylphenyl polyglycol ethers, alkylaryl polyether alcohols, isotridecyl alcohol, fatty alcohol ethylene oxide condensates, ethoxylated castor oil, polyoxyethylene alkyl ether or polyoxypropylene alkyl ether, lauryl alcohol polyglycol ether acetate, sorbitol esters, lignin-sulfite waste liquors or methylcellulose.

Powders, broadcasting agents and dusts can be prepared by mixing or grinding the active substances together with a solid carrier.

Granules, e.g. coated, impregnated and homogeneous granules, can be prepared by binding the active compounds to solid carriers. Solid carriers are mineral earths, such as silicic acids, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers, such as ammonium sulfate, ammonium phosphate, ammonium nitrate, ureas and vegetable products, such as cereal meal, treebark meal, wood meal and nutshell meal, cellulose powder or other solid carriers.

The concentrations of the active compounds I in the ready-to-use preparations can be varied within wide ranges, such as from 0.01 to 95% by weight, preferably from 0.5 to 90% by weight. The active compounds are employed in a purity of from 90% to 100%, preferably 95% to 100% (according to NMR spectrum).

The following formulation examples illustrate the production of such preparations:

I. 20 parts by weight of compound No. 1 are dissolved in a mixture which is composed of 80 parts by weight of alkylated benzene, 10 parts by weight of the adduct of from 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. By pouring and finely dispersing the solution in 100,000 parts by weight of water, an aqueous dispersion is obtained which comprises 0.02% by weight of the active compound.

II. 20 parts by weight of compound No. 5 are dissolved in a mixture which is composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. By pouring and finely dispersing the solution in 100,000 parts by weight of water, an aqueous dispersion is obtained which comprises 0.02% by weight of the active compound.

III. 20 parts by weight of active compound No. 7 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. By pouring and finely dispersing the solution in 100,000 parts by weight of water, an aqueous dispersion is obtained which comprises 0.02% by weight of the active compound.

IV. 20 parts by weight of active compound No. 15 are mixed thoroughly with 3 parts by weight of sodium diisobutylnaphthalene-α-sulfonate, 17 parts by weight of the sodium salt of a lignosulfonic acid from a sulfite waste liquor and 60 parts by weight of powdered silica gel and the mixture is ground in a hammer mill. By finely dispersing the mixture in 20,000 parts by weight of water, a spray mixture is obtained which comprises 0.1% by weight of the active compound.

V. 3 parts by weight of active compound No. 19 are mixed with 97 parts by weight of finely divided kaolin. This gives a dust which comprises 3% by weight of the active compound.

VI. 20 parts by weight of active compound No. 21 are intimately mixed with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. A stable oily dispersion is obtained.

The active compounds I, or their herbicides, can be applied pre-or post-emergence. If the active compounds are less compatible with certain crop plants, application techniques can be used in which the herbicides are sprayed with the aid of spray equipment in such a manner that the leaves of the sensitive crop plants are not affected if possible while the active compounds reach the leaves of undesirable plants which grow under them, or the uncovered soil surface (post-directed, lay-by).

Depending on the desired control effect, the season, the target plants and the growth stage, active compound I is applied at 0.001 to 3.0, preferably 0.01 to 1, kg/ha of active substance (a.s.).

To broaden the spectrum of action and to achieve synergistic effects, the N-phenyltetrahydroindazoles I can be mixed with a large number of representatives of other groups of herbicidal or growth-regulating active compounds and this mixture then applied.

Suitable components in mixtures are, for example, diazines, 4H-3,1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofurane derivatives, cyclohexane-1,3-dione derivatives which have attached to them in the 2-position for example a carboxyl or carbimino group, quinolinecarboxylic acid derivatives, imidazolinones, sulfonamides, sulfonylureas, aryloxy- and heteroaryloxyphenoxypropionic acids, the salts, esters and amides of these, and others.

It may additionally be useful to apply the compounds I, on their own or in combination with other herbicides, together with further crop protection agents, for example with pesticides or compositions for controlling phytopathogenic fungi or bacteria. Also of interest is the miscibility with mineral salt solutions which are employed for eliminating nutritional and trace element deficiencies. Non-phytotoxic oils and oil concentrates may also be added.

PREPARATION EXAMPLES

Example 1

3-Chloro-2-(4-chloro-5-cyanomethoxy-2-fluorophenyl)-4,5,6,7-tetrahydroindazole (compound 5)

4.52 g of 3-chloro-2-(4-chloro-2-fluoro-5-hydroxyphenyl)-4,5,6,7-tetrahydroindazole in 10 ml of diethyl ketone were added dropwise at approximately 20° C. to a suspension of 2.07 g of potassium carbonate and 2.49 g of potassium iodide in 150 ml of diethyl ketone. The reaction mixture was subsequently treated with 1.86 g of bromoacetonitrile in 10 ml of diethyl ketone. After the mixture had been refluxed for 10 hours, it was cooled, and the solvent was then removed. The residue was taken up in water, whereupon the solids formed were removed, washed with water and finally dried under reduced pressure at approximately 20° C. Yield: 3.20 g Example 2

3-Chloro-2-[4-chloro-2-fluoro-5-(1',1',1'-trifluoroeth-2'-oxy)-phenyl]-4,5,6,7-tetrahydroindazole (compound 11)

3.01 g of 3-chloro-2-(4-chloro-2-fluoro-5-hydroxyphenyl)-4,5,6,7-tetrahydroindazole in 10 ml of dimethylformamide and 2.10 g of 2,2,2-trifluoro-1-iodoethane in 10 ml of dimethylformamide were added dropwise at approximately 20° C. to a suspension of 1.38 g of potassium carbonate in 50 ml of dimethylformamide. After the mixture had been refluxed for 4 hours, it was cooled and the solvent subsequently removed. The residue was taken up in water, whereupon the solid formed was separated off and washed with water and dried under reduced pressure at 40° C. Yield: 2.84 g.

Example 3

3-Chloro-2-(4-chloro-3-(1'-fluoroprop-3'-oxy) phenyl)-4,5,6,7-tetrahydroindazole (compound 27)

2.88 g of triphenylphosphine were added to a mixture of 2.83 g of 3-chloro-2-(4-chloro-3-hydroxyphenyl)-4,5,6,7-tetrahydroindazole, 0.78 g of 1-fluoro-3-propanol and 60 ml of tetrahydrofuran. 5.04 g of diethyl azodicarboxylate in a mixture of 10 ml of toluene and 10 ml of tetrahydrofuran were subsequently added dropwise. After the mixture had been stirred at approximately 20° C. for 12 hours, a further 2.88 g of triphenylphosphine and 5.04 g of diethyl azodicarboxylate in a mixture of 10 ml of toluene and 10 ml of tetrahydrofuran were added to the reaction mixture. After the mixture had been stirred for a further 6 hours, it was treated with 1 ml of water and approximately 3 spatula-tipfuls of sodium sulfate. Stirring was continued at approximately 20° C. for 30 minutes, whereupon the solids were separated off. The filtrate was concentrated and the residue taken up in diethyl ether. The ether phase was filtered and the filtrate then concentrated. The crude product was purified by means of chromatography on silica gel (eluent: cyclohexane/methyl tert-butyl ether=3:1). Yield: 2.72 g.

Example 4

3-Chloro-2-[4-chloro-3-(1'-chloroeth-2'-oxy) phenyl]-4,5,6,7-tetrahydroindazole (compound 4)

11.2 g of 3-chloro-2-(4-chloro-3-hydroxyphenyl)-4,5,6,7-tetrahydroindazole in 20 ml of acetone were added dropwise to a suspension of 8.4 g of potassium carbonate and 10.0 g of potassium iodide in 200 ml of acetone. 8.8 g of 1-chloro-2-bromoethane in 10 ml of acetone were added to this mixture with stirring. There upon, the reaction mixture was refluxed for 5 hours and then cooled. After the solvent had been removed, a residue was obtained, and this was taken up in water. The aqueous phase was brought to a pH of 5-6 using dilute hydrochloric acid, during which process a solid precipitated which was separated off, washed with water and dried under reduced pressure at approximately 20° C. The crude product was purified by chromatography on silica gel (eluent: petroleum ether/diethyl ether=2:1). Yield: 4.0 g.

Example 5

3-Chloro-2-[4-chloro-3-(1'-cyanopent-1-oxy)phenyl] 4,5,6,7-tetrahydroindazole (compound 8)

Step 1

3-Chloro-2-[4-chloro-3-(1'-ethoxycarbonylpent-1'-oxy)phenyl]-4,5,6,7-tetrahydroindazole 6.2 g of ethyl 2-bromohexanoate in 10 ml of dimethylformamide were added dropwise at approximately 20° C. to a suspension of 8.0 g of 3-chloro-2-(4-chloro-3-hydroxyphenyl)-4,5,6,7-tetrahydroindazole and 4.1 g of potassium carbonate in 50 ml of dimethylformamide. After the reaction mixture had been refluxed for 5 hours, it was cooled and then treated with 150 ml of water. The mixture was subsequently extracted using methyl tert-butyl ether. The combined organic phases were dried over sodium sulfate and concentrated, whereupon the residue was dried under reduced pressure. Yield: 11.4 g.

Step 2

3-Chloro-2-[4-chloro-3-(1'-carboxypent-1'-oxy) phenyl]-4,5,6,7-tetrahydroindazole 10 g of 3-chloro-2-[4-chloro-3-(1'-ethoxycarbonylpent-1'-oxy)phenyl]-4,5,6,7-tetrahydroindazole in 10 ml of ethanol were added dropwise to a solution of 1.5 g of sodium hydroxide in 100 ml of ethanol. After the mixture had been stirred at approximately 20° C. for 12 hours, the solvent was removed. The residue was treated with water and acidified.

This gave a suspension whose solids were separated off, washed with water and dried under reduced pressure.

Yield: 9.1 g.

Step 3

3-Chloro-2-[4-chloro-3-(1'-chloroformylpent-1'-oxy) phenyl]-4,5,6,7-tetrahydroindazole 8.0 g of 3-chloro-2-[4-chloro-3-(1'-carboxypent-1'-oxy)phenyl]-4,5,6,7-tetrahydroindazole and 5.1 g of oxalyl chloride were refluxed for 5 hours in 150 ml of toluene. Then, a few drops of dimethylformamide were added at 100° C. to this mixture, whereupon the mixture was refluxed for a further 4 hours. It was then cooled and concentrated. The resulting product of value was reacted further in the following step 4 without further purification.

Step 4

3-Chloro-2-[4-chloro-3-(1'-aminocarbonylpent-1'-oxy)phenyl]-4,5,6,7-tetrahydroindazole The 3-chloro-2-[4-chloro-3-(1'-chloroformylpent-1'-oxy)phenyl]-4,5,6,7-tetrahydroindazole which had been obtained in step 3, 5 g of 25% strength aqueous ammonia solution and 200 ml of tetrahydrofuran were stirred at approximately 20° C. for 12 hours. The mixture was subsequently concentrated and the residue taken up in water, whereupon the mixture was acidified with dilute hydrochloric acid. This gave a suspension whose solids were separated off, washed with water and dried under reduced pressure. Yield: 4.7 g.

Step 5

3-Chloro-2-[4-chloro-3-(1'-cyanopent-1'-oxy) phenyl]-4,5,6,7-tetrahydroindazole 3.5 g of pyridine and then 4.6 g of trifluoroacetic anhydride were added dropwise at 0° C. to 4.5 g of 3-chloro-2-[4-chloro-3-(1'-aminocarbonylpent-1'-oxy)phenyl]-4,5,6,7-tetrahydroindazole in 200 ml of diethyl ether. After the reaction mixture had been stirred at approximately 20° C. for 12 hours, it was treated with water. The organic phase was separated off and washed with dilute hydrochloric acid, water and dilute sodium hydroxide solution. After the mixture was dried over sodium sulfate, the solvent was removed. Yield: 3.2 g.

Example 6

3-Chloro-2-[4-chloro-5-(1'-chloroeth-2'-oxy)-2-fluorophenyl]-4,5,6,7-tetrahydroindazole (compound 15)

1 drop of dimethylformamide was added to 1.55 g of 3-chloro-2-[4-chloro-5-(1'-hydroxyeth-2'-oxy)-2-fluorophenyl]-4,5,6,7-tetrahydroindazole in 50 ml of toluene. The mixture was subsequently heated at 50–60° C., and 0.59 g of thionyl chloride in 10 ml of toluene was added dropwise at this temperature. After the reaction mixture had been heated at 30–60° C. for 5 hours, a further 0.59 g of thionyl chloride in 10 ml of toluene was added dropwise The mixture was subsequently stirred at 50–60° C. for a further 6 hours. For working-up, the mixture was cooled, and the low-boiling components were subsequently removed under a water-pump vacuum. The residue was taken up in water, whereupon the mixture was extracted using ethyl acetate. The combined organic phases were dried over sodium sulfate and then concentrated.

Yield: 1.16 g.

Example 7

3-Chloro-2-[4-chloro-2-fluoro-5-(1'-iodoeth-2'-oxy) phenyl]-4,5,6,7-tetrahydroindazole (compound 18)

A mixture of 1.77 g of 3-chloro-2-[4-chloro-5-(1'-chloroeth-2'-oxy)-2-fluorophenyl]-4,5,6,7-tetrahydroindazole, 1.20 g of sodium iodide, a small amount of molecular sieve and 50 ml of acetone was refluxed for 4 hours. After a further 1.20 g of sodium iodide had been added, the mixture was refluxed for a further 6 hours. This process was repeated four more times. The cooled reaction mixture was finally freed from insoluble inorganic components, whereupon the liquid phase was concentrated. The residue was taken up in water, giving a suspension whose solids were separated off, washed with water and dried under reduced pressure. Yield: 1.10 g.

Example 8

3-Chloro-2-[4-chloro-3-(1'-bromo-2',2'-dimethyl-prop-3'-oxy)phenyl]-4,5,6,7-tetrahydroindazole (compound 29)

Precursor

3-Chloro-2-[4-chloro-3-(1'-hydroxy-2',2'-dimethyl-prop-3'-oxy)-phenyl]-4,5,6,7-tetrahydroindazole A mixture of 2.8 g of 3-chloro-2-[4-chloro-3-hydroxyphenyl]-4,5,6,7-tetrahydroindazole, 2.8 g of potassium carbonate, 1.5 g of potassium iodide, 1.2 g of 1-chloro-2,2-dimethyl-3-propanol and 100 ml of dimethylformamide was refluxed for 6 hours. The mixture was then treated with a further 2.8 g of potassium carbonate, 1.5 g of potassium iodide and 1.2 g of 1-chloro-2,2-dimethyl-3-propanol. The mixture was subsequently refluxed for another 6 hours. The cooled reaction mixture was concentrated, whereupon the residue was taken up in water. The product was extracted using ethyl acetate, isolated by drying the combined organic phases over sodium sulfate and removing the solvent, and purified by means of chromatography on silica gel (eluent: cyclohexane/methyl tert-butyl ether=7:3). Yield: 1.6 g.

Preparation of the end product 5.4 g of tetrabromomethane and 4.2 g of triphenylphosphine were added to 3.0 g of 3-chloro-2-[4-chloro-3-(1'-hydroxy-2',2'-dimethyl-prop-3'-oxy)phenyl]-4,5,6,7-tetrahydroindazole in 200 ml of acetonitrile. After the mixture had been stirred at approximately 20° C. for 12 hours, it was refluxed for a further 5 hours, subsequently cooled and then concentrated. The crude product was purified by filtration through silica gel (eluent: diethyl ether). Yield after drying the filtrate over sodium sulfate and removing the ether: 2.7 g.

Preparation Example 9

3-Methyl-1- and 3-methyl-2-[4-chloro-3-cyanomethoxyphenyl]-4,5,6,7-tetrahydroindazole (mixture of isomers; compound 30)

Step 1

3-Methyl-1- and 3-methyl-2-[4-chloro-3-methoxyphenyl]-4,5,6, 7-tetrahydroindazole A mixture of 5.0 g of 2-acetylcyclohexanone, 6.2 g of 4-chloro-3-methoxyphenylhydrazine, a spatula-tipful of p-toluenesulfonic acid and 100 ml of xylene was refluxed for 3 hours in a water separator. After cooling, the mixture was washed with water, dried and concentrated. Yield: 9.0 g.

Step 2

3-Methyl-1- and 3-methyl-2-[4-chloro-3-hydroxyphenyl]-4,5,6,7-tetrahydroindazole 7.0 g of the mixture of 3-methyl-1- and 3-methyl-2-[4-chloro-3-methoxyphenyl]-4,5,6,7-tetrahydroindazole which had been prepared in step 1 were added to 60 ml of 47% strength aqueous hydrobromic acid, whereupon the mixture was stirred at boiling point for 4 hours. The cooled reaction mixture was taken up in water and extracted using ethyl acetate. The combined organic phases are dried over sodium sulfate and concentrated. Yield: 1.6 g.

Step 3

3-Methyl-1- and 3-methyl-2-[4-chloro-3-cyanomethoxyphenyl]-4,5,6,7-tetrahydroindazole (mixture of isomers)

3.0 g of a mixture of 3-methyl-1- and 3-methyl-2-[4-chloro-3-hydroxyphenyl]-4,5,6,7-tetrahydroindazole, 1.3 g of bromoacetonitrile and 1.5 g of potassium carbonate in 50 ml of dimethylformamide were stirred at approximately 20° C. for 6 hours. The mixture was subsequently diluted with water, whereupon the product mixture was extracted using methylene chloride. The combined organic phases were dried over sodium sulfate and chromatographed on silica gel (eluent: cyclohexane/methyl tert-butyl ether=7:3). Yield: 1.3 g.

Table 6 which follows shows other compounds I which were prepared, or can be prepared, in analogy to the examples:

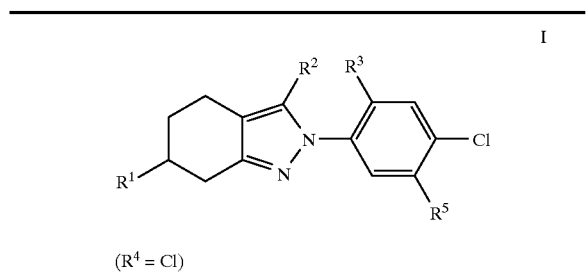

(R$^4$ = Cl)

I

| Compound No. | R$^1$ | R$^2$ | R$^3$ | R$^5$ | Melting point [° C.]/ $^1$H-NMR [ppm]/ IR [cm$^{-1}$] |
|---|---|---|---|---|---|
| 1 | H | Cl | H | OCH$_2$—CN | 114–116 |
| 2 | H | Cl | H | OCH(CH$_3$)—CN | 1.76(m, 7H), 2.54(m, 2H), 2.64(m, 2H), 5.64(q, 1H), 7.35(dd, 1H), 7.56(d, 1H), 7.70(d, 1H) |
| 3 | H | Cl | H | OCH$_2$CH$_2$CH$_2$—CN | 40–41 |
| 4 | H | Cl | H | OCH$_2$CH$_2$—Cl | 1.68(m, 4H), 2.44(m, 2H), 2.62(m, 2H), 3.99(t, 2H), 4.40(t, 2H), 7.16(dd, 1H), 7.35(d, 1H), 7.58(d, 1H) |
| 5 | H | Cl | F | OCH$_2$—CN | 1.75(m, 4H), 2.48(m, 2H), 2.65(m, 2H), 5.35(s, 2H), 7.60(d, 1H), 7.90(d, 1H) |
| 6 | H | Cl | F | OCH$_2$CH$_2$CH$_2$—CN | 80 |
| 7 | H | Cl | F | OCH(CH$_3$)—CN | 1.72(d, 3H), 1.75(m, 4H), 2.48(t, 2H), 2.64(t, 2H), 5.58(q, 1H), |

-continued

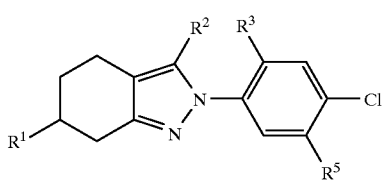

(R$^4$ = Cl)

I

| Compound No. | R$^1$ | R$^2$ | R$^3$ | R$^5$ | Melting point [° C.]/ $^1$H-NMR [ppm]/ IR [cm$^{-1}$] |
|---|---|---|---|---|---|
| 8 | H | Cl | H | OCH(CH$_2$CH$_2$CH$_2$CH$_3$)—CN | 7.65(d, 1H), 7.90(d, 1H) 0.92(t, 3H), 1.46(m, 4H), 1.74(m, 4H), 2.06(m, 2H), 2.44(m, 2H), 2.62(m, 2H), 5.60(t, 1H), 7.32(dd, 1H), 7.56(d, 1H), 7.66(d, 1H) |
| 9 | H | Cl | H | OCH$_2$—CF$_3$ | 83 |
| 10 | H | Cl | H | OCH(C$_2$H$_5$)—CN | 1.10(t, 3H), 1.73(m, 4H), 2.07(m, 2H), 2.47(m, 2H), 2.63(m, 2H), 5.57(m, 1H), 7.30(dd, 1H), 7.54(d, 1H), 7.67(d, 1H) |
| 11 | H | Cl | F | OCH$_2$—CF$_3$ | >200 |
| 12 | H | Cl | H | OCH$_2$CH(CH$_3$)—CH$_2$CN | 1.12(d, 3H), 1.74(m, 4H), 2.35(m, 1H), 2.42(m, 2H), 2.60(m, 3H), 2.74(dd, 1H), 3.96(dd, 1H), 4.06(dd, 1H), 7.16(dd, 1H), 7.32(dd, 1H), 7.59(d, 1H) |
| 13 | H | Cl | H | OCH$_2$CH$_2$—Br | 2930, 1595, 1495 |
| 14 | H | Cl | H | OCH$_2$CH$_2$—I | 74 |
| 15 | H | Cl | F | OCH$_2$CH$_2$—Cl | 1.72(m, 1H), 2.46(t, 2H), 2.60(t, 2H), 3.92(t, 2H), 4.37(t, 2H), 7.40(d, 1H), 7.78(d, 1H) |
| 16 | H | Cl | F | OCH$_2$CH$_2$—Br | 81 |
| 17 | H | Cl | F | OCH(C$_2$H$_5$)—CN | 01 |
| 18 | H | Cl | F | OCH$_2$CH$_2$—I | 69 |
| 19 | CH$_3$ | Cl | H | OCH$_2$—CN | 91 |
| 20 | H | Cl | H | OCH$_2$CH$_2$CH(CH$_3$)—CN | 1.35(d, 3H), 1.75(m, 4H), 2.06(q, 2H), 2.45(t, 2H), 2.62(t, 2H), 3.07(m, 1H), |

-continued

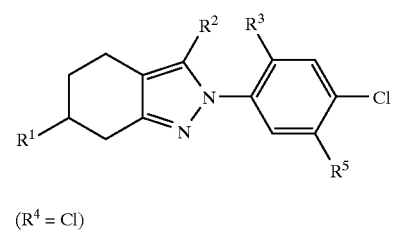

($R^4 = Cl$)

| Compound No. | $R^1$ | $R^2$ | $R^3$ | $R^5$ | Melting point [° C.]/ $^1$H-NMR [ppm]/ IR [cm$^{-1}$] |
|---|---|---|---|---|---|
| 21 | H | Cl | H | SCH$_2$—CN | 4.23(m, 2H), 7.18(dd, 1H), 7.36(d, 1H), 7.60(d, 1H) 137–138 |
| 22 | CH$_3$ | Cl | H | OCH(CH$_3$)—CN | 1.05(d, 3H), 1.35(m, 1H), 1.72(d, 3H), 1.85(m, 2H), 2.19(dd, 1H), 2.50(m, 2H), 2.75(dd, 1H), 5.62(q, 1H), 7.30(dd, 1H), 7.56(d, 1H), 7.60(d, 1H) |
| 23 | H | Cl | H | OCH(CH(CH$_3$)$_2$)—CN | 57–58 |
| 24 | H | Cl | H | OCH$_2$C(CH$_3$)$_2$CH$_2$—CN | 1.14(s, 6H), 1.76(m, 4H), 2.44(t, 2H), 2.62(t, 2H), 2.66(s, 2H), 3.90(s, 2H), 7.17(dd, 1H), 7.32(d, 1H), 7.60(d, 1H) |
| 25 | H | Cl | H | OCH$_2$CH$_2$CH$_2$CH$_2$—Cl | 1.76(m, 4H), 1.90(m, 4H), 2.42(m, 2H), 2.58(m, 2H), 3.72(m, 2H), 4.16(m, 2H), 7.13(d, 1H), 7.28(s, 1H), 7.56(d, 1H) |
| 26 | H | Cl | H | OCH(CH$_3$)CH$_2$—Br | 1.55(d, 3H), 1.82(m, 4H), 2.50(t, 2H), 2.70(t, 2H), 3.50(dd, 1H), 3.62(dd, 1H), 4.62(m, 1H), 7.16(m, 2H), 7.46(d, 1H) |
| 27 | H | Cl | H | OCH$_2$CH$_2$CH$_2$—F | 1.72(m, 2H), 2.15(dq, 2H), 2.44(m, 2H), 2.62(m, 2H), 4.22(t, 2H), 4.66(dt, 2H), 7.15(dd, 1H), 7.34(d, 1H), |

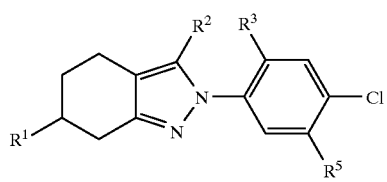

($R^4 = Cl$)

| Compound No. | $R^1$ | $R^2$ | $R^3$ | $R^5$ | Melting point [° C.]/ $^1$H-NMR [ppm]/ IR [cm$^{-1}$] |
|---|---|---|---|---|---|
| 28 | H | Cl | H | OCH$_2$C(CH$_3$)$_2$CH$_2$—Cl | 7.58(d, 1H) 1.12(s, 6H), 1.78(m, 4H), 2.46(m, 2H), 2.63(m, 2H), 3.70(s, 2H), 4.93(s, 2H), 7.17(dd, 1H), 7.30(d, 1H), 7.60(d, 1H) |
| 29 | H | Cl | H | OCH$_2$C(CH$_3$)$_2$CH$_2$—Br | 1.13(s, 6H), 1.76(m, 4H), 2.47(m, 2H), 2.63(m, 2H), 3.63(s, 2H), 3.93(s, 2H), 7.15(dd, 1H), 7.30(d, 1H), 7.60(d, 1H) |
| 30 | H | CH$_3$ | H | OCH$_2$—CN | 110–112 (mixtures of isomers) |
| 31 | H | Cl | H | SCH(CH$_3$)—CN | 101–102 |
| 32 | H | Cl | H | SCH$_2$CH$_2$CH$_2$CN | 1.80(m, 4H), 2.08(t, 2H), 2.54(m, 4H), 2.70(m, 2H), 3.12(t, 2H), 7.32(dd, 1H), 7.45(m, 2H) |
| 33 | H | Cl | H | SCH$_2$CF$_3$ | 1.82(m, 4H), 2.51(t, 2H), 2.69(t, 2H), 3.52(q, 2H), 7.47(m, 2H), 7.75(s, 1H) |
| 34 | H | Cl | H | OCH(CH$_2$F)$_2$ | 1.76(m, 4H), 2.47(t, 2H), 2.62(t, 2H), 4.73(m, 4H), 5.11(m, 1H), 7.21(dd, 1H), 7.50(d, 1H), 7.62(d, 1H) |
| 35 | H | Cl | H | OCH(CH$_2$Cl)CH$_2$OCH$_3$ | 1.75(m, 4H), 2.44(m, 2H), 2.60(m, 2H), 3.35(s, 3H), 3.65(m, 2H), 3.88(m, 2H), 4.86(m, 1H), 7.18(dd, 1H), 7.48(d, 1H), 7.58(d, 1H) |
| 36 | H | Cl | H | OCH$_2$C(CH$_3$)$_2$CH$_2$I | 1.22(s, 6H), 1.82(m, 4H), |

-continued

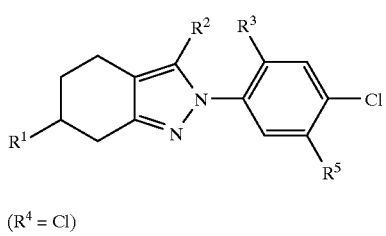

($R^4$ = Cl)

| Compound No. | $R^1$ | $R^2$ | $R^3$ | $R^5$ | Melting point [° C.]/ $^1$H-NMR [ppm]/ IR [cm$^{-1}$] |
|---|---|---|---|---|---|
| 37 (mixtures of isomers) | H | CH$_3$ | H | OCH(CH$_3$)CN | 2.50(t, 2H), 2.73(t, 2H), 3.42(s, 2H), 3.86(s, 2H), 7.08(m, 2H), 7.42(d, 1H) 1.84(m, 7H), 2.24, 2.30(s, 3H), 2.48(m, 2H), 2.76(m, 2H), 5.00(m, 1H), 7.15, 7.20(dd, 1H), 7.23, 7.28(d, 1H), 7.44, 7.48(d, 1H) |
| 38 | H | Cl | H | SCH$_2$CH$_2$CN | 68–70 |
| 39 | H | Cl | H | S(O)CH$_2$CH$_2$CN | 1.74(m, 4H), 2.45(t, 2H), 2.56(m, 1H), 2.74(t, 2H), 2.92(m, 1H), 3.25(m, 1H), 3.46(m, 1H), 7.52(d, 1H), 7.79(dd, 1H), 8.10(d, 1H) |

Use Examples
(herbicidal activity)

The herbicidal action of the N-phenyltetrahydroindazoles I was demonstrated by the following greenhouse tests:

Plastic flowerpots containing loamy sand and approximately 3.0% of humus as substrate were used as culture vessel. The seeds of the test plants were sown separately, according to species.

For the pre-emergence treatment, the active compounds which were suspended or emulsified in water were applied directly after the seeds had been sown using finely dispersing nozzles. The vessels were irrigated lightly to promote germination and growth and subsequently covered with transparent plastic hoods until the plants had rooted. This hood causes uniform germination of the test plants if this has not been adversely affected by the active compounds.

For post-emergence treatment, the test plants were first grown to a plant height of 3 to 15 cm, depending on the growth form, and only then treated with the active compounds which were suspended or emulsified in water. The test plants for this purpose were either sown directly and grown on in the same vessels, or first grown separately as seedlings and transplanted into the test containers a few days prior to treatment. The rate for post-emergence treatment was 0.0313, 0.0156 or 0.0078 kg/ha of a.s. (active substance).

Depending on the species, the plants were kept at 10–25° C. or 20–35° C. The test period extended over 2–4 weeks. During this time, the plants were tended and their response to the individual treatments was evaluated.

Assessment was carried out using a scale from 0 to 100. 100 means that no plants have emerged or that at least the aerial parts have been destroyed completely, and 0 means no damage or normal course of growth.

The plants used in the greenhouse tests comprised the following species:

| Botanical Name | Common Name |
|---|---|
| Abutilon theophrasti | velvet leaf |
| Amaranthus retroflexus | carelessweed; redroot pigweed |
| Chenopodium album | lambsquarters (goosefoot) |
| Crysanthanemum coronarium | garland chrysanthemum; crown daisy |
| Galium aparine | catchweed bedstraw |
| Ipomoea subspecies | morning glory |
| Sinapis alba | white mustard |
| Sida spinosa | prickly sida; teaweed |
| Solanum nigrum | black nightshade |
| Veronica subspecies | speedwell |
| Xanthium strumarium | cocklebur |

Compounds No. 5, 7 and 15 effect very good control of broad-leaf plants when used post-emergence at a rate of 0.0313 or 0.0156 kg/ha of a.s.

By contrast, EP-A 049 508 discloses comparative compound A (No. 228 therein)

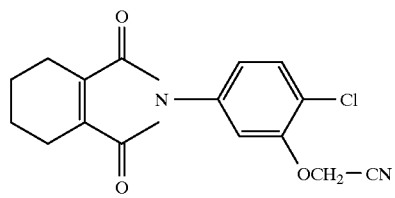

and EP-A 379 099 discloses comparative compounds B (No. 2.003 therein)

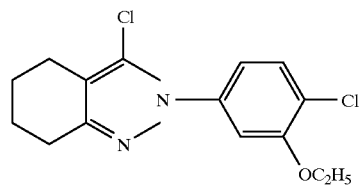

and C (No. 2.009 therein)

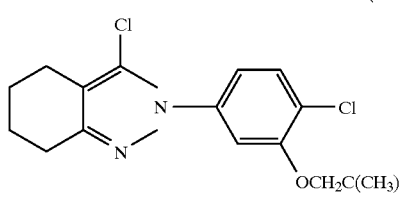

which had a lesser herbicidal action.

Use examples (desiccant/defoliant activity)

The test plants were young cotton plants having 4 leaves (without cotyledons) which had been grown under greenhouse conditions (relative atmospheric humidity 50 to 70%, day/night temperatures 27/20° C.).

The young cotton plants underwent leaf treatment to runoff point with aqueous preparations of the active compounds (with an addition of 0.15% by weight of the fatty alcohol alkoxylate Plurafac LF 700, based on the spray mixture). The amount of water applied was 1000 1/ha (converted). After 13 days, the number of leaves shed and the degree of defoliation in % were determined.

No leaf dehiscence was observed in the untreated control plants.

We claim:

1. An N-phenyltetrahydroindazole of the formula I

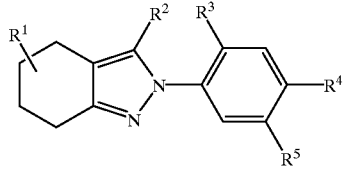

I where $R^1$ is hydrogen;

$R^2$ is halogen;

$R^3$ is hydrogen or halogen;

$R^4$ is halogen;

$R^5$ is —$OR^6$;

$R^6$ is —Alk—$R^7$;

$R^7$ is cyano;

Alk is a methylene, ethylene, propylene, butylene or pentamethylene chain, where any methylene unit which can be substituted can carry one —CO—($C_1$–$C_4$-alkoxy) or $C_1$–$C_6$-alkyl substituent.

2. A compound of the formula I or an agriculturally utilizable salt thereof as claimed in claim 1, where $R^3$ is hydrogen, fluorine or chlorine.

3. A process for the preparation of N-phenyltetrahydroindazoles of the formula I as claimed in claim 1 where $R^7$ is cyano which comprises reacting a compound of the formula III

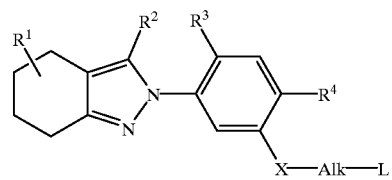

III in which L is a customary leaving group and X is oxygen, with a compound of the formula M-$R^7$ where M is an alkali metal, alkaline earth metal or transition metal.

4. A process for the preparation of N-phenyltetrahydroindazoles of the formula I as claimed in claim 1 where $R^7$ is cyano, which comprises eliminating water in a manner known per se from a compound of the formula IX

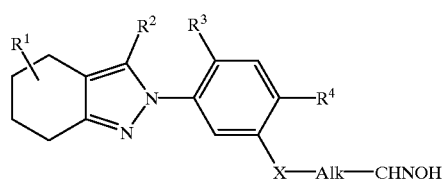

IX or XI

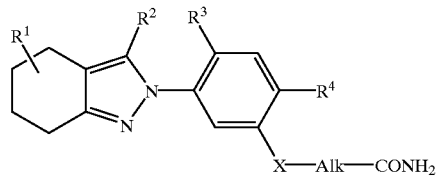

XI

5. A process for the preparation of N-phenyltetrahydroindazoles of the formula I as claimed in claim 1 where X is oxygen, which comprises reacting a phenol or thiophenol of the formula XII

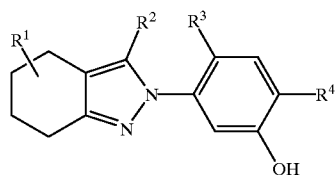

XII with a compound of the formula XIII

L—Alk—$R^7$   XIII where L is a customary leaving group.

6. A process for the preparation of N-phenyltetrahydroindazoles of the formula I as claimed in claim 1 where X is oxygen, which comprises reacting a compound of the formula XIV

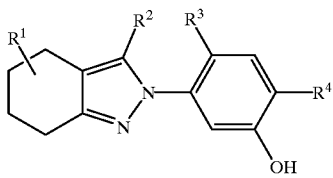

XIV with an alcohol HO—Alk—R⁷ (XV) by the Mitsunobu method.

7. A process for the preparation of N-phenyltetrahydroindazoles of the formula I as claimed in claim 1 where $R^2$ is halogen, which comprises reacting a cyclohexanonecarboxylic acid derivative of the formula XIX

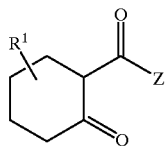

XIX where Z is a nucleophilic leaving group, with a hydrazine of the formula XVII

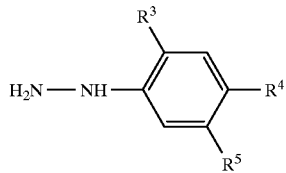

XVII and halogenating the process product XVIII

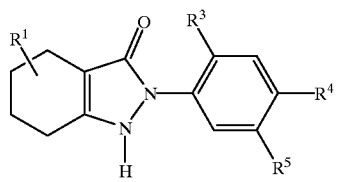

XVIII

8. A herbicide, comprising a herbicidally active amount of at least one N-phenyltetrahydroindazole of the formula I or of an agriculturally utilizable salt of I as claimed in claim 1 and at least one inert liquid and/or solid carrier and, if desired, at least one adjuvant.

9. A plant desiccant and/or defoliant, comprising an amount with a desiccant/defoliant action of at least one N-phenyltetrahydroindazole of the formula I or an agriculturally utilizable salt of I as claimed in claim 1, and at least one inert liquid and/or solid carrier and, if desired, at least one adjuvant.

10. A process for the preparation of herbicides, which comprises mixing a herbicidally active amount of at least one N-phenyltetrahydroindazole of the formula I or an agriculturally utilizable salt of I as claimed in claim 1, at least one inert liquid and/or solid carrier and, if desired, at least one adjuvant.

11. A process for the preparation of desiccants and/or defoliants, which comprises mixing an amount with a desiccant and/or defoliant action of at least one N-phenyltetrahydroindazole of the formula I or an agriculturally utilizable salt of I as claimed in claim 1, at least one inert liquid and/or solid carrier and, if desired, at least one adjuvant.

12. A method of controlling undesirable vegetation, which comprises allowing a herbicidally active amount of at least one N-phenyltetrahydroindazole of the formula I or of an agriculturally utilizable salt of I as claimed in claim 1 to act on plants, their environment or on seed.

13. A method for desiccating and/or defoliating plants, which comprises allowing an amount with a desiccant and/or defoliant action of at least one N-phenyltetrahydroindazole of the formula I or of an agriculturally utilizable salt of I as claimed in claim 1 to act on plants.

* * * * *

UNITED STATES PATENT AND TRADEMARK OFFICE
CERTIFICATE OF CORRECTION

PATENT NO.: 5,939,558

DATED: August 17, 1999

INVENTOR(S): HEISTRACHER et al.

It is certified that error appears in the above-identified patent and that said Letters Patent is hereby corrected as shown below:

In the abstract, item [57], line 29, "-$R^{11}$" should be -- -$OR^{11}$--.

Signed and Sealed this

First Day of February, 2000

Attest:

Attesting Officer

Q. TODD DICKINSON

Acting Commissioner of Patents and Trademarks